(12) United States Patent
Kim

(10) Patent No.: US 11,952,414 B2
(45) Date of Patent: Apr. 9, 2024

(54) PEPTIDE USED FOR IMMUNOTHERAPEUTICS

(71) Applicant: 3H BIO. CO., LTD., Gyeonggi-do (KR)

(72) Inventor: Hyo Joon Kim, Gyeonggi-Do (KR)

(73) Assignee: 3H BIO. CO., LTD., Gyeonggi-do (KR)

( * ) Notice: Subject to any disclaimer, the term of this patent is extended or adjusted under 35 U.S.C. 154(b) by 0 days.

(21) Appl. No.: 17/823,180

(22) Filed: Aug. 30, 2022

(65) Prior Publication Data

US 2023/0087676 A1 Mar. 23, 2023

Related U.S. Application Data

(63) Continuation of application No. 17/639,547, filed as application No. PCT/KR2021/009453 on Jul. 21, 2021.

(30) Foreign Application Priority Data

Jul. 22, 2020 (KR) .................. 10-2020-0091031
Jul. 22, 2020 (KR) .................. 10-2020-0091032
Jul. 22, 2020 (KR) .................. 10-2020-0091033

(51) Int. Cl.
| | | |
|---|---|---|
| *C07K 14/775* | (2006.01) | |
| *A61K 38/16* | (2006.01) | |
| *A61P 3/04* | (2006.01) | |
| *C07K 14/435* | (2006.01) | |
| *A61K 38/00* | (2006.01) | |

(52) U.S. Cl.
CPC ............ *C07K 14/775* (2013.01); *A61K 38/16* (2013.01); *A61P 3/04* (2018.01); *C07K 14/435* (2013.01); *A61K 38/00* (2013.01); *C07K 2319/00* (2013.01)

(58) Field of Classification Search
CPC .......... C07K 14/775; A61P 3/04; A61K 38/16
See application file for complete search history.

(56) References Cited

U.S. PATENT DOCUMENTS

| | | | | |
|---|---|---|---|---|
| 7,829,667 B2 * | 11/2010 | Kim | ................. | C07K 14/775 530/300 |
| 2011/0002955 A1 * | 1/2011 | Kim | ................. | C07K 14/775 536/23.4 |
| 2014/0220059 A1 * | 8/2014 | Asari | ................. | A61K 9/0043 424/185.1 |
| 2017/0165358 A1 | 6/2017 | Alving et al. | | |

FOREIGN PATENT DOCUMENTS

| | | |
|---|---|---|
| KR | 2002/0018971 A | 3/2002 |
| KR | 2005/0093280 A | 9/2005 |
| KR | 2008/0027753 A | 3/2008 |
| KR | 102261457 B1 | 6/2021 |
| WO | WO-97/26784 A1 | 7/1997 |
| WO | WO-2022/019665 A1 | 1/2022 |

OTHER PUBLICATIONS

International Search Report Translation for International Application No. PCT/KR2021/009453 dated Nov. 22, 2021.

\* cited by examiner

*Primary Examiner* — Amber D Steele
(74) *Attorney, Agent, or Firm* — Foley Hoag LLP; David P. Halstead

(57) ABSTRACT

Provided is a peptide provided herein includes at least one peptide unit, and the peptide unit may include at least one B-cell epitope, at least one Th epitope, and an appropriate number of auxiliary parts. The peptide unit is a portion designed to uniformly induce only the intended antibody while exhibiting a certain level of immunogenicity in the body of a subject. In addition, the peptide unit is designed with a relatively short length, and thus has the characteristics of easy synthesis and a low production cost. The peptide has properties suitable for use as an immunotherapeutic due to the characteristics of the peptide unit described above. In the present specification, the design principles of the peptide and the peptide unit are disclosed in detail.

3 Claims, 25 Drawing Sheets

Specification includes a Sequence Listing.

FIG. 8
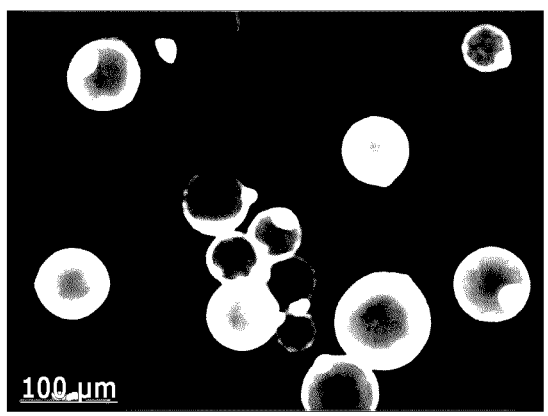
Lean
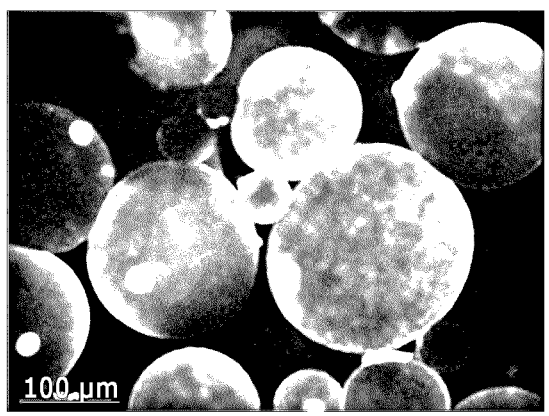
Obese
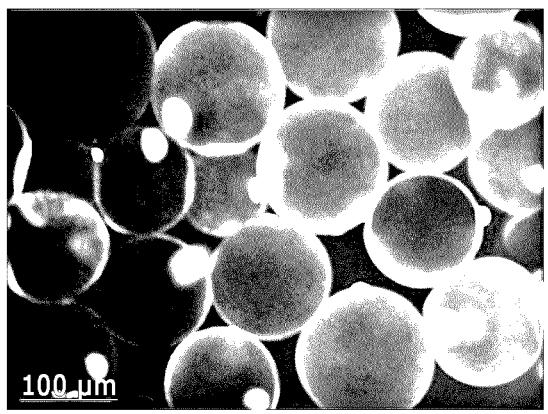
Mock
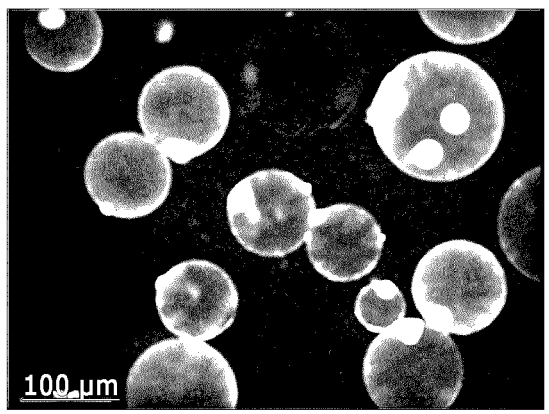
3H-OTP

FIG. 9
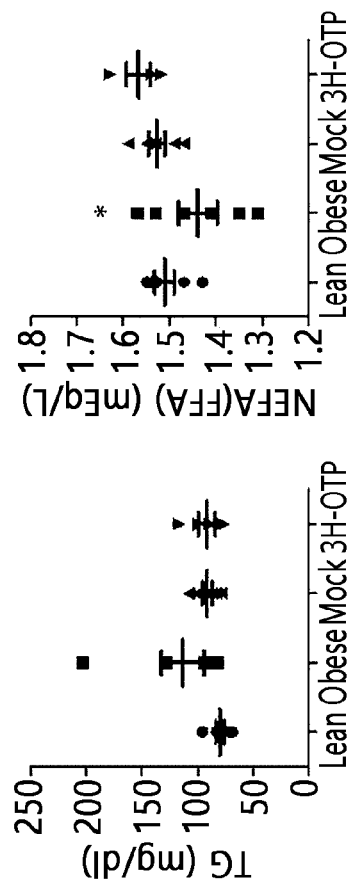
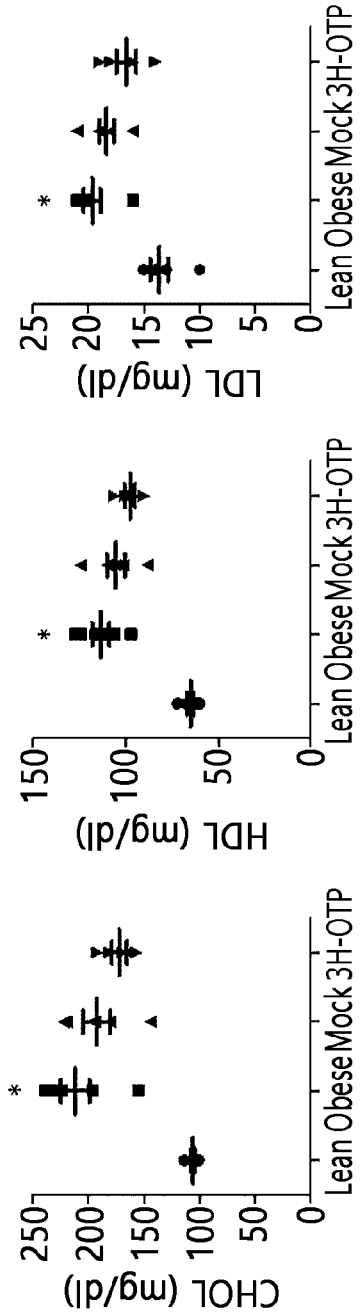

FIG. 23

Antibody Titer for each individual

| No | Lean 11 | 19 | No | Obese 11 | 19 | No | P1 11 | 19 | No | P3 11 | 19 | No | P4 11 | 19 |
|---|---|---|---|---|---|---|---|---|---|---|---|---|---|---|
| L1 | 0.0 | 0.0 | O1 | 0.0 | 0.0 | 1-1 | 10.6 | 37.8 | 3-1 | 0.0 | 0.1 | 4-1 | 0.0 | 0.0 |
| L2 | 0.0 | 0.0 | O2 | 0.0 | 0.0 | 1-2 | 0.4 | 0.2 | 3-2 | 51.6 | 18.9 | 4-2 | 0.0 | 0.0 |
| L3 | 0.0 | 0.0 | O3 | 0.0 | 0.0 | 1-3 | 178.1 | 21662.4 | 3-3 | 25.0 | 10.6 | 4-3 | 5.4 | 0.0 |
| L4 | 0.0 | 0.0 | O4 | 0.0 | 0.0 | 1-4 | 67.0 | 6184.6 | 3-4 | 0.0 | 0.0 | 4-5 | 0.0 | 0.0 |
| L5 | 0.0 | 0.0 | O5 | 0.0 | 0.0 | 1-5 | 0.0 | 0.0 | 3-5 | 27.2 | 0.3 | 4-6 | 0.0 | 0.0 |
| L6 | 0.0 | 0.0 | O6 | 0.0 | 0.0 | 1-6 | 252.5 | 2259.3 | 3-6 | 58.5 | 0.6 | 4-7 | 0.0 | 0.0 |
| L7 | 0.0 | 0.0 | O7 | 0.0 | 0.0 | 1-7 | 0.0 | 0.3 | 3-7 | 0.0 | 0.0 | 4-8 | 0.0 | 0.0 |
| L8 | 0.0 | 0.0 | O8 | 0.0 | 0.0 | 1-8 | 194.8 | 176.0 | 3-8 | 0.0 | 0.0 | | | |
| | | | O9 | 0.0 | 0.0 | 1-9 | 1274.4 | 573.0 | | | | | | |
| | | | O10 | 0.0 | 0.0 | 1-10 | 315.8 | 97.6 | | | | | | |
| | | | O11 | 0.0 | 0.0 | 1-11 | 47.2 | 23.6 | | | | | | |
| | | | O12 | 0.0 | 0.0 | 1-12 | 0.1 | 0.0 | | | | | | |
| ave | 0.0 | 0.0 | ave | 0.0 | 0.0 | ave | 195.1 | 2584.6 | ave | 20.3 | 3.8 | ave | 0.8 | 0.0 |
| sd | 0.0 | 0.0 | sd | 0.0 | 0.0 | sd | 357.7 | 6272.8 | sd | 24.4 | 7.1 | sd | 2.0 | 0.0 |
| se | 0.0 | 0.0 | se | 0.0 | 0.0 | se | 103.3 | 1810.8 | se | 8.6 | 2.1 | se | 0.7 | 0.0 |

FIG. 24

Antibody Titer for each individual

| No | Lean 11 | 19 | No | Obese 11 | 19 | No | P8 11 | 19 | No | P9 11 | 19 |
|---|---|---|---|---|---|---|---|---|---|---|---|
| L1 | 0.0 | 0.0 | O1 | 0.0 | 0.0 | 8-1 | 13634.7 | 1766.5 | 9-1 | 7.5 | 30.8 |
| L2 | 0.0 | 0.0 | O2 | 0.0 | 0.0 | 8-2 | 2865.4 | 2101.3 | 9-2 | 0.0 | 0.0 |
| L3 | 0.0 | 0.0 | O3 | 0.0 | 0.0 | 8-3 | 1630.4 | 3200.0 | 9-3 | 132.5 | 1164.8 |
| L4 | 0.0 | 0.0 | O4 | 0.0 | 0.0 | 8-4 | 891.7 | 776.6 | 9-4 | 2.6 | 0.0 |
| L5 | 0.0 | 0.0 | O5 | 0.0 | 0.0 | 8-5 | 2486.5 | 165.3 | 9-5 | 67.9 | 0.0 |
| L6 | 0.0 | 0.0 | O6 | 0.0 | 0.0 | 8-6 | 25829.2 | 5438.6 | 9-6 | 1.9 | 0.0 |
| L7 | 0.0 | 0.0 | O7 | 0.0 | 0.0 | 8-7 | 1307.1 | 432.0 | 9-7 | 9.3 | 38.5 |
| L8 | 0.0 | 0.0 | O8 | 0.0 | 0.0 | 8-8 | 1600.0 | 12504.4 | 9-8 | 0.0 | 1221.0 |
|  |  |  | O9 | 0.0 | 0.0 |  |  |  |  |  |  |
|  |  |  | O10 | 0.0 | 0.0 |  |  |  |  |  |  |
|  |  |  | O11 | 0.0 | 0.0 |  |  |  |  |  |  |
|  |  |  | O12 | 0.0 | 0.0 |  |  |  |  |  |  |
| ave | 0.0 | 0.0 | ave | 0.0 | 0.0 | ave | 6280.6 | 3298.1 | ave | 27.7 | 306.9 |
| sd | 0.0 | 0.0 | sd | 0.0 | 0.0 | sd | 8941.0 | 4097.3 | sd | 48.1 | 547.3 |
| se | 0.0 | 0.0 | se | 0.0 | 0.0 | se | 3161.1 | 1182.8 | se | 18.2 | 158.0 |

FIG. 25

Antibody Titer for each individual

| No | P2 11 | P2 16 | No | P5 11 | P5 16 | No | P7 11 | P7 16 |
|---|---|---|---|---|---|---|---|---|
| 2-1 | 0.4 | 1095.6 | 5-1 | 0.0 | 0.0 | 7-1 | 399.8 | 20.8 |
| 2-2 | 915.1 | 469.9 | 5-2 | 0.0 | 0.0 | 7-2 | 0.0 | 43.3 |
| 2-3 | 1926.3 | 3200.0 | 5-3 | 4344.9 | 293.3 | 7-3 | 0.0 | 0.0 |
| 2-4 | 2.4 | 9871.8 | 5-4 | 0.4 | 0.0 | 7-4 | 132.0 | 65.9 |
| 2-5 | 1.7 | 3200.0 | | | | 7-5 | 300.0 | 0.3 |
| 2-6 | 24.9 | 6436.4 | | | | 7-6 | 0.0 | 0.0 |
| 2-7 | 35.2 | 6611.6 | | | | 7-7 | 0.0 | 0.0 |
| 2-8 | 32.2 | 1147.4 | | | | 7-8 | 0.1 | 12.3 |
| ave | 367.3 | 4004.1 | ave | 1086.3 | 73.3 | ave | 104.0 | 17.8 |
| sd | 704.3 | 3328.4 | sd | 2172.4 | 146.6 | sd | 160.7 | 24.7 |
| se | 249.0 | 1176.8 | se | 768.1 | 51.8 | se | 56.8 | 8.7 |

PEPTIDE USED FOR IMMUNOTHERAPEUTICS

CROSS-REFERENCE TO RELATED APPLICATIONS

This Application is a Continuation of U.S. application Ser. No. 17/639,547, filed on Mar. 1, 2022, which is a U.S. § 371 National Stage Application based on PCT/KR2021/009453, filed on Jul. 21, 2021, which claims priority from Korean Application 10-2020-0091031, filed on Jul. 22, 2020; Korean Application 10-2020-0091032, filed on Jul. 22, 2020; and Korean Application 10-2020-0091033, filed on Jul. 22, 2020. The entire contents of PCT/KR2021/009453 are incorporated herein by reference in their entirety.

INCORPORATION BY REFERENCE OF SEQUENCE LISTING

The instant application contains a Sequence Listing which has been submitted electronically in .XML format and is hereby incorporated by reference in its entirety. Said XML copy, created on Nov. 8, 2022, is named "PYH-00902 Sequence Listing" and is 555,409 bytes in size.

TECHNICAL FIELD

The present disclosure relates to a peptide that is injected into the body of a subject to generate humoral immunity, which is a technology in the field of immunotherapeutics.

BACKGROUND ART

The purpose of an immunotherapeutic is to be introduced into the body of a subject to induce humoral immunity against the immunotherapeutic itself, and to thereby treat a specific illness or disease with the antibody produced as a result. In particular, the "treatment" also includes prevention of a specific illness or disease. Immunotherapeutics are similar to vaccines in that they induce antibody production through an antigen-antibody reaction in the body of a subject; however, they differ from vaccines in that the antibody has not only a binding ability to the immunotherapeutic itself, but also a binding ability to a specific target in the body (e.g., specific tissues and cells in the body, or substances generated in metabolic processes, etc.) thereby making it possible to treat a specific illness or disease, and administer repeatedly.

DISCLOSURE

Technical Problem

The present disclosure provides a peptide which has a function of inducing a pre-designed antibody in the body of a subject.

The present disclosure provides a composition for an immunotherapeutic including the peptide.

The present disclosure provides a nucleic acid sequence encoding the peptide.

The present disclosure provides uses of the peptide and a composition for an immunotherapeutic including the peptide.

Technical Solution

According to an aspect of the present disclosure, there is provided a peptide unit (a block of peptide) which is 23mer to 71mer in length, is recognized by CD4+ T-cells to induce a humoral immunity, and includes the following:
  at least one Th epitope, wherein the length of the Th epitope is 8mer to 32mer; and
  at least one B-cell epitope,
    wherein the B-cell epitope is a fragment or a mimotope of apolipoprotein B-100, which can induce an antibody targets apolipoprotein B-100.

In an embodiment, the peptide unit has a length in the range of 26mer to 50mer, and the Th epitope has a length in the range of 11mer to 13mer.

In an embodiment, the peptide unit includes one B-cell epitope and one Th epitope, and the peptide unit has a length in the range of 26mer to 45mer.

In an embodiment, the peptide unit includes one B-cell epitope and two Th epitopes (which are each referred to as a first Th epitope and a second Th epitope); the peptide unit has a length in the range of 37mer to 50mer; and the first Th epitope is linked between the B-cell epitope and the second Th epitope.

In an embodiment, the peptide unit includes two B-cell epitopes (which are each referred to as a first B-cell epitope and a second B-cell epitope) and one Th epitope; the peptide unit has a length in the range of 45mer to 50mer; and the second B-cell epitope is linked between the first B-cell epitope and the Th epitope.

In an embodiment, the peptide unit includes two B-cell epitopes (which are each referred to as a first B-cell epitope and a second B-cell epitope) and one Th epitope; the peptide unit has a length in the range of 45mer to 50mer; and the Th epitope is linked between the first B-cell epitope and the second B-cell epitope.

The present disclosure provides a nucleic acid encoding the peptide unit, or a peptide that does not include a nonstandard amino acid among the peptides.

The present disclosure provides a peptide in which 2 or more and 5 or less peptide units are linked.

The present disclosure provides a pharmaceutical composition for treating obesity including the following: the peptide unit or the peptide; and adjuvants.

The present disclosure provides a method for treating obesity including the following: administering the pharmaceutical composition into the body of a subject.

The present disclosure provides a use of the peptide unit or the peptide for treating obesity.

The present disclosure provides a use of the peptide unit or the peptide for preparing a therapeutic for obesity.

Advantageous Effects of Invention

When the peptide provided in the present disclosure is injected into the body of a subject, the peptide has the effect of inducing the production of an antibody with a specific physiological function, which specifically binds to a previously designed antigenic site.

BRIEF DESCRIPTION OF DRAWINGS

FIG. 8, which shows the results of the peptide effect confirmation experiment according to Experimental Example 3, is images showing the measured size of the adipocytes of a test subject for each experimental group (DAPI stained images of nuclei and lipids of adipocytes for each experimental group are shown), in which Lean denotes a control group with normal weight, Obese denotes an obesity group induced by high-fat diet, Mock denotes a group administered with placebo, and 3H-OTP denotes Group 2-1.

FIG. 9, which shows the results of the peptide effect confirmation experiment according to Experimental Example 3, is graphs showing the measured blood lipid concentration of a test subject for each experimental group, in which TG denotes triglyceride, NEFA denotes non-esterified fatty acid, CHOL denotes cholesterol, HDL denotes high-density lipoprotein, and LDL denotes low-density lipoprotein.

FIGS. 23 to 25, which show the results of the peptide effect confirmation experiment according to Experimental Example 7, and are tables describing the measured antibody titers at 11 weeks of age, 16 weeks of age, and 19 weeks of age of a test subject for each experimental group, in which Lean denotes a control group with normal weight, Obese denotes an obesity group induced by high-fat diet, P1 denotes Group 6-1, P2 denotes Group 6-2, P3 denotes Group 6-3, P4 denotes Group 6-4, P5 denotes Group 6-5, P6 denotes Group 6-6, P7 denotes Group 6-7, P8 denotes Group 6-8, and P9 denotes Group 6-9. In addition, the value identified by the label in the "No" column for each experimental group in each table denotes the experimental results of each individual subject in each experimental group, "ave" denotes the overall average, "sd" denotes the overall standard deviation, and "se" denotes the overall standard error.

DETAILED DESCRIPTION FOR CARRYING OUT THE INVENTION

Figure 1:
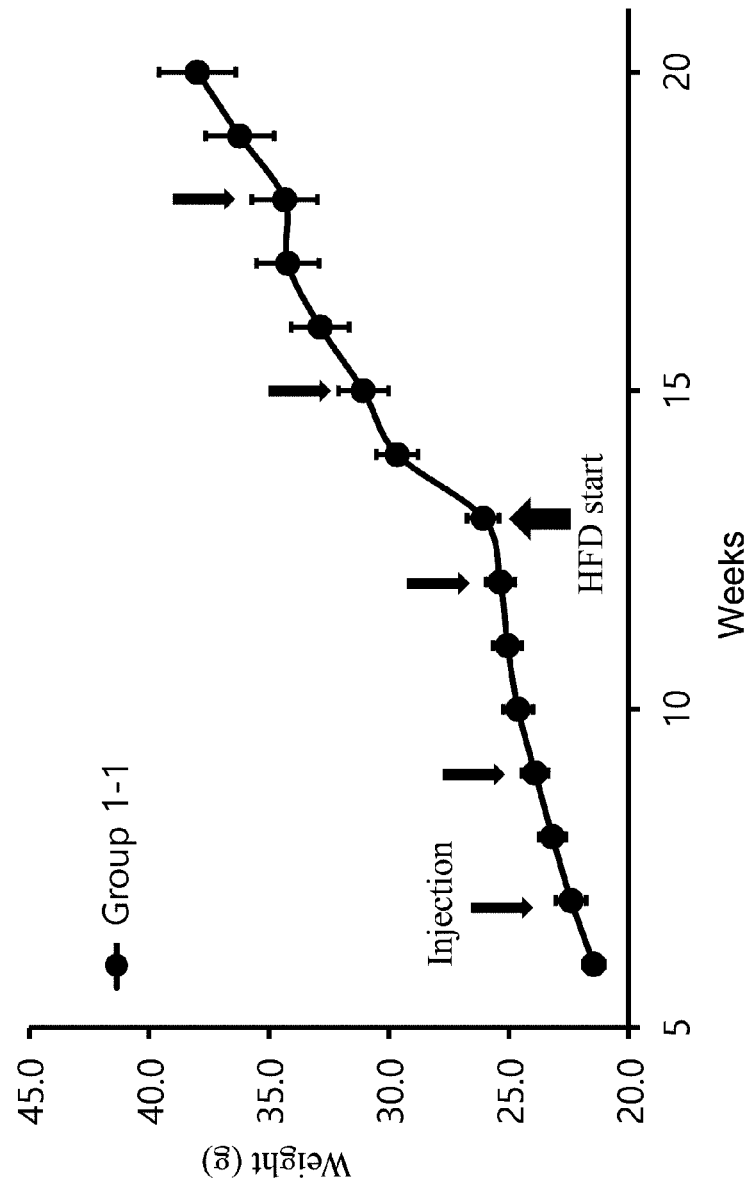
FIGS. 1 to 3, which show the results of the peptide effect confirmation experiment according to Experimental Example 2, are graphs showing the measured changes in body weight per week according to each experimental group.

Hereinafter, the presently disclosed subject matter now will be described in more detail in terms of some specific embodiments and examples with reference to the accompanying drawings. It should be noted that the accompanying drawings encompass some, but not all embodiments of the present disclosure. The presently disclosed subject matter may be embodied in many different forms and should not be construed as limited to the specific embodiments set forth herein. Rather, these embodiments are provided so that this disclosure will satisfy applicable legal requirements. Indeed, many modifications and other embodiments of the present disclosure will come to the mind of one skilled in the art to which the presently disclosed subject matter pertains. Therefore, it is to be understood that the presently disclosed subject matter is not to be limited to the specific embodiments disclosed and that modifications and other embodiments are intended to be included within the scope of the appended claims.

Definitions of General Terms About As used herein, the term "about" refers to a degree close to a certain quantity, and it refers to an amount, level, value, number, frequency, percent, dimension, size, amount, weight, or length that varies by to the extent of 30%, 25%, 20%, 25%, 10%, 9%, 8%, 7%, 6%, 5%, 4%, 3%, 2%, or 1% with respect to a reference amount, level, value, number, frequency, percentage, dimension, size, amount, weight, or length.

Peptide

As used herein, the term "peptide" refers to a polymer of amino acids. The term peptide refers to a form in which a small number of amino acids are linked, and is mainly used to distinguish it from a protein. There is no clear standard for distinguishing proteins from peptides, but as used herein, while about 200 amino acid polymers are referred to as peptides, those more than that are referred to as proteins, unless otherwise defined. The term "peptide" may include all other meanings recognized by those skilled in the art.

Subject

As used herein, the term "subject" refers to an organism that is an object exposed to a specific substance (e.g., peptide, etc.). The subject may refer to an independent organism (e.g., a human, animal, etc.) or may refer to a partial constitution of the independent organism (e.g., a part of a tissue, cell, etc.). This meaning may be appropriately interpreted according to the context. In addition, the term "subject" may further include all meanings recognized by those skilled in the art.

Immunotherapeutics

As used herein, the term "immunotherapeutics" is a concept distinguished from general therapeutics or vaccines. The immunotherapeutics are the same as existing vaccines in that they are injected into the body of a subject to induce a humoral immune response against the immunotherapeutics themselves. However, immunotherapeutics differ from existing vaccines in that the antibodies, which are induced as a result of the humoral immune response, have an ability being able to bind not only to the immunotherapeutics themselves, but also to specific tissues and cells in the body (e.g., receptors on the cell surface) or specific substances (e.g., peptides, lipids, proteins, and/or saccharides) produced during metabolism; thereby they can treat a specific illness or disease, and they can be administered continuously and repeatedly. Accordingly, the immunotherapeutics generally include antigens designed to induce antibodies having an ability to bind with a specific target tissue, cell, or substance in the body. Unless otherwise defined, the term "immunotherapeutics" is interpreted to include all antigens that can be appropriately used by those skilled in the art (e.g., peptides, proteins, lipids, saccharides, and/or complexes thereof, etc.) having the above-described functions. The term "immunotherapeutics" may be more limitedly referred to as "humoral-immunotherapeutics". In addition, the term "immunotherapeutics" may include all meanings recognized by those skilled in the art.

Treatment or Therapeutics

As used herein, the term "treatment" collectively refers to any direct or indirect action or measure to eliminate, alleviate, reduce, inhibit, or improve the disease, illness, disorder, and/or symptoms of a subject, or any direct or indirect action or measure to induce the results of preventing the disease, illness, disorder, and/or symptoms. As used herein, the term "therapeutics" refers to various substances (e.g., compounds or peptides) that can exhibit the "treatment" effect when administered in an appropriate way to a subject. In addition, the term "treatment" or "therapeutics" may include all other meanings recognized by those skilled in the art.

Immunogenicity

As used herein, the term "immunogenicity" collectively refers to "the property of acting as an antigen capable of inducing an immune response" in the dictionary. There are various methods for measuring the immunogenicity of a specific antigen, and the methods may be appropriately adopted or designed according to the purpose. For example, the methods may include 1) a method for confirming whether IgG, IgA, and/or IgE type antibodies are generated in the body of a subject when the antigen is administered into the body of the subject, 2) a method for confirming the time when the IgG, IgA, and/or IgE type antibodies are generated depending on the administration cycle, 3) a method for confirming the titer of the induced antibodies to the antigen, and 4) when the mechanism of action of the induced antibodies is found, a method for measuring the effect according to the mechanism of action, but the methods are not limited thereto. The expression "increase of immunogenicity" may be used interchangeably with, for example, "increase of the effect of inducing an immune response", "improvement of the ability to induce antibodies", and "increase of the effectiveness as an immunotherapeutic", and it includes all of the expressions which those skilled in the art can properly interpret according to the context.

Mer

As used herein, the term "mer" generally refers to the number of units in a high molecular weight polymer. As used herein, the term "mer" is generally expressed as "peptide with a length of an N mer" along with a number when expressing the length of a peptide, which refers to a peptide in which a N number of amino acids are polymerized. The unit indicated by the expression "mer" should be properly interpreted within the context, and it includes all other meanings that can be recognized by those skilled in the art.

Standard Amino Acid

As used herein, the term "standard amino acid" refers to 20 amino acids synthesized through the transcription and translation processes of genes in the body of an organism. Specifically, the standard amino acid includes alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys K), methionine (Met, M), phenylalanine (Phe, F), proline (Pro, P), serine (Ser, S), threonine (Thr, T), tryptophan (Trp, W), tyrosine (Tyr, Y), and valine (Val, V). The standard amino acid has a corresponding DNA codon and can be represented by a general one-letter or three-letter notation of an amino acid. The subjects being referred to by the term standard amino acid should be appropriately interpreted according to the context, and they include all other meanings that can be recognized by those skilled in the art.

Nonstandard Amino Acid

As used herein, the term "nonstandard amino acid" refers to an amino acid other than the standard amino acid. The nonstandard amino acid includes artificial and unnatural amino acids, and it includes those amino acids which are chemically modified through posttranslational modification within an organism, etc. The nonstandard amino acid includes, for example, D-form alanine, L-cyclohexylalanine, 6-aminohexanoic acid, etc. Since the nonstandard amino acid does not have a corresponding DNA codon, it cannot be represented by a general one-letter or three-letter notation of an amino acid, and it is written using other characters and explained via additional explanation. The subjects being referred to by the term nonstandard amino acids should be appropriately interpreted according to the context, and they include all other meanings that can be recognized by those skilled in the art.

Description of Peptide Sequence

Unless otherwise stated, when describing the sequence of a peptide in the present specification, single letter notation or three letter notation of an amino acid is used, and it is written in the direction from the N-terminus to the C-terminus. For example, when expressed as RNVP, it refers to a peptide in which arginine, asparagine, valine, and proline are sequentially linked in the direction from the N-terminus to the C-terminus. For another example, when expressed as Thr-Leu-Lys, it refers to a peptide in which threonine, leucine, and lysine are sequentially linked in the direction from the N-terminus to the C-terminus. In the case of amino acids that cannot be represented by the one-letter notation, other letters are used to describe these amino acids, and will be explained via additional explanation.

When expressing a peptide as a structural formula, N- and —C may be used to clearly indicate the N-terminus or C-terminus, and may be underlined so as to distinguish the N-terminus and/or C-terminus. For example, when the structural formula of a peptide is expressed as N̲-B-T-A-C̲, "N-" written at the beginning and "—C" written at the end are symbols to clarify the N-terminus and C-terminus directions unless otherwise specified. This refers to a peptide in which the sequences represented by B, T, and A are linked in the direction from the N-terminus to the C-terminus.

Background—Humoral Immunity

Humoral Immunity by Immunoglobulin M (IgM)

Among humoral immunities, an IgM-induced immune response is an innate immune function which is mainly active in the primary immune response, and it occurs rapidly in the early stages of infection. IgM is mainly secreted in the form of a pentamer, and theoretically has 10 antigen-binding sites, and thus, it can bind to a large number of antigens simultaneously. Although IgM can bind to a wide variety of types and forms of antigens and, the affinity and avidity of the binding are limited by the intrinsic affinity of IgM itself. Therefore, the affinity and avidity of IgM to an antigen are significantly lower than those of an antibody, such as IgG generated by the aid of helper T cells.

Limitations of Humoral Immunity by IgM

Although IgM-induced humoral immunity plays an important role in the initial immune response, the effect relying on humoral immunity by IgM is limited because 1) the production of IgM produced by B cells is low compared to those of other types of antibodies (e.g., IgG produced by differentiated B cells, etc.), 2) the specific binding ability of IgM to an antigen is low compared to that of IgG, and 3) the degree of a secondary immune response is weak when re-exposed to the same antigen. Therefore, from the viewpoint of designing an antigen that induces an immune response, in the case where the antigen injected into the body of a subject induces only a humoral immunity by IgM, it is highly likely that the desired effect will not be obtained. Therefore, it is very important to design an antigen so as to induce a humoral immunity by IgG.

Humoral Immunity by Immunoglobulin G (IgG) 1—Overview

The humoral immunity that produces IgG mainly occurs in the germinal center of the spleen or lymph node, and it proceeds by the complex action of B cells, helper T cells, and antigen-presenting cells (APCs). The overall process is as follows. 1) B cells recognize invading antigens (mainly proteins or peptide antigens). 2) After the antigen-presenting cells endocytose the antigens (or fragments thereof) and cut them into smaller fragments within the cells, and present some of the fragments to MHC Class II on the surface of the antigen-presenting cells. 3) Helper T cells recognize the antigen fragments presented to the MHC Class II. 4) The helper T cells transmit a differentiation signal to the B cells (antigen-recognized cells). 5) The B cells are activated and some differentiate into plasma cells to produce an IgG antibody having a high specific binding ability to the antigens. 6) As a result of the activation of the B cells, some cells differentiate into memory B cells and are stored in the body so that they can trigger an immune response that quickly produces an IgG antigen when the same antigens re-invade.

Humoral Immunity by IgG 2—Antigen-Recognized Cells

Antigen-presenting cells are a collective term for cells which are capable of endocytosing protein fragments or peptides, cleaving them into shorter peptide fragments, placing them on MHC Class II, and presenting them on the surface of the antigen-presenting cells. Major antigen-presenting cells include B cells, macrophages, dendritic cells, etc. Antigen-presenting cells transport the endocytosed antigen fragments from the site of infection to the lymph node, and present the antigen fragments to helper T cells by MHC Class II, and thereby play a role in inducing an immune response by activating helper T cells that recognize the same.

Humoral Immunity by IgG 3—MHC Class II

MHC Class II is a molecule expressed on the surface of antigen-presenting cells and has a heterodimer structure consisting of a/β chains. MHC Class II, due to its structure, can bind to a peptide of a certain length and present the same. Antigen-presenting cells allow peptide fragments derived from foreign antigens to bind to MHC Class II and present them on the cell surface. HLA gene complexes (human leukocyte antigen gene complexes) are involved in the expression of MHC Class II in humans, and among them, gene complexes such as HLA-DP, DQ, DR, etc. are known to be involved in the expression of MHC Class II cell surface receptors on the surface of antigen-presenting cells. In humans, the HLA-DR gene is known to have various alleles according to race, and about 12 types of HLA-DR genes are known as the most frequently found alleles.

Humoral Immunity by IgG 4—MHC Class II Presentation by Antigen Presenting Cells

Although there is a slight difference between the literatures, the length of the peptide presented in MHC Class II is known to be in the range of about a 17mer to about a 24mer. Therefore, antigen-presenting cells do not present the endocytosed antigen proteins or peptide fragments on MHC Class II as they are, but they undergo a process of cleavage making them into smaller fragments of 17mers to 24mers. The antigen fragments (proteins or peptide fragments) endocytosed by the antigen-presenting cells are present in the endosome, and the endosome is fused with the lysosome of the antigen-presenting cells. Thereafter, the antigen fragments are cleaved into shorter peptides by various kinds of degrading enzymes present in the lysosome. Examples of the degrading enzymes include endopeptidases and exopeptidases. While endopeptidases act to cleave the antigen fragments by acting on the peptide bond inside the antigen fragments, exopeptidases mainly act to cleave the antigen fragments by acting on peptide bonds at both ends of the antigen fragments. When the antigen fragments are cleaved into peptides of an appropriate size through the above process, some of them are bound to MHC Class II present in the inner membrane of the lysosome. The lysosome returns to the cell surface and fuses with the cell's plasma membrane, and thereby MHC Class II and the peptide fragments bound thereto are exposed on the surface of antigen-presenting cells. This whole process is also called "the process by which antigen-presenting cells present antigens".

Humoral Immunity by IgG 5—Helper T Cell

Helper T lymphocytes are also known as CD4+ cells because they express CD4. Helper T cells express T cell receptors (TCRs) which have the ability to bind to MHC Class II on the surface. The T cell receptors generally form a complex with CD3. When antigens (e.g., peptide fragments) transported by antigen-presenting cells to lymph nodes are presented through MHC Class II, helper T cells recognize the antigen fragments presented above. The T cell receptor-CD3 complex and CD4 are involved in this recognition process. When the helper T cells successfully recognize the antigen fragments, they are activated to secrete various cytokines or differentiate themselves. The secreted cytokines are involved in the differentiation of B cells, which will be described later.

Humoral Immunity by IgG 6—B Cell Differentiation

Under the influence of the cytokines (e.g., interleukin-4 (IL-4), etc.) secreted by helper T cells, there occurs an immunoglobulin class switching of the B cells, thereby changing the isotypes of the antibodies produced by the B cells (e.g., from IgM to IgG). In addition, some of the B cells are differentiated into memory B cells and stored so as to induce a rapid immune response when the same antigens invade again, and some are differentiated into plasma cells and actively produce IgG antibodies.

Humoral Immunity by IgG 7—Conditions for IgG Production

For the occurrence of a humoral immunity by IgG, it is essential that 1) a specific three-dimensional structure of an antigen be recognized by B cells, and 2) some fragments of the antigen be recognized by helper T cells through MHC Class II. In general, although the part of an antigen recognized by B cells and the part of an antigen recognized by helper T cells are different from each other, and they activate an immune response through pathways different from each other, it is generally known that the immune response occurs only when the part recognized by B cells (B-cell epitope) and the part recognized by helper T cells (Th epitope) have at least a certain linkage. For example, the B-cell epitope and the Th epitope may be included in one molecule, form a conjugate, or have other linkages.

Limitations of Prior Art

Things to Consider in Designing Peptides that can be Used as Immunotherapeutics

As described above, immunotherapeutics are required due to their characteristics that 1) they be able to stably induce an immune response in the body of a subject, 2) they be able to minimize side effects by uniformly inducing only the intended antibody in the body of a subject; and 3) for their commercialization, they be easily synthesized and their production cost be reasonable. Therefore, in designing a peptide that can be used as an immunotherapeutic, the following three conditions should be essentially considered: 1) the peptide should exhibit a certain level of immunogenicity, 2) the peptide should trigger an immune response in the body of a subject that uniformly induces antigen recognition specificity of the antibody intended in advance, the isotype that controls physiological functions of the antibody, etc., and 3) the peptide should be easy to synthesize in consideration of economic feasibility.

Limitations of Prior Art

As disclosed in previously filed patent application U.S. Ser. No. 10/378,707 and PCT/KR2005/000784, and Kim et al. (2016, An apolipoprotein B100 mimotope prevents obesity in mice, Clinical Science 130, 105-116), it is known that antibodies specific to an artificially produced peptide with a specific sequence can also bind to an exposed site of the ApoB-100 protein in an LDL molecule, and thereby it can function as immunotherapeutics. Using such a characteristic, immunotherapeutics including the peptide were designed and are disclosed in the above patent applications, etc. However, the prior art was mainly focused on improving the immunogenicity of the peptide, for example, 1) preparing a long continuous identical sequence (concatemer) of the peptide, 2) designing an immunotherapeutic by linking a helper T cell epitope (that is sufficiently long at a protein level) to the concatemer, etc. Accordingly, conventionally designed immunotherapeutics had limitations in that 1) various types of antibodies were induced and the uniformity was decreased due to the presence of various epitopes (antigenic determinants), and 2) the economic feasibility was low due to their high production cost.

Necessity for Establishment of Method for Peptide Design

As for the peptides for use as immunotherapeutics, no principle has been established with regard to 1) uniform induction of only the intended immune response and 2) design of a peptide that is easy to synthesize and has a low production cost. Accordingly, in the present specification, technical matters to be considered in the design of peptides for use as immunotherapeutics and methods for designing the same will be provided.

a Peptide

Peptide Overview

The peptides provided herein include at least one peptide unit (a block of peptide). The peptide unit includes at least one B-cell epitope, at least one Th epitope, and an appropriate number of auxiliary parts. In an embodiment, the peptide may include one peptide unit. In another embodiment, the peptide may include two or more peptide units.

Characteristic of Peptide 1—a Peptide Unit is Included

The peptide unit is a part designed 1) to exhibit immunogenicity beyond a certain level, and 2) to uniformly induce only the intended antibody in advance. Therefore, the peptide unit provided herein has properties suitable for use as an immunotherapeutic.

Characteristic of Peptide 2—Relatively Short Length of Peptide Unit

Since the peptide unit is designed with a relatively short length, it is easy to synthesize and the production cost is low. The peptide is designed using a peptide unit as a component thereof, and specifically, it is designed in a form in which one or more of the peptide units are linked. When the peptide includes only a small number of the peptide units, the overall peptide length is short, thus having the advantage of easy synthesis. Even when the peptide has a relatively long sequence including a plurality of peptide units, the peptide unit itself is well designed for easy synthesis, and thus, it is possible to prepare the peptide in such a manner by synthesizing the peptide units in parallel and then linking these peptide units. As a result, the peptide provided herein has a characteristic of being easy to synthesize, which is the characteristic suitable for the use of the peptide as an immunotherapeutic, in addition to the characteristics of the peptide unit described above.

Functions of Peptide

When the peptide is injected into the body of a subject, it has a function of uniformly inducing only antibodies capable of specifically binding to the B-cell epitope included in the peptide.

B-Cell Epitope

Definition of B-Cell Epitope

The peptides provided herein include one or more B-cell epitopes. As used herein, the term B-cell epitope refers to a unit of peptide that is intentionally designed to induce a homogeneous antibody of one type. Therefore, when the peptide including the B-cell epitope is injected into the body of a subject, it results in that one type of antibody is dominantly induced per type of a B-cell epitope.

Structure of B-Cell Epitope

The B-cell epitope includes a part for forming a three-dimensional structure and an adjacent part thereof. The part for forming a three-dimensional structure is the part that forms a peptide with a higher order structure, and this part is designed so that B cells can recognize the peptide with a higher order structure and produce an antibody that can specifically bind to the same. The adjacent part is a part which directly or indirectly influences the part for forming a three-dimensional structure to stably form a higher order structure. Specifically, the adjacent part may have functions such as 1) a function of the part for forming a three-dimensional structure to form a specific structure, 2) a linker function that does not affect the part for forming a three-dimensional structure when the B-cell epitope is linked to another part within a peptide unit, 3) a function of protecting the part for forming a three-dimensional structure, etc., but their functions are not limited thereto. In an embodiment, the B-cell epitope may have a sequence in which a first part for forming a three-dimensional structure and a first adjacent part thereof is linked in order from the N-terminus to the C-terminus. In another embodiment, the B-cell epitope may have a sequence in which a second adjacent part, a second part for forming a three-dimensional structure, and a third adjacent part are sequentially linked in order from the N-terminus to the C-terminus. In still another embodiment, the B-cell epitope may have a sequence in which a third part for forming a three-dimensional structure and a fourth adjacent part are sequentially linked in order from the N-terminus to the C-terminus.

Design of B-Cell Epitope 1—Designing of Part for Forming Three-Dimensional Structure The B-cell epitope should be able to uniformly induce the production of antibodies capable of recognizing the three-dimensional structure of B cells and specifically binding thereto. The three-dimensional structure recognized by B cells can be expressed through an appropriate peptide with a higher order structure. Therefore, the B-cell epitope is designed to include a part for forming a three-dimensional structure that forms a peptide with a higher order structure. The part for forming a three-dimensional structure may form an intended peptide with a higher order structure depending on the purpose. In an embodiment, the part for forming a three-dimensional structure may include an α-helix structure. In another embodiment, the part for forming a three-dimensional structure may include a β structure. In still another embodiment, the part for forming a three-dimensional structure may include α-helix and/or β structures. In another embodiment, the part for forming a three-dimensional structure may include a peptide with a tertiary structure. In still another embodiment, the part for forming a three-dimensional structure may include a peptide with a quaternary structure.

Design of B-Cell Epitope 2—Adjacent Part

When designing the B-cell epitope, it is not essential that all sequences form a peptide with a higher order structure. In other words, the B-cell epitope may be designed to additionally include an adjacent part, in addition to the part for forming a three-dimensional structure. The adjacent part may affect the part for forming a three-dimensional structure so that it stably forms a higher order structure. The adjacent part may perform various other functions, and its role may overlap with that of an auxiliary part. In an embodiment, the adjacent part may have a linker function. In another embodiment, the adjacent part may have a protective function for the part for forming a three-dimensional structure. In still another embodiment, the adjacent part may have one or more functions.

Length of B-Cell Epitope

The B-cell epitope should have 1) a size large enough to be recognized by B cells and 2) one type or a very few types of antibodies that specifically binds to the B-cell epitope. The length of the B-cell epitope should be limited to an appropriate level. When the length of the B-cell epitope is too short, it is not recognized by B cells and thus does not have an antibody inducing ability, whereas when the length of the B-cell epitope is too long, various types of antibodies may be induced, which deviates from the intended purpose. In an embodiment, the length of the B-cell epitope may be about 8mer, about 9mer, about 10mer, about 11mer, about 12mer, about 13mer, about 14mer, about 15mer, about 16mer, about 17mer, about 18mer, about 20mer, about 21mer, about 22mer, about 23mer, about 24mer, about 25mer, about 26mer, about 27mer, about 28mer, about 29mer, or about 30mer.

In another embodiment, the length of the B-cell epitope may have a value within the two numerical ranges selected in the immediately preceding sentence.

Embodiments of B-Cell Epitope

In an embodiment, the B-cell epitope may be one that induces an antibody targeting apolipoprotein B-100. In another embodiment, the B-cell epitope may be a fragment of apolipoprotein B-100, and/or a mimotope of apolipoprotein B-100. In still another embodiment, the B-cell epitope is characterized in that it induces an antibody that targets a site selected from the following:
an externally exposed site of apolipoprotein B-100 included in low-density lipoprotein (LDL); and an externally exposed site of apolipoprotein B-100 included in very low-density lipoprotein (VLDL).

Embodiments of Sequences of B-Cell Epitope

In an embodiment, the B-cell epitope is a peptide includes a sequence selected from a group consisting of RNVPPIFNDVYWIAF (SEQ ID NO: 6), CRFRGLISLSQVYLS (SEQ ID NO: 7), KTTKQSFDLSVKAQYKKNKH (SEQ ID NO: 8), RNVPPIFNDVY (SEQ ID NO: 9), CRFRGLISLSQ (SEQ ID NO: 10), KTTKQSFDLSVK (SEQ ID NO: 11), RNVPPIFNDVYW (SEQ ID NO: 12), CRFRGLISLSQV (SEQ ID NO: 13), KTTKQSFDLSVKAQYKK (SEQ ID NO: 14), RNVPPIFNDVYWI (SEQ ID NO: 15), CRFRGLISLSQVY (SEQ ID NO: 16), KTTKQSFDLSVKAQYKKN (SEQ ID NO: 17), PIFNDVYWIAF (SEQ ID NO: 18), GLISLSQVYLS (SEQ ID NO: 19), QSFDLSVKAQYKKNKH (SEQ ID NO: 20), PPIFNDVYWIAF (SEQ ID NO: 21), RGLISLSQVYLS (SEQ ID NO: 22), KQSFDLSVKAQYKKNKH (SEQ ID NO: 23), VPPIFNDVYWIAF (SEQ ID NO: 24), FRGLIS-LSQVYLS (SEQ ID NO: 25), TKQSFDLSVKAQYK-KNKH (SEQ ID NO: 26), NVPPIFNDVYWIA (SEQ ID NO: 27), RFRGLISLSQVYL (SEQ ID NO: 28), TKQSFDLSVKAQYKKN (SEQ ID NO: 29), VPPIFNDVYWI (SEQ ID NO: 30), FRGLISLSQVY (SEQ ID NO: 31), TKQSFDLSVKAQYKKN (SEQ ID NO: 32), PPIFNDVYW (SEQ ID NO: 33), RGLISLSQV (SEQ ID NO: 34), KQSFDLSVKAQYKK (SEQ ID NO: 35), RFR-GLISLSQVYLDP (SEQ ID NO: 221), 5J SVCGCPVGHHDVVGL (SEQ ID NO: 222).

In another embodiment, the B-cell epitope may be a peptide which includes an epitope that is included in a peptide selected from the group consisting of SEQ ID NOS: 6 to 35 and 221 to 222.

Sequences Similar to Exemplary Sequences of B-Cell Epitope

In the present specification, sequences similar to the exemplary sequences of the B-cell epitope are disclosed. In an embodiment, the B-cell epitope may have a sequence having an identity of 80%, 81%, 82%, 83%, 84%, 85%, 86%, 87%, 88%, 89%, 90%, 91%, 92%, 93%, 94%, 95%, 96%, 97%, 98%, 99%, or 100%, to those sequences selected from the group consisting of SEQ ID NOS: 6 to 34 and SEQ ID NO: 221 to 222. In another embodiment, the B-cell epitope may be a sequence that matches the selected sequence by more than a value selected in the immediately preceding sentence. For example, the B-cell epitope may have a sequence that is 90% or more identical to SEQ ID NO: 6.

Th Epitope

Definition of Th Epitope

The Th epitope included in the peptide provided herein refers to a part which is designed such that after the peptide is endocytosed by antigen-presenting cells, it binds to MHC Class II, is presented on the surface of the antigen-presenting cell, and functions to be recognized by helper T cells (Th, helper-T-lymphocytes), in the process of being presented on the surface of the antigen-presenting cells by MHC Class II. The process of presenting antigens in which antigen-presenting cells process the endocytosed peptide and allow it to bind to MHC Class II was described previously. In other words, the Th epitope is a part that plays a role to be recognized by helper T cells when the peptide is injected into the body of a subject; therefore, it plays a direct role in inducing an IgG-type antibody against the peptide.

Design of Th Epitope 1—Anchor Residue

The Th epitope is designed to have an anchor residue capable of binding to MHC Class II in its sequence. Whether an anchor residue is included in the sequence is an important factor that affects the function of the Th epitope. In an embodiment, the Th epitope may include as anchor residues one or more amino acids selected from the group consisting of tyrosine (Y), phenylalanine (F), tryptophan (W), arginine (R), leucine (L), valine (V), isoleucine (I), and methionine (M).

Design of Th Epitope 2—Species-Specific Th Epitope

As the Th epitope, a Th epitope having an ability to bind to MHC Class II of a certain species may be selected according to its purpose. In an embodiment, the Th epitope may be a Th epitope having the ability to bind to human MHC Class II. In another embodiment, the Th epitope may be a Th epitope having the ability to bind to MHC Class II of a species belonging to a mammal. Specifically, the Th epitope may be a Th epitope having the ability to bind to MHC Class II of a mouse.

Design of Th Epitope 3—Gene-Specific Th Epitope

Due to the diverse traits of HLA gene complex, the structure of MHC Class II may vary between races and individuals. Accordingly, it is possible to design a Th epitope having an ability to bind to HLA-DP, HLA-DQ, and/or HLA-DR, which are MHC Class II molecules of a specific genetic trait. In an embodiment, the Th epitope may be a peptide sequence, which has a high binding ability to MHC Class II expressed by one or more HLA-DR genes selected from 2w2b, 2w2a, 3, 4w4, 4w14, 5, 7, 52a, 52b, 52c, and 53, which are HLA-DR1 alleles.

In an embodiment, the Th epitope may be a peptide sequence, which has a high binding ability to MHC Class II expressed by one or more genes selected from HLA-DQ5, HLA-DR, HLA-DR1 to HLA-DR8, HLA-DR11, HLA-DR13, HLA-DR14, HLA-DRw52, HLA-DR2w15, HLA-DPw4, each subtype of HLA-DRB1 (e.g., 0301, 01, 03, 04, 07, 08, 09, 11, 12, 13, 15, and 0301), and HLA-DRB5.

In another embodiment, the Th epitope may be a sequence named HA307-312 disclosed in Cara C. Wilson et al. (2001, Identification and Antigenicity of Broadly Cross-Reactive and Conserved Human Immunodeficiency Virus Type 1-Derived Helper T-Lymphocyte Epitopes, *Journal of Virology*, 75(9) 4195-4207).

In still another embodiment, the Th epitope may be one of the HLA Class II restricted epitopes disclosed in Table 2 of Christopher P Desmond et al. (2008, A systematic review of T-cell epitopes in hepatitis B virus: identification, genotypic variation and relevance to antiviral therapeutics, *Antiviral Therapy* 13:161-175).

Design of Th Epitope 4—Gene-Nonspecific Th Epitope

Irrespective of the traits of the HLA gene complex, Th epitopes having an ability to bind to various MHC Class II are known, and it is possible to design a Th epitope that can bind to various MHC Class II regardless of genetic traits. In an embodiment, the Th epitope may be a sequence named "pan DR-binding peptide" disclosed in the U.S. Patent Application No. 305,871.

Design of Th Epitope 5—Excluding Possibility Acting as B-Cell Epitope

The Th epitope is designed to be presented by MHC Class II of antigen-presenting cells and recognized by helper T cells. Therefore, the Th epitope generally has a very high binding capacity to MHC Class II, and thus, the probability that the Th epitope may act as a B-Cell epitope is very low. In other words, the Th epitope is designed such that it does not induce an antibody which specifically binds to the three-dimensional structure of the Th epitope itself.

Design of Length of Th Epitope

The Th epitope should be designed to have an appropriate length so that it can bind to one unit of MHC Class II. It is generally known that one unit of Th epitope that can directly bind to MHC Class II is at a length of about a 30mer (Abbas, A. K., Lichtman, A. H. and Pillai, S. *Cellular and molecular immunology* (pp 124-126), 7th Ed. (2012) Philadelphia PA, Elsevier Saunder, etc.). In addition, 1) when the length of the Th epitope becomes too short, there is a risk for the Th epitope to lose the ability to bind to MHC Class II, whereas 2) when the length of the Th epitope is too long, there is a room for the Th epitope to act independently as a B-cell epitope, thus deviating from the intended purpose. Therefore, it is necessary to design a Th epitope with an appropriate length.

Range of Length of Th Epitope

In an embodiment, the length of Th epitope may be 7mer, 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, 32mer, or 33mer. In another embodiment, the length of Th epitope may have a value within the two numerical ranges selected in the immediately preceding sentence. For example, the length of Th epitope may be in the range of 8mer to 32mer. For another example, the length of Th epitope may be in the range of 11 mer to 13mer.

Embodiments of Th Epitope—Design of PADRE

In an embodiment, the Th epitope may be a peptide named "pan DR-binding peptide" disclosed in US Patent Application No. 305,871. In another embodiment, the Th epitope may be one of the peptides disclosed in Tables VIII A and IX of U.S. Pat. No. 6,413,935 B1. In still another embodiment, the Th epitope may have a peptide sequence satisfying the following structural Formula I.

$$\underline{N}\text{-Lys-}X_1\text{-}X_2\text{-Ala-Ala-}X_3\text{-Thr-}X_4\text{-}X_5\text{-Ala-Ala-}\underline{C} \qquad \text{[Formula I]}$$

in which the $X_1$ may be tyrosine (Tyr), phenylalanine (Phe), or L-cyclohexylalanine, but the $X_1$ is not limited thereto.

The $X_2$ may be a hydrophobic amino acid, or may be leucine (Leu) or isoleucine (Ile), but the $X_2$ is not limited thereto.

The $X_3$ may be an aromatic or cyclic amino acid, or may be phenylalanine (Phe), tyrosine (Tyr), or histidine (His), but the $X_3$ is not limited thereto.

The $X_4$ may be an aliphatic long chain amino acid, or may be isoleucine (Ile) or valine (Val), but the $X_4$ is not limited thereto.

$X_5$ may be a charged amino acid, or may be arginine (Arg), leucine (Leu), aspartic acid (Asp), glutamine (Gln), or glycine (Gly), but the $X_5$ is not limited thereto.

In an embodiment, the Th epitope may have a peptide sequence satisfying the following structural Formula II:

$$\underline{N}\text{-}X_1\text{-}X_2\text{-Val-}X_3\text{-Ala-}X_4\text{-Thr-Leu-Lys-Ala-Ala-}\underline{C} \qquad \text{[Formula II]}$$

in which the $X_1$ is lysine (Lys) or arginine (Arg), the $X_2$ is tyrosine (Tyr), phenylalanine (Phe), or L-cyclohexylalanine, the $X_3$ is lysine (Lys), tryptophan (Trp), tyrosine (Tyr), arginine (Arg), alanine (Ala), or methionine (Met), and the $X_4$ is asparagine (Asn), tryptophan (Trp), tyrosine (Tyr), valine (Val), histidine (His), lysine (Lys), or alanine (Ala).

Embodiments of Sequences of Th Epitope

In an embodiment, the Th epitope may be selected from a group consist of K(Cha)VAAWTLKAA (SEQ ID NO: 1), PKYVKQNTLKLAT (SEQ ID NO: 2), ILMQYIKANSKFIGI (SEQ ID NO: 3), QSIALSSLMVAQAIP (SEQ ID NO: 4), ILMQYIKANSKFIGIPMGLPQSIALSSLMVAQ (SEQ ID NO: 5), PLGFFPDHQL (SEQ ID NO: 162), WPEANQVGAGAFGPGF (SEQ ID NO: 163), MQWNSTALHQALQDP (SEQ ID NO: 164), MQWNSTTFHQTLQDPRVRGLYFPAGG (SEQ ID NO: 165), FFLLTRILTI (SEQ ID NO: 166), FFLLTRILTIPQSLD (SEQ ID NO: 167), TSLNFLGGTTVCLGQ (SEQ ID NO: 168), 17 QSPTSNHSPTSCPPIC (SEQ ID NO: 169), IIFLFILLLCLIFLLVLLD (SEQ ID NO: 170), CTTPAQGNSMFPSC (SEQ ID NO: 171), CTKPTDGN (SEQ ID NO: 172), WASVRFSW (SEQ ID NO: 173), LLPIFFCLW (SEQ ID NO: 174), MDIDPYKEFGATVELLSFLP (SEQ ID NO: 175), FLPSDFFPSV (SEQ ID NO: 176), RDLLDTASALYREALESPEH (SEQ ID NO: 177), PHHTALRQAILCWGELMTLA(SEQ ID NO: 178), GRETVIEYLVSFGVW (SEQ ID NO: 179), EYLVSFGVWIRTPPA (SEQ ID NO: 180), VSFGVWIRTPPAYRPPNAPI (SEQ ID NO: 181), TVVRRRGRSP (SEQ ID NO: 182), VGPLTVNEKRRLKLI (SEQ ID NO: 183), RHYLHTLWKAGILYK (SEQ ID NO: 184), ESRLVVDFSQFSRGN (SEQ ID NO: 185), LQSLTNLLSSNLSWL (SEQ ID NO: 186), SSNLSWLSLDVSAAF (SEQ ID NO: 187), LHLYSHPIILGFRKI (SEQ ID NO: 188), KQCFRKLPVNRPIDW (SEQ ID NO: 189), LCQVFADATPTGWGL (SEQ ID NO: 190), AANWILRGTSFVYVP (SEQ ID NO: 191), EIRLKVFVLGGCRHK (SEQ ID NO: 192), KFVAAWTLKAA (SEQ ID NO: 195), KYVAAWTLKAA (SEQ ID NO: 196), DIEKKIAKMEKASSVFNVVNS (SEQ ID NO: 223), YSGPLKAEIAQRLEDV (SEQ ID NO: 224), K(Cha)VKANTLKAA (SEQ ID NO: 225), K(Cha)VKANTLKAA (SEQ ID NO: 226), K(Cha)VKAWTLKAA (SEQ ID NO: 227), K(Cha)VKAWTLKAA (SEQ ID NO: 228), K(Cha)VWANTLKAA (SEQ ID NO: 229), K(Cha)VWANTLKAA (SEQ ID NO: 230), K(Cha)VWAYTLKAA (SEQ ID NO: 231), K(Cha)VWAVTLKAA (SEQ ID NO: 232), K(Cha)VYAWTLKAA (SEQ ID NO: 233), K(Cha)VYAWTLKAA (SEQ ID NO: 234), R(Cha)VRANTLKAA (SEQ ID NO: 235), K(Cha)VKAHTLKAA (SEQ ID NO: 236), K(Cha)VKAHTLKAA (SEQ ID NO: 237), K(Cha)VAANTLKAA (SEQ ID NO: 238), K(Cha)VAANTLKAA (SEQ ID NO: 239), K(Cha)VAAYTLKAA (SEQ ID NO: 240), K(Cha)VAAYTLKAA (SEQ ID NO: 241), K(Cha)VAAWTLKAA (SEQ ID NO: 242), K(Cha)VAAKTLKAA (SEQ ID NO: 243), K(Cha)VAAHTLKAA (SEQ ID NO: 244), K(Cha)VAAATLKAA (SEQ ID NO: 245), K(Cha)VAAWTLKAA (SEQ ID NO: 246), and K(Cha)VMAATLKAA (SEQ ID NO: 247). In this case, "a" denotes D-form alanine, "Z" denotes 6-aminohexanoic acid, and "(Cha)" denotes L-cyclohexylalanine.

Sequences Similar to Exemplary Sequences of Th Epitope

In the present specification, sequences similar to the exemplary sequences of the Th epitope are disclosed. In an embodiment, the Th epitope may have a sequence, which have an identity of 80%, 81%, 82%, 83%, 84%, 85%, 86%, 87%, 88%, 89%, 90%, 91%, 92%, 93%, 94%, 95%, 96%, 97%, 98%, 99%, or 100% to SEQ ID NO: 1 to SEQ ID NO: 5, SEQ ID NO: 162 to SEQ ID NO: 192, SEQ ID NO: 195 to SEQ ID NO: 196, and SEQ ID NO: 223 to SEQ ID NO: 247, a sequence satisfying the above [Formula I], or a sequence satisfying the above [Formula II]. In another embodiment, the Th epitope may have a sequence which matches, by the number selected in the immediately preceding sentence or more, to SEQ ID NO: 1 to SEQ ID NO: 5, SEQ ID NO: 162 to SEQ ID NO: 192, SEQ ID NO: 195 to SEQ ID NO: 196, and SEQ ID NO: 223 to SEQ ID NO: 247, a sequence satisfying the above [Formula I], or a sequence satisfying the above [Formula II]. For example, the Th epitope may have a sequence which has an identity of 90% or more to the sequence of SEQ ID NO: 1.

Auxiliary Part

Definition of Auxiliary Part

The peptides disclosed herein may include one or more auxiliary parts. The auxiliary part collectively refers to an additional part which can directly or indirectly affect the peptide to cause an intended immune response in the body of a subject. The auxiliary part may have one or more functions, and the constitution of the peptide sequence and/or the position of the sequence may appropriately be designed according to the purpose.

Function of Auxiliary Part 1—Function as Linker

The auxiliary part may function as a linker linking a B-cell epitope and a Th epitope. The B-cell epitope and the Th epitope may be directly linked or they may be linked through an auxiliary part serving as a linker. In addition, the auxiliary part may be designed to have a linker function that links a plurality of units included in the peptide. In an embodiment, the sequence of the auxiliary part may be located between the sequence of the B-cell epitope and the sequence of the Th epitope. In particular, the auxiliary part has a linker function that links the B-cell epitope and the Th epitope. In another embodiment, the sequence of the auxiliary part may be located between the sequence of the first peptide unit and the sequence of the second peptide unit in the peptide. In particular, the auxiliary part has a linker function for linking the first peptide unit and the second peptide unit.

Function of Auxiliary Part 2—Function for Protection

In the case of the peptide unit provided herein, it is characterized by having a relatively short sequence length. Accordingly, when a peptide including the peptide unit is injected into the body of a subject, the Th epitope sequence may be degraded before being recognized by helper T cells, and thus, the intended immune response may not occur. In an embodiment, the protective unit may protect the Th epitope from being cleaved by an enzyme in the body of the subject. For example, the enzyme in the body of the subject may be a peptidase. Specifically, the peptidase may be an exopeptidase and/or an endopeptidase, but the peptidase is not limited thereto. In another embodiment, the auxiliary part may be linked to the N-terminus and/or C-terminus of the Th epitope. In particular, the auxiliary part has a function of protecting the Th epitope. In still another embodiment, the auxiliary part may include at least one nonstandard amino acid.

Function of Auxiliary Part 3—Function for Forming Cyclic Form

The auxiliary part may be designed to be linked to both ends of the peptide unit to thereby have a function of allowing the peptide to form a cyclic form. In an embodiment, the peptide may include a first auxiliary part at the N-terminus and a second auxiliary part at the C-terminus. In particular, the first auxiliary part and the second auxiliary part may each include one or more cysteines (S). In another embodiment, the peptide may exist in a cyclic form. In particular, the N-terminus and C-terminus of the peptide may be linked through an auxiliary part.

Function of Auxiliary Part 3—Other Functions

The auxiliary part may have an additional function in addition to the above functions. In an embodiment, the auxiliary part may include a hydrophilic amino acid and may have a function of increasing the solubility of a peptide. In another embodiment, the auxiliary part may consist of a sequence that is biologically inactive in the body of a subject. In particular, the auxiliary part has no effect on the functions of the B-cell epitope and the Th epitope, and may have a dummy function to extend the length of the peptide. Specifically, the peptide may be a His-tag, but is not limited thereto.

Capable of Performing Multiple Functions

The auxiliary part may have one or more functions. In an embodiment, the auxiliary part may have a linker function, a protective function, a cyclic form forming function, a dummy function, and/or a solubility increasing function.

May Include Nonstandard Amino Acid

The auxiliary part may include one or more nonstandard amino acids. The artificial amino acid may be necessary for an auxiliary part to exhibit the linker function, protective function, and/or other functions. In an embodiment, the auxiliary part may include at least one nonstandard amino acid. Specifically, the nonstandard amino acid may be one or more nonstandard amino acids selected from the group consisting of L-cyclohexylalanine, D-form alanine, and 6-aminohexanoic acid, but the nonstandard amino acid is not limited thereto.

Length of Auxiliary Part

The auxiliary part may be designed to have an appropriate length according to its function. When the auxiliary part has multiple functions, it may be designed to have an appropriate length to exhibit all of the multiple functions. In an embodiment, the length of the auxiliary part may be 1mer, 2mer, 3mer, 4mer, 5mer, 6mer, 7mer, 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, or 31mer or longer. In another embodiment, the length of the auxiliary part may have a value within the two numerical ranges of the immediately preceding sentence. For example, the length of the auxiliary part may be in the range of 1mer to 8mer. For another example, the length of the auxiliary part may be in the range of 15mer to 26mer.

Characteristics of Auxiliary Part—has Little Effect on Function of B-Cell Epitope The auxiliary part does not significantly affect the function of the peptide unit and/or peptide disclosed herein to induce an antibody that specifically binds to the B-cell epitope in the body of a subject.

Embodiments of Sequences of Auxiliary Part

In an embodiment, the auxiliary part may be a peptide selected from a group consisting of a, Z, aZ, Za, RN, AF, CR, LS, KT, KH, RF, DP, SV, GL, ZRNV (SEQ ID NO: 36), aZRN (SEQ ID NO: 37), IAFZ (SEQ ID NO: 38), AFZa (SEQ ID NO: 39), RNVP(SEQ ID NO: 40), WIAF (SEQ ID NO: 41), ZCRF (SEQ ID NO: 42), aZCR (SEQ ID NO: 43), YLSZ (SEQ ID NO: 44), LSZa (SEQ ID NO: 45), CRFR (SEQ ID NO: 46), VYLS (SEQ ID NO: 47), ZKTT (SEQ ID NO: 48), aZKT (SEQ ID NO: 49), NKHZ (SEQ ID NO: 50), KHZa (SEQ ID NO: 51), GSHIHIH GSDDDDK (SEQ ID NO: 52), HIIHIHH (SEQ ID NO: 53), MRGSHIIIHHGSDDDDKIVD (SEQ ID NO: 54), GGGGSGGGGGGSS(SEQ ID NO: 55), RRRRRR (SEQ ID NO: 159), GSHHHHHIHGSDDDDKaZ (SEQ ID NO: 193), and ZaGSHIIIHHGSDDDDK (SEQ ID NO: 194). In particular, "a" denotes D-form alanine and "Z" denotes 6-aminohexanoic acid.

Designing Peptide Unit—Overall

A method for designing a possible peptide unit and a form thereof will be described hereinbelow. Each unit may include at least one B-cell epitope and at least one Th epitope, and may include an appropriate number of auxiliary parts. The linking order of the B-cell epitope, the Th epitope, and the auxiliary part is exemplified for each type. Unless otherwise specified, the design of each part included in the peptide unit basically follows the design principle described above.

Designing Unit-A

Structure of Unit-A 1—Overview

As a peptide unit provided herein, a peptide unit, which can include 1) one B-cell epitope and one Th epitope and 2) one or more an auxiliary part, is named "unit-A". The function of the auxiliary part is not particularly limited as long as it does not impair the functions of the B-cell epitope and the Th epitope, and is appropriately designed as necessary.

In an embodiment, the unit-A may be one in which the first B-cell epitope and the first Th epitope are sequentially linked in the direction from the N-terminus to the C-terminus.

Furthermore, the unit-A may further include a first auxiliary part. When the unit-A includes the first auxiliary part, the sequence of the first auxiliary part is located at the N-terminal side relative to the sequence of the first B-cell epitope within the unit-A sequence. In particular, the first auxiliary part may have a dummy function, a solubility improving function, a linker function, and/or a cyclic form-forming function, but the functions of the first auxiliary part are not limited thereto.

Furthermore, the unit-A may further include a second auxiliary part. When the unit-A includes the second auxiliary part, the sequence of the second auxiliary part is located between the sequence of the first B-cell epitope and the sequence of the first Th epitope within the unit-A sequence. In particular, the second auxiliary part may have a dummy function, a solubility improving function, a linker function, and/or a protective function, but the functions of the second auxiliary part are not limited thereto.

Furthermore, the unit-A may further include a third auxiliary part. When the unit-A includes the third auxiliary part, the sequence of the third auxiliary part is located at the C-terminal side relative to the sequence of the first Th epitope within the unit-A sequence. In particular, the third auxiliary part may have a dummy function, a solubility improving function, a linker function, a protective function and/or a cyclic form-forming function, but the functions of the third auxiliary part are not limited thereto.

In another embodiment, the unit-A may be one in which a second Th epitope and a second B-cell epitope are sequentially linked in the direction from the N-terminus to the C-terminus.

Furthermore, the unit-A may further include a fourth auxiliary part. When the unit-A includes the fourth auxiliary part, the sequence of the fourth auxiliary part is located at the N-terminal side relative to the sequence of the second Th epitope within the unit-A sequence. In particular, the fourth auxiliary part may have a dummy function, a solubility improving function, a linker function, and/or a cyclic form-forming function, but the functions of the fourth auxiliary part are not limited thereto.

Furthermore, the unit-A may further include a fifth auxiliary part. When the unit-A includes the fifth auxiliary part, the sequence of the fifth auxiliary part is located between the sequence of the second B-cell epitope and the sequence of the second Th epitope within the unit-A sequence. In particular, the fifth auxiliary part may have a dummy function, a solubility improving function, a linker function, and/or a cyclic form-forming function, but the functions of the fifth auxiliary part are not limited thereto.

Furthermore, the unit-A may further include a sixth auxiliary part. When the unit-A includes the sixth auxiliary part, the sequence of the sixth auxiliary part is located at the C-terminal side relative to the sequence of the second B-cell epitope within the unit-A sequence. In particular, the sixth auxiliary part may have a dummy function, a solubility improving function, a linker function, and/or a cyclic form-forming function, but the functions of the sixth auxiliary part are not limited thereto.

Structure of Unit-A 2—Formula

In an embodiment, the unit-A is a peptide represented by the following [Formula A] or [Formula A'].

$$\underline{N}\text{-}A_1\text{-}B_1\text{-}A_2\text{-}T_1\text{-}A_3\text{-}\underline{C} \quad \text{[Formula A]}$$

$$\underline{N}\text{-}A_4\text{-}T_2\text{-}A_5\text{-}B_2\text{-}A_6\text{-}\underline{C} \quad \text{[Formula A']}$$

The $B_1$ and $B_2$ are B-cell epitopes, and they follow the design principle described above.

The $T_1$ and $T_2$ are Th epitopes, and they follow the design principle described above.

The $A_1$ to $A_6$ are auxiliary parts and they may be omitted.

In particular, the $A_1$ to $A_6$ may have a dummy function, a solubility improving function, a linker function, and/or a cyclic form forming function, but the $A_1$ to $A_6$ are not limited thereto.

Length of Unit-A

In an embodiment, the length of the unit-A may be about 16mer, about 17mer, about 18mer, about 19mer, about 20mer, about 21mer, about 22mer, about 23mer, about 24mer, about 25mer, about 26mer, about 27mer, about 28mer, about 29mer, about 30mer, about 31mer, about 32mer, about 33mer, about 34mer, about 35mer, about 36mer, about 37mer, about 38mer, about 39mer, about 40mer, about 41mer, about 42mer, about 43mer, about 44mer, about 45mer, about 46mer, about 47mer, about 48mer, about 49mer, about 50mer, about 51mer, about 52mer, about 53mer, about 54mer, about 55mer, about 56mer, about 57mer, about 58mer, about 59mer, about 60mer, about 61mer, about 62mer, about 63mer, about 64mer, about 65mer, about 66mer, about 67mer, about 68mer, about 69mer, about 70mer, about 71mer, about 72mer, about 73mer, about 74mer, about 75mer, about 76mer, about 77mer, about 78mer, about 79mer, about 80mer, about 81mer, about 82mer, about 83mer, about 84mer, about 85mer, about 86mer, about 87mer, about 88mer, about 89mer, about 90mer, about 91mer, about 92mer, about 93mer, about 94mer, about 95mer, about 96mer, about 97mer, about 98mer, about 99mer, or about 100mer. In another embodiment, the length of the unit-A may have a value within the two numerical ranges selected in the immediately preceding sentence. For example, the length of the unit-A may be in the range of about 16mer to about 30mer. For another example, the length of the unit-A may be in the range of about 23mer to about 60mer.

Embodiment of Unit-A—Exemplary Design

In an embodiment, the unit-A may have a sequence in which a first B-cell epitope, a first auxiliary part, and a first Th epitope are sequentially linked. In particular, the first auxiliary part has a linker function and it includes one or more artificial amino acids.

In another embodiment, the unit-A may have a sequence in which a second auxiliary part, a second B-cell epitope, a third auxiliary part, and a second Th epitope are sequentially linked. In particular, the second auxiliary part is His-tag, and the third auxiliary part has a linker function and it includes one or more artificial amino acids.

In still another embodiment, the unit-A may have a sequence in which a third B-cell epitope, a fourth auxiliary part, a third Th epitope, and a fifth auxiliary part are sequentially linked. In particular, the fourth auxiliary part has a linker function and a protective function, and the fifth auxiliary part has a protective function. The fourth auxiliary part and the fifth auxiliary part each include one or more artificial amino acids.

In still another embodiment, the unit-A may have a sequence in which a 6th an auxiliary part, a 4th B-cell epitope, a 7th auxiliary part, a 4th Th epitope, and an eighth auxiliary part are sequentially linked. In particular, the sixth auxiliary part is His-tag, the seventh auxiliary part has a linker function and a protective function, and the eighth auxiliary part has a protective function. The seventh auxiliary part and the eighth auxiliary part include one or more artificial amino acids.

Embodiments of Unit-A Sequence

In an embodiment, the Unit-A is a unit peptide selected from a group consisting of RNVPPIFNDVYWIAFZaK(Cha)VAAWTLKAAaZ (SEQ ID NO: 56), ZaK(Cha)VAAWTLKAAaZRNVPPIFNDVYWIAF (SEQ ID NO: 57), CRFRGLISLSQVYLSZaK(Cha)VAAWTLKAAaZ (SEQ ID NO: 58), ZaK(Cha)VAAWTLKAAaZCRFRGLISLSQVYLS (SEQ ID NO: 59), KTTKQSFDLSVKAQYKKNKHZaK(Cha)VAAWTLKAAaZ (SEQ ID NO: 60), ZaK(Cha)VAAWTLKAAaZKTTKQSFDLSVKAQYKKNKH (SEQ ID NO: 61), RNVPPIFNDVYWIAFK(Cha)VAAWTLKAA (SEQ ID NO: 62), K(Cha)VAAWTLKAARNVPPIFNDVYWIAF (SEQ ID NO: 63), RNVPPIFNDVYK(Cha)VAAWTLKAA (SEQ ID NO: 64), PIFNDVYWIAFK(Cha)VAAWTLKAA (SEQ ID NO: 65), PPIFNDVYWK(Cha)VAAWTLKAA (SEQ ID NO: 66), RNVPPIFNDVYWIAFK(Cha)VAAWTLKAAHHHHHHIH (SEQ ID NO: 67), RNVPPIFNDVYWIAFZaK(Cha)VAAWTLKAAaZGSHIHIH GSDDDDK (SEQ ID NO: 68), GSHIiHIHHGSDDDDKZaK(Cha)VAAWTLKAAaZRNVPPIFNDVYWIAF (SEQ ID NO: 69), RNVPPIFNDVYWIAFGSHHHHHHGSDDDDKZaK(Cha)VAAWTLKAAaZ (SEQ ID NO: 70), GSHIiHIHHGSDDDDKZaK(Cha)VAAWTLKAAaZCRFRGLISLSQVYLS (SEQ ID NO: 71), GSHHHHHHGSDDDDKCRFRGLISLSQVYLSZaK(Cha)VAAWTLKAAaZ (SEQ ID NO: 72), CRFRGLISLSQVYLSZaK(Cha)VAAWTLKAAaZGSHIiIHIHHGSDDDDK (SEQ ID NO: 73), GSHIiIHIHHGSDDDDKZaK(Cha)VAAWTLKAAaZKTTKQSFDLSVKAQYKKNK H (SEQ ID NO: 74), GSHHHHHHGSDDDDKKTTKQSFDLSVKAQYKKNKHZaK(Cha)VAAWTLKAA aZ (SEQ ID NO: 75), KTTKQSFDLSVKAQYKKNKHZaK(Cha)VAAWTLKAAaZGSHHHHHHGSDDDD K (SEQ ID NO: 76), MRGSHHHHHHGSDDDDKIVDRNVPPIFNDVYWIAFZaK(Cha)VAAWTLKAAaZ (SEQ ID NO: 77), MRGSHHHHHHGSDDDD-KIVDGSHHHHHHGSDDDDKRNVPPIFNDVYWIAFZaK(Cha)VAAWTLKAAaZ (SEQ ID NO: 78), MRGSHHHHHHGSDDDDKIVDRNVPPIFNDVYWIAFZaK(Cha)VAAWTLKAAaZ GSHHHHHHGSDDDDK (SEQ ID NO: 79), RNVPPIFNDVYWIAFILMQYIKANSKFIGI (SEQ ID NO: 80), RNVPPIFNDVYWIAFILMQYIKANSKFIGIPMGLPQSIALSSLMVAQ (SEQ ID NO: 81), CRNVPPIFNDVYWIAFZaK(Cha)VAAWTLKAAaZC (SEQ ID NO: 82), RNVPPIFNDVYWIAFZaK(Cha)VAAWTLKAACR (SEQ ID NO: 161), RNVPPIFNDVYWIAFXXKXVAAWTLKAAXXGSHHHHHHGSDDDDK (SEQ ID NO: 199), GSHHHHHHGSDDDDKXXKXVAAWTLKAAXXRNVPPIFNDVYWIAF(SEQ ID NO: 200), RNVPPIFNDVYWIAFXXKXVAAWTLKAAXX (SEQ ID NO: 204), RNVPPIFNDVYWIAFKXVAAWTLKAA (SEQ ID NO: 205), RNVPPIFNDVYWIAFKXVAAWTLKAAHHHHHH (SEQ ID NO: 206), RNVPPIFNDVYWIAFXXKXVAAWTLKAACR (SEQ ID NO: 208), RNVPPIFNDVYWIAFXXKFVAAWTLKAAXX (SEQ ID NO: 210), RNVPPIFNDVYWIAFXXKFVAAWTLKAACR (SEQ ID NO: 212), RNVPPIFNDVYWIAFCTKPTDGN (SEQ ID NO: 213), RNVPPIFNDVYWIAFLLPIFFCLW (SEQ ID NO: 214), RNVPPIFNDVYWIAFFLPSDFFPSV (SEQ ID NO: 215), RNVPPIFNDVYWIAFILMQYIKANSKFIGIHHHHHH (SEQ ID NO: 219), and RNVPPIFNDVYWIAFMDIDPYKEFGATVELLSFLPHHHHHH (SEQ ID NO: 220). In this case, the "a" denotes D-form alanine, the "Z" denotes 6-aminohexanoic acid, the "(Cha)" denotes L-cyclohexylalanine, and the "X" denotes any standard amino acid.

Designing Unit-B

Structure of Unit-B 1—Overview

As a peptide unit provided herein, a peptide unit 1) which includes two B-cell epitopes and one Th epitope, 2) in which the sequence of one B-cell epitope of the two B-cell epitopes is located between the sequence of the other B-cell epitope the sequence of the Th epitope, and 3) which may include one or more auxiliary parts, is named "unit-B". The function of the auxiliary part is not particularly limited as long as it does not impair the functions of the B-cell epitope and the Th epitope, and is appropriately designed as necessary.

In an embodiment, the unit-B may be one in which the first B-cell epitope, the second B-cell epitope, and the first Th epitope are sequentially linked in the direction from the N-terminus to the C-terminus.

Furthermore, the unit-B may further include a first auxiliary part. When the unit-B includes the first auxiliary part, the sequence of the first auxiliary part is located at the N-terminal side relative to the sequence of the first B-cell epitope within the unit-B sequence. In particular, the first auxiliary part may have a dummy function, a solubility improving function, a linker function, and/or a cyclic form-forming function, but the functions of the first auxiliary part are not limited thereto.

Furthermore, the unit-B may further include a second auxiliary part. When the unit-B includes the second auxiliary part, the sequence of the second auxiliary part is located between the sequence of the first B-cell epitope and the sequence of the second B-cell epitope within the unit-B sequence. In particular, the second auxiliary part may have a dummy function, a solubility improving function, a linker function, and/or a protective function, but the functions of the second auxiliary part are not limited thereto.

Furthermore, the unit-B may further include a third auxiliary part. When the unit-B includes the third auxiliary part, the sequence of the third auxiliary part is located between the sequence of the second B-cell epitope and the sequence of the first Th epitope within the unit-B sequence. In particular, the third auxiliary part may have a dummy function, a solubility improving function, a linker function, and/or a protective function, but the functions of the third auxiliary part are not limited thereto.

Furthermore, the unit-B may further include a fourth auxiliary part. When the unit-B includes the fourth auxiliary part, the sequence of the fourth auxiliary part is located at the C-terminal side relative to the sequence of the first Th epitope within the unit-B sequence. In particular, the fourth auxiliary part may have a dummy function, a solubility improving function, a linker function, and/or a cyclic form-forming function, but the functions of the fourth auxiliary part are not limited thereto.

In another embodiment, the unit-B may be one in which a second Th epitope, a third B-cell epitope, and a fourth B-cell epitope are sequentially linked in the direction from the N-terminus to the C-terminus.

Furthermore, the unit-B may further include a fifth auxiliary part. When the unit-B includes the fifth auxiliary part, the sequence of the fifth auxiliary part is located at the N-terminal side relative to the sequence of the second Th epitope within the unit-B sequence. In particular, the fifth auxiliary part may have a dummy function, a solubility improving function, a linker function, and/or a cyclic form-forming function, but the functions of the fifth auxiliary part are not limited thereto.

Furthermore, the unit-B may further include a sixth auxiliary part. When the unit-B includes the sixth auxiliary part, the sequence of the sixth auxiliary part is located between the sequence of the second Th epitope and the sequence of the third B-cell epitope within the unit-B sequence. In particular, the sixth auxiliary part may have a dummy function, a solubility improving function, a linker function, and/or a protective function, but the functions of the sixth auxiliary part are not limited thereto.

Furthermore, the unit-B may further include a seventh auxiliary part. When the unit-B includes the seventh auxiliary part, the sequence of the seventh auxiliary part is located between the sequence of the third B-cell epitope and the sequence of the fourth B-cell epitope within the unit-B sequence. In particular, the seventh auxiliary part may have a dummy function, a solubility improving function, a linker function, and/or a protective function, but the functions of the seventh auxiliary part are not limited thereto.

Furthermore, the unit-B may further include an eighth auxiliary part. When the unit-B includes the eighth auxiliary part, the sequence of the eighth auxiliary part is located at the C-terminal side relative to the sequence of the fourth B-cell epitope within the unit-B sequence. In particular, the eighth auxiliary part may have a dummy function, a solubility improving function, a linker function, and/or a cyclic form-forming function, but the functions of the eighth auxiliary part are not limited thereto.

Structure of Unit-B 2—Formula

In an embodiment, the unit-B is a peptide represented by the following [Formula B] or [Formula B'].

  [Formula B]

  [Formula B']

The $B_1$ to $B_4$ are B-cell epitopes, and they follow the design principle described above.

The $T_1$ and $T_2$ are Th epitopes, and they follow the design principle described above.

The $A_1$ to $A_8$ are auxiliary parts and they may be omitted.

In particular, the $A_1$ to $A_8$ may have a dummy function, a solubility improving function, a linker function, and/or a cyclic form forming function, but the $A_1$ to $A_8$ are not limited thereto.

Length of Unit-B

In an embodiment, the length of the unit-B may be about 24mer, about 25mer, about 26mer, about 27mer, about 28mer, about 29mer, about 30mer, about 31mer, about 32mer, about 33mer, about 34mer, about 35mer, about 36mer, about 37mer, about 38mer, about 39mer, about 40mer, about 41mer, about 42mer, about 43mer, about 44mer, about 45mer, about 46mer, about 47mer, about 48mer, about 49mer, about 50mer, about 51mer, about 52mer, about 53mer, about 54mer, about 55mer, about 56mer, about 57mer, about 58mer, about 59mer, about 60mer, about 61mer, about 62mer, about 63mer, about 64mer, about 65mer, about 66mer, about 67mer, about 68mer, about 69mer, about 70mer, about 71mer, about 72mer, about 73mer, about 74mer, about 75mer, about 76mer, about 77mer, about 78mer, about 79mer, about 80mer, about 81mer, about 82mer, about 83mer, about 84mer, about 85mer, about 86mer, about 87mer, about 88mer, about 89mer, about 90mer, about 91mer, about 92mer, about 93mer, about 94mer, about 95mer, about 96mer, about 97mer, about 98mer, about 99mer, or about 100mer. In another embodiment, the length of the unit-B may have a value within the two numerical ranges selected in the immediately preceding sentence. For example, the length of the unit-B may be in the range of about 24mer to about 45mer. For another example, the length of the unit-A may be in the range of about 40mer to about 80mer.

Embodiment of Unit-B—Exemplary Design

In an embodiment, the unit-B may have a sequence in which a first auxiliary part, a first B-cell epitope, a second B-cell epitope, a second auxiliary part, and a first Th epitope are sequentially linked. In particular, the first auxiliary part is His-tag, the second auxiliary part and it includes one or more artificial amino acids.

In another embodiment, the unit-B may have a sequence in which a third B-cell epitope, a fourth B-cell epitope, a third auxiliary part, and a second Th epitope are sequentially linked. In particular, the third auxiliary part has a linker function and it includes one or more artificial amino acids.

In another embodiment, the unit-B may have a sequence in which a fourth auxiliary part, a fifth B-cell epitope, a sixth B-cell epitope, a fifth an auxiliary part, a third Th epitope, and a sixth auxiliary part are sequentially linked. In particular, the fourth auxiliary part is His-tag, the fifth auxiliary part has a linker function and a protective function and includes one or more artificial amino acids, and the sixth auxiliary part has a protective function and includes one or more artificial amino acids.

In still another embodiment, the unit-B may have a sequence in which a seventh B-cell epitope, an eighth B-cell epitope, a seventh auxiliary part, a fourth Th epitope, and an eighth auxiliary part are sequentially linked. In particular, the seventh auxiliary part has a linker function, a protective function, and includes one or more artificial amino acids, and the eighth auxiliary part has a protective function and includes one or more LSQVYLSCRFRGLISLSQVYLSZaK(Cha)VAAWTL-KAAaZ (SEQ ID NO: 87), CRFRGLISLSQVYLSKTTKQSFDLSVKAQYK-KNKHZaK(Cha)VAAWTLKAAaZ(SEQ ID NO: 88), KTTKQSFDLSVKAQYKKNKHRNVPPIFNDVYWI-AFZaK(Cha)VAAWTLKAAaZ 28 (SEQ ID NO: 89), KTTKQSFDLSVKAQYKKNKHCRFRGLIS-LSQVYLSZaK(Cha)VAAWTLKAAaZ (SEQ ID NO: 90), KTTKQSFDLSVKAQYK-KNKHKTTKQSFDLSVKAQYKKNKHZaK(Cha) VAAWT LKAAaZ (SEQ ID NO: 91), RNVPPIFNDVYWI-AFCRFRGLISLSQVYLSK(Cha)VAAWTLKAA (SEQ ID NO: 92), PIFNDVYWIAFGLISLSQVYLSK(Cha)VAAW-TLKAA (SEQ ID NO: 93), RNVPPIFNDVYCRFRGLIS-LSQK(Cha)VAAWTLKAA (SEQ ID NO: 94), PIFNDVY-WIAFCRFRGLISLSQK(Cha)VAAWTLKAA (SEQ ID NO: 95), PPIFNDVYWRGLISLSQVK(Cha)VAAWTL-KAA (SEQ ID NO: 96), RNVPPIFNDVYWIAFCRFRG-LISLSQVYLSK(Cha)VAAWTLKAAHHHHHH (SEQ ID NO: 97), MRGSHHHHHHGSDDDDKIVDRNVP-PIFNDVYWIAFCRFRGLISLSQVYLSZaK(Ch a)VAAW-TLKAAaZ (SEQ ID NO: 98), MRGSHHHHHHGSDDDD-KIVDRNVPPIFNDVYWIAFCRFRGLISLSQVYLSZaK (Ch a)VAAWTLKAA (SEQ ID NO: 99), RNVPPIFNDVYWIAFCRFRGLISLSQVYLSZaK(Cha) VAAWTLKAA (SEQ ID NO: 100), MRGSHHHHHHGSDDDDKIVDRNVPPIFNDVYWI-AFGGGGSGGGGGGSSRNVP PIFNDVYWIAFZaK(Cha) VAAWTLKAA (SEQ ID NO: 101), RNVPPIFNDVYWI-AFGGGGSGGGGGGSSRNVPPIFNDVYWIAFZaK(Cha) VAA WTLKAA (SEQ ID NO: 102), RNVPPIFNDVYWIAFGGGGSGGGGGGSSRNVP-PIFNDVYWIAFZaK(Cha)VAA WTLKAAaZ (SEQ ID NO: 103), RNVPPIFNDVYWIAFRNVPPIFNDVYWIA-FILMQYIKANSKFIGI (SEQ ID NO: 104), RNVP-PIFNDVYWIAFRNVPPIFNDVYWIAFILMQYIKANSK-FIGIPMGLPQSIALS SLMVAQ (SEQ ID NO: 105), CRNVPPIFNDVYWIAFCRFRGLISLSQVYLSZaK(Cha) VAAWTLKAAaZC (SEQ ID NO: 106), and RNVP-PIFNDVYWIAFCRFRGLISLSQVYLSXXK(Cha)VAAW-TLKAAXX (SEQ ID NO: 202). In this case, the "a" denotes D-form alanine, the "Z" denotes 6-aminohexanoic acid, the "(Cha)" denotes L-cyclohexylalanine, and the "X" denotes any standard amino acid.

Designing Unit-C

Structure of Unit-C1—Overview

As a peptide unit provided herein, a peptide unit 1) which includes two B-cell epitopes and one Th epitope, 2) in which the sequence of the Th epitope is located between may have a value within the two numerical ranges selected in the immediately preceding sentence. For example, the length of the unit-C may be in the range of about 24mer to about 45mer. For another example, the length of the unit-A may be in the range of about 40mer to about 80mer.

Embodiment of Unit-C—Exemplary Design

In an embodiment, the unit-C may have a sequence in which a first B-cell epitope, a first auxiliary part, a first Th epitope, a second auxiliary part, and a second B-cell epitope are sequentially linked. In particular, the first auxiliary part and the second auxiliary part each have a linker function and a protective function. The first auxiliary part and the second auxiliary part each include one or more artificial amino acids.

In another embodiment, the unit-C may have a sequence in which a third auxiliary part, a third B-cell epitope, a fourth auxiliary part, a second Th epitope, a fifth auxiliary part, and a fourth B-cell epitope are sequentially linked. In particular, the third auxiliary part is His-tag, and the fourth auxiliary part and the fifth auxiliary part each have a linker function and a protective function. The fourth auxiliary part and the fifth auxiliary part each include one or more artificial amino acids.

Embodiments of Unit-C Sequence

In an embodiment, the unit-C is a peptide unit selected from a group consisting of RNVPPIFNDVYWIAFZaK(Cha)VAAWTLKAAaZRNVPPIFNDVYWIAF (SEQ ID NO: 107), RNVPPIFNDVYWIAFZaK(Cha)VAAWTLKAAaZCRFRGLISLSQVYLS (SEQ ID NO: 108), RNVPPIFNDVYWIAFZaK(Cha)VAAWTLKAAaZKTTKQSFDLSVKAQYKKNKH (SEQ ID NO: 109), CRFRGLISLSQVYLSZaK(Cha)VAAWTLKAAaZRNVPPIFNDVYWIAF (SEQ ID NO: 110), CRFRGLISLSQVYLSZaK(Cha)VAAWTLKAAaZCRFRGLISLSQVYLS (SEQ ID NO: 111), RNVPPIFNDVYWIAFZaK(Cha)VAAWTLKAAaZKTTKQSFDLSVKAQYKKNKH (SEQ ID NO: 112), KTTKQSFDLSVKAQYKKNKHZaK(Cha)VAAWTLKAAaZRNVPPIFNDVYWIAF (SEQ ID NO: 113), KTTKQSFDLSVKAQYKKNKHZaK(Cha)VAAWTLKAAaZCRFRGLISLSQVYLS (SEQ ID NO: 114), KTTKQSFDLSVKAQYKKNKHZaK(Cha)VAAWTLKAAaZKTTKQSFDLSVKAQ YKKNKH (SEQ ID NO: 115), PIFNDVYWIAFK(Cha)VAAWTLKAACRFRGLISLSQ (SEQ ID NO: 116), PPIFNDVYWK(Cha)VAAWTLKAARGLISLSQV (SEQ ID NO: 117), MRGSHHHHHHGSDDDDKIVD RNVPPIFNDVYWIAFZaK(Cha)VAAWTLKAAaZRNVPPIFNDVYWIAF (SEQ ID NO: 118), MRGSHHHHHHGSDDDDKIVDRNVPPIFNDVYWIAF GGGGSGGGGGGSS ILMQYIKANSKFIGIPMGLPQSIALSSLMVAQ GGGGSGGGGGGSSCRFRGLISLSQVYLS (SEQ ID NO: 119), RNVPPIFNDVYWIAFILMQYIKANSKFIGICRFRGLISLSQVYLS (SEQ ID NO: 120), RNVPPIFNDVYWIAFZPKYVKQNTLKLATZCRFRGLISLSQVYLS (SEQ ID NO: 121), CRNVPPIFNDVYWIAFZaK(Cha)VAAWTLKAAaZRNVPPIFNDVYWIAFC (SEQ ID NO: 122), RNVPPIFNDVYWIAFZaK(Cha)VAAWTLKAACRFRGLISLSQVYLS(SEQ ID NO: 160), RNVPPIFNDVYWIAFXXKXVAAWTLKAAXXCRFRGLISLSQVYLS (SEQ ID NO: 198), KTTKQSFDLSVKAQYKKNKHXXKXVAAWTLKAAXXCRFRGLISLSQVYLS (SEQ ID NO: 201), RNVPPIFNDVYWIAFXPKYVKQNTLKLATXCRFRGLISLSQVYLS (SEQ ID NO: 203), RNVPPIFNDVYWIAFXXKXVAAWTLKAACRFRGLISLSQVYLS (SEQ ID NO: 207), RNVPPIFNDVYWIAFXXKFVAAWTLKAAXXCRFRGLISLSQVYLS (SEQ ID NO: 209), RNVPPIFNDVYWIAFXXKFVAAWTLKAACRFRGLISLSQVYLS (SEQ ID NO: 211), KTTKQSFDLSVKAQYKKNKHZaWPEANQVGAGAFGPGFaZCRFRGLISLSQVYLS (SEQ ID NO: 216), KTTKQSFDLSVKAQYKKNKHZaMDIDPYKEFGATVELLSFLPaZCRFRGLISLS QVYLS (SEQ ID NO: 217), 5 KTTKQSFDLSVKAQYKKNKHZaILMQYIKANSKFIGIPMGLPQSIALSSLMVAQ 32 aZCRFRGLISLSQVYLS (SEQ ID NO: 218). In this case, the "a" denotes D-form alanine, the "Z" denotes 6-aminohexanoic acid, the "(Cha)" denotes L-cyclohexylalanine, and the "X" denotes any standard amino acid.

Designing Unit-D

Structure of Unit-D 1—Overview

As a peptide unit provided herein, a peptide unit, 1) which includes one B-cell epitope and two Th epitopes, 2) in which, the sequence of one Th epitope of the two Th epitopes is located between the sequence of the other Th epitope and the sequence of the B-cell epitope, and 3) which may include one or more auxiliary parts, is named "unit-C". The function of the auxiliary part is not particularly limited as long as it does not impair the functions of the B-cell epitope and the Th epitope, and is appropriately designed as necessary.

In an embodiment, the unit-D may be one in which a first B-cell epitope, a first Th epitope, and a second Th epitope are sequentially linked in the direction from the N-terminus to the C-terminus.

Furthermore, the unit-D may further include a first auxiliary part. When the unit-D includes the first auxiliary part, the sequence of the first auxiliary part is located at the N-terminal side relative to the sequence of the first B-cell epitope within the unit-D sequence. In particular, the first auxiliary part may have a dummy function, a solubility improving function, a linker function, and/or a cyclic form-forming function, but the functions of the first auxiliary part are not limited thereto.

Furthermore, the unit-D may further include a second auxiliary part. When the unit-D includes the second auxiliary part, the sequence of the second auxiliary part is located between the sequence of the first B-cell epitope and the sequence of the first Th epitope within the unit-D sequence. In particular, the second auxiliary part may have a dummy function, a solubility improving function, a linker function, and/or a protective function, but the functions of the second auxiliary part are not limited thereto.

Furthermore, the unit-D may further include a third auxiliary part. When the unit-D includes the third auxiliary part, the sequence of the third auxiliary part is located between the sequence of the first Th epitope and the sequence of the second Th epitope within the unit-D sequence. In particular, the third auxiliary part may have a dummy function, a solubility improving function, a linker function, and/or a protective function, but the functions of the third auxiliary part are not limited thereto.

Furthermore, the unit-D may further include a fourth auxiliary part. When the unit-D includes the fourth auxiliary part, the sequence of the fourth auxiliary part is located at the C-terminal side relative to the sequence of the second Th epitope within the unit-D sequence. In particular, the fourth auxiliary part may have a dummy function, a solubility improving function, a linker function, and/or a cyclic form-forming function, but the functions of the fourth auxiliary part are not limited thereto.

In another embodiment, the unit-D may be one in which a third Th epitope, a fourth Th epitope, and a second B-cell epitope are sequentially linked in the direction from the N-terminus to the C-terminus.

Furthermore, the unit-D may further include a fifth auxiliary part. When the unit-D includes the fifth auxiliary part, the sequence of the fifth auxiliary part is located at the N-terminal side relative to the sequence of the third Th epitope within the unit-D sequence. In particular, the fifth auxiliary part may have a dummy function, a solubility improving function, a linker function, and/or a cyclic form-forming function, but the functions of the fifth auxiliary part are not limited thereto.

Furthermore, the unit-D may further include a sixth auxiliary part. When the unit-D includes the sixth auxiliary part, the sequence of the sixth auxiliary part is located between the sequence of the third Th epitope and the sequence of the fourth Th epitope within the unit-D sequence. In particular, the sixth auxiliary part may have a dummy function, a solubility improving function, a linker function, and/or a protective function, but the functions of the sixth auxiliary part are not limited thereto.

Furthermore, the unit-D may further include a seventh auxiliary part. When the unit-D includes the seventh auxiliary part, the sequence of the seventh auxiliary part is located between the sequence of the fourth Th epitope and the sequence of the second B-cell epitope within the unit-D sequence. In particular, the seventh auxiliary part may have a dummy function, a solubility improving function, a linker function, and/or a protective function, but the functions of the seventh auxiliary part are not limited thereto.

Furthermore, the unit-D may further include an eighth auxiliary part. When the unit-D includes the eighth auxiliary part, the sequence of the eighth auxiliary part is located at the C-terminal side relative to the sequence of the second B-cell epitope within the unit-D sequence. In particular, the eighth auxiliary part may have a dummy function, a solubility improving function, a linker function, and/or a cyclic form-forming function, but the functions of the eighth auxiliary part are not limited thereto.

Structure of Unit-D 2—Formula

In an embodiment, the unit-B is a peptide represented by the following [Formula D] or [Formula D'].

[Formula D]

[Formula D']

The $B_1$ and $B_2$ are B-cell epitopes, and they follow the design principle described above.

The $T_1$ to $T_4$ are Th epitopes, and they follow the design principle described above.

The $A_1$ to $A_8$ are auxiliary parts and they may be omitted.

In particular, the $A_1$ to $A_8$ may have a dummy function, a solubility improving function, a linker function, and/or a cyclic form forming function, but the $A_1$ to $A_8$ are not limited thereto.

Length of Unit-D

In an embodiment, the length of the unit-D may be about 24mer, about 25mer, about 26mer, about 27mer, about 28mer, about 29mer, about 30mer, about 31mer, about 32mer, about 33mer, about 34mer, about 35mer, about 36mer, about 37mer, about 38mer, about 39mer, about 40mer, about 41mer, about 42mer, about 43mer, about 44mer, about 45mer, about 46mer, about 47mer, about 48mer, about 49mer, about 50mer, about 51mer, about 52mer, about 53mer, about 54mer, about 55mer, about 56mer, about 57mer, about 58mer, about 59mer, about 60mer, about 61mer, about 62mer, about 63mer, about 64mer, about 65mer, about 66mer, about 67mer, about 68mer, about 69mer, about 70mer, about 71mer, about 72mer, about 73mer, about 74mer, about 75mer, about 76mer, about 77mer, about 78mer, about 79mer, about 80mer, about 81mer, about 82mer, about 83mer, about 84mer, about 85mer, about 86mer, about 87mer, about 88mer, about 89mer, about 90mer, about 91mer, about 92mer, about 93mer, about 94mer, about 95mer, about 96mer, about 97mer, about 98mer, about 99mer, or about 100mer. In another embodiment, the length of the unit-B may have a value within the two numerical ranges selected in the immediately preceding sentence. For example, the length of the unit-D may be in the range of about 24mer to about 45mer. For another example, the length of the unit-A may be in the range of about 40mer to about 80mer.

Embodiment of Unit-D—Exemplary Design

In an embodiment, the unit-D may have a sequence in which a first auxiliary part, a first B-cell epitope, a second auxiliary part, a first Th epitope, a third auxiliary part, and a second Th epitope are sequentially linked. In particular, the first auxiliary part is His-tag, the second auxiliary part and the third auxiliary part each have a linker function. The second auxiliary part and the third auxiliary part each include one or more artificial amino acids.

In another embodiment, the unit-D may have a sequence in which a fourth auxiliary part, a second B-cell epitope, a fifth auxiliary part, a third Th epitope, a sixth auxiliary part, a fourth Th epitope, and a seventh auxiliary part are sequentially linked. In particular, the fourth auxiliary part is His-tag, the fifth auxiliary part and the sixth auxiliary part each have a linker function, and the seventh auxiliary part has a protective function. The fifth auxiliary part, the sixth auxiliary part, and the seventh auxiliary part each include one or more artificial amino acids.

In still another embodiment, the unit-D includes a third B-cell epitope, an eighth auxiliary part, a fifth Th epitope, a ninth auxiliary part, and a sixth Th epitope. In particular, the eighth auxiliary part and the ninth auxiliary part each have a linker function. The eighth auxiliary part and the ninth auxiliary part each have a protective function each include one or more artificial amino acids.

In still another embodiment, the unit-D includes a fourth B-cell epitope, a tenth auxiliary part, a seventh Th epitope, an eleventh auxiliary part, an eighth Th epitope, and a twelfth auxiliary part. In particular, the tenth auxiliary part and the eleventh auxiliary part each have a linker function. The twelfth auxiliary part has a protective function. The tenth auxiliary part, the eleventh auxiliary part, and the twelfth auxiliary part each include one or more artificial amino acids.

Embodiments of Unit-D Sequence

In an embodiment, the unit-D is a unit peptide selected from a group consisting of RNVPPIFNDVYWIAF ZaK(Cha)VAAWTLKAAaZ ILMQYIKANSKFIGI (SEQ ID NO: 123), CRFRGLISLSQVYLS ZaK(Cha)VAAWTL-KAAaZ ILMQYIKANSKFIGI (SEQ ID NO: 124), KTTKQSFDLSVKAQYKKNKH ZaK(Cha)VAAWTL-KAAaZ ILMQYIKANSKFIGI (SEQ ID NO: 125), ILMQYIKANSKFIGI ZaK(Cha)VAAWTLKAAaZ RNVP-PIFNDVYWIAF (SEQ ID NO: 126), ILMQYIKANSKFIGI ZaK(Cha)VAAWTLKAAaZ CRFRGLISLSQVYLS (SEQ ID NO: 127), ILMQYIKANSKFIGI ZaK(Cha)VAAWTL-KAAaZ KTTKQSFDLSVKAQYKKNKH (SEQ ID NO: 128), PIFNDVYWIAF K(Cha)VAAWTLKAA K(Cha)VAAWTLKAA (SEQ ID NO: 129), PPIFNDVYW K(Cha)VAAWTLKAA K(Cha)VAAWTLKAA (SEQ ID NO: 130), MRGSHHHHHHGSDDDDKIVDRNVPPIFNDVYWI-AFZaK(Cha)VAAWTLKAAaZ ILMQYIKANSKFIGI (SEQ ID NO: 131), MRGSHHHHHHGSDDDD-KIVDILMQYIKANSKFIGIZaK(Cha)VAAWTLKAAaZ (SEQ ID NO: 132), MRGSHHHHHHGSDDDD-KIVDRNVPPIFNDVYWIAFGGGGSGGGGGGSSZaK (Cha) VAAWTLKAAaZILMQYIKANSKFIGI (SEQ ID NO: 133), MRGSHHHHHHGSDDDDKIVDRNVP-PIFNDVYWIAFGGGGSGGGGGGSSILMQ YIKANSK-FIGIPMGLPQSIALSSLMVAQGGGGSGGGGGGSSIL-MQYIKANSKFI GIPMGLPQSIALSSLMVAQ (SEQ ID NO: 134), RNVPPIFNDVYWIAFZaK(Cha)VAAWTL-KAAaZK(Cha)LAAFTIRAAaZ (SEQ ID NO: 135), CRNVPPIFNDVYWIAFZaK(Cha)VAAWTL-KAAaZILMQYIKANSKFIGIC (SEQ ID NO: 136). In this case, the "a" denotes D-form alanine, the "Z" denotes 6-aminohexanoic acid, the "(Cha)" denotes L-cyclohexyl-alanine, and the "X" denotes any standard amino acid.

Designing Unit-E

Structure of Unit-E 1—Overview

As a peptide unit provided herein, a peptide unit 1) which includes two B-cell epitopes and two Th epitopes, 2) in which each sequence of the two Th epitopes is located between the sequence of one B-cell epitope of the two B-cell epitopes and the sequence of the other B-cell epitope, and 3) which may include one or more auxiliary parts, is named "unit-E". The function of the auxiliary part is not particularly limited as long as it does not impair the functions of the B-cell epitope and the Th epitope, and is appropriately designed as necessary.

In an embodiment, the unit-E may be one in which a first B-cell epitope, a first Th epitope, a second Th epitope, and a second B-cell epitope are sequentially linked in the direction from the N-terminus to the C-terminus.

Furthermore, the unit-E may further include a first auxiliary part. When the unit-E includes the first auxiliary part, the sequence of the first auxiliary part is located at the N-terminal side relative to the sequence of the first B-cell epitope within the unit-E sequence. In particular, the first auxiliary part may have a dummy function, a solubility improving function, a linker function, and/or a cyclic form-forming function, but the functions of the first auxiliary part are not limited thereto.

Furthermore, the unit-E may further include a second auxiliary part. When the unit-E includes the second auxiliary part, the sequence of the second auxiliary part is located between the sequence of the first B-cell epitope and the sequence of the first Th epitope within the unit-E sequence. In particular, the second auxiliary part may have a dummy function, a solubility improving function, a linker function, and/or a protective function, but the functions of the second auxiliary part are not limited thereto.

Furthermore, the unit-E may further include a third auxiliary part. When the unit-E includes the third auxiliary part, the sequence of the third auxiliary part is located between the sequence of the first Th epitope and the sequence of the second Th epitope within the unit-E sequence. In particular, the third auxiliary part may have a dummy function, a solubility improving function, a linker function, and/or a protective function, but the functions of the third auxiliary part are not limited thereto.

Furthermore, the unit-E may further include a fourth auxiliary part. When the unit-E includes the fourth auxiliary part, the sequence of the fourth auxiliary part is located between the sequence of the second B-cell epitope and the second B-cell epitope within the unit-E sequence. In particular, the fourth auxiliary part may have a dummy function, a solubility improving function, a linker function, and/or a protective function, but the functions of the fourth auxiliary part are not limited thereto.

Furthermore, the unit-E may further include a fifth auxiliary part. When the unit-E includes the fifth auxiliary part, the sequence of the fifth auxiliary part is located at the N-terminal side relative to the sequence of the second B-cell epitope within the unit-E sequence. In particular, the fifth auxiliary part may have a dummy function, a solubility improving function, a linker function, and/or a cyclic form-forming function, but the functions of the fifth auxiliary part are not limited thereto.

Structure of Unit-E 2—Formula

In an embodiment, the unit-E is a peptide represented by the following [Formula E].

$$\underline{N}\text{-}A_1\text{-}B_1\text{-}A_2\text{-}T_1\text{-}A_3\text{-}T_2\text{-}A_4\text{-}B_2\text{-}A_5\text{-}\underline{C} \qquad \text{[Formula E]}$$

The $B_1$ and $B_2$ are B-cell epitopes, and they follow the design principle described above.

The $T_1$ and $T_2$ are Th epitopes, and they follow the design principle described above.

The $A_1$, $A_2$, $A_3$, $A_4$, and $A_5$ are auxiliary parts and they may be omitted.

In particular, the $A_1$, $A_2$, $A_3$, $A_4$, and $A_5$ may have a dummy function, a solubility improving function, a linker function, and/or a cyclic form forming function, but the $A_1$, $A_2$, $A_3$, $A_4$, and $A_5$ are not limited thereto.

Length of Unit-E

In an embodiment, the length of the unit-E may be about 32mer, about 33mer, about 34mer, about 35mer, about 36mer, about 37mer, about 38mer, about 39mer, about 40mer, about 41mer, about 42mer, about 43mer, about 44mer, about 45mer, about 46mer, about 47mer, about 48mer, about 49mer, about 50mer, about 51mer, about 52mer, about 53mer, about 54mer, about 55mer, about 56mer, about 57mer, about 58mer, about 59mer, about 60mer, about 61mer, about 62mer, about 63mer, about 64mer, about 65mer, about 66mer, about 67mer, about 68mer, about 69mer, about 70mer, about 71mer, about 72mer, about 73mer, about 74mer, about 75mer, about 76mer, about 77mer, about 78mer, about 79mer, about 80mer, about 81mer, about 82mer, about 83mer, about 84mer, about 85mer, about 86mer, about 87mer, about 88mer, about 89mer, about 90mer, about 91mer, about 92mer, about 93mer, about 94mer, about 95mer, about 96mer, about 97mer, about 98mer, about 99mer, or about 100mer. In another embodiment, the length of the unit-E may have a value within the two numerical ranges selected in the immediately preceding sentence. For example, the length of the unit-E may be in the range of about 32mer to about 60mer. For another example, the length of the unit-A may be in the range of about 50mer to about 100mer.

Embodiment of Unit-E—Exemplary Design

In an embodiment, the unit-E may have a sequence in which a first auxiliary part, a first B-cell epitope, a second auxiliary part, a first Th epitope, a third auxiliary part, a second Th epitope, a fourth auxiliary part, and a second B-cell epitope are sequentially linked. In particular, the first auxiliary part is His-tag. The second auxiliary part and the fourth auxiliary part each have a linker function and a protective function. The third auxiliary part has a linker function. The second auxiliary part, the third auxiliary part, and the fourth auxiliary part include one or more artificial amino acids.

In another embodiment, the unit-E may have a sequence in which a third B-cell epitope, a fifth auxiliary part, a third Th epitope, a sixth auxiliary part, a fourth Th epitope, a seventh auxiliary part, and a fourth B-cell epitope are sequentially linked. In particular, the fifth auxiliary part and the seventh auxiliary part each have a linker function and a protective function. The sixth auxiliary part has a linker function. The fifth auxiliary part, the sixth auxiliary part, and the seventh auxiliary part include one or more artificial amino acids.

Embodiments of Unit-E Sequence

In an embodiment, the unit-E is a peptide unit selected from a group consisting of RNVPPIFNDVYWIAFZaK(Cha)VAAWTLKAAaZILMQYIKANSKFIGIRNVPPIFN DVYWIAF (SEQ ID NO: 137), RNVPPIFNDVYWI-AFZaK(Cha)VAAWTLKAAaZILMQYIKANSKFIGICR-FRGLIS LSQVYLS (SEQ ID NO: 138), RNVPPIFNDVY-WIAFZaK(Cha)VAAWTLKAAaZILMQYIKANSKFIGIKTTKQSF DLSVKAQYKKNKH (SEQ ID NO: 139), CRFRGLIS-LSQVYLSZaK(Cha)VAAWTLKAAaZILMQYIKANSK-FIGIRNVPPIFN DVYWIAF (SEQ ID NO: 140), CRFRG-LISLSQVYLSZaK(Cha)VAAWTLKAAaZILMQYIKANSKFIGICRFRGLIS LSQVYLS (SEQ ID NO: 141), CRFRGLISLSQVYLSZaK(Cha)VAAWTLKAAaZILMQYIKANSKFIGIKTTKQSF DLSVKAQYKKNKH (SEQ ID NO: 142), KTTKQSFDLSVKAQYKKNKHZaK(Cha)VAAWTL-KAAaZILMQYIKANSKFIGIR NVPPIFNDVYWIAF (SEQ ID NO: 143), KTTKQSFDLSVKAQYKKNKHZaK(Cha)VAAWTLKAAaZILMQYIKANSKFIGIC RFRGLIS-LSQVYLS (SEQ ID NO: 144), KTTKQSFDLSVKAQYK-KNKHZaK(Cha)VAAWTLKAAaZILMQYIKANSKFIGIK TTKQSFDLSVKAQYKKNKH (SEQ ID NO: 145), MRGSHHHHHHGSDDDDKIVDRNVPPIFNDVYWI-AFZaK(Cha)VAAWTLKAAaZ ILMQYIKANSKFI-GIRNVPPIFNDVYWIAF (SEQ ID NO: 146), MRGSHHHHHHGSDDDDKIVDRNVPPIFNDVYWI-AFGGGGSGGGGGGSSILMQ YIKANSKFIGIPMGLPQ-SIALSSLMVAQILMQYIKANSKFIGIPMGLPQSIALSSL MVAQGGGGSGGGGGGSSCRFRGLISLSQVYLS (SEQ ID NO: 147), PIFNDVYWIAFK(Cha)VAAWTLKAAK(Cha)VAAWTLKAACRFRGLISLSQ (SEQ ID NO: 148), PPIFNDVYWK(Cha)VAAWTLKAAK(Cha)VAAWTL-KAARGLISLSQV (SEQ ID NO: 149), and CRNVP-PIFNDVYWIAFZaK(Cha)VAAWTLKAAaZILMQYI-KANSKFIGIRNVPPIF NDVYWIAFC (SEQ ID NO: 150). In this case, the "a" denotes D-form alanine, the "Z" denotes 6-aminohexanoic acid, the "(Cha)" denotes L-cyclohexyl-alanine.

Designing a Peptide

Designing a Peptide—Overview

The peptides provided herein can be designed using one or more of the peptide units disclosed above. These peptides include one or more of peptide units and may include one or more types of peptide units. For example, the peptide may be designed by 1) including only one peptide unit, 2) designing a concatemer by linking multiple peptide units of one type having the same sequence, 3) designing the peptide in the form of string-of-beads by linking one or more types of the peptide units with different sequences, 4) by mixing the design methods of 1) to 3) above, and 5) designing the peptide in a cyclic form by connecting both ends of the peptide designed in the above method, but the design methods are not limited thereto. Hereinafter, each design method will be described in detail.

One Unit Design

The peptide may be designed to include only one of the peptide units described above. In an embodiment, the peptide may include one peptide unit selected from the group consisting of unit-A, unit-B, unit-C, unit-D, and unit-E. In particular, the peptide unit has the constitution described above.

Concatemer Design 1—Overview

The peptide may be designed in the form of a concatemer in which multiple peptide units having the same sequence are linked. The peptide designed in the concatemer form consists of 1) one type of a peptide unit and 2) multiple peptide units having the same or equivalent sequence.

In particular, two peptide units with "an equivalent sequence" refers to cases where 1) when an auxiliary part is present at the N-terminus and/or C-terminus of each of the two peptides, and 2) when the auxiliary part exists, its sequence, even if the two are different, the rest of the sequence is the same. For example, when a first peptide has a sequence in which a first auxiliary part and a first unit-A are linked in the direction from the N-terminus to C-terminus, a second peptide has a sequence in which the first unit-A and a first auxiliary part are linked in the direction from the N-terminus to the C-terminus, a third peptide has a sequence in which a second auxiliary part, the first unit-A, and a third auxiliary part are linked in the direction from the N-terminus to the C-terminus, and a fourth peptide has the first unit-A sequence, the first to fourth peptides are said to have an equivalent sequence.

In an embodiment, the peptide may include one in which a first a peptide unit and a second a peptide unit are linked in order. In particular, the first peptide unit is a peptide unit selected from the group consisting of unit-A, unit-B, unit-C, unit-D, and unit-E; and the second a peptide unit has a sequence which is the same as or equivalent to the first peptide unit.

In another embodiment, the peptide may include one in which a third peptide unit, a fourth peptide unit, and a fifth peptide unit are linked in order. In particular, the third peptide unit is a peptide unit selected from the group consisting of unit-A, unit-B, unit-C, unit-D, and unit-E; and the fourth peptide unit and the fifth peptide unit each have a sequence which is the same as or equivalent to the third peptide unit.

In still another embodiment, the peptide may include one in which a sixth peptide unit, a seventh peptide unit, an eighth peptide unit, and a ninth peptide unit are linked in order. In particular, the third peptide unit is a peptide unit selected from the group consisting of unit-A, unit-B, unit-C, unit-D, and unit-E; and the seventh peptide unit, the eighth peptide unit, and the ninth peptide unit each have a sequence which is the same as or equivalent to the sixth peptide unit.

Concatemer Design 2—Formula

In an embodiment, the peptide may be a peptide represented by the following [Formula 1].

$$\underline{N}\text{-}U_1\text{-}U_2\text{-}\ldots\text{-}U_n\text{-}\underline{C} \qquad \text{[Formula 1]}$$

in which $U_1$ to $U_n$ are each a peptide unit selected from the group consisting of unit-A, unit-B, unit-C, unit-D, and unit-E, and they have the constitutions of peptide units described above.

The $U_1$ to $U_n$ have the same or equivalent sequence.

The n is an integer of 2 or greater.

Concatemer Design 3—Exemplary Sequences

In an embodiment, the peptide is a peptide selected from a group consisting of MRGSHHIHIHGSDDDD-KIVDRNVPPIFNDVYWIAFZaK(Cha)VAAWTLKAAaZ RNVPPIFNDVYWIAFZaK(Cha)VAAWTLKAAaZ (SEQ ID NO: 151), RNVPPIFNDVYWIAFCRFRGLIS-LSQVYLSZaK(Cha)VAAWTLKAAaZRNVPPIF NDVY-WIAFCRFRGLISLSQVYLSZaK(Cha)VAAWTLKAAaZ (SEQ ID NO: 152), RNVPPIFNDVYWIAFZaK(Cha)
VAAWTLKAAaZCRFRGLISLSQVYLSRNVPPIF
NDVYWIAFZaK(Cha)VAAWTLKAAaZCRFRGLIS-
LSQVYLS (SEQ ID NO: 153), RNVPPIFNDVYWIAFZaK
(Cha)VAAWTLKAAaZILMQYIKANSKFIGIRNVPPIFN
DVYWIAFZaK(Cha)VAAWTLKAAaZILMQYIKANSK-
FIGI (SEQ ID NO: 154), and RNVPPIFNDVYWIAFZaK
(Cha)VAAWTLKAAaZILMQYIKANSKFIGIRNVPPIFN
DVYWIAFRNVPPIFNDVYWIAFZaK(Cha)VAAWTL-
KAAaZILMQYIKANSKFIGI RNVPPIFNDVYWIAF
(SEQ ID NO: 155). In this case, the "a" denotes D-form alanine, the "Z" denotes 6-aminohexanoic acid, the "(Cha)" denotes L-cyclohexylalanine.

String-of-Beads Design 1—Overview

The peptide may be designed in the form of string-of-beads in which multiple peptide units having different sequences are linked. The peptide designed in the form of string-of-beads consists of 1) at least one kind of a peptide unit and 2) multiple peptide units having different sequences.

In an embodiment, the peptide may include one in which the first peptide unit and the second peptide unit are sequentially linked. In particular, the first peptide unit and the second peptide unit are each a peptide unit selected from the group consisting of unit-A, unit-B, unit-C, unit-D, and unit-E; and the first peptide unit and the second peptide unit have sequences different from each other.

In another embodiment, the peptide may include one in which the third peptide unit, the fourth peptide unit, and the fifth peptide unit are sequentially linked. In particular, the third peptide unit, the fourth peptide unit, and the fifth peptide are each a peptide unit selected from the group consisting of unit-A, unit-B, unit-C, unit-D, and unit-E; and the third peptide unit, the fourth peptide unit, and the fifth peptide unit have sequences different from one other.

In still another embodiment, the peptide may include one in which the sixth peptide unit, the seventh peptide unit, the eighth peptide unit, and the ninth peptide unit are sequentially linked. In particular, the sixth peptide unit, the seventh peptide unit, the eighth peptide unit, and the ninth peptide unit are each a peptide unit selected from the group consisting of unit-A, unit-B, unit-C, unit-D, and unit-E; and the sixth peptide unit, the seventh peptide unit, the eighth peptide unit, and the ninth peptide unit have sequences different from one other.

String-of-Beads Design 2—Formula

In an embodiment, the peptide may be a peptide represented by the following [Formula 2]:

$$\underline{N}\text{-}U_1\text{-}U_2\text{-}\ldots\text{-}U_n\text{-}\underline{C} \quad\quad\quad [\text{Formula 2}]$$

in which $U_1$ to $U_n$ are each a peptide unit selected from the group consisting of unit-A, unit-B, unit-C, unit-D, and unit-E, and they have the constitutions of peptide units described above.

The $U_1$ to $U_n$ have the same or equivalent sequence.

The n is an integer of 2 or greater.

String-of-Beads Design 3—Exemplary Sequences

In an embodiment, the peptide may be a peptide of RNVPPIFNDVYWIAFZaK(Cha)VAAWTLKAAaZRNVP-
PIFNDVYWIAFCRFRGLI SLSQVYLSZaK(Cha)VAAW-
TLKAAaZ (SEQ ID NO: 156), in which "a" denotes D-form alanine, Z denotes 6-aminohexanoic acid, and (Cha) denotes L-cyclohexylalanine.

Mixed Design 1—Overview

The peptide may be designed by appropriately mixing the above-mentioned 1) one unit design, 2) concatemer design, and 3) string-of-beads design. In an embodiment, the peptide may be designed by first designing a unit peptide according to the design methods described above, and then linking multiple unit peptides.

In an embodiment, the peptide may be one in which a first unit peptide and a second unit peptide are sequentially linked. In particular, the first unit peptide and the second unit peptide each have a peptide constitution according to any one of the one unit design, the concatemer design, and the string-of-beads design, and the sequence of the first unit peptide and the sequence of the second unit peptide are different from each other.

In another embodiment, the peptide may be one in which a third unit peptide, a fourth unit peptide, and a fifth unit peptide are sequentially linked. In particular, the third unit peptide, the fourth unit peptide, and the fifth unit peptide each have a peptide constitution according to any one of the one unit design, the concatemer design, and the string-of-beads design, and the sequences of the third unit peptide, the fourth unit peptide, and the fifth unit peptide are different from one other.

In still another embodiment, the peptide may be one in which a sixth unit peptide, a seventh unit peptide, an eighth unit peptide, and a ninth unit peptide are sequentially linked. In particular, the sixth unit peptide, the seventh unit peptide, the eighth unit peptide, and the ninth unit peptide each have a peptide constitution according to any one of the one unit design, the concatemer design, and the string-of-beads design, and the sequences of the sixth unit peptide, the seventh unit peptide, the eighth unit peptide, and the ninth unit peptide are different from one other.

Mixed Design 2—Formula

In an embodiment, the peptide may be a peptide represented by the following [Formula 3]:

$$\underline{N}\text{N-}P_1\text{-}P_2\text{-}\ldots\text{-}P_n\text{-}\underline{C} \quad\quad\quad [\text{Formula 3}]$$

in which $P_1$ to $P_1$ are each a unit peptide designed by a method selected from the group consisting of a one unit design, a concatemer design, and a string-of-beads design, and they have the designs and constitutions of peptides described above.

The n is an integer of 2 or greater.

Mixed Design 3—Exemplary Sequences

In an embodiment, the peptide is a peptide selected from a group consisting of RNVPPIFNDVYWIAFZaK(Cha)
VAAWTLKAAaZRNVPPIFNDVYWIAFZRNVPPI
FNDVYWIAFZaK(Cha)VAAWTLKAAaZILMQYIKAN-
SKFIGIZRNVPPIFNDVY WIAFZaK(Cha)VAAWTL-
KAAaZILMQYIKANSKFIGICRFRGLISLSQVYLS (SEQ ID NO: 157), and RNVPPIFNDVYWIAFZaK(Cha)VAAW-
TLKAAaZRNVPPIFNDVYWIAFCRFRGLI
SLSQVYLSZaK(Cha)VAAWTLKAAaZRNVPPIFNDVY-
WIAFCRFRGLISLSQVYLSZ aK(Cha)VAAWTL-
KAAaZRNVPPIFNDVYWIAFZaK(Cha)VAAWTL-
KAAaZRNVPPIF
NDVYWIAFZRNVPPIFNDVYWIAFZaK(Cha)VAAW-
TLKAAaZILMQYIKANSKFIGI ZRNVPPIFNDVYWI-
AFZaK(Cha)VAAWTLKAAaZ ILMQYIKANSKFIGICR-
FRGLISLSQVYLS (SEQ ID NO: 158). In this case, the "a" denotes D-form alanine, the "Z" denotes 6-aminohexanoic acid, and the "(Cha)" denotes L-cyclohexylalanine.

Designing of Cyclic Form

The peptide may be designed to form a cyclic form. When the peptide is in a cyclic form, the stability in the body of a subject is increased; therefore, an improved effect can be expected when the peptide with a cyclic form is used as an immunotherapeutic. In an embodiment, with regard to the peptide designed by a design method selected from the group consisting of a one unit design, a concatemer design, a string-of-beads design, and a mixed design method, the peptide may be designed to further have an auxiliary part having a function for forming a cyclic form at the N-terminus and C-terminus. In another embodiment, with regard to the peptide designed by a design method selected from the group consisting of a one unit design, a concatemer design, a string-of-beads design, and a mixed design method, the peptide may be designed to further include an auxiliary part and to form a cyclic form through the auxiliary part.

Other Designs

The peptide may be designed by other methods as necessary, in addition to the design methods described above. In an embodiment, with regard to the peptide designed by a design method selected from the group consisting of a one unit design, a concatemer design, a string-of-beads design, and a mixed design method, the peptide may further include one or more auxiliary parts, one or more B-cell epitopes, and/or one or more Th epitopes.

Sequences Similar to Peptide Units and/or Peptides Disclosed

In the present specification, peptide units and/or peptide which have a sequence similar to those disclosed in the paragraphs of "unit-A design", "unit-B design", "unit-C design", "unit-D design", "unit-E design", and "peptide design" above are disclosed.

In an embodiment, the peptide unit may have a sequence having an identity of 80%, 81%, 82%, 83%, 84%, 85%, 86%, 87%, 88%, 89%, 90%, 91%, 92%, 93%, 94%, 95%, 96%, 97%, 98%, 99%, or 100% to any one of the sequences disclosed in the paragraphs of "unit-A design", "unit-B design", "unit-C design", "unit-D design", and "unit-E design". In another embodiment, the peptide unit may have a sequence that matches with any one of the sequences disclosed in the paragraphs of "unit-A design", "unit-B design", "unit-C design", "unit-D design", and "unit-E design" by at least a numerical value selected in the immediately preceding sentence. In still another embodiment, the peptide unit may have a sequence which has an identity of 80%, 81%, 82%, 83%, 84%, 85%, 86%, 87%, 88%, 89%, 90%, 91%, 92%, 93%, 94%, 95%, 96%, 97%, 98%, 99%, or 100% to any one selected from SEQ ID NO: 56 to SEQ ID NO: 150, SEQ ID NO: 160 to SEQ ID NO: 161, and SEQ ID NO: 198 to SEQ ID NO: 220. In still another embodiment, the peptide unit may have a sequence which matches with any one of the sequences disclosed selected from SEQ ID NO: 56 to SEQ ID NO: 150, SEQ ID NO: 160 to SEQ ID NO: 161, and SEQ ID NO: 198 to SEQ ID NO: 220 by at least a numerical value selected in the immediately preceding sentence. For example, the peptide unit may have a sequence which has an identity of 90% or more to SEQ ID NO: 56.

In still another embodiment, the peptide may have a sequence which has an identity of 80%, 81%, 82%, 83%, 84%, 85%, 86%, 87%, 88%, 89%, 90%, 91%, 92%, 93%, 94%, 95%, 96%, 97%, 98%, 99%, or 100% to any one of the sequences disclosed in the paragraph of "peptide design". In still another embodiment, the peptide may have a sequence that matches with any one of the sequences disclosed in the paragraph of "peptide design" by at least a numerical value selected in the immediately preceding sentence. In still another embodiment, the peptide may have a sequence which has an identity of 80%, 81%, 82%, 83%, 84%, 85%, 86%, 87%, 88%, 89%, 90%, 91%, 92%, 93%, 94%, 95%, 96%, 97%, 98%, 99%, or 100% to any one selected from SEQ ID NO: 151 to SEQ ID NO: 158. In still another embodiment, the peptide may have a sequence that matches with any one of SEQ ID NO: 151 to SEQ ID NO: 158 by at least a numerical value selected in the immediately preceding sentence. For example, the peptide may have a sequence which has an identity of 90% or more to SEQ ID NO: 151.

Use of Peptides

Use of Peptides—Overview

The peptides provided herein are suitable as an immunotherapeutic because they have the following characteristics when introduced into the body of a subject: 1) they induce the production of antibodies that specifically bind to intentionally designed B-cell epitopes, and 2) they induce the production of uniform antibodies. Therefore, the peptides can be used as an immunotherapeutic. In an embodiment, the peptides provided herein can be used as an immunotherapeutic for obesity. In another embodiment, the peptide units and/or peptides including the same provided herein may be used for the treatment of obesity.

Use of Peptides for Treatment of Obesity

The peptides provided herein include a B-cell epitope. In an embodiment, the B-cell epitope may be a B-cell epitope included in SEQ ID NOS: 41 to 75. In particular, the B-cell epitope is known to induce antibodies having an ability to bind to ApoB-100 (U.S. patent application Ser. No. 10/378,707, PCT/KR2005/000784, and Kim et al., 2016, An apolipoprotein B100 mimotope prevents obesity in mice, Clinical Science 130, 105-116). It is known from the prior documents above that when an antibody having an ability to bind to ApoB-100 is induced by the B-cell epitope in the body of a subject, it has an immunotherapeutic effect on obesity. Accordingly, in the present specification, the uses of the peptides for the treatment of obesity and a method thereof are disclosed. In order to describe the immunotherapeutic effects of the peptides on obesity, U.S. patent application Ser. No. 10/378,707, PCT/KR2005/000784, and Kim et al., 2016, An apolipoprotein B100 mimotope prevents obesity in mice, Clinical Science 130, 105-116 are incorporated herein by reference. In the event of a conflict between the referenced part and the description of the present specification, it should be construed that the description in the present specification takes precedence over the referenced part.

Pharmaceutical Composition Including Peptide

The present specification discloses a pharmaceutical composition including the peptide described above. The peptide can be used as an immunotherapeutic and has in common with vaccines in that it induces a humoral immunity when injected into the body. Therefore, those skilled in the art may include, in the pharmaceutical composition including the peptide, an appropriate constitution that can be added for administration of general vaccines and/or to enhance the effect of inducing an immune response. For example, the pharmaceutical composition may include the formulated peptide, pharmaceutically acceptable carriers, supplements and/or adjuvants, but are not limited thereto. Specifically, the pharmaceutical composition may include water, saline, dextrose, ethanol, glycerol, sodium chloride, dextrose, mannitol, sorbitol, lactose, gelatin, albumin, aluminum hydroxide, Freund's Incomplete Adjuvant and Complete Adjuvant (Pifco Laboratories, Detroit, Mich.), Merck adjuvant 65(Merck and Company, Inc., Rahway, NJ), aluminum hydroxide gel (Alum), or aluminum salts such as aluminum phosphate, AS04 series, MF, squalene, MF59, QS21, calcium, iron or zinc salts, insoluble suspensions of acylated tyrosine, acylated fructose, cationically or anionically derived poly saccharides, polyphosphazenes, biodegradable microspheres, Quil A, toll-like receptor (TLR) agonists, PHAD [Avanti polar lipid, Monophosphoryl Lipid A (synthetic)], monophosphoryl lipid A (MPL, monophosphoryl Lipid A), synthetic lipid A, lipid A mimics or analogues, aluminum salts, cytokines, saponins, prolactin, growth hormone deoxycholic acid, betaglucan, polyribonucleotides, muramyl dipeptide (MDP) derivatives, CpG oligos, gram-negative bacterial lipopolysaccharide (LPS), polyphosphazene, emulsion, virosome, cochleate, poly(lactide-co-glycolide) (PLG) microparticles, poloxamer particles, microparticles, liposomes, or an appropriate combination thereof.

Manufacturing Method of the Peptides

The peptides provided herein may be prepared by a known method that can be adopted by those skilled in the art, and the preparation method is not particularly limited. In an embodiment, the peptide may be prepared by a recombinant protein preparation method. In another embodiment, the peptide may be chemically synthesized. Specifically, the peptide may be synthesized by a liquid-phase peptide synthesis method, a solid-phase peptide synthesis method, or a convergent method of small peptide fragments, but the methods are not limited thereto.

Nucleic Acid Encoding Peptide Unit and/or Peptide

Nucleic Acid Encoding Peptide Unit and/or Peptide—Overview

In the present specification, nucleic acids which encode peptide units and/or peptides disclosed above (hereinafter, "encoding nucleic acid") are disclosed. While the peptide units and peptides disclosed herein may include nonstandard amino acids, there are no codons corresponding to the nonstandard amino acids in nature. Therefore, the nonstandard amino acids cannot be encoded by a general method. Accordingly, it is necessary to replace these nonstandard amino acids with appropriate standard amino acids to encode them in the form of nucleic acids. When the peptide unit and/or peptide do not include a nonstandard amino acid, the encoding nucleic acid can be designed using a nucleic acid codon corresponding to each standard amino acid.

For convenience of description, in the present specification, the peptide unit and/or peptide including the substitution of the nonstandard amino acid with an appropriate standard amino acid; and the peptide unit and/or peptide including only standard amino acids are referred to as a target peptide to be encoded, and the DNA and/or RNA encoding the target peptide to be encoded is referred to as an encoding nucleic acid. In particular, when the peptide unit and/or peptide do not include a nonstandard amino acid, the peptide unit and/or peptide has the same amino acid sequence as the target peptide to be encoded.

As used herein, the term "target peptide to be encoded" is a conceptual term introduced to easily describe the resultant encoding nucleic acid, and is independent of the method or procedure for preparing the encoding nucleic acid.

Design of Target Peptide to be Encoded

When a peptide unit and peptide disclosed herein include a nonstandard amino acid, the target peptide to be encoded is designed by replacing the same with an appropriate standard amino acid. When a peptide unit and peptide disclosed herein do not include a nonstandard amino acid, the corresponding target peptide to be encoded has the same sequence as the peptide unit and peptide. In an embodiment, the target peptide to be encoded may be one in which the nonstandard amino acid is replaced with any standard amino acid. In another embodiment, the target peptide to be encoded may be one in which the nonstandard amino acid is replaced with a standard amino acid that is identical to the same or has an equivalent function. In still another embodiment, the target peptide to be encoded may have a same sequence as the peptide unit and/or the peptide. In particular, the peptide unit and/or peptide are characterized by having no nonstandard amino acids.

Embodiments of Designing Target Peptide to be Encoded—Cases Including PADRE

The peptide unit and peptide disclosed herein include one or more Th epitopes. In particular, when the Th epitope is a sequence named PADRE disclosed in US Patent Application No. 305,871, it may include a nonstandard amino acid, L-cyclohexylalanine. According to the literature, the L-cyclohexylalanine may have both a function of protecting the PADRE from a peptide degrading enzyme and a function of an anchor residue capable of binding to MHC Class II. Therefore, the target peptide to be encoded is designed by replacing the L-cyclohexylalanine with an appropriate standard amino acid having the same or equivalent function. In an embodiment, the L-cyclohexylalanine may be substituted with any standard amino acid. In another embodiment, the L-cyclohexylalanine may be substituted with phenylalanine or tyrosine. In still another embodiment, the sequence of the target peptide to be encoded corresponding to the PADRE may be KFVAAWTLKAA (SEQ ID NO: 195), KYVAAWTLKAA (SEQ ID NO: 196), or KXVAAWTLKAA (SEQ ID NO: 197), in which the X refers to any standard amino acid.

Embodiments of Sequence of Target Peptide to be Encoded

In an embodiment, a sequence of the target peptide to be encoded is selected from RNVPPIFNDVYWIAFXXKXVAAWTLKAAXXCRFRGLISLSQVYLS (SEQ ID NO: 198), RNVPPIFNDVYWIAFXXKXVAAWTLKAAXXGSHHHHHHGSDDDDK(SEQ ID NO: 199), GSHHHHHHGSDDDDKXXKXVAAWTLKAAXXRNVPPIFNDVYWIAF (SEQ ID NO: 200), KTTKQSFDLSVKAQYKKNKHXXKXVAAWTLKAAXXCRFRGLISLSQVYLS(SEQ ID NO: 201), RNVPPIFNDVYWIAFCRFRGLISLSQVYLSXXK(Cha)VAAWTLKAAXX (SEQ ID NO: 202), RNVPPIFNDVYWIAFXPKYVKQNTLKLATXCRFRGLISLSQVYLS(SEQ ID NO: 203), RNVPPIFNDVYWIAFXXKXVAAWTLKAAXX (SEQ ID NO: 204), RNVPPIFNDVYWIAFKXVAAWTLKAA (SEQ ID NO: 205), RNVPPIFNDVYWIAFKXVAAWTLKAAHHHHHH (SEQ ID NO: 206), RNVPPIFNDVYWIAFXXKXVAAWTLKAACRFRGLISLSQVYLS (SEQ ID NO: 207), RNVPPIFNDVYWIAFXXKXVAAWTLKAACR (SEQ ID NO: 208), RNVPPIFNDVYWIAFXXKFVAAWTLKAAXXCRFRGLISLSQVYLS (SEQ ID NO: 209), RNVPPIFNDVYWIAFXXKFVAAWTLKAAXX (SEQ ID NO: 210), RNVPPIFNDVYWIAFXXKFVAAWTLKAACRFRGLISLSQVYLS (SEQ ID NO: 211), and RNVPPIFNDVYWIAFXXKFVAAWTLKAACR (SEQ ID NO: 212). In this case, the "X" denotes any standard amino acid.

Design of Encoding Nucleic Acid 1—Nucleic Acid Codon Based

The encoding nucleic acid disclosed herein refers to a nucleic acid codon encoding the encoding target peptide. Since the sequences of the target peptides to be encoded are all standard amino acids, the encoding nucleic acid is designed based on the nucleic acid codon corresponding to each amino acid of the target peptide to be encoded. In particular, since one or more nucleic acid codons can correspond to one standard amino acid, two or more encoding nucleic acids encoding one target peptide to be encoded can eventually be designed. In an embodiment, the encoding nucleic acid may be a DNA and/or RNA codon encoding the target peptide to be encoded. In another embodiment, the encoding nucleic acid may have sequence, which is capable of a complementary binding to a DNA and/or RNA codon encoding the target peptide to be encoded.

The sequence of the encoding nucleic acid may be codon optimized, which is described in more detail below.

Design of Encoding Nucleic Acid 2—Codon Optimization

As described above, if the encoding nucleic acid is designed by simply linking the nucleic acid codon corresponding to each amino acid of the target peptide to be encoded, multiple encoding nucleic acids may be designed for one target nucleic acid to be encoded. Since 1 to 6 nucleic acid codons correspond per standard amino acid on average, the number of possible nucleic acid codon combinations increases exponentially as the amino acid sequence length increases. However, not all of these combinations are of equal importance. In general, there is a combination of nucleic acid codons capable of better expressing the target peptide to be encoded in cells, the combination may vary depending on the higher-order structure of the sequence itself, the type of the target cell into which the encoding nucleic acid is to be injected, etc. Discovering a combination of such a nucleic acid codon and specifying the discovered combination as a sequence of an encoding nucleic acid is called codon optimization. There is not necessarily only one codon-optimized sequence for one coding target peptide, and there may be two or more codon-optimized sequences.

In an embodiment, the encoding nucleic acid may have a codon optimized DNA and/or RNA sequence. In another embodiment, the encoding nucleic acid may have non-codon optimized DNA and/or RNA sequences.

Codon Optimization of Encoding Nucleic Acid 1—Consideration of Higher-Order Structure of Encoding Nucleic Acid Codon optimization of the encoding nucleic acid may be performed in consideration of a higher-order structure of the nucleic acid sequence itself. In an embodiment, the encoding nucleic acid may be codon-optimized in consideration of the GC contents of the sequence. In another embodiment, the sequence of the encoding nucleic acid may have a GC content in the range of about less than 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In still another embodiment, the sequence of the encoding nucleic acid may have a GC content within the numerical range selected in the immediately preceding sentence. For example, the sequence of the encoding nucleic acid may have a GC content in the range of about 20% to about 50%. In still another embodiment, the sequence of the encoding nucleic acid may have a GC content less than the value selected in the immediately preceding sentence. For example, the sequence of the encoding nucleic acid may have a GC content of less than about 25%.

Codon Optimization of Encoding Nucleic Acid 2—Consideration of Target Cells to be Expressed Codon optimization of the encoding nucleic acid may be achieved in consideration of into which cell the encoding nucleic acid is to be injected and expressed. In an embodiment, the codon optimization of the encoding nucleic acid may be achieved in consideration of the codon usage in prokaryotic or eukaryotic cells. In another embodiment, the codon optimization of the encoding nucleic acid may be achieved in consideration of codon usage of animal cells. In still another embodiment, the codon optimization of the encoding nucleic acid may be achieved in consideration of mammalian codon usage. In still another embodiment, the codon optimization of the encoding nucleic acid may be achieved in consideration of human codon usage. In still another embodiment, the encoding nucleic acid may be *E. coli* codon optimized one. In still another embodiment, the encoding nucleic acid may be mammalian codon optimized one. In still another embodiment, the encoding nucleic acid may be human codon optimized one.

Embodiments of Encoding Nucleic Acid Sequences

In an embodiment, the encoding nucleic acid may be represented by a sequence selected from 5'-CGTAATGTTCCTCCTATCTTCAATGATGTTTATTG-GATTGCATTCNNNNN NAAGNNNGTGGCAGCTTGGACCCT-GAAGGCAGCANNNNNNTGCCGTTTCC GTGGACT-GATTTCCCTGTCCCAGGTTTATCTGTCC-3' (SEQ ID NO: 248), 5'-CGTAATGTTCCTCCTATCTTCAAT-GATGTTTATTGGATTGCATTCNNNNN NAAGTTCGTGGCAGCTTGGACCCT-GAAGGCAGCANNNNNNTGCCGTTTCC GTGGACT-GATTTCCCTGTCCCAGGTTTATCTGTCC-3' (SEQ ID NO: 249), 49 5'-CGTAATGTTCCTCCTATCTTCAAT-GATGTTTATTGGATTGCATTCNNNNN NAAGTATGTGGCAGCTTGGACCCT-GAAGGCAGCANNNNNNTGCCGTTTCC GTGGACT-GATTTCCCTGTCCCAGGTTTATCTGTCC-3' (SEQ ID NO: 250), 5'-CGTAATGTTCCTCCTATCTTCAAT-GATGTTTATTGGATTGCATTCNNNNN NAAGNNNGTGGCAGCTTGGACCCT-GAAGGCAGCANNNNNNGGATCGCATC ACCATCAC-CATCACGGATCCGATGATGATGACAAG-3' (SEQ ID NO: 251), 5'-ACGTAATGTTCCTCCTATCTTCAAT-GATGTTTATTGGATTGCATTCNNNN NNAAGTTCGTGGCAGCTTGGACCCT-GAAGGCAGCANNNNNNGGATCGCAT CACCATCAC-CATCACGGATCCGATGATGATGACAAG-3' (SEQ ID NO: 252), 5'-CGTAATGTTCCTCCTATCTTCAAT-GATGTTTATTGGATTGCATTCNNNNN NAAGTATGTGGCAGCTTGGACCCT-GAAGGCAGCANNNNNNGGATCGCATC ACCATCAC-CATCACGGATCCGATGATGATGACAAG-3' (SEQ ID NO: 253), 5'-GGATCGCATCACCATCACCATCACG-GATCCGATGATGATGACAAGNNNN NNAAGNNNGTGGCAGCTTGGACCCT-GAAGGCAGCANNNNNNCGTAATGTT CCTCC-TATCTTCAATGATGTTTATTGGATTGCATTC-3' (SEQ ID NO: 254), 5'-GGATCGCATCACCATCACCATCACG-GATCCGATGATGATGACAAGNNNN NNAAGTTCGTGGCAGCTTGGACCCT-GAAGGCAGCANNNNNNCGTAATGTT CCTCC-TATCTTCAATGATGTTTATTGGATTGCATTC-3' (SEQ ID NO: 255), 5'-GGATCGCATCACCATCACCATCACG-GATCCGATGATGATGACAAGNNNN NNAAGTATGTGGCAGCTTGGACCCT-GAAGGCAGCANNNNNNCGTAATGTT CCTCC-TATCTTCAATGATGTTTATTGGATTGCATTC-3' (SEQ ID NO: 256), 5'-AAAACGACAAAGCAATCATTTGATT-TAAGTGTAAAAGCTCAGTATNNNN NNAAGNNNGTGGCAGCTTGGACCCT-GAAGGCAGCANNNNNNTGCCGTTTC CGTGGACT-GATTTCCCTGTCCCAGGTTTATCTGTCC-3' (SEQ ID NO: 257), 5'-AAAACGACAAAGCAATCATTTGATT-TAAGTGTAAAAGCTCAGTATNNNN NNAAGTTCGTGGCAGCTTGGACCCT-GAAGGCAGCANNNNNNTGCCGTTTC CGTGGACT-GATTTCCCTGTCCCAGGTTTATCTGTCC-3' (SEQ ID NO: 258), 5'-AAAACGACAAAGCAATCATTTGATT-TAAGTGTAAAAGCTCAGTATNNNN NNAAGTATGTGGCAGCTTGGACCCT-GAAGGCAGCANNNNNNTGCCGTTTC CGTGGACT-GATTTCCCTGTCCCAGGTTTATCTGTCC-3' (SEQ ID NO: 259), 5'-CGTAATGTTCCTCCTATCTTCAAT-GATGTTTATTGGATTGCATTCTGCCGT TTCCGTGGACTGATTTCCCTGTCCAGGTT-TATCTGTCCNNNNNNAAGNNN GTGGCAGCTTGGACCCTGAAGGCAGCANNNNNN-3' (SEQ ID NO: 260), 5'-CGTAATGTTCCTCCTATCTT-CAATGATGTTTATTGGATTGCATTCTGCCGT TTCCGTGGACTGATTTCCCTGTCCAGGTT-TATCTGTCCNNNNNNAAGTTCG TGGCAGCTTGGACCCTGAAGGCAGCANNNNNN-3' (SEQ ID NO: 261), 5'-CGTAATGTTCCTCCTATCTT-CAATGATGTTTATTGGATTGCATTCTGCCGT TTCCGTGGACTGATTTCCCTGTCCAGGTT-TATCTGTCCNNNNNNAAGTATG TGGCAGCTTGGACCCTGAAGGCAGCANNNNNN-3' (SEQ ID NO: 262), 5'-CGTAATGTTCCTCCTATCTT-CAATGATGTTTATTGGATTGCATTCNNNCCT AAGTATGTGAAGCAGAATACACT-GAAGCTGGCAACCNNNTGCCGTTTCCGT GGACT-GATTTCCCTGTCCCAGGTTTATCTGTCC-3' (SEQ ID NO: 263), 5'-CGTAATGTTCCTCCTATCTTCAAT-GATGTTTATTGGATTGCATTCNNNNN NAAGNNNGTGGCAGCTTGGACCCT-GAAGGCAGCANNNNNN-3' (SEQ ID NO: 264), 5'-CGTAATGTTCCTCCTATCTTCAATGATGTTTATTG-GATTGCATTCNNNNN NAAGTTCGTGGCAGCTTGGACCCT-GAAGGCAGCANNNNNN-3' (SEQ ID NO: 265), 5'-CGTAATGTTCCTCCTATCTTCAATGATGTTTATTG-GATTGCATTCNNNNN NAAGTATGTGGCAGCTTGGACCCT-GAAGGCAGCANNNNNN-3' (SEQ ID NO: 266), 5'-CGTAATGTTCCTCCTATCTTCAATGATGTTTATTG-GATTGCATTCAAGNN NGTGGCAGCTTGGACCCT-GAAGGCAGCA-3' (SEQ ID NO: 267), 5'-CGTAATGTTCCTCCTATCTTCAATGATGTTTATTG-GATTGCATTCAAGTTC GTGGCAGCTTGGACCCT-GAAGGCAGCA-3' (SEQ ID NO: 268), 5'-CGTAATGTTCCTCCTATCTTCAATGATGTTTATTG-GATTGCATTCAAGTAT GTGGCAGCTTGGACCCT-GAAGGCAGCA-3' (SEQ ID NO: 269), 5'-CGTAATGTTCCTCCTATCTTCAATGATGTTTATTG-GATTGCATTCAAGNN NGTGGCAGCTTGGACCCT-GAAGGCAGCACATCACCATCACCATCAC-3' (SEQ ID NO: 270), 5'-CGTAATGTTCCTCCTATCTTCAAT-GATGTTTATTGGATTGCATTCAAGTTC GTGGCAGCTTGGACCCTGAAGGCAGCACATCAC-CATCACCATCAC-3' (SEQ ID NO: 271), 5'-CGTAATGTTCCTCCTATCTTCAATGATGTTTATTG-GATTGCATTCAAGTAT GTGGCAGCTTGGACCCT-GAAGGCAGCACATCACCATCACCATCAC-3' (SEQ ID NO: 272), 5'-CGTAATGTTCCTCCTATCTTCAAT-GATGTTTATTGGATTGCATTCNNNNN NAAGNNNGTGGCAGCTTGGACCCTGAAGGCAG-CATGCCGTTTCCGTGGAC TGAT-TTCCCTGTCCCAGGTTTATCTGTCC-3' (SEQ ID NO: 273), 5'-CGTAATGTTCCTCCTATCTTCAATGATGTTT-ATTGGATTGCATTCNNNNN NAAGTTCGTGGCAGCTTGGACCCTGAAGGCAG-CATGCCGTTTCCGTGGACT GAT-TTCCCTGTCCCAGGTTTATCTGTCC-3' (SEQ ID NO: 274), 5'-CGTAATGTTCCTCCTATCTTCAATGATGTTT-ATTGGATTGCATTCNNNNN NAAGTATGTGGCAGCTTGGACCCTGAAGGCAG-CATGCCGTTTCCGTGGACT GAT-TTCCCTGTCCCAGGTTTATCTGTCC-3' (SEQ ID NO: 275), 5'-CGTAATGTTCCTCCTATCTTCAATGATGTTT-ATTGGATTGCATTCNNNNN NAAGNNNGTGGCAGCTTGGACCCTGAAGGCAG-CATGCCGT-3' (SEQ ID NO: 276), 5'-CGTAATGTTCCTCCTATCTTCAATGATGTTTATTG-GATTGCATTCNNNNN NAAGTTCGTGGCAGCTTGGACCCTGAAGGCAG-CATGCCGT-3' (SEQ ID NO: 277), and 5'-CGTAATGTTCCTCCTATCTTCAATGATGTTTATTG-GATTGCATTCNNNNN NAAGTATGTGGCAGCTTGGACCCTGAAGGCAG-CATGCCGT-3' (SEQ ID NO: 278).

In an embodiment, the encoding nucleic acid may be represented by an RNA sequence equivalent to the sequence selected from SEQ ID NO: 248 to SEQ ID NO: 278.

In another embodiment, the encoding nucleic acid may be one in which at least one codon is substituted with a codon encoding the same amino acid in the sequence selected from SEQ ID NO: 248 to SEQ ID NO: 278. For example, the encoding nucleic acid may be one in which the first codon (the first to third nucleic acids at the 5' end) in the SEQ ID NO: 248 sequences (i.e., CGT) is substituted with CGC, CGG, CGA, AGA, or AGG.

In still another embodiment, the encoding nucleic acid may be represented by an RNA sequence equivalent to that in the sequence selected from SEQ ID NO: 248 to SEQ ID NO: 278, in which one or more codons are substituted with a codon encoding the same amino acid.

Pharmaceutical Composition Including Nucleic Acid Encoding Peptide Unit and/or Peptide Pharmaceutical Composition Including Encoding Nucleic Acid—Overview The present specification provides a pharmaceutical composition including a nucleic acid encoding a peptide unit and/or peptide (i.e., encoding nucleic acid). In order to deliver the encoding nucleic acid to a subject to exhibit an intended effect of inducing an immune response, it needs to formulate the encoding nucleic acid by an appropriate method. The encoding nucleic acid may be formulated by a known method, for example, methods disclosed in W. K. KIM (2019, mRNA vaccine—new era in vaccinology, BRIC View 2019-R11), Zhang et al. (2019, Advances in mRNA Vaccines for Infectious Diseases, Frontiers in Immunology, Vol. 10, Article 594), Reichmuth et al. (2016, mRNA vaccine delivery using lipid nanoparticles, *Therapeutic Delivery*, 7(5), 319-334), Miao et al. (2021, mRNA vaccine for cancer immunotherapy, *Molecular Cancer*, 20:41), Boen et al. (2021, Identification of T Cell Ligands in a Library of Peptides Covalently Attached to HLA-DR4, *The Journal of Immunology*, 165:2040-2047), Pardi et al. (2018, mRNA vaccines—a new era in vaccinology, *Nature Reviews*, Vol. 17, 261-279) and Korean Patent Application No. 10-2017-0054429, but the method is not limited thereto.

The pharmaceutical composition including the encoding nucleic acid may further include adjuvants and/or additional ingredients, in addition to the formulated encoding nucleic acid. In an embodiment, the pharmaceutical composition including the encoding nucleic acid includes the following: formulated encoding nucleic acids; optionally, adjuvants; and optionally, additional ingredients.

Formulated Encoding Nucleic Acid

The formulated encoding nucleic acid may be formulated by those skilled in the art by selecting an appropriate delivery means (vector) for the encoding nucleic acid. The encoding nucleic acid may be formulated using a viral vector and/or a non-viral vector. In an embodiment, the formulated encoding nucleic acid may include a viral vector. In another embodiment, the formulated encoding nucleic acid may include a non-viral vector. Specifically, the non-viral vector may include lipids, polymers, and inorganic nanoparticles, but is not limited thereto.

In still another embodiment, the formulated encoding nucleic acid may include one or more selected from the following:

a naked nucleic acid; a cationic peptide-complex nucleic acid (protamine); positively-charged oil-water cationic nanoemulsion (cationic nanoemulsion); a nucleic acid which is bound to chemically a modified dendrimer, and complexed with polyethylene glycol and PEG-lipids (modified dendrimer nanoparticle); a nucleic acid complexed with protamine in PEG-lipid nanoparticles (protamine liposome); a nucleic acid complexed with a cationic polymer (e.g., polyethylenimine (PEI)) (cationic polymer); a nucleic acid complexed with cationic polymers such as PEI and lipid components(cationic polymer liposomes); a nucleic acid complexed with a polysaccharide polymer (e.g., chitosan) (polysaccharide particles); a nucleic acid complexed with cationic lipid nanoparticle polymers (cationic lipid nanoparticle); a nucleic acid complexed with cationic lipid and cholesterol (cationic lipid-cholesterol nanoparticles); and a nucleic acid complexed with cationic lipid, cholesterol, and PEG-lipid (cationic lipid-cholesterol-PEG nanoparticles).

In still another embodiment, the formulated encoding nucleic acid may include lipid nanoparticles (LNPs). In the specific embodiment above, the lipid nanoparticles may be ionizable cationic lipids, phospholipids, cholesterol, and/or lipid-anchored polyethylene glycol. Specifically, the ionizable cationic lipid may be one or more selected from the following: DLin-DMA; DLin-KC2-DMA; DLin-MC3-DMA; C12-200; cKK-E12; DLin-MC3-DMA derivative L319 (Alnylam and AlCana Technologies); C12-200 and cKK-E12 derivative (Anderson Group); COVID-19 vaccine lipid ALC-0315 and SM-102; TT3 and biodegradable derivative FTT5 (Dong's group); vitamin-derived lipids ssPalmE and VcLNP; A9 (Acuitas); L5 (Moderna); A18 Lipid; ATX Lipid (LUNAR® composition; Arcturus); and LP01 (Intellia Therapeutics). Specifically, the phospholipid may be one or more selected from the following: 1,2-dioleoyl-sn-glycero-3-phosphoethanolamine (DOPE); and 1,2-distearoyl-sn-glycero-3- phosphocholine (DSPC).

In a specific embodiment, the formulated encoding nucleic acid may include a polymer-based delivery system. In the specific embodiment, the polymer-based delivery system may include one or more selected from the following: polyethyleneimine (PEI); polyamidoamine (PAMAM); polypropyleneimine; and a polymer-based dendrimer.

In still another embodiment, the formulated encoding nucleic acid may include a peptide-based delivery system. In the specific embodiment, the peptide-based delivery system may include protamine. Specifically, the formulated encoding nucleic acid may be a protamine-mRNA complex.

In still another embodiment, the formulated encoding nucleic acid may include cationic lipid constituting liposomes, lipoplexes and/or cationic emulsions (CNE). In the specific embodiment, the cationic lipid may be 1,2-di-O-octadecenyl-3-trimethylammonium propane (DOTMA) and/or 1,2-dioleoyl3-trimethylammonium-propane (DOTAP).

Adjuvants

In an embodiment, the pharmaceutical composition including the encoding nucleic acid may include lipid nanoparticles (LNPs), aluminum salts, 1,2-dioleyl-3-trimethyl-ammonium-propane chloride, MF59 (Novartis) adjuvant, CD70, CD40 ligand (CD40L), TriMix, protamine acting through TLR7 signaling, and/or bacteria-derived monophosphoryl lipid A, as adjuvants.

Ingredients

In an embodiment, the pharmaceutical composition including the encoding nucleic acid may optionally include various additional ingredients. In another embodiment, the additional ingredients may be one or more selected from the following:

lipids; salts to balance body acidity; sucrose to maintain stability during repeated freezing-thawing; and vaccine stability enhancing substances Specifically, the lipid may be SM-102, PEG2000-DMG, DPSC, cholesterol, and/or ALC-0315, but is not limited thereto. Specifically, the salt may be sodium acetate, potassium chloride, monobasic potassium phosphate, sodium chloride, and/or dibasic sodium phosphate dehydrate, but is not limited thereto. Specifically, the vaccine stability enhancing substance may be acetic acid, an acid stabilizer (tromethamine), and/or ethanol, but is not limited thereto.

The Peptide—Summary

The peptide provided herein includes at least one peptide unit, and the peptide unit includes at least one B-cell epitope and at least one Th epitope, and may include an appropriate number of auxiliary parts. The peptide unit is a part designed to uniformly induce only the intended antibody while exhibiting a certain level of immunogenicity in the body of a subject. In addition, since the peptide unit is designed with a relatively short length, it has the characteristics of easy synthesis and a low production cost. The peptide has properties suitable for use as an immunotherapeutic due to the characteristics of the peptide unit described above. In the present specification, the design principles of the peptide and the peptide unit are disclosed in detail.

The names for each part of the peptide disclosed herein (e.g., an auxiliary part) are given for convenience of explanation. Accordingly, the scope and name for each part may vary depending on the viewpoint. For example, the auxiliary part may be referred to as a protective part, a dummy part, and/or a linker, but is not limited thereto. For another example, the B-cell epitope may be referred to as a Th-epitope-protective epitope, but is not limited thereto.

Possible Examples of the Invention

Hereinafter, possible examples of the invention provided in the present specification are listed. The following Examples provided in this paragraph merely correspond to embodiments of the invention. Therefore, the invention provided in the present specification cannot be interpreted as being limited to the following examples.

Symbols Used in Each Example

Hereinafter, symbols used for a brief description of each Example, in addition to numbers to distinguish each Example, will be described.

"B" denotes a B-cell epitope. "T" denotes Th epitope. "A" denotes an auxiliary part (Auxiliary part). "U" denotes a peptide unit.

When each component is linked by "-", the component means that the components on either side of the "-" are directly linked or linked through any other component. For example, when it is described as B-T, it includes all of the peptides in which a B-cell epitope and a Th epitope are directly linked, and a peptide in which a B-cell epitope and a Th epitope are linked via any other sequence.

If necessary, each component may be marked with a subscript number, representing that the two components are different. For example, when expressed as B1-B2-T, B1 and B2 represent different B-cell epitopes.

The above symbols are only those for schematically describing Examples, and they should not be interpreted by limiting Examples with these symbols.

Peptide Unit 1

Example 1, Peptide Unit that can Induce Humoral Immunity

A peptide unit that can induce a humoral immunity by being recognized by CD4+ T-cells, including the following: at least one Th epitope; and at least one B-cell epitope, in which the peptide unit is characterized in that the length of the Th epitope is 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, or 30mer; the length of the B-cell epitope is 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, or 32mer; and the length of the peptide unit is 16mer, 17mer, 18mer, 19mer, 20mer, 21mer, 22mer, 23mer, 24mer, 25mer, 26mer, 27mer, 28mer, 29mer, 30mer, 31mer, 32mer, 33mer, 34mer, 35mer, 36mer, 37mer, 38mer, 39mer, 40mer, 41mer, 42mer, 43mer, 44mer, 45mer, 46mer, 47mer, 48mer, 49mer, 50mer, 51mer, 52mer, 53mer, 54mer, 55mer, 56mer, 57mer, 58mer, 59mer, 60mer, 61mer, 62mer, 63mer, 64mer, 65mer, 66mer, 67mer, 68mer, 69mer, 70mer, 71mer, 72mer, 73mer, 74mer, 75mer, 76mer, 77mer, 78mer, 79mer, 80mer, 81mer, 82mer, 83mer, 84mer, 85mer, 86mer, 87mer, 88mer, 89mer, 90mer, 91mer, 92mer, 93mer, 94mer, 95mer, 96mer, 97mer, 98mer, 99mer, or 100mer.

Example 2, Peptide Unit that Induces Antibodies Targeting Apolipoprotein B-100

A peptide unit that can induce a humoral immunity by being recognized by CD4+ T-cells, including the following: at least one Th epitope; and at least one B-cell epitope, in which the peptide unit is characterized in that the length of the Th epitope is 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, or 30mer; the B-cell epitope is able to induce antibodies that target apolipoprotein B-100; and the length of the peptide unit is 16mer, 17mer, 18mer, 19mer, 20mer, 21mer, 22mer, 23mer, 24mer, 25mer, 26mer, 27mer, 28mer, 29mer, 30mer, 31mer, 32mer, 33mer, 34mer, 35mer, 36mer, 37mer, 38mer, 39mer, 40mer, 41mer, 42mer, 43mer, 44mer, 45mer, 46mer, 47mer, 48mer, 49mer, 50mer, 51mer, 52mer, 53mer, 54mer, 55mer, 56mer, 57mer, 58mer, 59mer, 60mer, 61mer, 62mer, 63mer, 64mer, 65mer, 66mer, 67mer, 68mer, 69mer, 70mer, 71mer, 72mer, 73mer, 74mer, 75mer, 76mer, 77mer, 78mer, 79mer, 80mer, 81mer, 82mer, 83mer, 84mer, 85mer, 86mer, 87mer, 88mer, 89mer, 90mer, 91mer, 92mer, 93mer, 94mer, 95mer, 96mer, 97mer, 98mer, 99mer, or 100mer.

Example 3, Peptide Unit that Induces Antibody which Targets Apolipoprotein B-100 Included in LDL and/or VLDL The peptide unit of Example 2, wherein the B-cell epitope is characterized in that it induces an antibody targeting a site selected from the following: an externally exposed site of apolipoprotein B-100 included in low-density lipoprotein (LDL); and an externally exposed site of apolipoprotein B-100 included in ultra-low-density lipoprotein (VLDL).

Example 4, Limitation on Type B

The peptide unit of Example 2, wherein the peptide unit is characterized in that the B-cell epitope is a fragment of apolipoprotein B-100 and/or a mimotope of apolipoprotein B-100.

Example 5, Limitation on Sequence of B

The peptide unit of Example 4, wherein the peptide unit is characterized in that the B-cell epitope is a sequence being selected from the group consisting of RNVPPIFNDVYWIAF (SEQ ID NO: 6), CRFRGLISLSQVYLS (SEQ ID NO: 7), KTTKQSFDLSVKAQYKKNKH (SEQ ID NO: 8), RFRGLISLSQVYLDP (SEQ ID NO: 221), and SVCGCPVGHHDVVGL (SEQ ID NO: 222) or an epitope included in the sequence selected from SEQ ID NOS: 6 to 8 and 221 to 222.

Example 6, Limitation on Full-Length Sequence Length of Peptide Unit

The peptide unit of any one of Examples 1 to 5, wherein the peptide unit is characterized in that the length of the peptide unit is 23mer to 71mer or 26mer to 50mer.

Peptide Unit 2—Unit A

Example 7, B-T and T-B

The peptide unit of any one of Examples 1 to 4, wherein the peptide unit is characterized in that the peptide unit includes one B-cell epitope and one Th epitope.

Example 8, Limitation on Sequence B, Limitation on Length T, and Limitation on Length U The peptide unit of Example 7, wherein the peptide unit is characterized in that the length of the peptide unit is 26mer to 45mer; the B-cell epitope is selected from RNVPPIFNDVYWIAF (SEQ ID NO: 6), CRFRGLISLSQVYLS (SEQ ID NO: 7), KTTKQSFDLSVKAQYKKNKH (SEQ ID NO: 8), RFRGLISLSQVYLDP (SEQ ID NO: 221), and SVCGCPVGHHDVVGL (SEQ ID NO: 222); and the length of the Th epitope is 11mer to 13mer.

Example 9, Limitation on Sequence T

The peptide unit of any one of Examples 7 and 8, wherein the Th epitope is characterized in that it is selected from the group consisting of the following: K(Cha)VAAWTLKAA (SEQ ID NO: 1); PKYVKQNTLKLAT (SEQ ID NO: 2); ILMQYIKANSKFIGI (SEQ ID NO: 3); QSIALSSLMVAQAIP (SEQ ID NO: 4); ILMQYIKANSKFIGIPMGLPQSIALSSLMVAQ (SEQ ID NO: 5); PLGFFPDHQL (SEQ ID NO: 162); WPEANQVGAGAFGPGF (SEQ ID NO: 163); MQWNSTALHQALQDP (SEQ ID NO: 164); MQWNSTTFHQTLQDPRVRGLYFPAGG (SEQ ID NO: 165); FFLLTRILTI (SEQ ID NO: 166); FFLLTRILTIPQSLD (SEQ ID NO: 167); TSLNFLGGTTVCLGQ (SEQ ID NO: 168); QSPTSNHSPTSCPPIC (SEQ ID NO: 169); IIFLFILLLCLIFLLVLLD (SEQ ID NO: 170); CTTPAQGNSMFPSC (SEQ ID NO: 171); CTKPTDGN (SEQ ID NO: 172); WASVRFSW (SEQ ID NO: 173); LLPIFFCLW (SEQ ID NO: 174); MDIDPYKEFGATVELLSFLP (SEQ ID NO: 175); FLPSDFFPSV (SEQ ID NO: 176); RDLLDTASALYREALESPEH (SEQ ID NO: 177); PHHTALRQAILCWGELMTLA (SEQ ID NO: 178); GRETVIEYLVSFGVW (SEQ ID NO: 179); EYLVSFGVWIRTPPA (SEQ ID NO: 180); VSFGVWIRTPPAYRPPNAPI (SEQ ID NO: 181); TVVRRRGRSP (SEQ ID NO: 182); VGPLTVNEKRRLKLI (SEQ ID NO: 183); RHYLHTLWKAGILYK (SEQ ID NO: 184); ESRLVVDFSQFSRGN (SEQ ID NO: 185); LQSLTNLLSSNLSWL (SEQ ID NO: 186); SSNLSWLSLDVSAAF (SEQ ID NO: 187); LHLYSHPIILGFRKI (SEQ ID NO: 188); KQCFRKLPVNRPIDW (SEQ ID NO: 189); LCQVFADATPTGWGL (SEQ ID NO: 190); AANWILRGTSFVYVP (SEQ ID NO: 191); and EIRLKVFVLGGCRHK (SEQ ID NO: 192), in which the (Cha) denotes L-cyclohexylalanins.

Example 10, BAT and TAB

The peptide unit of any one of Examples 7 and 8, wherein the peptide unit is characterized in that it further includes an auxiliary part, and that the auxiliary part is linked between the B-cell epitope and the Th epitope.

Example 11, Limitation on a, Including Nonstandard Amino Acid

The peptide unit of Example 10, wherein the peptide unit is characterized in that the auxiliary part includes one or more nonstandard amino acids.

Example 12, Limitation on Sequence of a Including Nonstandard Amino Acid

The peptide unit of Example 11, wherein the peptide unit is characterized in that the auxiliary part is selected from a, Z, aZ, Za, GSHHHHHHGSDDDKZa (SEQ ID NO: 193), and aZGSHHHHHHGSDDDK (SEQ ID NO: 194).

Example 13, Limitation on Sequence a not Including Nonstandard Amino Acid

The peptide unit of Example 10, wherein the peptide unit is characterized in that the auxiliary part is selected from CR, HHHHHH (SEQ ID NO: 53), and RRRRRR (SEQ ID NO: 159).

Peptide Unit 3—Unit D

Example 14, $B$-$T_1$-$T_2$ and $T_2$-$T_1$-$B$

The peptide unit of any one of Examples 1 to 4, wherein the peptide unit is characterized in that it includes one B-cell epitope, and two Th epitopes which are referred to as the first Th epitope and the second Th epitope, respectively, and that the first Th epitope is linked between the B-cell epitope and the second Th epitope.

Example 15, Limitation on Sequence B, Limitation on Length T, and Limitation on Length U The peptide unit of Example 14, wherein the peptide unit is characterized in that the length of the peptide unit is 37mer to 50mer; the B-cell epitope is selected from RNVPPIFNDVYWIAF (SEQ ID NO: 6), CRFRGLISLSQVYLS (SEQ ID NO: 7), KTTKQSFDLSVKAQYKKNKH (SEQ ID NO: 8), RFRGLISLSQVYLDP (SEQ ID NO: 221), and SVCGCPVGHHDVVGL (SEQ ID NO: 222); and the length of the first Th epitope and the second Th epitope is 11 mer to 13mer, respectively.

Example 16, Limitation on Sequence T

The peptide unit of any one of Examples 14 and 15, wherein the Th epitope is characterized in that it is selected from the group consisting of the following: K(Cha)VAAWTLKAA (SEQ ID NO: 1); PKYVKQNTLKLAT (SEQ ID NO: 2); ILMQYIKANSKFIGI (SEQ ID NO: 3); QSIALSSLMVAQAIP (SEQ ID NO: 4); ILMQYIKANSKFIGIPMGLPQSIALSSLMVAQ (SEQ ID NO: 5); PLGFFPDHQL (SEQ ID NO: 162); WPEANQVGAGAFGPGF (SEQ ID NO: 163); MQWNSTALHQALQDP (SEQ ID NO: 164); MQWNSTTFHQTLQDPRVRGLYFPAGG (SEQ ID NO: 165); FFLLTRILTI (SEQ ID NO: 166); FFLLTRILTIPQSLD (SEQ ID NO: 167); TSLNFLGGTTVCLGQ (SEQ ID NO: 168); QSPTSNHSPTSCPPIC (SEQ ID NO: 169); IIFLFILLLCLIFLLVLLD (SEQ ID NO: 170); CTTPAQGNSMFPSC (SEQ ID NO: 171); CTKPTDGN (SEQ ID NO: 172); WASVRFSW (SEQ ID NO: 173); LLPIFFCLW (SEQ ID NO: 174); MDIDPYKEFGATVELLSFLP (SEQ ID NO: 175); FLPSDFFPSV (SEQ ID NO: 176); RDLLDTASALYREALESPEH (SEQ ID NO: 177); PHHTALRQAILCWGELMTLA (SEQ ID NO: 178); GRETVIEYLVSFGVW (SEQ ID NO: 179); EYLVSFGVWIRTPPA (SEQ ID NO: 180); VSFGVWIRTPPAYRPPNAPI (SEQ ID NO: 181); TVVRRRGRSP (SEQ ID NO: 182); VGPLTVNEKRRLKLI (SEQ ID NO: 183); RHYLHTLWKAGILYK (SEQ ID NO: 184); ESRLVVDFSQFSRGN (SEQ ID NO: 185); LQSLTNLLSSNLSWL (SEQ ID NO: 186); SSNLSWLSLDVSAAF (SEQ ID NO: 187); LHLYSHPIILGFRKI (SEQ ID NO: 188); KQCFRKLPVNRPIDW (SEQ ID NO: 189); LCQVFADATPTGWGL (SEQ ID NO: 190); AANWILRGTSFVYVP (SEQ ID NO: 191); and EIRLKVFVLGGCRHK (SEQ ID NO: 192), in which the a denotes D-form alanine, the (Cha) denotes L-cyclohexylalanins, and the Z denotes 6-aminohexanoic acid.

Example 17, $BAT_1$-$T_2$ and $T_2$-$T_1AB$

The peptide unit of any one of Examples 14 and 15, wherein the peptide unit is characterized in that it further includes an auxiliary part, and the auxiliary part is linked between the B-cell epitope and the first Th epitope.

Example 18, B-T$_1$AT$_2$ and T$_2$AT$_1$-B

The peptide unit of any one of Examples 14 and 15, wherein the peptide unit is characterized in that it further includes an auxiliary part, and the auxiliary part is linked between the first Th epitope and the second Th epitope.

Example 19, Limitation on a, Including Nonstandard Amino Acid

The peptide unit of any one of Examples 17 and 18, wherein the peptide unit is characterized in that the auxiliary part includes one or more nonstandard amino acids.

Example 20, Limitation on Sequence a Including Nonstandard Amino Acid

The peptide unit of Example 19, wherein the peptide unit is characterized in that the auxiliary part is selected from a, Z, aZ, Za, GSHHHHHHGSDDDKZa (SEQ ID NO: 193), and aZGSHHHHHHGSDDDK (SEQ ID NO: 194).

Example 21, Limitation on Sequence a not Including Nonstandard Amino Acid

The peptide unit of any one of Examples 17 and 18, wherein the peptide unit is characterized in that the auxiliary part is selected from CR, HHHHHH (SEQ ID NO: 53), and RRRRRR (SEQ ID NO: 159).

Example 22, BAT$_1$AT$_2$ and T$_2$AT$_1$AB

The peptide unit of any one of Examples 14 and 15, wherein the peptide unit is characterized in that it further includes a first auxiliary part and a second auxiliary part, and that the first auxiliary part is linked between the B-cell epitope and the Th epitope and the second auxiliary part is linked between the first Th epitope and the second Th epitope.

Example 23, Limitation on a, Including Nonstandard Amino Acid

The peptide unit of Example 22, wherein the peptide unit is characterized in that the first auxiliary part and/or the second auxiliary part include one or more nonstandard amino acids.

Example 24, Limitation on Sequence of a Including Nonstandard Amino Acid

The peptide unit of Example 23, wherein the peptide unit is characterized in that the auxiliary part including one or more nonstandard amino acids is independently selected from a, Z, aZ, Za, GSHHHHHHGSDDDKZa (SEQ ID NO: 193), and aZGSHHHHHHGSDDDK (SEQ ID NO: 194).

Example 25, Limitation on Sequence a not Including Nonstandard Amino Acid

The peptide unit of Example 22, wherein the peptide unit is characterized in that the first auxiliary part and/or the second auxiliary part are independently selected from CR, HHHHHH (SEQ ID NO: 53), and RRRRRR (SEQ ID NO: 159).

Peptide Unit 4—Unit B

Example 26, B$_1$-B$_2$-T and T-B$_2$-B$_1$

The peptide unit of any one of Examples 1 to 4, wherein the peptide unit is characterized in that it includes two B-cell epitopes, which are referred to as a first B-cell epitope and a second B-cell epitope, respectively, and that the second B-cell epitope is linked between the first B-cell epitope and the Th epitope.

Example 27, Limitation on Sequence B, Limitation on Length T, and Limitation on Length U The peptide unit of Example 26, wherein the peptide unit is characterized in that the length of the peptide unit is 45mer to 50mer; the first B-cell epitope and the second B-cell epitope are independently selected from RNVPPIFNDVY-WIAF (SEQ ID NO: 6), CRFRGLISLSQVYLS (SEQ ID NO: 7), KTTKQSFDLSVKAQYKKNKH (SEQ ID NO: 8), RFRGLISLSQVYLDP (SEQ ID NO: 221), and SVCGCPVGHHDVVGL (SEQ ID NO: 222); and the length of the Th epitope is 11mer to 13mer.

Example 28, Limitation on Sequence T

The peptide unit of any one of Examples 26 and 27, wherein the Th epitope is characterized in that it is selected from the group consisting of the following: K(Cha)VAAW-TLKAA (SEQ ID NO: 1); PKYVKQNTLKLAT (SEQ ID NO: 2); ILMQYIKANSKFIGI (SEQ ID NO: 3); QSIALSSLMVAQAIP (SEQ ID NO: 4); ILMQYIKANSK-FIGIPMGLPQSIALSSLMVAQ (SEQ ID NO: 5); PLGFFPDHQL (SEQ ID NO: 162); WPEANQVGAGAFGPGF (SEQ ID NO: 163); MQWN-STALHQALQDP (SEQ ID NO: 164); MQWN-STTFHQTLQDPRVRGLYFPAGG (SEQ ID NO: 165); FFLLTRILTI (SEQ ID NO: 166); FFLLTRILTIPQSLD (SEQ ID NO: 167); TSLNFLGGTTVCLGQ (SEQ ID NO: 168); QSPTSNHSPTSCPPIC (SEQ ID NO: 169); IIFL-FILLLCLIFLLVLLD (SEQ ID NO: 170); CTT-PAQGNSMFPSC (SEQ ID NO: 171); CTKPTDGN (SEQ ID NO: 172); WASVRFSW (SEQ ID NO: 173); LLPIFFCLW (SEQ ID NO: 174); MDIDPYKEF-GATVELLSFLP (SEQ ID NO: 175); FLPSDFFPSV (SEQ ID NO: 176); RDLLDTASALYREALESPEH (SEQ ID NO: 177); PHHTALRQAILCWGELMTLA (SEQ ID NO: 178); GRETVIEYLVSFGVW (SEQ ID NO: 179); EYL-VSFGVWIRTPPA (SEQ ID NO: 180); VSFGVWIRTPPAY-RPPNAPI (SEQ ID NO: 181); TVVRRRGRSP (SEQ ID NO: 182); VGPLTVNEKRRLKLI (SEQ ID NO: 183); RHYLHTLWKAGILYK (SEQ ID NO: 184); ESRLVVDFSQFSRGN (SEQ ID NO: 185); LQSLTNLLSSNLSWL (SEQ ID NO: 186); SSNLSWLSLDVSAAF (SEQ ID NO: 187); LHLYSH-PIILGFRKI (SEQ ID NO: 188); KQCFRKLPVNRPIDW (SEQ ID NO: 189); LCQVFADATPTGWGL (SEQ ID NO: 190); AANWILRGTSFVYVP (SEQ ID NO: 191); and EIRLKVFVLGGCRHK (SEQ ID NO: 192), in which the a denotes D-form alanine, the (Cha) denotes L-cyclohexyl-alanins, and the Z denotes 6-aminohexanoic acid.

Example 29, B$_1$-B$_2$AT and TAB$_2$-B$_1$

The peptide unit of any one of Examples 26 and 27, wherein the peptide unit is characterized in that it further includes an auxiliary part, and the auxiliary part is linked between the second B-cell epitope and the Th epitope.

Example 30, B₁AB₂-T and T-B₂AB₁

The peptide unit of any one of Examples 26 and 27, wherein the peptide unit is characterized in that it further includes an auxiliary part, and the auxiliary part is linked between the first B-cell epitope and the second B-cell epitope.

Example 31, Limitation on a, Including Nonstandard Amino Acid

The peptide unit of any one of Examples 29 and 30, wherein the peptide unit is characterized in that the auxiliary part includes one or more nonstandard amino acids.

Example 32, Limitation on Sequence a Including Nonstandard Amino Acid

The peptide unit of Example 31, wherein the peptide unit is characterized in that the auxiliary part is selected from a, Z, aZ, Za, GSHHHHHHGSDDDKZa (SEQ ID NO: 193), and aZGSHHHHHHGSDDDK (SEQ ID NO: 194).

Example 33, a, Limitation on Sequence not Including Nonstandard Amino Acid

The peptide unit of any one of Examples 29 and 30, wherein the peptide unit is characterized in that the auxiliary part is selected from CR, HHHHHH (SEQ ID NO: 53), and RRRRRR (SEQ ID NO: 159).

Example 34, B₁A₁B₂A₂T and TA₂B₂A₁B₁

The peptide unit of any one of Examples 26 and 27, wherein the peptide unit is characterized in that it further includes a first auxiliary part and a second auxiliary part, and the first auxiliary part is linked between the first B-cell epitope and the second B-cell epitope, and the second auxiliary part is linked between the second B-cell epitope and Th epitope.

Example 35, Limitation on a, Including Nonstandard Amino Acid

The peptide unit of Example 34, wherein the peptide unit is characterized in that the first auxiliary part and/or the second auxiliary part include one or more nonstandard amino acids.

Example 36, Limitation on Sequence a Including Nonstandard Amino Acid

The peptide unit of Example 35, wherein the peptide unit is characterized in that the auxiliary parts including one or more nonstandard amino acids are each independently selected from a, Z, aZ, Za, GSHHHHHHGSDDDKZa (SEQ ID NO: 193), and aZGSHHHHHHGSDDDK (SEQ ID NO: 194).

Example 37, Limitation on Sequence a not Including Nonstandard Amino Acid

The peptide unit of Example 34, wherein the peptide unit is characterized in that the first auxiliary part and/or the second auxiliary part are each independently selected from CR, HHHHHH (SEQ ID NO: 53), and RRRRRR (SEQ ID NO: 159).

Peptide Unit 5—Unit C

Example 38, B₁-T-B₂

The peptide unit of any one of Examples 1 to 4, wherein the peptide unit is characterized in that the peptide unit includes two B-cell epitopes, which are referred to as a first B-cell epitope and a second B-cell epitope, and one Th epitope, and the Th epitope is linked between the first B-cell epitope and the second B-cell epitope.

Example 39, Limitation on Sequence B, Limitation on Length T, and Limitation on Length U The peptide unit of Example 38, wherein the peptide unit is characterized in that the length of the peptide unit is 45mer to 50mer; the first B-cell epitope and the second B-cell epitope are each independently selected from RNVPPIFNDVYWIAF (SEQ ID NO: 6), CRFRGLISLSQVYLS (SEQ ID NO: 7), KTTKQSFDLSVKAQYKKNKH (SEQ ID NO: 8), RFRGLISLSQVYLDP (SEQ ID NO: 221), and SVCGCPVGHHDVVGL (SEQ ID NO: 222); and the length of the Th epitope is 11mer to 13mer.

Example 40, Limitation on Sequence T

The peptide unit of any one of Examples 38 and 39, wherein the Th epitope is characterized in that it is selected from the group consisting of the following: K(Cha)VAAWTLKAA (SEQ ID NO: 1); PKYVKQNTLKLAT (SEQ ID NO: 2); ILMQYIKANSKFIGI (SEQ ID NO: 3); QSIALSSLMVAQAIP (SEQ ID NO: 4); ILMQYIKANSKFIGIPMGLPQSIALSSLMVAQ (SEQ ID NO: 5); PLGFFPDHQL (SEQ ID NO: 162); WPEANQVGAGAFGPGF (SEQ ID NO: 163); MQWNSTALHQALQDP (SEQ ID NO: 164); MQWNSTTFHQTLQDPRVRGLYFPAGG (SEQ ID NO: 165); FFLLTRILTI (SEQ ID NO: 166); FFLLTRILTIPQSLD (SEQ ID NO: 167); TSLNFLGGTTVCLGQ (SEQ ID NO: 168); QSPTSNHSPTSCPPIC (SEQ ID NO: 169); IIFLFILLLCLIFLLVLLD (SEQ ID NO: 170); CTTPAQGNSMFPSC (SEQ ID NO: 171); CTKPTDGN (SEQ ID NO: 172); WASVRFSW (SEQ ID NO: 173); LLPIFFCLW (SEQ ID NO: 174); MDIDPYKEFGATVELLSFLP (SEQ ID NO: 175); FLPSDFFPSV (SEQ ID NO: 176); RDLLDTASALYREALESPEH (SEQ ID NO: 177); PHHTALRQAILCWGELMTLA (SEQ ID NO: 178); GRETVIEYLVSFGVW (SEQ ID NO: 179); EYLVSFGVWIRTPPA (SEQ ID NO: 180); VSFGVWIRTPPAYRPPNAPI (SEQ ID NO: 181); TVVRRRGRSP (SEQ ID NO: 182); VGPLTVNEKRRLKLI (SEQ ID NO: 183); RHYLHTLWKAGILYK (SEQ ID NO: 184); ESRLVVDFSQFSRGN (SEQ ID NO: 185); LQSLTNLLSSNLSWL (SEQ ID NO: 186); SSNLSWLSLDVSAAF (SEQ ID NO: 187); LHLYSHPIILGFRKI (SEQ ID NO: 188); KQCFRKLPVNRPIDW (SEQ ID NO: 189); LCQVFADATPTGWGL (SEQ ID NO: 190); AANWILRGTSFVYVP (SEQ ID NO: 191); and EIRLKVFVLGGCRHK (SEQ ID NO: 192), in which the a denotes D-form alanine, the (Cha) denotes L-cyclohexylalanins, and the Z denotes 6-aminohexanoic acid.

Example 41, B₁AT-B₂ and B₂-TAB₁

The peptide unit of any one of Examples 38 and 39, wherein the peptide unit is characterized in that it further includes an auxiliary part, and the auxiliary part is linked between the first B-cell epitope and the Th epitope.

Example 42, Limitation on a, Including Nonstandard Amino Acid

The peptide unit of Example 41, wherein the peptide unit is characterized in that the auxiliary part includes one or more nonstandard amino acids, Example 43, Limitation on Sequence a Including Nonstandard Amino Acid The peptide unit of Example 42, wherein the peptide unit is characterized in that the auxiliary part is selected from a, Z, aZ, Za, GSHHHHHHGSDDDKZa (SEQ ID NO: 193), and aZGSHHHHHHGSDDDK (SEQ ID NO: 194).

Example 44, Limitation on Sequence a not Including Nonstandard Amino Acid

The peptide unit of Example 41, wherein the peptide unit is characterized in that the auxiliary part is selected from CR, HHHHHH (SEQ ID NO: 53), and RRRRRR (SEQ ID NO: 159).

Example 45, $B_1A_1TA_2B_2$

The peptide unit of any one of Examples 38 and 39, wherein the peptide unit is characterized in that it further includes a first auxiliary part and a second auxiliary part; the first auxiliary part is linked between the first B-cell epitope and the Th epitope; and the second auxiliary part is linked between the second B-cell epitope and the Th epitope.

Example 46, Limitation on a, Including Nonstandard Amino Acid

The peptide unit of Example 45, wherein the peptide unit is characterized in that the first auxiliary part and/or the second auxiliary part include one or more nonstandard amino acids.

Example 47, Limitation on Sequence a Including Nonstandard Amino Acid

The peptide unit of Example 46, wherein the peptide unit is characterized in that the auxiliary parts including one or more nonstandard amino acids are each independently selected from a, Z, aZ, Za, GSHHHHHHGSDDDKZa (SEQ ID NO: 193), and aZGSHHHHHHGSDDDK (SEQ ID NO: 194).

Example 48, Limitation on Sequence a not Including Nonstandard Amino Acid

The peptide unit of Example 45, wherein the peptide unit is characterized in that the first auxiliary part and/or the second auxiliary part are each independently selected from CR, HHHHHH (SEQ ID NO: 53), and RRRRRR (SEQ ID NO: 159).

Peptide Unit 6—Unit E

Example 49, $B_1$-$T_1$-$T_2$-$B_2$

The peptide unit of any one of Examples 1 to 4, wherein the peptide unit is characterized in that it includes two B-cell epitopes, which are each referred to as a first B-cell epitope and a second B-cell epitope, and two Th epitopes, which are each referred to as a first Th epitope and a second Th epitope, a first B-cell epitope, a first Th epitope, a second Th epitope, and a second B-cell epitope are sequentially linked, in the direction from the N-terminus to the C-terminus.

Example 50, Limitation on Sequence B, Limitation on Length T, and Limitation on Length U The peptide unit of Example 49, wherein the peptide unit is characterized in that the length of the peptide unit is 52mer to 90mer; the first B-cell epitope and the second B-cell epitope are each independently selected from RNVPPIFNDVYWIAF (SEQ ID NO: 6), CRFRGLISLSQVYLS (SEQ ID NO: 7), KTTKQSFDLSVKAQYKKNKH (SEQ ID NO: 8), RFRGLISLSQVYLDP (SEQ ID NO: 221), and SVCGCPVGHHDVVGL (SEQ ID NO: 222); and the length of the first Th epitope and the second Th epitope are each 11mer to 13mer.

Example 51, Limitation on Sequence T

The peptide unit of Example 50, wherein the first Th epitope and the second Th epitope are characterized in that they are each independently selected from the group consisting of the following: K(Cha)VAAWTLKAA (SEQ ID NO: 1); PKYVKQNTLKLAT (SEQ ID NO: 2); ILMQYIKANSKFIGI (SEQ ID NO: 3); QSIALSSLMVAQAIP (SEQ ID NO: 4); ILMQYIKANSKFIGIPMGLPQSIALSSLMVAQ (SEQ ID NO: 5); PLGFFPDHQL (SEQ ID NO: 162); WPEANQVGAGAFGPGF (SEQ ID NO: 163); MQWNSTALHQALQDP (SEQ ID NO: 164); MQWNSTTFHQTLQDPRVRGLYFPAGG (SEQ ID NO: 165); FFLLTRILTI (SEQ ID NO: 166); FFLLTRILTIPQSLD (SEQ ID NO: 167); TSLNFLGGTTVCLGQ (SEQ ID NO: 168); QSPTSNHSPTSCPPIC (SEQ ID NO: 169); IIFLFILLLCLIFLLVLLD (SEQ ID NO: 170); CTTPAQGNSMFPSC (SEQ ID NO: 171); CTKPTDGN (SEQ ID NO: 172); WASVRFSW (SEQ ID NO: 173); LLPIFFCLW (SEQ ID NO: 174); MDIDPYKEFGATVELLSFLP (SEQ ID NO: 175); FLPSDFFPSV (SEQ ID NO: 176); RDLLDTASALYREALESPEH (SEQ ID NO: 177); PHHTALRQAILCWGELMTLA (SEQ ID NO: 178); GRETVIEYLVSFGVW (SEQ ID NO: 179); EYLVSFGVWIRTPPA (SEQ ID NO: 180); VSFGVWIRTPPAYRPPNAPI (SEQ ID NO: 181); TVVRRRGRSP (SEQ ID NO: 182); VGPLTVNEKRRLKLI (SEQ ID NO: 183); RHYLHTLWKAGILYK (SEQ ID NO: 184); ESRLVVDFSQFSRGN (SEQ ID NO: 185); LQSLTNLLSSNLSWL (SEQ ID NO: 186); SSNLSWLSLDVSAAF (SEQ ID NO: 187); LHLYSHPIILGFRKI (SEQ ID NO: 188); KQCFRKLPVNRPIDW (SEQ ID NO: 189); LCQVFADATPTGWGL (SEQ ID NO: 190); AANWILRGTSFVYVP (SEQ ID NO: 191); and EIRLKVFVLGGCRHK (SEQ ID NO: 192), in which the a denotes D-form alanine, the (Cha) denotes L-cyclohexylalanins, and the Z denotes 6-aminohexanoic acid.

Example 52, $B_1AT_1$-$T_2$-$B_2$ and $B_2$-$T_2$-$T_1AB_1$

The peptide unit of any one of Examples 49 and 50, wherein the peptide unit is characterized in that it further includes an auxiliary part, and the auxiliary part is linked between the first B-cell epitope and the first Th epitope.

Example 53, $B_1$-$T_1AT_2$-$B_2$

The peptide unit of any one of Examples 49 and 50, wherein the peptide unit is characterized in that it further includes an auxiliary part, and the auxiliary part is linked between the first Th epitope and the second Th epitope.

Example 54, $B_1$-$T_1$-$T_2AB_2$ and $B_2AT_2$-$T_1$-$B_1$

The peptide unit of any one of Examples 49 and 50, wherein the peptide unit is characterized in that it further includes an auxiliary part, and the auxiliary part is linked between the second Th epitope and the second B-cell epitope.

Example 55, Limitation on a, Including Nonstandard Amino Acid

The peptide unit of any one of Examples 52 to 54, wherein the peptide unit is characterized in that the auxiliary part includes one or more nonstandard amino acids.

Example 56, Limitation on a Including Nonstandard Amino Acid

The peptide unit of any one of Examples 52 to 54, wherein the peptide unit is characterized in that the auxiliary part is selected from a, Z, aZ, Za, GSHHHHHHGSDDDKZa (SEQ ID NO: 193), and aZGSHHHHHHGSDDDK (SEQ ID NO: 194).

Example 57, Limitation on Sequence a not Including Nonstandard Amino Acid

The peptide unit of any one of Examples 52 to 54, wherein the peptide unit is characterized in that the auxiliary part is selected from CR, HHHHHH (SEQ ID NO: 53), and RRRRRR (SEQ ID NO: 159).

Example 58, $B_1A_1T_1A_2T_2$-$B_2$ and $B_2$-$T_2A_2T_1A_1B_1$

The peptide unit of any one of Examples 49 and 50, wherein the peptide unit is characterized in that it further includes a first auxiliary part and a second auxiliary part, and the auxiliary part is linked between the first B-cell epitope and the first Th epitope, and the second auxiliary part is linked between the first Th epitope and the second Th epitope.

Example 59, $B_1A_1T_1$-$T_2A_2B_2$

The peptide unit of any one of Examples 49 and 50, wherein the peptide unit is characterized in that it further includes a first auxiliary part and a second auxiliary part, and the auxiliary part is linked between the first B-cell epitope and the first Th epitope, and the second auxiliary part is linked between the second Th epitope and the second B-cell epitope.

Example 60, $B_1$-$T_1A_1T_2A_2B_2$ and $B_2$-$T_2A_2T_1A_1B_1$

The peptide unit of any one of Examples 49 and 50, wherein the peptide unit is characterized in that it further includes a first auxiliary part and a second auxiliary part, and the auxiliary part is linked between the first Th epitope and the second Th epitope the first Th epitope and the second Th epitope is linked between the second Th epitope and the second B-cell epitope.

Example 61, Limitation on a, Including Nonstandard Amino Acid

The peptide unit of any one of Examples 58 to 60, wherein the peptide unit is characterized in that the first auxiliary part and/or a second auxiliary part include one or more nonstandard amino acids.

Example 62, Limitation on Sequence a Including Nonstandard Amino Acid

The peptide unit of any one of Examples 58 to 60, wherein the peptide unit is characterized in that the auxiliary parts including one or more nonstandard amino acids are each independently selected from a, Z, aZ, Za, GSHHHHHHGSDDDKZa (SEQ ID NO: 193), and aZGSHHHHHHGSDDDK (SEQ ID NO: 194).

Example 63, Limitation on Sequence a Including Nonstandard Amino Acid

The peptide unit of any one of Examples 58 to 60, wherein the peptide unit is characterized in that the first auxiliary part and/or a second auxiliary part are each independently selected from CR, HHHHHH (SEQ ID NO: 53), and RRRRRR (SEQ ID NO: 159).

Example 64, $B_1A_1T_1A_2T_2A_3B_2$

The peptide unit of any one of Examples 49 and 50, wherein the peptide unit is characterized in that it further includes a first auxiliary part, a second auxiliary part, and a third auxiliary part; the first auxiliary part is linked between the first B-cell epitope and the first Th epitope; the second auxiliary part is linked between the first Th epitope and the second Th epitope; and the third auxiliary part is linked between the second Th epitope and the second B-cell epitope.

Example 65, Limitation on a, Including Nonstandard Amino Acid

The peptide unit of Example 64, wherein the peptide unit is characterized in that the first auxiliary part, a second auxiliary part, and/or a third auxiliary part include one or more nonstandard amino acids.

Example 66, Limitation on Sequence a Including Nonstandard Amino Acid

The peptide unit of Example 65, wherein the peptide unit is characterized in that the auxiliary parts including one or more nonstandard amino acids are each independently selected from a, Z, aZ, Za, GSHHHHHHGSDDDKZa (SEQ ID NO: 193), and aZGSHHHHHHGSDDDK (SEQ ID NO: 194).

Example 67, Limitation on Sequence a not Including Nonstandard Amino Acid

The peptide unit of Example 64, wherein the peptide unit is characterized in that the first auxiliary part, the second auxiliary part, and/or the third auxiliary part are each independently selected from CR, HHHHHH (SEQ ID NO: 53), and RRRRRR (SEQ ID NO: 159).

Peptide Unit 7—Unit and Additional Auxiliary Part

Example 68, AU and UA a peptide unit including the following: a peptide unit of any one of Examples 1 to 67; and an additional auxiliary part.

Example 69, Limitation on a, Including Nonstandard Amino Acid

The peptide unit of Example 67, wherein the peptide unit is characterized in that the additional auxiliary part includes one or more nonstandard amino acids.

Example 70, Limitation on Sequence a Including Nonstandard Amino Acid

The peptide unit of Example 69, wherein the peptide unit is characterized in that the additional auxiliary part is selected from a, Z, aZ, Za, GSHHHHHHGSDDDKZa (SEQ ID NO: 193), and aZGSHHHHHHGSDDDK (SEQ ID NO: 194).

Example 71, Limitation on Sequence a not Including Nonstandard Amino Acid

The peptide unit of Example 68, wherein the peptide unit is characterized in that the additional auxiliary part is selected from CR, HHHHHH (SEQ ID NO: 53), and RRRRRR (SEQ ID NO: 159).

Example 72, AUA a peptide unit including the following: a peptide unit of any one of Examples 1 to 67; and a first additional auxiliary part and a second additional auxiliary part. In particular, the peptide unit is linked between the first additional auxiliary part and the second additional auxiliary part.

Example 73, Limitation on a, Including Nonstandard Amino Acid

The peptide unit of Example 72, wherein the peptide unit is characterized in that the first additional auxiliary part and/or the second additional auxiliary part include one or more nonstandard amino acids.

Example 74, Limitation on Sequence a Including Nonstandard Amino Acid

The peptide unit of Example 73, wherein the peptide unit is characterized in that the additional auxiliary parts including one or more nonstandard amino acids are each independently selected from a, Z, aZ, Za, GSHHHHHHGSDDDKZa (SEQ ID NO: 193), and aZGSHHHHHHGSDDDK (SEQ ID NO: 194).

Example 75, Limitation on Sequence a not Including Nonstandard Amino Acid

The peptide unit of Example 72, wherein the peptide unit is characterized in that the first additional auxiliary part and/or and the second additional auxiliary part are each independently selected from CR, HHHHHH (SEQ ID NO: 53), and RRRRRR (SEQ ID NO: 159).

Peptide Unit 8—Limitation on Unit Sequence

Example 76, Limitation on Sequence of Unit-A

The peptide unit of any one of Examples 1 to 8 and 68 to 75, wherein the peptide unit is selected from the following: RNVPPIFNDVYWIAFZaK(Cha)VAAWTLKAAaZ (SEQ ID NO: 56); ZaK(Cha)VAAWTLKAAaZRNVPPIFNDVYWIAF (SEQ ID NO: 57); CRFRGLISLSQVYLSZaK(Cha)VAAWTLKAAaZ (SEQ ID NO: 58); ZaK(Cha)VAAWTLKAAaZCRFRGLISLSQVYLS (SEQ ID NO: 59); KTTKQSFDLSVKAQYKKNKHZaK(Cha)VAAWTLKAAaZ (SEQ ID NO: 60); ZaK(Cha)VAAWTLKAAaZKTTKQSFDLSVKAQYKKNKH (SEQ ID NO: 61); RNVPPIFNDVYWIAFK(Cha)VAAWTLKAA (SEQ ID NO: 62); K(Cha)VAAWTLKAARNVPPIFNDVYWIAF (SEQ ID NO: 63); RNVPPIFNDVYK(Cha)VAAWTLKAA (SEQ ID NO: 64); PIFNDVYWIAFK(Cha)VAAWTLKAA (SEQ ID NO: 65); PPIFNDVYWK(Cha)VAAWTLKAA (SEQ ID NO: 66); RNVPPIFNDVYWIAFK(Cha)VAAWTLKAAHHHHHH (SEQ ID NO: 67); RNVPPIFNDVYWIAFZaK(Cha)VAAWTLKAAaZGSHIHIH GSDDDDK (SEQ ID NO: 68); GSHHHHHHGSDDDDKZaK(Cha)VAAWTLKAAaZRNVPPIFNDVYWIAF (SEQ ID NO: 69); RNVPPIFNDVYWIAFGSHHHHHHGSDDDDKZaK(Cha)VAAWTLKAAaZ (SEQ ID NO: 70); GSHHHHHHGSDDDDKZaK(Cha)VAAWTLKAAaZCRFRGLISLSQVYLS (SEQ ID NO: 71); GSHHHHHHGSDDDDKCRFRGLISLSQVYLSZaK(Cha)VAAWTLKAAaZ (SEQ ID NO: 72); CRFRGLISLSQVYLSZaK(Cha)VAAWTLKAAaZGSHHHHHHGSDDDDK (SEQ ID NO: 73); GSHIiHIHHGSDDDDKZaK(Cha)VAAWTLKAAaZKTTKQSFDLSVKAQYKKNKH (SEQ ID NO: 74); GSHHHHHHGSDDDDKKTTKQSFDLSVKAQYKKNKHZaK(Cha)VAAWTLKAAaZ (SEQ ID NO: 75); KTTKQSFDLSVKAQYKKNKHZaK(Cha)VAAWTLKAAaZGSHHHHHHGSDDDDK (SEQ ID NO: 76); MRGSHHHHHHGSDDDDKIVDRNVPPIFNDVYWIAFZaK(Cha)VAAWTLKAAaZ (SEQ ID NO: 77); MRGSHHHHHHGSDDDDKIVDGSHHHHHHGSDDDDKRNVPPIFNDVYWIAFZaK(Cha)VAAWTLKAAaZ (SEQ ID NO: 78); MRGSHHHHHHGSDDDDKIVDRNVPPIFNDVYWIAFZaK(Cha)VAAWTLKAAaZGS HHHHHHGSDDDDK (SEQ ID NO: 79); RNVPPIFNDVYWIAFILMQYIKANSKFIGI (SEQ ID NO: 80); RNVPPIFNDVYWIAFILMQYIKANSKFIGIPMGLPQSIALSSLMVAQ (SEQ ID NO: 81); CRNVPPIFNDVYWIAFZaK(Cha)VAAWTLKAAaZC (SEQ ID NO: 82); RNVPPIFNDVYWIAFZaK(Cha)VAAWTLKAACR (SEQ ID NO: 161); RNVPPIFNDVYWIAFXXKXVAAWTLKAAXXGSHHHHHHGSDDDDK (SEQ ID NO: 199); GSHHHHHHGSDDDDKXXKXVAAWTLKAAXXRNVPPIFNDVYWIAF (SEQ ID NO: 200); RNVPPIFNDVYWIAFXXKXVAAWTLKAAXX (SEQ ID NO: 204); RNVPPIFNDVYWIAFKXVAAWTLKAA (SEQ ID NO: 205); RNVPPIFNDVYWIAFKXVAAWTLKAAHHHHHH (SEQ ID NO: 206); RNVPPIFNDVYWIAFXXKXVAAWTLKAACR (SEQ ID NO: 208); RNVPPIFNDVYWIAFXXKFVAAWTLKAAXX (SEQ ID NO: 210); RNVPPIFNDVYWIAFXXKFVAAWTLKAACR (SEQ ID NO: 212); RNVPPIFNDVYWIAFCTKPTDGN (SEQ ID NO: 213); RNVPPIFNDVYWIAFLLPIFFCLW (SEQ ID NO: 214); RNVPPIFNDVYWIAFFLPSDFFPSV (SEQ ID NO: 215); RNVPPIFNDVYWIAFILMQYIKANSKFIGIHHHHHH (SEQ ID NO: 219); and RNVP- PIFNDVYWIAFMDIDPYKEFGATVELLSFLPHHHHHH (SEQ ID NO: 220), in which the a denotes D-form alanine, the Z denotes 6-aminohexanoic acid, the (Cha) denotes L-cyclohexylalanine, and the X denotes any standard amino acid.

Example 77, Limitation on Sequence of Unit-D

The peptide unit of any one of Examples 1 to 6, 14 to 15, and 68 to 75, wherein the peptide unit is selected from the following: RNVPPIFNDVYWIAF ZaK(Cha)VAAWTLKAAaZ ILMQYIKANSKFIGI (SEQ ID NO: 123); CRFRGLISLSQVYLS ZaK(Cha)VAAWTLKAAaZ ILMQYIKANSKFIGI (SEQ ID NO: 124); KTTKQSFDLSVKAQYKKNKH ZaK(Cha)VAAWTLKAAaZ ILMQYIKANSKFIGI (SEQ ID NO: 125); ILMQYIKANSKFIGI ZaK(Cha)VAAWTLKAAaZ RNVPPIFNDVYWIAF (SEQ ID NO: 126); ILMQYIKANSKFIGI ZaK(Cha)VAAWTLKAAaZ CRFRGLISLSQVYLS (SEQ ID NO: 127); ILMQYIKANSKFIGI ZaK(Cha)VAAWTLKAAaZ KTTKQSFDLSVKAQYKKNKH (SEQ ID NO: 128); PIFNDVYWIAF K(Cha)VAAWTLKAA K(Cha)VAAWTLKAA (SEQ ID NO: 129); PPIFNDVYW K(Cha)VAAWTLKAA K(Cha)VAAWTLKAA (SEQ ID NO: 130); MRGSHHHHHHGSDDDDKIVDRNVPPIFNDVYWIAFZaK(Cha)VAAWTLKAAaZIL MQYIKANSKFIGI (SEQ ID NO: 131); MRGSHHHHHHGSDDDDKIVDILMQYIKANSKFIGIZaK(Cha)VAAWTLKAAaZ (SEQ ID NO: 132); MRGSHHHHHHGSDDDDKIVDRNVPPIFNDVYWIAFGGGGSGGGGGGSSZaK(Cha) VAAWTLKAAaZILMQYIKANSKFIGI (SEQ ID NO: 133); MRGSHHHHHHGSDDDDKIVDRNVPPIFNDVYWIAFGGGGSGGGGGGSSILMQYI KANSKFIGIPMGLPQSIALSSLMVAQGGGGSGGGGGGSSILMQYIKANSKFIGIPM GLPQSIALSSLMVAQ (SEQ ID NO: 134); RNVPPIFNDVYWIAFZaK(Cha)VAAWTLKAAaZK(Cha)LAAFTIRAAaZ (SEQ ID NO: 135); and CRNVPPIFNDVYWIAFZaK(Cha)VAAWTLKAAaZILMQYIKANSKFIGIC (SEQ ID NO: 136), in which the a denotes D-form alanine, the Z denotes 6-aminohexanoic acid, and (Cha) denotes L-cyclohexylalanine.

Example 78, Limitation on Sequence of Unit-B

The peptide unit of any one of Examples 1 to 6, 26 to 27, and 68 to 75, wherein the peptide unit is selected from the group consisting of the following: RNVPPIFNDVYWIAFRNVPPIFNDVYWIAFZaK(Cha)VAAWTLKAAaZ (SEQ ID NO: 83), RNVPPIFNDVYWIAFCRFRGLISLSQVYLSZaK(Cha)VAAWTLKAAaZ (P5: SEQ ID NO: 84), RNVPPIFNDVYWIAFKTTKQSFDLSVKAQYKKNKHZaK(Cha)VAAWTLKAAaZ (SEQ ID NO: 85), CRFRGLISLSQVYLSRNVPPIFNDVYWIAFZaK(Cha)VAAWTLKAAaZ (SEQ ID NO: 86), CRFRGLISLSQVYLSCRFRGLISLSQVYLSZaK(Cha)VAAWTLKAAaZ (SEQ ID NO: 87), CRFRGLISLSQVYLSKTTKQSFDLSVKAQYKKNKHZaK(Cha)VAAWTLKAAaZ (SEQ ID NO: 88), KTTKQSFDLSVKAQYKKNKHRNVPPIFNDVYWIAFZaK(Cha)VAAWTLKAAaZ (SEQ ID NO: 89), KTTKQSFDLSVKAQYKKNKHCRFRGLISLSQVYLSZaK(Cha)VAAWTLKAAaZ (SEQ ID NO: 90), KTTKQSFDLSVKAQYKKNKHKTTKQSFDLSVKAQYKKNKHZaK(Cha)VAAWTLK AAaZ (SEQ ID NO: 91), RNVPPIFNDVYWIAFCRFRGLISLSQVYLSK(Cha)VAAWTLKAA (SEQ ID NO: 92), PIFNDVYWIAFGLISLSQVYLSK(Cha)VAAWTLKAA (SEQ ID NO: 93), RNVPPIFNDVYCRFRGLISLSQK(Cha)VAAWTLKAA (SEQ ID NO: 94), PIFNDVYWIAFCRFRGLISLSQK(Cha)VAAWTLKAA (SEQ ID NO: 95), PPIFNDVYWRGLISLSQVK(Cha)VAAWTLKAA (SEQ ID NO: 96), RNVPPIFNDVYWIAFCRFRGLISLSQVYLSK(Cha)VAAWTLKAAHHHHHH (SEQ ID NO: 97), MRGSHHHHHHGSDDDDKIVDRNVPPIFNDVYWIAFCRFRGLISLSQVYLSZaK(Cha)VAAWTLKAAaZ (SEQ ID NO: 98), MRGSHHHHHHGSDDDDKIVDRNVPPIFNDVYWIAFCRFRGLISLSQVYLSZaK(Cha)VAAWTLKAA (SEQ ID NO: 99), RNVPPIFNDVYWIAFCRFRGLISLSQVYLSZaK(Cha)VAAWTLKAA (SEQ ID NO: 100), MRGSHHHHHHGSDDDDKIVD RNVPPIFNDVYWIAF GGGGSGGGGGGSS RNVPPIFNDVYWIAFZaK(Cha) VAAWTLKAA (SEQ ID NO: 101), RNVPPIFNDVYWIAF GGGGSGGGGGGSS RNVPPIFNDVYWIAFZaK(Cha) VAAWTLKAA (SEQ ID NO: 102), RNVPPIFNDVYWIAF GGGGSGGGGGGSS RNVPPIFNDVYWIAFZaK(Cha) VAAWTLKAAaZ (SEQ ID NO: 103), RNVPPIFNDVYWIAFRNVPPIFNDVYWIAF ILMQYIKANSKFIGI (SEQ ID NO: 104), RNVPPIFNDVYWIAFRNVPPIFNDVYWIAF ILMQYIKANSKFIGIPMGLPQSIALSSLMVAQ (SEQ ID NO: 105), CRNVPPIFNDVYWIAFCRFRGLISLSQVYLSZaK(Cha)VAAWTLKAAaZC (SEQ ID NO: 106), and RNVPPIFNDVYWIAFCRFRGLISLSQVYLSXXXK(Cha)VAAWTLKAAXX (SEQ ID NO: 202), in which the a denotes D-form alanine, the (Cha) denotes L-cyclohexylalanins, the Z denotes 6-aminohexanoic acid, and the X denotes any standard amino acid.

Example 79, Limitation on Sequence of Unit-C

The peptide unit of any one of Examples 1 to 6, 38 to 39, and 68 to 75, wherein the peptide unit is selected from the group consisting of the following: RNVPPIFNDVYWIAFZaK(Cha)VAAWTLKAAaZRNVPPIFNDVYWIAF (SEQ ID NO: 107); RNVPPIFNDVYWIAFZaK(Cha) VAAWTLKAAaZCRFRGLISLSQVYLS (P1: SEQ ID NO: 108); RNVPPIFNDVYWIAFZaK(Cha)VAAWTLKAAaZKTTKQSFDLSVKAQYKKNKH (SEQ ID NO: 109); CRFRGLISLSQVYLSZaK(Cha)VAAWTLKAAaZRNVPPIFNDVYWIAF (SEQ ID NO: 110); CRFRGLISLSQVYLSZaK(Cha)VAAWTLKAAaZCRFRGLISLSQVYLS (SEQ ID NO: 111); RNVPPIFNDVYWIAFZaK(Cha)VAAWTLKAAaZKTTKQSFDLSVKAQYKKNKH (SEQ ID NO: 112); KTTKQSFDLSVKAQYKKNKHZaK(Cha)VAAWTLKAAaZRNVPPIFNDVYWIAF (SEQ ID NO: 113); KTTKQSFDLSVKAQYKKNKHZaK(Cha)VAAWTLKAAaZCRFRGLISLSQVYLS (P4: SEQ ID NO: 114); KTTKQSFDLSVKAQYKKNKHZaK(Cha)VAAWTLKAAaZKTTKQSFDLSVKAQYK KNKH (SEQ ID NO: 115); PIFNDVYWIAFK(Cha)VAAWTLKAACRFRGLISLSQ (SEQ ID NO: 116); PPIFNDVYWK(Cha)VAAWTLKAARGLISLSQV (SEQ ID NO: 117); MRGSHIIHGSDDDDKIVD RNVPPIFNDVYWIAFZaK(Cha)VAAWTLKAAaZRNVPPIFNDVYWIAF (SEQ ID NO: 118); MRGSHHHHHHGSDDDDKIVDRNVPPIFNDVYWIAF GGGGSGGGGGGSS ILMQYIKANSKFIGIPMGLPQSIALSSLMVAQ GGGGSGGGGGGSSCRFRGLISLSQVYLS (SEQ ID NO: 119); RNVPPIFNDVYWIAFILMQYIKANSKFIGICRFRGLISLSQVYLS (SEQ ID NO: 120); RNVPPIFNDVYWIAFZPKYVKQNTLKLATZCRFRGLISLSQVYLS (P5: SEQ ID NO: 121); CRNVPPIFNDVYWIAFZaK(Cha)VAAWTLKAAaZRNVPPIFNDVYWIAFC (SEQ ID NO: 122); RNVPPIFNDVYWIAFZaK(Cha)VAAWTLKAACR- FRGLISLSQVYLS (SEQ ID NO: 160); RNVPPIFNDVYWIAFXXKXVAAWTLKAAXXCRFRGLISLSQVYLS (SEQ ID NO: 198); KTTKQSFDLSVKAQYKKNKHXXKXVAAWTLKAAXXCRFRGLISLSQVYLS (SEQ ID NO: 201); RNVPPIFNDVYWIAFXPKYVKQNTLKLATXCRFRGLISLSQVYLS (SEQ ID NO: 203); RNVPPIFNDVYWIAFXXKXVAAWTLKAACRFRGLISLSQVYLS (SEQ ID NO: 207); RNVPPIFNDVYWIAFXXKFVAAWTLKAAXXCRFRGLISLSQVYLS (SEQ ID NO: 209); RNVPPIFNDVYWIAFXXKFVAAWTLKAACRFRGLISLSQVYLS (SEQ ID NO: 211); KTTKQSFDLSVKAQYKKNKHZaWPEANQVGAGAFGPGFaZCRFRGLISLSQVYLS (SEQ ID NO: 216); KTTKQSFDLSVKAQYKKNKHZaMDIDPYKEFGATVELLSFLPaZCRFRGLISLSQV YLS (SEQ ID NO: 217); and KTTKQSFDLSVKAQYKKNKHZaILMQYIKANSKFIGIPMGLPQSIAL SSLMVAQaZ CRFRGLISLSQVYLS (SEQ ID NO: 218), in which the a denotes D-form alanine, the (Cha) denotes L-cyclohexylalanins, the Z denotes 6-aminohexanoic acid, and the X denotes any standard amino acid.

Example 80, Limitation on Sequence of Unit-E

The peptide unit of any one of Examples 1 to 6, 49 to 50, and 68 to 75, wherein the peptide unit is selected from the group consisting of the following: RNVPPIFNDVYWIAFZaK(Cha)VAAWTLKAAaZILMQYIKANSKFIGIRNVPPIFND YWIAF (SEQ ID NO: 137), RNVPPIFNDVYWIAFZaK(Cha) VAAWTLKAAaZILMQYIKANSKFIGICRFRGLISLS QVYLS (SEQ ID NO: 138), RNVPPIFNDVYWIAFZaK(Cha)VAAWTLKAAaZILMQYIKANSKFIGIKTTKQSFDL SVKAQYKKNKH (SEQ ID NO: 139), CRFRGLISLSQVYLSZaK(Cha)VAAWTLKAAaZILMQYIKANSKFIGIRNVPPIFNDV YWIAF (SEQ ID NO: 140), CRFRGLISLSQVYLSZaK(Cha) VAAWTLKAAaZILMQYIKANSKFIGICRFRGLISLS QVYLS (SEQ ID NO: 141), CRFRGLISLSQVYLSZaK(Cha)VAAWTLKAAaZILMQYIKANSKFIGIKTTKQSFDLS VKAQYKKNKH (SEQ ID NO: 142), KTTKQSFDLSVKAQYKKNKHZaK(Cha)VAAWTLKAAaZILMQYIKANSKFIGIRNV PPIFNDVYWIAF (SEQ ID NO: 143), KTTKQSFDLSVKAQYKKNKHZaK(Cha)VAAWTLKAAaZILMQYIKANSKFIGICRF RGLISLSQVYLS (SEQ ID NO: 144), KTTKQSFDLSVKAQYKKNKHZaK(Cha) VAAWTLKAAaZILMQYIKANSKFIGIKTT KQSFDLSVKAQYKKNKH (SEQ ID NO: 145), MRGSHHHHHHGSDDDDKIVDRNVPPIFNDVYWIAFZaK(Cha)VAAWTLKAAaZIL MQYIKANSKFIGIRNVPPIFNDVYWIAF (SEQ ID NO: 146), MRGSHHHHHHGSDDDDKIVDRNVPPIFNDVYWIAFGGGGSGGGGGGSSILMQYI KANSKFIGIPMGLPQSIALSSLMVAQILMQYIKANSKFIGIPMGLPQSIALSSLMVA QGGGGSGGGGGGSSCRFRGLISLSQVYLS (SEQ ID NO: 147), PIFNDVYWIAFK(Cha)VAAWTLKAAK(Cha)VAAWTLKAACRFRGLISLSQ (SEQ ID NO: 148), PPIFNDVYWK(Cha)VAAWTLKAAK(Cha)VAAWTLKAARGLISLSQV (SEQ ID NO: 149), and CRNVPPIFNDVYWIAFZaK(Cha)VAAWTLKAAaZILMQYIKANSKFIGIRNVPPIFND VYWIAFC (SEQ ID NO: 150), in which the a denotes D-form alanine, the (Cha) denotes L-cyclohexylalanins, and the Z denotes 6-aminohexanoic acid.

Peptide Unit 9—Formula

Example 81, Higher Concept of Unit-A Formula

The peptide unit of any one of Examples 1 to 2, wherein the peptide unit is represented by the following [Formula A] or [Formula A']:

$$A_1\text{-}B\text{-}A_2\text{-}T\text{-}A_3 \quad \text{[Formula A]}$$

$$A_1\text{-}T\text{-}A_2\text{-}B\text{-}A_3 \quad \text{[Formula A']}$$

in which the peptide unit is one which can induce a humoral immunity by being recognized by CD4+ T-cells and has a length of 23mer, 24mer, 25mer, 26mer, 27mer, 28mer, 29mer, 30mer, 31mer, 32mer, 33mer, 34mer, 35mer, 36mer, 37mer, 38mer, 39mer, 40mer, 41mer, 42mer, 43mer, 44mer, 45mer, 46mer, 47mer, 48mer, 49mer, 50mer, 51mer, 52mer, 53mer, 54mer, 55mer, 56mer, 57mer, 58mer, 59mer, 60mer, 61mer, 62mer, 63mer, 64mer, 65mer, 66mer, 67mer, 68mer, 69mer, 70mer, or 71mer;

in which the $A_1$ is a first auxiliary part or absent; wherein the first auxiliary part has a linker function, a protective function, a cyclic form forming function, a dummy function, and/or a solubility increasing function, and may optionally have a nonstandard amino acid;

the $A_2$ is a second auxiliary part or absent; wherein the second auxiliary part has a linker function, a protective function, a cyclic form forming function, a dummy function, and/or a solubility increasing function, and may optionally have a nonstandard amino acid;

the $A_3$ is a third auxiliary part or absent; wherein the third auxiliary part has a linker function, a protective function, a cyclic form forming function, a dummy function, and/or a solubility increasing function, and may optionally have a nonstandard amino acid;

the B, which is a B-cell epitope, is a fragment of apolipoprotein B-100 or a mimotope of apolipoprotein B-100 and can induce an antibody which targets apolipoprotein B-100;

the T, which is a Th epitope, can be recognized by CD4+ T-cells and has a length of 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, or 32mer.

Example 82, Combination of Unit-A Sequences

In Example 81,
the $A_1$, $A_2$, and $A_3$ may be each independently selected from the group consisting of a, Z, aZ, Za, RN, AF, CR, LS, KT, KH, RF, DP, SV, GL, ZRNV (SEQ ID NO: 36), aZRN (SEQ ID NO: 37), IAFZ (SEQ ID NO: 38), AFZa (SEQ ID NO: 39), RNVP (SEQ ID NO: 40), WIAF (SEQ ID NO: 41), ZCRF (SEQ ID NO: 42), aZCR (SEQ ID NO: 43), YLSZ (SEQ ID NO: 44), LSZa (SEQ ID NO: 45), CRFR (SEQ ID NO: 46), VYLS (SEQ ID NO: 47), ZKTT (SEQ ID NO: 48), aZKT (SEQ ID NO: 49), NKHZ (SEQ ID NO: 50), KHZa (SEQ ID NO: 51), GSHHHHHHGSDDDDK (SEQ ID NO: 52), HHHHHH (SEQ ID NO: 53), MRGSHHHHHHGSDDDDKIVD (SEQ ID NO: 54), GGGGSGGGGGGSS (SEQ ID NO: 55), RRRRRR (SEQ ID NO: 159), GSHHHHHHGSDDDDKZa (SEQ ID NO: 193), and aZGSHHHHHHGSDDDDK (SEQ ID NO: 194) or may be absent, in which the a denotes D-form alanine, and the Z denotes 6-aminohexanoic acid;

the B has:

one selected from the group consisting of RNVPPIFNDVYWIAF (SEQ ID NO: 6), CRFRGLISLSQVYLS (SEQ ID NO: 7), KTTKQSFDLSVKAQYKKNKH (SEQ ID NO: 8), RNVPPIFNDVY (SEQ ID NO: 9), CRFRGLISLSQ (SEQ ID NO: 10), KTTKQSFDLSVK (SEQ ID NO: 11), RNVPPIFNDVYW (SEQ ID NO: 12), CRFRGLISLSQV (SEQ ID NO: 13), KTTKQSFDLSVKAQYKK (SEQ ID NO: 14), RNVPPIFNDVYWI (SEQ ID NO: 15), CRFRGLISLSQVY (SEQ ID NO: 16), KTTKQSFDLSVKAQYKKN (SEQ ID NO: 17), PIFNDVYWIAF (SEQ ID NO: 18), GLISLSQVYLS (SEQ ID NO: 19), QSFDLSVKAQYKKNKH (SEQ ID NO: 20), PPIFNDVYWIAF (SEQ ID NO: 21), RGLISLSQVYLS (SEQ ID NO: 22), KQSFDLSVKAQYKKNKH (SEQ ID NO: 23), VPPIFNDVYWIAF (SEQ ID NO: 24), FRGLISLSQVYLS (SEQ ID NO: 25), TKQSFDLSVKAQYKKNKH (SEQ ID NO: 26), NVPPIFNDVYWIA (SEQ ID NO: 27), RFRGLISLSQVYL (SEQ ID NO: 28), TKQSFDLSVKAQYKKN (SEQ ID NO: 29), VPPIFNDVYWI (SEQ ID NO: 30), FRGLISLSQVY (SEQ ID NO: 31), TKQSFDLSVKAQYKKN (SEQ ID NO: 32), PPIFNDVYW (SEQ ID NO: 33), RGLISLSQV (SEQ ID NO: 34), KQSFDLSVKAQYKK (SEQ ID NO: 35), RFRGLISLSQVYLDP (SEQ ID NO: 221), and SVCGCPVGHHDVVGL (SEQ ID NO: 222);

an epitope, which is included in any one of SEQ ID NO: 6 to SEQ ID NO: 35, and SEQ ID NO: 221 to SEQ ID NO: 222; or a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of SEQ ID NO: 6 to SEQ ID NO: 35, and SEQ ID NO: 221 to SEQ ID NO: 222;

in which the a denotes D-form alanine, and the Z denotes 6-aminohexanoic acid;

the T is selected from the group consisting of the following:

one selected from a group consisting of K(Cha)VAAWTLKAA (SEQ ID NO: 1), PKYVKQNTLKLAT (SEQ ID NO: 2), ILMQYIKANSKFIGI (SEQ ID NO: 3), QSIALSSLMVAQAIP (SEQ ID NO: 4), ILMQYIKANSKFIGIPMGLPQSIALSSLMVAQ (SEQ ID NO: 5), PLGFFPDHQL (SEQ ID NO: 162), WPEANQVGAGAFGPGF (SEQ ID NO: 163), MQWNSTALHQALQDP (SEQ ID NO: 164), MQWNSTTFHQTLQDPRVRGLYFPAGG (SEQ ID NO: 165), FFLLTRILTI (SEQ ID NO: 166), FFLLTRILTIPQSLD (SEQ ID NO: 167), TSLNFLGGTTVCLGQ (SEQ ID NO: 168), QSPTSNHSPTSCPPIC (SEQ ID NO: 169), IIFLFILLLCLIFLLVLLD (SEQ ID NO: 170), CTTPAQGNSMFPSC (SEQ ID NO: 171), CTKPTDGN (SEQ ID NO: 172), WASVRFSW (SEQ ID NO: 173), LLPIFFCLW (SEQ ID NO: 174), MDIDPYKEFGATVELLSFLP (SEQ ID NO: 175), FLPSDFFPSV (SEQ ID NO: 176), RDLLDTASALYREALESPEH (SEQ ID NO: 177), PHHTALRQAILCWGELMTLA (SEQ ID NO: 178), GRETVIEYLVSFGVW (SEQ ID NO: 179), EYLVSFGVWIRTPPA (SEQ ID NO: 180), VSFGVWIRTPPAYRPPNAPI (SEQ ID NO: 181), TVVRRRGRSP (SEQ ID NO: 182), VGPLTVNEKRRLKLI (SEQ ID NO: 183), RHYLHTLWKAGILYK (SEQ ID NO: 184), ESRLVVDFSQFSRGN (SEQ ID NO: 185), LQSLTNLLSSNLSWL (SEQ ID NO: 186), SSNLSWLSLDVSAAF (SEQ ID NO: 187), LHLYSHPIILGFRKI (SEQ ID NO: 188), KQCFRKLPVNRPIDW (SEQ ID NO: 189), LCQVFADATPTGWGL (SEQ ID NO: 190), AANWILRGTSFVYVP (SEQ ID NO: 191), EIRLKVFVLGGCRHK (SEQ ID NO: 192), KFVAAWTLKAA (SEQ ID NO: 195), KYVAAWTLKAA (SEQ ID NO: 196), DIEKKIAKMEKASSVFNVVNS (SEQ ID NO: 223), YSGPLKAEIAQRLEDV (SEQ ID NO: 224), K(Cha)VKANTLKAA (SEQ ID NO: 225), K(Cha)VKANTLKAA (SEQ ID NO: 226), K(Cha)VKAWTLKAA (SEQ ID NO: 227), K(Cha)VKAWTLKAA (SEQ ID NO: 228), K(Cha)VWANTLKAA (SEQ ID NO: 229), K(Cha)VWANTLKAA (SEQ ID NO: 230), K(Cha)VWAYTLKAA (SEQ ID NO: 231), K(Cha)VWAVTLKAA (SEQ ID NO: 232), K(Cha)VYAWTLKAA (SEQ ID NO: 233), K(Cha)VYAWTLKAA (SEQ ID NO: 234), R(Cha)VRANTLKAA (SEQ ID NO: 235), K(Cha)VKAHTLKAA (SEQ ID NO: 236), K(Cha)VKAHTLKAA (SEQ ID NO: 237), K(Cha)VAANTLKAA (SEQ ID NO: 238), K(Cha)VAANTLKAA (SEQ ID NO: 239), K(Cha)VAAYTLKAA (SEQ ID NO: 240), K(Cha)VAAYTLKAA (SEQ ID NO: 241), K(Cha)VAAWTLKAA (SEQ ID NO: 242), K(Cha)VAAKTLKAA (SEQ ID NO: 243), K(Cha)VAAHTLKAA (SEQ ID NO: 244), K(Cha)VAAATLKAA (SEQ ID NO: 245), K(Cha)VAAWTLKAA (SEQ ID NO: 246), and K(Cha)VMAATLKAA (SEQ ID NO: 247);

a sequence represented by the following [Formula I] or [Formula II];

N-Lys-$X_1$-$X_2$-Ala-Ala-$X_3$-Thr-$X_4$-$X_5$-Ala-Ala-C     [Formula I]

in which the $X_1$ is tyrosine (Tyr), phenylalanine (Phe), or L-cyclohexylalanine;

the $X_2$ is a hydrophobic amino acid, or leucine (Leu), or isoleucine (Ile);

the $X_3$ is an aromatic or cyclic amino acid, or phenylalanine (Phe), tyrosine (Tyr), or histidine (His);

the $X_4$ is an aliphatic long chain amino acid, or isoleucine (Ile), or valine (Val); and the $X_5$ is a charged amino acid, or arginine (Arg), leucine (Leu), aspartic acid (Asp), glutamine (Gln), or glycine (Gly);

N-Lys-$X_1$-Val-$X_2$-Ala-$X_3$-Thr-Leu-Lys-Ala-Ala-C     [Formula II]

in which $X_1$ is tyrosine (Tyr), phenylalanine (Phe), or L-cyclohexylalanine;

the $X_2$ is lysine (Lys), tryptophan (Trp), tyrosine (Tyr), arginine (Arg), alanine (Ala), or methionine (Met); and the X₃ is asparagine (Asn), tryptophan (Trp), tyrosine (Tyr), valine (Val), histidine (His), lysine (Lys), or alanine (Ala); and a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of the sequences represented by SEQ ID NO: 1 to SEQ ID NO: 5, SEQ ID NO: 162 to SEQ ID NO: 192, SEQ ID NO: 195 to SEQ ID NO: 196, SEQ ID NO: 223 to SEQ ID NO: 247, and [Formula I] or [Formula II];

in which (Cha) denotes L-cyclohexylalanins, and X denotes any standard amino acid.

Example 83, Higher Concept of Unit-B Formula

The peptide unit of any one of Examples 1 and 2, wherein the peptide unit is represented by the following [Formula B] or [Formula B']:

A₁-B₁-A₂-B₂-A₃-T-A₄    [Formula B]

A₁-T-A₂-B₁-A₃-B₂-A₄    [Formula B']

in which the peptide unit is characterized in that it can induce a humoral immunity by being recognized by CD4+ T-cells and has a length of 23mer, 24mer, 25mer, 26mer, 27mer, 28mer, 29mer, 30mer, 31mer, 32mer, 33mer, 34mer, 35mer, 36mer, 37mer, 38mer, 39mer, 40mer, 41mer, 42mer, 43mer, 44mer, 45mer, 46mer, 47mer, 48mer, 49mer, 50mer, 51mer, 52mer, 53mer, 54mer, 55mer, 56mer, 57mer, 58mer, 59mer, 60mer, 61mer, 62mer, 63mer, 64mer, 65mer, 66mer, 67mer, 68mer, 69mer, 70mer, or 71mer;

in which the A₁ is a first auxiliary part or absent; wherein the first auxiliary part has a linker function, a protective function, a cyclic form forming function, a dummy function, and/or a solubility increasing function, and may optionally have a nonstandard amino acid;

the A₂ is a second auxiliary part or absent; wherein the second auxiliary part has a linker function, a protective function, a cyclic form forming function, a dummy function, and/or a solubility increasing function, and may optionally have a nonstandard amino acid;

the A₃ is a third auxiliary part or absent; wherein the third auxiliary part has a linker function, a protective function, a cyclic form forming function, a dummy function, and/or a solubility increasing function, and may optionally have a nonstandard amino acid;

the A₄ is a fourth auxiliary part or absent; wherein the fourth auxiliary part has a linker function, a protective function, a cyclic form forming function, a dummy function, and/or a solubility increasing function, and may optionally have a nonstandard amino acid;

the B₁, which is a B-cell epitope, is a fragment of apolipoprotein B-100 or a mimotope of apolipoprotein B-100 and can induce an antibody which targets apolipoprotein B-100;

the B₂, which is a B-cell epitope, is a fragment of apolipoprotein B-100 or a mimotope of apolipoprotein B-100 and can induce an antibody which targets apolipoprotein B-100; and the T, which is a Th epitope, can be recognized by CD4+ T-cells and has a length of 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, or 32mer.

Example 84, Combination of Unit-B Sequences

In Example 83, the A₁, A₂, and A₃ are each independently selected from the group consisting of a, Z, aZ, Za, RN, AF, CR, LS, KT, KH, RF, DP, SV, GL, ZRNV (SEQ ID NO: 36), aZRN (SEQ ID NO: 37), IAFZ (SEQ ID NO: 38), AFZa (SEQ ID NO: 39), RNVP (SEQ ID NO: 40), WIAF (SEQ ID NO: 41), ZCRF (SEQ ID NO: 42), aZCR (SEQ ID NO: 43), YLSZ (SEQ ID NO: 44), LSZa (SEQ ID NO: 45), CRFR (SEQ ID NO: 46), VYLS (SEQ ID NO: 47), ZKTT (SEQ ID NO: 48), aZKT (SEQ ID NO: 49), NKHZ (SEQ ID NO: 50), KHZa (SEQ ID NO: 51), GSHHHHHHGSDDDDK (SEQ ID NO: 52), HHHHHH (SEQ ID NO: 53), MRGSHHHHHHGSDDDDKIVD (SEQ ID NO: 54), GGGGSGGGGGGSS (SEQ ID NO: 55), RRRRRR (SEQ ID NO: 159), GSHHHHHHGSDDDDKZa (SEQ ID NO: 193), and aZGSHHHHHHGSDDDDK (SEQ ID NO: 194) or is absent; in which the a denotes D-form alanine, and the Z denotes 6-aminohexanoic acid;

the B₁ and the B₂ are each independently, selected from the group consisting of RNVPPIFNDVYWIAF (SEQ ID NO: 6), CRFRGLISLSQVYLS (SEQ ID NO: 7), KTTKQSFDLSVKAQYKKNKH (SEQ ID NO: 8), RNVPPIFNDVY (SEQ ID NO: 9), CRFRGLISLSQ (SEQ ID NO: 10), KTTKQSFDLSVK (SEQ ID NO: 11), RNVPPIFNDVYW (SEQ ID NO: 12), CRFRGLISLSQV (SEQ ID NO: 13), KTTKQSFDLSVKAQYKK (SEQ ID NO: 14), RNVPPIFNDVYWI (SEQ ID NO: 15), CRFRGLISLSQVY (SEQ ID NO: 16), KTTKQSFDLSVKAQYKKN (SEQ ID NO: 17), PIFNDVYWIAF (SEQ ID NO: 18), GLISLSQVYLS (SEQ ID NO: 19), QSFDLSVKAQYKKNKH (SEQ ID NO: 20), PPIFNDVYWIAF (SEQ ID NO: 21), RGLISLSQVYLS (SEQ ID NO: 22), KQSFDLSVKAQYKKNKH (SEQ ID NO: 23), VPPIFNDVYWIAF (SEQ ID NO: 24), FRGLISLSQVYLS (SEQ ID NO: 25), TKQSFDLSVKAQYKKNKH (SEQ ID NO: 26), NVPPIFNDVYWIA (SEQ ID NO: 27), RFRGLISLSQVYL (SEQ ID NO: 28), TKQSFDLSVKAQYKKN (SEQ ID NO: 29), VPPIFNDVYWI (SEQ ID NO: 30), FRGLISLSQVY (SEQ ID NO: 31), TKQSFDLSVKAQYKKN (SEQ ID NO: 32), PPIFNDVYW (SEQ ID NO: 33), RGLISLSQV (SEQ ID NO: 34), KQSFDLSVKAQYKK (SEQ ID NO: 35), RFRGLISLSQVYLDP (SEQ ID NO: 221), and SVCGCPVGHHDVVGL (SEQ ID NO: 222);

an epitope, which is included in any one of SEQ ID NO: 6 to SEQ ID NO: 35, and SEQ ID NO: 221 to SEQ ID NO: 222; or has a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more with any one of SEQ ID NO: 6 to SEQ ID NO: 35, and SEQ ID NO: 221 to SEQ ID NO: 222;

in which the a denotes D-form alanine, and the Z denotes 6-aminohexanoic acid;

the T is selected from the group consisting of the following:

one selected from a group consisting of K(Cha)VAAWTLKAA (SEQ ID NO: 1), PKYVKQNTLKLAT (SEQ ID NO: 2), ILMQYIKANSKFIGI (SEQ ID NO: 3), QSIALSSLMVAQAIP (SEQ ID NO: 4), ILMQYIKANSKFIGIPMGLPQSIALSSLMVAQ (SEQ ID NO: 5), PLGFFPDHQL (SEQ ID NO: 162), WPEANQVGAGAFGPGF (SEQ ID NO: 163), MQWNSTALHQALQDP (SEQ ID NO: 164), MQWNSTTFHQTLQDPRVRGLYFPAGG (SEQ ID NO: 165), FFLLTRILTI (SEQ ID NO: 166), FFLLTRILTIPQSLD (SEQ ID NO: 167), TSLNFLGGTTVCLGQ (SEQ ID NO: 168), QSPTSNHSPTSCPPIC (SEQ ID NO: 169), IIFLFILLLCLIFLLVLLD (SEQ ID NO: 170), CTTPAQGNSMFPSC (SEQ ID NO: 171), CTKPTDGN (SEQ ID NO: 172), WASVRFSW (SEQ ID NO: 173), LLPIFFCLW (SEQ ID NO: 174), MDIDPYKEFGATVELLSFLP (SEQ ID NO: 175), FLPSDFFPSV (SEQ ID NO: 176), RDLLDTASALYREALESPEH (SEQ ID NO: 177), PHHTALRQAILCWGELMTLA (SEQ ID NO: 178), GRETVIEYLVSFGVW (SEQ ID NO: 179), EYLVSFGVWIRTPPA (SEQ ID NO: 180), VSFGVWIRTPPAYRPPNAPI (SEQ ID NO: 181), TVVRRRGRSP (SEQ ID NO: 182), VGPLTVNEKRRLKLI (SEQ ID NO: 183), RHYLHTLWKAGILYK (SEQ ID NO: 184), ESRLVVDFSQFSRGN (SEQ ID NO: 185), LQSLTNLLSSNLSWL (SEQ ID NO: 186), SSNLSWLSLDVSAAF (SEQ ID NO: 187), LHLYSHPIILGFRKI (SEQ ID NO: 188), KQCFRKLPVNRPIDW (SEQ ID NO: 189), LCQVFADATPTGWGL (SEQ ID NO: 190), AANWILRGTSFVYVP (SEQ ID NO: 191), EIRLKVFVLGGCRHK (SEQ ID NO: 192), KFVAAWTLKAA (SEQ ID NO: 195), KYVAAWTLKAA (SEQ ID NO: 196), DIEKKIAKMEKASSVFNVVNS (SEQ ID NO: 223), YSGPLKAEIAQRLEDV (SEQ ID NO: 224), K(Cha)VKANTLKAA (SEQ ID NO: 225), K(Cha)VKANTLKAA (SEQ ID NO: 226), K(Cha)VKAWTLKAA (SEQ ID NO: 227), K(Cha)VKAWTLKAA (SEQ ID NO: 228), K(Cha)VWANTLKAA (SEQ ID NO: 229), K(Cha)VWANTLKAA (SEQ ID NO: 230), K(Cha)VWAYTLKAA (SEQ ID NO: 231), K(Cha)VWAVTLKAA (SEQ ID NO: 232), K(Cha)VYAWTLKAA (SEQ ID NO: 233), K(Cha)VYAWTLKAA (SEQ ID NO: 234), R(Cha)VRANTLKAA (SEQ ID NO: 235), K(Cha)VKAHTLKAA (SEQ ID NO: 236), K(Cha)VKAHTLKAA (SEQ ID NO: 237), K(Cha)VAANTLKAA (SEQ ID NO: 238), K(Cha)VAANTLKAA (SEQ ID NO: 239), K(Cha)VAAYTLKAA (SEQ ID NO: 240), K(Cha)VAAYTLKAA (SEQ ID NO: 241), K(Cha)VAAWTLKAA (SEQ ID NO: 242), K(Cha)VAAKTLKAA (SEQ ID NO: 243), K(Cha)VAAHTLKAA (SEQ ID NO: 244), K(Cha)VAAATLKAA (SEQ ID NO: 245), K(Cha)VAAWTLKAA (SEQ ID NO: 246), and K(Cha)VMAATLKAA (SEQ ID NO: 247);

a sequence represented by the following [Formula I] or [Formula II]:

$$\underline{N}\text{-Lys-}X_1\text{-}X_2\text{-Ala-Ala-}X_3\text{-Thr-}X_4\text{-}X_5\text{-Ala-Ala-}\underline{C} \quad \text{[Formula I]}$$

in which the $X_1$ is tyrosine (Tyr), phenylalanine (Phe), or L-cyclohexylalanine;

the $X_2$ is a hydrophobic amino acid, or leucine (Leu), or isoleucine (Ile);

the $X_3$ is an aromatic or cyclic amino acid, or phenylalanine (Phe), tyrosine (Tyr), or histidine (His);

the $X_4$ is an aliphatic long chain amino acid, or isoleucine (Ile), or valine (Val); and the $X_5$ is a charged amino acid, or arginine (Arg), leucine (Leu), aspartic acid (Asp), glutamine (Gln), or glycine (Gly);

$$\underline{N}\text{-Lys-}X_1\text{-Val-}X_2\text{-Ala-}X_3\text{-Thr-Leu-Lys-Ala-Ala-}\underline{C} \quad \text{[Formula II]}$$

in which $X_1$ is tyrosine (Tyr), phenylalanine (Phe), or L-cyclohexylalanine;

the $X_2$ is lysine (Lys), tryptophan (Trp), tyrosine (Tyr), arginine (Arg), alanine (Ala), or methionine (Met); and the $X_3$ is asparagine (Asn), tryptophan (Trp), tyrosine (Tyr), valine (Val), histidine (His), lysine (Lys), or alanine (Ala); and a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of the sequences represented by SEQ ID NO: 1 to SEQ ID NO: 5, SEQ ID NO: 162 to SEQ ID NO: 192, SEQ ID NO: 195 to SEQ ID NO: 196, SEQ ID NO: 223 to SEQ ID NO: 247, and [Formula I] or [Formula II];

in which (Cha) denotes L-cyclohexylalanins, and X denotes any standard amino acid.

Example 85, Higher Concept of Unit-C Formula

The peptide unit of any one of Examples 1 and 2, wherein the peptide unit is represented by the following [Formula C]:

$$A_1\text{-}B_1\text{-}A_2\text{-}T\text{-}A_3\text{-}B_2\text{-}A_4 \quad \text{[Formula C]}$$

in which the peptide unit is characterized in that it can induce a humoral immunity by being recognized by CD4+ T-cells and has a length of 23mer, 24mer, 25mer, 26mer, 27mer, 28mer, 29mer, 30mer, 31mer, 32mer, 33mer, 34mer, 35mer, 36mer, 37mer, 38mer, 39mer, 40mer, 41mer, 42mer, 43mer, 44mer, 45mer, 46mer, 47mer, 48mer, 49mer, 50mer, 51mer, 52mer, 53mer, 54mer, 55mer, 56mer, 57mer, 58mer, 59mer, 60mer, 61mer, 62mer, 63mer, 64mer, 65mer, 66mer, 67mer, 68mer, 69mer, 70mer, or 71mer;

in which the $A_1$ is a first auxiliary part or absent; wherein the first auxiliary part has a linker function, a protective function, a cyclic form forming function, a dummy function, and/or a solubility increasing function, and may optionally have a nonstandard amino acid;

the $A_2$ is a second auxiliary part or absent; wherein the second auxiliary part has a linker function, a protective function, a cyclic form forming function, a dummy function, and/or a solubility increasing function, and may optionally have a nonstandard amino acid;

the $A_3$ is a third auxiliary part or absent; wherein the third auxiliary part has a linker function, a protective function, a cyclic form forming function, a dummy function, and/or a solubility increasing function, and may optionally have a nonstandard amino acid;

the $A_4$ is a fourth auxiliary part or absent; wherein the fourth auxiliary part has a linker function, a protective function, a cyclic form forming function, a dummy function, and/or a solubility increasing function, and may optionally have a nonstandard amino acid;

the B₁, which is a B-cell epitope, is a fragment of apolipoprotein B-100 or a mimotope of apolipoprotein B-100 and can induce an antibody which targets apolipoprotein B-100;

the B₂, which is a B-cell epitope, is a fragment of apolipoprotein B-100 or a mimotope of apolipoprotein B-100 and can induce an antibody which targets apolipoprotein B-100; and the T, which is a Th epitope, can be recognized by CD4+ T-cells and has a length of 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, or 32mer.

Example 86, Combination of Unit-C Sequences

In Example 85, the A₁, A₂, A₃, and A₄ are each independently selected from the group consisting of a, Z, aZ, Za, RN, AF, CR, LS, KT, KH, RF, DP, SV, GL, ZRNV (SEQ ID NO: 36), aZRN (SEQ ID NO: 37), IAFZ (SEQ ID NO: 38), AFZa (SEQ ID NO: 39), RNVP (SEQ ID NO: 40), WIAF (SEQ ID NO: 41), ZCRF (SEQ ID NO: 42), aZCR (SEQ ID NO: 43), YLSZ (SEQ ID NO: 44), LSZa (SEQ ID NO: 45), CRFR (SEQ ID NO: 46), VYLS (SEQ ID NO: 47), ZKTT (SEQ ID NO: 48), aZKT (SEQ ID NO: 49), NKHZ (SEQ ID NO: 50), KHZa (SEQ ID NO: 51), GSHHHHHHGSDDDDK (SEQ ID NO: 52), HHHHHH (SEQ ID NO: 53), MRGSHHHHHHGSDDDDKIVD (SEQ ID NO: 54), GGGGSGGGGGSS (SEQ ID NO: 55), RRRRRR (SEQ ID NO: 159), GSHHHHHHGSDDDDKZa (SEQ ID NO: 193), and aZGSHHHHHHGSDDDDK (SEQ ID NO: 194), or is absent; in which a denotes D-form alanine, and Z denotes 6-aminohexanoic acid;

the B₁ and B₂ each independently have one selected from the group consisting of:

one selected from a group consisting of RNVPPIFNDVYWIAF (SEQ ID NO: 6), CRFRGLISLSQVYLS (SEQ ID NO: 7), KTTKQSFDLSVKAQYKKNKH (SEQ ID NO: 8), RNVPPIFNDVY (SEQ ID NO: 9), CRFRGLISLSQ (SEQ ID NO: 10), KTTKQSFDLSVK (SEQ ID NO: 11), RNVPPIFNDVYW (SEQ ID NO: 12), CRFRGLISLSQV (SEQ ID NO: 13), KTTKQSFDLSVKAQYKK (SEQ ID NO: 14), RNVPPIFNDVYWI (SEQ ID NO: 15), CRFRGLISLSQVY (SEQ ID NO: 16), KTTKQSFDLSVKAQYKKN (SEQ ID NO: 17), PIFNDVYWIAF (SEQ ID NO: 18), GLISLSQVYLS (SEQ ID NO: 19), QSFDLSVKAQYKKNKH (SEQ ID NO: 20), PPIFNDVYWIAF (SEQ ID NO: 21), RGLISLSQVYLS (SEQ ID NO: 22), KQSFDLSVKAQYKKNKH (SEQ ID NO: 23), VPPIFNDVYWIAF (SEQ ID NO: 24), FRGLISLSQVYLS (SEQ ID NO: 25), TKQSFDLSVKAQYKKNKH (SEQ ID NO: 26), NVPPIFNDVYWIA (SEQ ID NO: 27), RFRGLISLSQVYL (SEQ ID NO: 28), TKQSFDLSVKAQYKKN (SEQ ID NO: 29), VPPIFNDVYWI (SEQ ID NO: 30), FRGLISLSQVY (SEQ ID NO: 31), TKQSFDLSVKAQYKKN (SEQ ID NO: 32), PPIFNDVYW (SEQ ID NO: 33), RGLISLSQV (SEQ ID NO: 34), KQSFDLSVKAQYKK (SEQ ID NO: 35), RFRGLISLSQVYLDP (SEQ ID NO: 221), and SVCGCPVGHHDVVGL (SEQ ID NO: 222);

an epitope, which is included in any one of SEQ ID NO: 6 to SEQ ID NO: 35, and SEQ ID NO: 221 to SEQ ID NO: 222; or a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of the sequences represented by SEQ ID NO: 6 to SEQ ID NO: 35, and SEQ ID NO: 221 to SEQ ID NO: 222;

in which "a" denotes D-form alanine, and "Z" denotes 6-aminohexanoic acid;

the T is selected from the group consisting of the following:

one selected from a group consisting of K(Cha)VAAWTLKAA (SEQ ID NO: 1), PKYVKQNTLKLAT (SEQ ID NO: 2), ILMQYIKANSKFIGI (SEQ ID NO: 3), QSIALSSLMVAQAIP (SEQ ID NO: 4), ILMQYIKANSKFIGIPMGLPQSIALSSLMVAQ (SEQ ID NO: 5), PLGFFPDHQL (SEQ ID NO: 162), WPEANQVGAGAFGPGF (SEQ ID NO: 163), MQWNSTALHQALQDP (SEQ ID NO: 164), MQWNSTTFHQTLQDPRVRGLYFPAGG (SEQ ID NO: 165), FFLLTRILTI (SEQ ID NO: 166), FFLLTRILTIPQSLD (SEQ ID NO: 167), TSLNFLGGTTVCLGQ (SEQ ID NO: 168), QSPTSNHSPTSCPPIC (SEQ ID NO: 169), IIFLFILLLCLIFLLVLLD (SEQ ID NO: 170), CTTPAQGNSMFPSC (SEQ ID NO: 171), CTKPTDGN (SEQ ID NO: 172), WASVRFSW (SEQ ID NO: 173), LLPIFFCLW (SEQ ID NO: 174), MDIDPYKEFGATVELLSFLP (SEQ ID NO: 175), FLPSDFFPSV (SEQ ID NO: 176), RDLLDTASALYREALESPEH (SEQ ID NO: 177), PHHTALRQAILCWGELMTLA (SEQ ID NO: 178), GRETVIEYLVSFGVW (SEQ ID NO: 179), EYLVSFGVWIRTPPA (SEQ ID NO: 180), VSFGVWIRTPPAYRPPNAPI (SEQ ID NO: 181), TVVRRRGRSP (SEQ ID NO: 182), VGPLTVNEKRRLKLI (SEQ ID NO: 183), RHYLHTLWKAGILYK (SEQ ID NO: 184), ESRLVVDFSQFSRGN (SEQ ID NO: 185), LQSLTNLLSSNLSWL (SEQ ID NO: 186), SSNLSWLSLDVSAAF (SEQ ID NO: 187), LHLYSHPIILGFRKI (SEQ ID NO: 188), KQCFRKLPVNRPIDW (SEQ ID NO: 189), LCQVFADATPTGWGL (SEQ ID NO: 190), AANWILRGTSFVYVP (SEQ ID NO: 191), EIRLKVFVLGGCRHK (SEQ ID NO: 192), KFVAAWTLKAA (SEQ ID NO: 195), KYVAAWTLKAA (SEQ ID NO: 196), DIEKKIAKMEKASSVFNVVNS (SEQ ID NO: 223), YSGPLKAEIAQRLEDV (SEQ ID NO: 224), K(Cha)VKANTLKAA (SEQ ID NO: 225), K(Cha)VKANTLKAA (SEQ ID NO: 226), K(Cha)VKAWTLKAA (SEQ ID NO: 227), K(Cha)VKAWTLKAA (SEQ ID NO: 228), K(Cha)VWANTLKAA (SEQ ID NO: 229), K(Cha)VWANTLKAA (SEQ ID NO: 230), K(Cha)VWAYTLKAA (SEQ ID NO: 231), K(Cha)VWAVTLKAA (SEQ ID NO: 232), K(Cha)VYAWTLKAA (SEQ ID NO: 233), R(Cha)VYAWTLKAA (SEQ ID NO: 234), VRANTLKAA (SEQ ID NO: 235), K(Cha)
VKAHTLKAA (SEQ ID NO: 236), K(Cha)
VKAHTLKAA (SEQ ID NO: 237), K(Cha)
VAANTLKAA (SEQ ID NO: 238), K(Cha)
VAANTLKAA (SEQ ID NO: 239), K(Cha)
VAAYTLKAA (SEQ ID NO: 240), K(Cha)
VAAYTLKAA (SEQ ID NO: 241), K(Cha)
VAAWTLKAA (SEQ ID NO: 242), K(Cha)
VAAKTLKAA (SEQ ID NO: 243), K(Cha)
VAAHTLKAA (SEQ ID NO: 244), K(Cha)
VAAATLKAA (SEQ ID NO: 245), K(Cha)
VAAWTLKAA (SEQ ID NO: 246), and K(Cha)
VMAATLKAA (SEQ ID NO: 247);
a sequence represented by the following [Formula I] or [Formula II]:

$$\underline{N}\text{-Lys-}X_1\text{-}X_2\text{-Ala-Ala-}X_3\text{-Thr-}X_4\text{-}X_5\text{-Ala-Ala-}\underline{C} \qquad \text{[Formula I]}$$

in which the $X_1$ is tyrosine (Tyr), phenylalanine (Phe), or L-cyclohexylalanine;
the $X_2$ is a hydrophobic amino acid, or leucine (Leu), or isoleucine (Ile);
the $X_3$ is an aromatic or cyclic amino acid, or phenylalanine (Phe), tyrosine (Tyr), or histidine (His);
the $X_4$ is an aliphatic long chain amino acid, or isoleucine (Ile), or valine (Val); and
the $X_5$ is a charged amino acid, or arginine (Arg), leucine (Leu), aspartic acid (Asp), glutamine (Gln), or glycine (Gly);

$$\underline{N}\text{-Lys-}X_1\text{-Val-}X_2\text{-Ala-}X_3\text{-Thr-Leu-Lys-Ala-Ala-}\underline{C} \qquad \text{[Formula II]}$$

in which $X_1$ is tyrosine (Tyr), phenylalanine (Phe), or L-cyclohexylalanine;
the $X_2$ is lysine (Lys), tryptophan (Trp), tyrosine (Tyr), arginine (Arg), alanine (Ala), or methionine (Met); and
the $X_3$ is asparagine (Asn), tryptophan (Trp), tyrosine (Tyr), valine (Val), histidine (His), lysine (Lys), or alanine (Ala); and
a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of the sequences represented by SEQ ID NO: 1 to SEQ ID NO: 5, SEQ ID NO: 162 to SEQ ID NO: 192, SEQ ID NO: 195 to SEQ ID NO: 196, SEQ ID NO: 223 to SEQ ID NO: 247, and [Formula I] or [Formula II];
in which (Cha) denotes L-cyclohexylalanins, and X denotes any standard amino acid.

Example 87, Higher Concept of Unit-D Formula

The peptide unit of any one of Examples 1 and 2, wherein the peptide unit is represented by the following [Formula I] or [Formula II]:

$$A_1\text{-}B\text{-}A_2\text{-}T_1\text{-}A_3\text{-}T_2\text{-}A_4 \qquad \text{[Formula D]}$$

$$A_1\text{-}T_1\text{-}A_2\text{-}T_2\text{-}A_3\text{-}B\text{-}A_4 \qquad \text{[Formula D']}$$

in which the peptide unit is characterized in that it can induce a humoral immunity by being recognized by CD4+ T-cells and has a length of 23mer, 24mer, 25mer, 26mer, 27mer, 28mer, 29mer, 30mer, 31mer, 32mer, 33mer, 34mer, 35mer, 36mer, 37mer, 38mer, 39mer, 40mer, 41mer, 42mer, 43mer, 44mer, 45mer, 46mer, 47mer, 48mer, 49mer, 50mer, 51mer, 52mer, 53mer, 54mer, 55mer, 56mer, 57mer, 58mer, 59mer, 60mer, 61mer, 62mer, 63mer, 64mer, 65mer, 66mer, 67mer, 68mer, 69mer, 70mer, or 71mer;
in which the $A_1$ is a first auxiliary part or absent; wherein the first auxiliary part has a linker function, a protective function, a cyclic form forming function, a dummy function, and/or a solubility increasing function, and may optionally have a nonstandard amino acid;
the $A_2$ is a second auxiliary part or absent; wherein the second auxiliary part has a linker function, a protective function, a cyclic form forming function, a dummy function, and/or a solubility increasing function, and optionally may have a nonstandard amino acid;
the $A_3$ is a third auxiliary part or absent; wherein the third auxiliary part has a linker function, a protective function, a cyclic form forming function, a dummy function, and/or a solubility increasing function, and may optionally have a nonstandard amino acid;
the $A_4$ is a fourth auxiliary part or absent; wherein the fourth auxiliary part has a linker function, a protective function, a cyclic form forming function, a dummy function, and/or a solubility increasing function, and may optionally have a nonstandard amino acid;
the B, which is a B-cell epitope, is a fragment of apolipoprotein B-100 or a mimotope of apolipoprotein B-100 and can induce an antibody which targets apolipoprotein B-100;
the $T_1$, which is a Th epitope, can be recognized by CD4+ T-cells and has a length of 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, or 32mer; and
the $T_2$, which is a Th epitope, can be recognized by CD4+ T-cells and has a length of 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, or 32mer.

Example 88, Combination of Unit-D Sequences

In Example 87,
the $A_1$, $A_2$, $A_3$, and $A_4$ are each independently selected from the group consisting of a, Z, aZ, Za, RN, AF, CR, LS, KT, KH, RF, DP, SV, GL, ZRNV (SEQ ID NO: 36), aZRN (SEQ ID NO: 37), IAFZ (SEQ ID NO: 38), AFZa (SEQ ID NO: 39), RNVP (SEQ ID NO: 40), WIAF (SEQ ID NO: 41), ZCRF (SEQ ID NO: 42), aZCR (SEQ ID NO: 43), YLSZ (SEQ ID NO: 44), LSZa (SEQ ID NO: 45), CRFR (SEQ ID NO: 46), VYLS (SEQ ID NO: 47), ZKTT (SEQ ID NO: 48), aZKT (SEQ ID NO: 49), NKHZ (SEQ ID NO: 50), KHZa (SEQ ID NO: 51), GSHHHHHHGSDDDDK (SEQ ID NO: 52), HHHHHH (SEQ ID NO: 53), MRGSHHHHHHGSDDDDKIVD (SEQ ID NO: 54), GGGGSGGGGGSS (SEQ ID NO: 55), RRRRRR (SEQ ID NO: 159), GSHHHHHHGSDDDDKZa (SEQ ID NO: 193), and aZGSHHHHHHGSDDDDK (SEQ ID NO: 194)), or is absent; in which a denotes D-form alanine, and Z denotes 6-aminohexanoic acid;
the B has:
one selected from the group consisting of RNVPPIFNDVYWIAF (SEQ ID NO: 6), CRFRGLISLSQVYLS (SEQ ID NO: 7), KTTKQSFDLSVKAQYKKNKH (SEQ ID NO: 8), RNVPPIFNDVY (SEQ ID NO: 9), CRFRGLISLSQ (SEQ ID NO: 10), KTTKQSFDLSVK (SEQ ID NO:

11), RNVPPIFNDVYW (SEQ ID NO: 12), CRFRGLISLSQV (SEQ ID NO: 13), KTTKQSFDLSVKAQYKK (SEQ ID NO: 14), RNVPPIFNDVYWI (SEQ ID NO: 15), CRFRGLISLSQVY (SEQ ID NO: 16), KTTKQSFDLSVKAQYKKN (SEQ ID NO: 17), PIFNDVYWIAF (SEQ ID NO: 18), GLISLSQVYLS (SEQ ID NO: 19), QSFDLSVKAQYKKNKH (SEQ ID NO: 20), PPIFNDVYWIAF (SEQ ID NO: 21), RGLISLSQVYLS (SEQ ID NO: 22), KQSFDLSVKAQYKKNKH (SEQ ID NO: 23), VPPIFNDVYWIAF (SEQ ID NO: 24), FRGLISLSQVYLS (SEQ ID NO: 25), TKQSFDLSVKAQYKKNKH (SEQ ID NO: 26), NVPPIFNDVYWIA (SEQ ID NO: 27), RFRGLISLSQVYL (SEQ ID NO: 28), TKQSFDLSVKAQYKKN (SEQ ID NO: 29), VPPIFNDVYWI (SEQ ID NO: 30), FRGLISLSQVY (SEQ ID NO: 31), TKQSFDLSVKAQYKKN (SEQ ID NO: 32), PPIFNDVYW (SEQ ID NO: 33), RGLISLSQV (SEQ ID NO: 34), KQSFDLSVKAQYKK (SEQ ID NO: 35), RFRGLISLSQVYLDP (SEQ ID NO: 221), and SVCGCPVGHHDVVGL (SEQ ID NO: 222);

an epitope, which is included in any one of SEQ ID NO: 6 to SEQ ID NO: 35, and SEQ ID NO: 221 to SEQ ID NO: 222; or a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of the sequences represented by SEQ ID NO: 6 to SEQ ID NO: 35, and SEQ ID NO: 221 to SEQ ID NO: 222;

in which a denotes D-form alanine, and Z denotes 6-aminohexanoic acid;

the $T_1$ and $T_2$ are each independently selected from the group consisting of the following:

one selected from a group consisting of K(Cha)VAAWTLKAA (SEQ ID NO: 1), PKYVKQNTLKLAT (SEQ ID NO: 2), ILMQYIKANSKFIGI (SEQ ID NO: 3), QSIALSSLMVAQAIP (SEQ ID NO: 4), ILMQYIKANSKFIGIPMGLPQSIALSSLMVAQ (SEQ ID NO: 5), PLGFFPDHQL (SEQ ID NO: 162), WPEANQVGAGAFGPGF (SEQ ID NO: 163), MQWNSTALHQALQDP (SEQ ID NO: 164), MQWNSTTFHQTLQDPRVRGLYFPAGG (SEQ ID NO: 165), FFLLTRILTI (SEQ ID NO: 166), FFLLTRILTIPQSLD (SEQ ID NO: 167), TSLNFLGGTTVCLGQ (SEQ ID NO: 168), QSPTSNHSPTSCPPIC (SEQ ID NO: 169), IIFLFILLLCLIFLLVLLD (SEQ ID NO: 170), CTTPAQGNSMFPSC (SEQ ID NO: 171), CTKPTDGN (SEQ ID NO: 172), WASVRFSW (SEQ ID NO: 173), LLPIFFCLW (SEQ ID NO: 174), MDIDPYKEFGATVELLSFLP (SEQ ID NO: 175), FLPSDFFPSV (SEQ ID NO: 176), RDLLDTASALYREALESPEH (SEQ ID NO: 177), PHHTALRQAILCWGELMTLA (SEQ ID NO: 178), GRETVIEYLVSFGVW (SEQ ID NO: 179), EYLVSFGVWIRTPPA (SEQ ID NO: 180), VSFGVWIRTPPAYRPPNAPI (SEQ ID NO: 181), TVVRRRGRSP (SEQ ID NO: 182), VGPLTVNEKRRLKLI (SEQ ID NO: 183), RHYLHTLWKAGILYK (SEQ ID NO: 184), ESRLVVDFSQFSRGN (SEQ ID NO: 185), LQSLTNLLSSNLSWL (SEQ ID NO: 186), SSNLSWLSLDVSAAF (SEQ ID NO: 187), LHLYSHPIILGFRKI (SEQ ID NO: 188), KQCFRKLPVNRPIDW (SEQ ID NO: 189), LCQVFADATPTGWGL (SEQ ID NO: 190), AANWILRGTSFVYVP (SEQ ID NO: 191), EIRLKVFVLGGCRHK (SEQ ID NO: 192), KFVAAWTLKAA (SEQ ID NO: 195), KYVAAWTLKAA (SEQ ID NO: 196), DIEKKIAKMEKASSVFNVVNS (SEQ ID NO: 223), YSGPLKAEIAQRLEDV (SEQ ID NO: 224), K(Cha)VKANTLKAA (SEQ ID NO: 225), K(Cha) VKANTLKAA (SEQ ID NO: 226), K(Cha) VKAWTLKAA (SEQ ID NO: 227), K(Cha) VKAWTLKAA (SEQ ID NO: 228), K(Cha) VWANTLKAA (SEQ ID NO: 229), K(Cha) VWANTLKAA (SEQ ID NO: 230), K(Cha) VWAYTLKAA (SEQ ID NO: 231), K(Cha) VWAVTLKAA (SEQ ID NO: 232), K(Cha) VYAWTLKAA (SEQ ID NO: 233), K(Cha) VYAWTLKAA (SEQ ID NO: 234), R(Cha) VRANTLKAA (SEQ ID NO: 235), K(Cha) VKAHTLKAA (SEQ ID NO: 236), K(Cha) VKAHTLKAA (SEQ ID NO: 237), K(Cha) VAANTLKAA (SEQ ID NO: 238), K(Cha) VAANTLKAA (SEQ ID NO: 239), K(Cha) VAAYTLKAA (SEQ ID NO: 240), K(Cha) VAAYTLKAA (SEQ ID NO: 241), K(Cha) VAAWTLKAA (SEQ ID NO: 242), K(Cha) VAAKTLKAA (SEQ ID NO: 243), K(Cha) VAAHTLKAA (SEQ ID NO: 244), K(Cha) VAAATLKAA (SEQ ID NO: 245), K(Cha) VAAWTLKAA (SEQ ID NO: 246), and K(Cha) VMAATLKAA (SEQ ID NO: 247);

a sequence represented by the following [Formula I] or [Formula II]:

N-Lys-$X_1$-$X_2$-Ala-Ala-$X_3$-Thr-$X_4$-$X_5$-Ala-Ala-C   [Formula I]

in which the $X_1$ is tyrosine (Tyr), phenylalanine (Phe), or L-cyclohexylalanine;

the $X_2$ is a hydrophobic amino acid, or leucine (Leu), or isoleucine (Ile);

the $X_3$ is an aromatic or cyclic amino acid, or phenylalanine (Phe), tyrosine (Tyr), or histidine (His);

the $X_4$ is an aliphatic long chain amino acid, or isoleucine (Ile), or valine (Val); and the $X_5$ is a charged amino acid, or arginine (Arg), leucine (Leu), aspartic acid (Asp), glutamine (Gln), or glycine (Gly);

N-Lys-$X_1$-Val-$X_2$-Ala-$X_3$-Thr-Leu-Lys-Ala-Ala-C   [Formula II]

in which the $X_1$ is tyrosine (Tyr), phenylalanine (Phe), or L-cyclohexylalanine;

the $X_2$ is lysine (Lys), tryptophan (Trp), tyrosine (Tyr), arginine (Arg), alanine (Ala), or methionine (Met);

the $X_3$ is asparagine (Asn), tryptophan (Trp), tyrosine (Tyr), valine (Val), histidine (His), lysine (Lys), or alanine (Ala); and a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of the sequences represented by SEQ ID NO: 1 to SEQ ID NO: 5, SEQ ID NO: 162 to SEQ ID NO: 192, SEQ ID NO: 195 to SEQ ID NO: 196, SEQ ID NO: 223 to SEQ ID NO: 247, and [Formula I] or [Formula II];

in which (Cha) denotes L-cyclohexylalanins, and X denotes any standard amino acid.

Example 89, Higher Concept of Unit-E Formula

The peptide unit of any one of Examples 1 and 2, wherein the peptide unit is represented by the following [Formula E]:

$A_1$-$B_1$-$A_2$-$T_1$-$A_3$-$T_2$-$A_4$-$B_2$-$A_5$    [Formula E]

in which the peptide unit is one which can induce a humoral immunity by being recognized by CD4+ T-cells and has a length of 23mer, 24mer, 25mer, 26mer, 27mer, 28mer, 29mer, 30mer, 31mer, 32mer, 33mer, 34mer, 35mer, 36mer, 37mer, 38mer, 39mer, 40mer, 41mer, 42mer, 43mer, 44mer, 45mer, 46mer, 47mer, 48mer, 49mer, 50mer, 51mer, 52mer, 53mer, 54mer, 55mer, 56mer, 57mer, 58mer, 59mer, 60mer, 61mer, 62mer, 63mer, 64mer, 65mer, 66mer, 67mer, 68mer, 69mer, 70mer, or 71mer;

in which the $A_1$ is a first auxiliary part or absent; wherein the first auxiliary part has a linker function, a protective function, a cyclic form forming function, a dummy function, and/or a solubility increasing function, and may optionally have a nonstandard amino acid;

the $A_2$ is a second auxiliary part or absent; wherein the second auxiliary part has a linker function, a protective function, a cyclic form forming function, a dummy function, and/or a solubility increasing function, and optionally may have a nonstandard amino acid;

the $A_3$ is a third auxiliary part or absent; wherein the third auxiliary part has a linker function, a protective function, a cyclic form forming function, a dummy function, and/or a solubility increasing function, and may optionally have a nonstandard amino acid;

the $A_4$ is a fourth auxiliary part or absent; wherein the fourth auxiliary part has a linker function, a protective function, a cyclic form forming function, a dummy function, and/or a solubility increasing function, and may optionally have a nonstandard amino acid;

the $B_1$, which is a B-cell epitope, is a fragment of apolipoprotein B-100 or a mimotope of apolipoprotein B-100 and can induce an antibody which targets apolipoprotein B-100;

the $B_2$, which is a B-cell epitope, is a fragment of apolipoprotein B-100 or a mimotope of apolipoprotein B-100 and can induce an antibody which targets apolipoprotein B-100;

the $T_1$, which is a Th epitope, is characterized in that it can be recognized by CD4+ T-cells and has a length of 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, or 32mer; and the $T_2$, which is a Th epitope, is characterized in that it can be recognized by CD4+ T-cells and has a length of 8mer, 9mer, 10mer, 11mer, 12mer, 13mer, 14mer, 15mer, 16mer, 17mer, 18mer, 19mer, 20mer, 21mer, 22mer, 23mer, 24mer, 25mer, 26mer, 27mer, 28mer, 29mer, 30mer, 31mer, or 32mer.

Example 90, Combination of Unit-E Sequences

In Example 89,
the $A_1$, $A_2$, $A_3$, and $A_4$ are each independently selected from the group consisting of a, Z, aZ, Za, RN, AF, CR, LS, KT, KH, RF, DP, SV, GL, ZRNV (SEQ ID NO: 36), aZRN (SEQ ID NO: 37), IAFZ (SEQ ID NO: 38), AFZa (SEQ ID NO: 39), RNVP (SEQ ID NO: 40), WIAF (SEQ ID NO: 41), ZCRF (SEQ ID NO: 42), aZCR (SEQ ID NO: 43), YLSZ (SEQ ID NO: 44), LSZa (SEQ ID NO: 45), CRFR (SEQ ID NO: 46), VYLS (SEQ ID NO: 47), ZKTT (SEQ ID NO: 48), aZKT (SEQ ID NO: 49), NKHZ (SEQ ID NO: 50), KHZa (SEQ ID NO: 51), GSHHHHHHGSDDDDK (SEQ ID NO: 52), HHHHHH (SEQ ID NO: 53), MRGSHHHHHHGSDDDDKIVD (SEQ ID NO: 54), GGGGSGGGGGGSS (SEQ ID NO: 55), RRRRRR (SEQ ID NO: 159), GSHHHHHHGSDDDDKZa (SEQ ID NO: 193), and aZGSHHHHHHGSDDDDK (SEQ ID NO: 194), or is absent; in which a denotes D-form alanine, and Z denotes 6-aminohexanoic acid;

the $B_1$ and $B_2$ each independently have one selected from the group consisting of, one selected from a group consisting of RNVPPIFNDVYWIAF (SEQ ID NO: 6), CRFRGLISLSQVYLS (SEQ ID NO: 7), KTTKQSFDLSVKAQYKKNKH (SEQ ID NO: 8), RNVPPIFNDVY (SEQ ID NO: 9), CRFRGLISLSQ (SEQ ID NO: 10), KTTKQSFDLSVK (SEQ ID NO: 11), RNVPPIFNDVYW (SEQ ID NO: 12), CRFRGLISLSQV (SEQ ID NO: 13), KTTKQSFDLSVKAQYKK (SEQ ID NO: 14), RNVPPIFNDVYWI (SEQ ID NO: 15), CRFRGLISLSQVY (SEQ ID NO: 16), KTTKQSFDLSVKAQYKKN (SEQ ID NO: 17), PIFNDVYWIAF (SEQ ID NO: 18), GLISLSQVYLS (SEQ ID NO: 19), QSFDLSVKAQYKKNKH (SEQ ID NO: 20), PPIFNDVYWIAF (SEQ ID NO: 21), RGLISLSQVYLS (SEQ ID NO: 22), KQSFDLSVKAQYKKNKH (SEQ ID NO: 23), VPPIFNDVYWIAF (SEQ ID NO: 24), FRGLISLSQVYLS (SEQ ID NO: 25), TKQSFDLSVKAQYKKNKH (SEQ ID NO: 26), NVPPIFNDVYWIA (SEQ ID NO: 27), RFRGLISLSQVYL (SEQ ID NO: 28), TKQSFDLSVKAQYKKN (SEQ ID NO: 29), VPPIFNDVYWI (SEQ ID NO: 30), FRGLISLSQVY (SEQ ID NO: 31), TKQSFDLSVKAQYKKN (SEQ ID NO: 32), PPIFNDVYW (SEQ ID NO: 33), RGLISLSQV (SEQ ID NO: 34), KQSFDLSVKAQYKK (SEQ ID NO: 35), RFRGLISLSQVYLDP (SEQ ID NO: 221), and SVCGCPVGHHDVVGL (SEQ ID NO: 222);

an epitope, which is included in any one of SEQ ID NO: 6 to SEQ ID NO: 35, and SEQ ID NO: 221 to SEQ ID NO: 222; or a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of the sequences represented by SEQ ID NO: 6 to SEQ ID NO: 35, and SEQ ID NO: 221 to SEQ ID NO: 222;

in which a denotes D-form alanine, and Z denotes 6-aminohexanoic acid;

the $T_1$ and $T_2$ are each independently selected from the group consisting of the following:

one selected from a group consisting of K(Cha)VAAWTLKAA (SEQ ID NO: 1), PKYVKQNTLKLAT (SEQ ID NO: 2), ILMQYIKANSKFIGI (SEQ ID NO: 3), QSIALSSLMVAQAIP (SEQ ID NO: 4), ILMQYIKANSKFIGIPMGLPQSIALSSLMVAQ (SEQ ID NO: 5), PLGFFPDHQL (SEQ ID NO: 162), WPEANQVGAGAFGPGF (SEQ ID NO: 163), MQWNSTALHQALQDP (SEQ ID NO: 164), MQWNSTTFHQTLQDPRVRGLYFPAGG (SEQ ID NO: 165), FFLLTRILTI (SEQ ID NO: 166), FFLLTRILTIPQSLD (SEQ ID NO: 167), TSLNFLGGTTVCLGQ (SEQ ID NO: 168), QSPTSNHSPTSCPPIC (SEQ ID NO: 169), IIFLFILLLCLIFLLVLLD (SEQ ID NO: 170), CTTPAQGNSMFPSC (SEQ ID NO: 171), CTKPTDGN (SEQ ID NO: 172), WASVRFSW (SEQ ID NO: 173), LLPIFFCLW (SEQ ID NO: 174), MDIDPYKEFGATVELLSFLP (SEQ ID NO: 175), FLPSDFFPSV (SEQ ID NO: 176), RDLLDTASALYREALESPEH (SEQ ID NO: 177), PHHTALRQAILCWGELMTLA (SEQ ID NO: 178), GRETVIEYLVSFGVW (SEQ ID NO: 179), EYLVSFGVWIRTPPA (SEQ ID NO: 180), VSFGVWIRTPPAYRPPNAPI (SEQ ID NO: 181), TVVRRRGRSP (SEQ ID NO: 182), VGPLTVNEKRRLKLI (SEQ ID NO: 183), RHYLHTLWKAGILYK (SEQ ID NO: 184), ESRLVVDFSQFSRGN (SEQ ID NO: 185), LQSLTNLLSSNLSWL (SEQ ID NO: 186), SSNLSWLSLDVSAAF (SEQ ID NO: 187), LHLYSHPIILGFRKI (SEQ ID NO: 188), KQCFRKLPVNRPIDW (SEQ ID NO: 189), LCQVFADATPTGWGL (SEQ ID NO: 190), AANWILRGTSFVYVP (SEQ ID NO: 191), EIRLKVFVLGGCRHK (SEQ ID NO: 192), KFVAAWTLKAA (SEQ ID NO: 195), KYVAAWTLKAA (SEQ ID NO: 196), DIEKKIAKMEKASSVFNVVNS (SEQ ID NO: 223), YSGPLKAEIAQRLEDV (SEQ ID NO: 224), K(Cha)VKANTLKAA (SEQ ID NO: 225), K(Cha)VKANTLKAA (SEQ ID NO: 226), K(Cha)VKAWTLKAA (SEQ ID NO: 227), K(Cha)VKAWTLKAA (SEQ ID NO: 228), K(Cha)VWANTLKAA (SEQ ID NO: 229), K(Cha)VWANTLKAA (SEQ ID NO: 230), K(Cha)VWAYTLKAA (SEQ ID NO: 231), K(Cha)VWAVTLKAA (SEQ ID NO: 232), K(Cha)VYAWTLKAA (SEQ ID NO: 233), K(Cha)VYAWTLKAA (SEQ ID NO: 234), R(Cha)VRANTLKAA (SEQ ID NO: 235), K(Cha)VKAHTLKAA (SEQ ID NO: 236), K(Cha)VKAHTLKAA (SEQ ID NO: 237), K(Cha)VAANTLKAA (SEQ ID NO: 238), K(Cha)VAANTLKAA (SEQ ID NO: 239), K(Cha)VAAYTLKAA (SEQ ID NO: 240), K(Cha)VAAYTLKAA (SEQ ID NO: 241), K(Cha)VAAWTLKAA (SEQ ID NO: 242), K(Cha)VAAKTLKAA (SEQ ID NO: 243), K(Cha)VAAHTLKAA (SEQ ID NO: 244), K(Cha)VAAATLKAA (SEQ ID NO: 245), K(Cha)VAAWTLKAA (SEQ ID NO: 246), and K(Cha)VMAATLKAA (SEQ ID NO: 247);

a sequence represented by the following [Formula I] or [Formula II]:

N-Lys-$X_1$-$X_2$-Ala-Ala-$X_3$-Thr-$X_4$-$X_5$-Ala-Ala-C        [Formula I]

in which the $X_1$ is tyrosine (Tyr), phenylalanine (Phe), or L-cyclohexylalanine;
the $X_2$ is a hydrophobic amino acid, or leucine (Leu), or isoleucine (Ile);
the $X_3$ is an aromatic or cyclic amino acid, or phenylalanine (Phe), tyrosine (Tyr), or histidine (His);
the $X_4$ is an aliphatic long chain amino acid, or isoleucine (Ile), or valine (Val); and
the $X_5$ is a charged amino acid, or arginine (Arg), leucine (Leu), aspartic acid (Asp), glutamine (Gln), or glycine (Gly);

N-Lys-$X_1$-Val-$X_2$-Ala-$X_3$-Thr-Leu-Lys-Ala-Ala-C:        [Formula II]

in which $X_1$ is tyrosine (Tyr), phenylalanine (Phe), or L-cyclohexylalanine;
the $X_2$ is lysine (Lys), tryptophan (Trp), tyrosine (Tyr), arginine (Arg), alanine (Ala), or methionine (Met); and
the $X_3$ is asparagine (Asn), tryptophan (Trp), tyrosine (Tyr), valine (Val), histidine (His), lysine (Lys), or alanine (Ala); and a sequence which matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one of the sequences represented by SEQ ID NO: 1 to SEQ ID NO: 5, SEQ ID NO: 162 to SEQ ID NO: 192, SEQ ID NO: 195 to SEQ ID NO: 196, SEQ ID NO: 223 to SEQ ID NO: 247, and [Formula I] or [Formula II];

in which (Cha) denotes L-cyclohexylalanins, and X denotes any standard amino acid.

Peptide Including Peptide Unit

Example 91, Peptide Including 2 or More Peptide Units

A peptide, in which 2 or more peptide units of any one of Examples 1 to 90 are linked.

Example 92, Peptide Including Two to Eight Peptide Units

A peptide, in which 2, 3, 4, 5, 6, 7, or 8 of peptide units of any one of Examples 1 to 90 are linked.

Example 93, Concatemer Sequence

The peptide of Example 91, wherein each of the peptide units has the same or equivalent sequence.

Example 94, String of Beads

The peptide of Example 91, wherein each of the peptide units has a different sequence.

Example 95, Cyclic Form

The peptide of Example 91, in which the peptide is characterized in that it further includes an auxiliary part having a cyclic-form-forming function at the N-terminus and C-terminus, and the peptide forms a cyclic form through the auxiliary part.

Nucleic Acid Encoding Peptide Unit and/or Peptide

Example 96, Encoding Nucleic Acid, not Including Nonstandard Amino Acid

A nucleic acid which encodes a peptide unit of any one of Examples 1 to 6 and/or a peptide of any one of Example 91 to Example 95, in which the peptide unit and the peptide do not include a nonstandard amino acid.

Example 97, Encoding Nucleic Acid of Each Unit Formula, not Including Nonstandard Amino Acid A nucleic acid, which encodes a peptide unit of any one of Example 7 to Example 10, Example 14 to Example 18, Example 22, Example 26 to Example 30, Example 34, Example 38 to Example 41, Example 45, Example 49 to Example 54, Example 58 to Example 60, Example 64, Example 68, and Example 72, in which the peptide unit is characterized in that it does not include a nonstandard amino acid.

Example 98, Limitation on Sequence of Unit Peptide

The nucleic acid of any one of Examples 96 and 97, wherein the nucleic acid encoding a peptide unit selected from the following: RNVPPIFNDVYWIAFXXKXVAAWTLKAAXXCRFRGLISLSQVYLS (SEQ ID NO: 198); RNVPPIFNDVYWIAFXXKXVAAWTLKAAXXGSHHHHHHGSDDDDK (SEQ ID NO: 199); GSHHHHHHGSDDDDKXXKXVAAWTLKAAXXRNVPPIFNDVYWIAF (SEQ ID NO: 200); KTTKQSFDLSVKAQYKKNKHXXKXVAAWTLKAAXXCRFRGLISLSQVYLS (SEQ ID NO: 201); RNVPPIFNDVYWIAFCRFRGLISLSQVYLSXXKXVAAWTLKAAXX (SEQ ID NO: 202); RNVPPIFNDVYWIAFXPKYVKQNTLKLATXCRFRGLISLSQVYLS (SEQ ID NO: 203); RNVPPIFNDVYWIAFXXKXVAAWTLKAAXX (SEQ ID NO: 204); RNVPPIFNDVYWIAFKXVAAWTLKAA (SEQ ID NO: 205); RNVPPIFNDVYWIAFKXVAAWTLKAAHHHHHH (SEQ ID NO: 206); RNVPPIFNDVYWIAFXXKXVAAWTLKAACRFRGLISLSQVYLS (SEQ ID NO: 207); RNVPPIFNDVYWIAFXXKXVAAWTLKAACR (SEQ ID NO: 208); RNVPPIFNDVYWIAFXXKFVAAWTLKAAXXCRFRGLISLSQVYLS (SEQ ID NO: 209); RNVPPIFNDVYWIAFXXKFVAAWTLKAAXX (SEQ ID NO: 210); RNVPPIFNDVYWIAFXXKFVAAWTLKAACRFRGLISLSQVYLS (SEQ ID NO: 211); and RNVPPIFNDVYWIAFXXKFVAAWTLKAACR (SEQ ID NO: 212), in which the X denotes any standard amino acid.

Example 99, Limitation on Sequence of Unit-Encoding DNA

The nucleic acid of Example 98, a DNA which is represented by a sequence selected from the following:

```
                                              (SEQ ID NO: 248)
5'-CGTAATGTTCCTCCTATCTTCAATGATGTTTATTGGATTGCATTCNNNNNNAAG

NNNGTGGCAGCTTGGACCCTGAAGGCAGCANNNNNNNTGCCGTTTCCGTGGAC

TGATTTCCCTGTCCCAGGTTTATCTGTCC-3';

(SEQ ID NO: 249)
5'-CGTAATGTTCCTCCTATCTTCAATGATGTTTATTGGATTGCATTCNNNNNNAAG

TTCGTGGCAGCTTGGACCCTGAAGGCAGCANNNNNNNTGCCGTTTCCGTGGACT

GATTTCCCTGTCCCAGGTTTATCTGTCC-3';

(SEQ ID NO: 250)
5'-CGTAATGTTCCTCCTATCTTCAATGATGTTTATTGGATTGCATTCNNNNNNAAG

TATGTGGCAGCTTGGACCCTGAAGGCAGCANNNNNNNTGCCGTTTCCGTGGACT

GATTTCCCTGTCCCAGGTTTATCTGTCC-3';

(SEQ ID NO: 251)
5'-CGTAATGTTCCTCCTATCTTCAATGATGTTTATTGGATTGCATTCNNNNNNAAG

NNNGTGGCAGCTTGGACCCTGAAGGCAGCANNNNNNNGGATCGCATCACCATC

ACCATCACGGATCCGATGATGATGACAAG-3';

(SEQ ID NO: 252)
5'-ACGTAATGTTCCTCCTATCTTCAATGATGTTTATTGGATTGCATTCNNNNNNAA

GTTCGTGGCAGCTTGGACCCTGAAGGCAGCANNNNNNNGGATCGCATCACCAT

CACCATCACGGATCCGATGATGATGACAAG-3';

(SEQ ID NO: 253)
5'-CGTAATGTTCCTCCTATCTTCAATGATGTTTATTGGATTGCATTCNNNNNNAAG

TATGTGGCAGCTTGGACCCTGAAGGCAGCANNNNNNNGGATCGCATCACCATC

ACCATCACGGATCCGATGATGATGACAAG-3';

(SEQ ID NO: 254)
5'-GGATCGCATCACCATCACCATCACGGATCCGATGATGATGACAAGNNNNNNA

AGNNNNGTGGCAGCTTGGACCCTGAAGGCAGCANNNNNNNCGTAATGTTCCTCC

TATCTTCAATGATGTTTATTGGATTGCATTC-3';
```

```
                                              (SEQ ID NO: 255)
5'-GGATCGCATCACCATCACCATCACGGATCCGATGATGATGACAAGNNNNNNA

AGTTCGTGGCAGCTTGGACCCTGAAGGCAGCANNNNNNCGTAATGTTCCTCCT

ATCTTCAATGATGTTTATTGGATTGCATTC-3';

(SEQ ID NO: 256)
5'-GGATCGCATCACCATCACCATCACGGATCCGATGATGATGACAAGNNNNNNA

AGTATGTGGCAGCTTGGACCCTGAAGGCAGCANNNNNNCGTAATGTTCCTCCT

ATCTTCAATGATGTTTATTGGATTGCATTC-3';

(SEQ ID NO: 257)
5'-AAAACGACAAAGCAATCATTTGATTTAAGTGTAAAAGCTCAGTATNNNNNNA

AGNNNGTGGCAGCTTGGACCCTGAAGGCAGCANNNNNNTGCCGTTTCCGTGG

ACTGATTTCCCTGTCCCAGGTTTATCTGTCC-3';

(SEQ ID NO: 258)
5'-AAAACGACAAAGCAATCATTTGATTTAAGTGTAAAAGCTCAGTATNNNNNNA

AGTTCGTGGCAGCTTGGACCCTGAAGGCAGCANNNNNNTGCCGTTTCCGTGGA

CTGATTTCCCTGTCCCAGGTTTATCTGTCC-3';

(SEQ ID NO: 259)
5'-AAAACGACAAAGCAATCATTTGATTTAAGTGTAAAAGCTCAGTATNNNNNNA

AGTATGTGGCAGCTTGGACCCTGAAGGCAGCANNNNNNTGCCGTTTCCGTGG

ACTGATTTCCCTGTCCCAGGTTTATCTGTCC-3';

(SEQ ID NO: 260)
5'-CGTAATGTTCCTCCTATCTTCAATGATGTTTATTGGATTGCATTCTGCCGTTTCC

GTGGACTGATTTCCCTGTCCCAGGTTTATCTGTCCNNNNNNNAAGNNNGTGGCA

GCTTGGACCCTGAAGGCAGCANNNNNN-3';

(SEQ ID NO: 261)
5'-CGTAATGTTCCTCCTATCTTCAATGATGTTTATTGGATTGCATTCTGCCGTTTCC

GTGGACTGATTTCCCTGTCCCAGGTTTATCTGTCCNNNNNNNAAGTTCGTGGCA

GCTTGGACCCTGAAGGCAGCANNNNNN-3';

(SEQ ID NO: 262)
5'-CGTAATGTTCCTCCTATCTTCAATGATGTTTATTGGATTGCATTCTGCCGTTTCC

GTGGACTGATTTCCCTGTCCCAGGTTTATCTGTCCNNNNNNNAAGTATGTGGCA

GCTTGGACCCTGAAGGCAGCANNNNNN-3';

(SEQ ID NO: 263)
5'-CGTAATGTTCCTCCTATCTTCAATGATGTTTATTGGATTGCATTCNNNCCTAAG

TATGTGAAGCAGAATACACTGAAGCTGGCAACCNNNTGCCGTTTCCGTGGACT

GATTTCCCTGTCCCAGGTTTATCTGTCC-3';

(SEQ ID NO: 264)
5'-CGTAATGTTCCTCCTATCTTCAATGATGTTTATTGGATTGCATTCNNNNNNAAG

NNNGTGGCAGCTTGGACCCTGAAGGCAGCANNNNNN-3';

(SEQ ID NO: 265)
5'-CGTAATGTTCCTCCTATCTTCAATGATGTTTATTGGATTGCATTCNNNNNNAAG

TTCGTGGCAGCTTGGACCCTGAAGGCAGCANNNNNN-3';

(SEQ ID NO: 266)
5'-CGTAATGTTCCTCCTATCTTCAATGATGTTTATTGGATTGCATTCNNNNNNAAG

TATGTGGCAGCTTGGACCCTGAAGGCAGCANNNNNN-3';
```

-continued (SEQ ID NO: 267)
5'-CGTAATGTTCCTCCTATCTTCAATGATGTTTATTGGATTGCATTCAAGNNNGTGGCAGCTTGGACCCTGAAGGCAGCA-3';

(SEQ ID NO: 268)
5'-CGTAATGTTCCTCCTATCTTCAATGATGTTTATTGGATTGCATTCAAGTTCGTGGCAGCTTGGACCCTGAAGGCAGCA-3';

(SEQ ID NO: 269)
5'-CGTAATGTTCCTCCTATCTTCAATGATGTTTATTGGATTGCATTCAAGTATGTGGCAGCTTGGACCCTGAAGGCAGCA-3';

(SEQ ID NO: 270)
5'-CGTAATGTTCCTCCTATCTTCAATGATGTTTATTGGATTGCATTCAAGNNNGTGGCAGCTTGGACCCTGAAGGCAGCACATCACCATCACCATCAC-3';

(SEQ ID NO: 271)
5'-CGTAATGTTCCTCCTATCTTCAATGATGTTTATTGGATTGCATTCAAGTTCGTGGCAGCTTGGACCCTGAAGGCAGCACATCACCATCACCATCAC-3';

(SEQ ID NO: 272)
5'-CGTAATGTTCCTCCTATCTTCAATGATGTTTATTGGATTGCATTCAAGTATGTGGCAGCTTGGACCCTGAAGGCAGCACATCACCATCACCATCAC-3';

(SEQ ID NO: 273)
5'-CGTAATGTTCCTCCTATCTTCAATGATGTTTATTGGATTGCATTCNNNNNNAAGNNNGTGGCAGCTTGGACCCTGAAGGCAGCATGCCGTTTCCGTGGACTGATTTCCCTGTCCCAGGTTTATCTGTCC-3';

(SEQ ID NO: 274)
5'-CGTAATGTTCCTCCTATCTTCAATGATGTTTATTGGATTGCATTCNNNNNNAAGTTCGTGGCAGCTTGGACCCTGAAGGCAGCATGCCGTTTCCGTGGACTGATTTCCCTGTCCCAGGTTTATCTGTCC-3';

(SEQ ID NO: 275)
5'-CGTAATGTTCCTCCTATCTTCAATGATGTTTATTGGATTGCATTCNNNNNNAAGTATGTGGCAGCTTGGACCCTGAAGGCAGCATGCCGTTTCCGTGGACTGATTTCCCTGTCCCAGGTTTATCTGTCC-3';

(SEQ ID NO: 276)
5'-CGTAATGTTCCTCCTATCTTCAATGATGTTTATTGGATTGCATTCNNNNNNAAGNNNGTGGCAGCTTGGACCCTGAAGGCAGCATGCCGT-3';

(SEQ ID NO: 277)
5'-CGTAATGTTCCTCCTATCTTCAATGATGTTTATTGGATTGCATTCNNNNNNAAGTTCGTGGCAGCTTGGACCCTGAAGGCAGCATGCCGT-3';
and (SEQ ID NO: 278)
5'-CGTAATGTTCCTCCTATCTTCAATGATGTTTATTGGATTGCATTCNNNNNNAAGTATGTGGCAGCTTGGACCCTGAAGGCAGCATGCCGT-3'.

Example 100, Limitation on Sequence of Unit-Encoding RNA

The nucleic acid of Example 98, a RNA represented by a sequence selected from the following:

(SEQ ID NO: 279)
5'-CGUAAUGUUCCUCCUAUCUUCAAUGAUGUUUAUUGGAUUGCAUUCNNNNNN
AAGNNNGUGGCAGCUUGGACCCUGAAGGCAGCANNNNNNUGCCGUUUCCGU
GGACUGAUUUCCCUGUCCCAGGUUUAUCUGUCC-3';

(SEQ ID NO: 280)
5'-CGUAAUGUUCCUCCUAUCUUCAAUGAUGUUUAUUGGAUUGCAUUCNNNNNN
AAGUUCGUGGCAGCUUGGACCCUGAAGGCAGCANNNNNNUGCCGUUUCCGU
GGACUGAUUUCCCUGUCCCAGGUUUAUCUGUCC-3';

(SEQ ID NO: 281)
5'-CGUAAUGUUCCUCCUAUCUUCAAUGAUGUUUAUUGGAUUGCAUUCNNNNNN
AAGUAUGUGGCAGCUUGGACCCUGAAGGCAGCANNNNNNUGCCGUUUCCGU
GGACUGAUUUCCCUGUCCCAGGUUUAUCUGUCC-3';

(SEQ ID NO: 282)
5'-CGUAAUGUUCCUCCUAUCUUCAAUGAUGUUUAUUGGAUUGCAUUCNNNNNN
AAGNNNGUGGCAGCUUGGACCCUGAAGGCAGCANNNNNNGGAUCGCAUCAC
CAUCACCAUCACGGAUCCGAUGAUGAUGACAAG-3';

(SEQ ID NO: 283)
5'-CGUAAUGUUCCUCCUAUCUUCAAUGAUGUUUAUUGGAUUGCAUUCNNNNNN
AAGUUCGUGGCAGCUUGGACCCUGAAGGCAGCANNNNNNGGAUCGCAUCAC
CAUCACCAUCACGGAUCCGAUGAUGAUGACAAG-3';

(SEQ ID NO: 284)
5'-CGUAAUGUUCCUCCUAUCUUCAAUGAUGUUUAUUGGAUUGCAUUCNNNNNN
AAGUAUGUGGCAGCUUGGACCCUGAAGGCAGCANNNNNNGGAUCGCAUCAC
CAUCACCAUCACGGAUCCGAUGAUGAUGACAAG-3';

(SEQ ID NO: 285)
5'-GGAUCGCAUCACCAUCACCAUCACGGAUCCGAUGAUGAUGACAAGNNNNNN
AAGNNNGUGGCAGCUUGGACCCUGAAGGCAGCANNNNNNCGUAAUGUUCCU
CCUAUCUUCAAUGAUGUUUAUUGGAUUGCAUUC-3';

(SEQ ID NO: 286)
5'-GGAUCGCAUCACCAUCACCAUCACGGAUCCGAUGAUGAUGACAAGNNNNNN
AAGUUCGUGGCAGCUUGGACCCUGAAGGCAGCANNNNNNCGUAAUGUUCCU
CCUAUCUUCAAUGAUGUUUAUUGGAUUGCAUUC-3';

(SEQ ID NO: 287)
5'-GGAUCGCAUCACCAUCACCAUCACGGAUCCGAUGAUGAUGACAAGNNNNNN
AAGUAUGUGGCAGCUUGGACCCUGAAGGCAGCANNNNNNCGUAAUGUUCCU
CCUAUCUUCAAUGAUGUUUAUUGGAUUGCAUUC-3';

(SEQ ID NO: 288)
5'-AAAACGACAAAGCAAUCAUUUGAUUUAAGUGUAAAAGCUCAGUAUNNNNN
NAAGNNNGUGGCAGCUUGGACCCUGAAGGCAGCANNNNNNUGCCGUUUCCG
UGGACUGAUUUCCCUGUCCCAGGUUUAUCUGUCC-3';

```
                                                     (SEQ ID NO: 289)
5'-AAAACGACAAAGCAAUCAUUUGAUUUAAGUGUAAAAGCUCAGUAUNNNNN

NAAGUUCGUGGCAGCUUGGACCCUGAAGGCAGCANNNNNNUGCCGUUUCCG

UGGACUGAUUUCCCUGUCCCAGGUUUAUCUGUCC-3';

(SEQ ID NO: 290)
5'-AAAACGACAAAGCAAUCAUUUGAUUUAAGUGUAAAAGCUCAGUAUNNNNN

NAAGUAUGUGGCAGCUUGGACCCUGAAGGCAGCANNNNNNUGCCGUUUCCG

UGGACUGAUUUCCCUGUCCCAGGUUUAUCUGUCC-3';

(SEQ ID NO: 291)
5'-CGUAAUGUUCCUCCUAUCUUCAAUGAUGUUUAUUGGAUUGCAUUCUGCCGU

UUCCGUGGACUGAUUUCCCUGUCCCAGGUUUAUCUGUCCNNNNNNAAGNNN

GUGGCAGCUUGGACCCUGAAGGCAGCANNNNNN-3';

(SEQ ID NO: 292)
5'-CGUAAUGUUCCUCCUAUCUUCAAUGAUGUUUAUUGGAUUGCAUUCUGCCGU

UUCCGUGGACUGAUUUCCCUGUCCCAGGUUUAUCUGUCCNNNNNNAAGUUC

GUGGCAGCUUGGACCCUGAAGGCAGCANNNNNN-3';

(SEQ ID NO: 293)
5'-CGUAAUGUUCCUCCUAUCUUCAAUGAUGUUUAUUGGAUUGCAUUCUGCCGU

UUCCGUGGACUGAUUUCCCUGUCCCAGGUUUAUCUGUCCNNNNNNAAGUAU

GUGGCAGCUUGGACCCUGAAGGCAGCANNNNNN-3';

(SEQ ID NO: 294)
5'-CGUAAUGUUCCUCCUAUCUUCAAUGAUGUUUAUUGGAUUGCAUUCNNNCCU

AAGUAUGUGAAGCAGAAUACACUGAAGCUGGCAACCNNNUGCCGUUUCCGU

GGACUGAUUUCCCUGUCCCAGGUUUAUCUGUCC-3';

(SEQ ID NO: 295)
5'-CGUAAUGUUCCUCCUAUCUUCAAUGAUGUUUAUUGGAUUGCAUUCNNNNNN

AAGNNNGUGGCAGCUUGGACCCUGAAGGCAGCANNNNNN-3';

(SEQ ID NO: 296)
5'-CGUAAUGUUCCUCCUAUCUUCAAUGAUGUUUAUUGGAUUGCAUUCNNNNNN

AAGUUCGUGGCAGCUUGGACCCUGAAGGCAGCANNNNNN-3';

(SEQ ID NO: 297)
5'-CGUAAUGUUCCUCCUAUCUUCAAUGAUGUUUAUUGGAUUGCAUUCNNNNNN

AAGUAUGUGGCAGCUUGGACCCUGAAGGCAGCANNNNNN-3';

(SEQ ID NO: 298)
5'-CGUAAUGUUCCUCCUAUCUUCAAUGAUGUUUAUUGGAUUGCAUUCAAGNNN

GUGGCAGCUUGGACCCUGAAGGCAGCA-3';

(SEQ ID NO: 299)
5'-CGUAAUGUUCCUCCUAUCUUCAAUGAUGUUUAUUGGAUUGCAUUCAAGUUC

GUGGCAGCUUGGACCCUGAAGGCAGCA-3';

(SEQ ID NO: 300)
5'-CGUAAUGUUCCUCCUAUCUUCAAUGAUGUUUAUUGGAUUGCAUUCAAGUAU

GUGGCAGCUUGGACCCUGAAGGCAGCA-3';

(SEQ ID NO: 301)
5'-CGUAAUGUUCCUCCUAUCUUCAAUGAUGUUUAUUGGAUUGCAUUCAAGNNN

GUGGCAGCUUGGACCCUGAAGGCAGCACAUCACCAUCACCAUCAC-3'

(SEQ ID NO: 302)
5'-CGUAAUGUUCCUCCUAUCUUCAAUGAUGUUUAUUGGAUUGCAUUCAAGUUC

GUGGCAGCUUGGACCCUGAAGGCAGCACAUCACCAUCACCAUCAC-3'
```

-continued (SEQ ID NO: 303)
5'-CGUAAUGUUCCUCCUAUCUUCAAUGAUGUUUAUUGGAUUGCAUUCAAGUAU
GUGGCAGCUUGGACCCUGAAGGCAGCACAUCACCAUCACCAUCAC-3'

(SEQ ID NO: 304)
5'-CGUAAUGUUCCUCCUAUCUUCAAUGAUGUUUAUUGGAUUGCAUUCNNNNNN
AAGNNNGUGGCAGCUUGGACCCUGAAGGCAGCAUGCCGUUUCCGUGGACUG
AUUUCCCUGUCCCAGGUUUAUCUGUCC-3';

(SEQ ID NO: 305)
5'-CGUAAUGUUCCUCCUAUCUUCAAUGAUGUUUAUUGGAUUGCAUUCNNNNNN
AAGUUCGUGGCAGCUUGGACCCUGAAGGCAGCAUGCCGUUUCCGUGGACUG
AUUUCCCUGUCCCAGGUUUAUCUGUCC-3';

(SEQ ID NO: 306)
5'-CGUAAUGUUCCUCCUAUCUUCAAUGAUGUUUAUUGGAUUGCAUUCNNNNNN
AAGUAUGUGGCAGCUUGGACCCUGAAGGCAGCAUGCCGUUUCCGUGGACUG
AUUUCCCUGUCCCAGGUUUAUCUGUCC-3';

(SEQ ID NO: 307)
5'-CGUAAUGUUCCUCCUAUCUUCAAUGAUGUUUAUUGGAUUGCAUUCNNNNNN
AAGNNNGUGGCAGCUUGGACCCUGAAGGCAGCAUGCCGU-3';

(SEQ ID NO: 308)
5'-CGUAAUGUUCCUCCUAUCUUCAAUGAUGUUUAUUGGAUUGCAUUCNNNNNN
AAGUUCGUGGCAGCUUGGACCCUGAAGGCAGCAUGCCGU-3';
and (SEQ ID NO: 309)
5'-CGUAAUGUUCCUCCUAUCUUCAAUGAUGUUUAUUGGAUUGCAUUCNNNNNN
AAGUAUGUGGCAGCUUGGACCCUGAAGGCAGCAUGCCGU-3'.

Example 101, Vector

A vector including any one nucleic acid of Example 96 to Example 100.

Example 102, Limitation on Vector

The vector of Example 101, wherein the vector is selected from the group consisting of plasmids, retroviruses, lentiviruses, adenoviruses, adeno-associated viruses, vaccinia viruses, poxviruses, and herpes simplex viruses.

Example 103, Mammalian Codon-Optimized Nucleic Acid

A nucleic acid of any one of Examples 96 to 98, wherein the nucleic acid is codon-optimized for a species selected from mammals.

Example 104, Human Codon-Optimized Nucleic Acid

A nucleic acid of any one of Examples 96 to 98, wherein the nucleic acid is human codon-optimized.

Example 105, Prokaryotic Codon-Optimized Nucleic Acid

A nucleic acid of any one of Examples 96 to 98, wherein the nucleic acid is codon-optimized for a species selected from prokaryotes.

Example 106, E. coli Codon-Optimized Nucleic Acid

A nucleic acid of any one of Examples 96 to 98, wherein the nucleic acid is E. coli codon-optimized.

Pharmaceutical Composition Including Peptide

Example 107, Pharmaceutical Composition for Immunotherapy

A pharmaceutical composition for immunotherapy including the following:
a peptide unit of any one of Examples 1 to 90, and/or a peptide of any one of Examples 91 to 95; and
adjuvants.

Example 108, Pharmaceutical Composition for Obesity Treatment

A pharmaceutical composition for obesity treatment including the following:
a peptide unit of any one of Examples 1 to 90, and/or a peptide of any one of Examples 91 to 95; and
adjuvants.

Example 109, Limitation on Adjuvants

In any one of Examples 107 to 108, the adjuvant is water, saline, dextrose, ethanol, glycerol, sodium chloride, dextrose, mannitol, sorbitol, lactose, gelatin, albumin, aluminum hydroxide, Freund's Incomplete Adjuvant and Complete Adjuvant (Pifco Laboratories, Detroit, Mich.), a Merck antigen adjuvant 65 (Merck and Company, Inc., Rahway, NJ), alhydrogel (Al(OH)$_3$), aluminum hydroxide gel (alum), or aluminum salts such as aluminum phosphate, AS04 series, MF, squalene, MF59, QS21, calcium, iron or zinc salts, insoluble suspensions of acylated tyrosine, acylated fructose, cationically or anionically derived polysaccharides, polyphosphazenes, biodegradable microspheres, Quil A, toll-like receptor (TLR) agonists, PHAD [Avanti polar lipid, Monophosphoryl Lipid A (synthetic)], monophosphoryl lipid A (MPL, monophosphoryl Lipid A), synthetic lipid A, lipid A mimics or analogues, aluminum salts, cytokines, saponins, prolactin, growth hormone deoxycholic acid, beta-glucan, polyribonucleotides, muramyl dipeptide (MDP) derivatives, CpG oligos, gram-negative bacterial lipopolysaccharide (LPS), polyphosphazene, emulsions, virosome, cochleate, poly(lactide-co-glycolide) (PLG) microparticles, poloxamer particles, microparticles, liposomes, or appropriate combinations thereof.

Pharmaceutical Composition Including Encoding Nucleic Acid

Example 110, Formulated Encoding Nucleic Acid

Formulated encoding nucleic acid, which is characterized in that the nucleic acid of any one of Examples 96 to 106 is formulated using a viral vector and/or non-viral vector.

Example 111, Limitation on Viral Vector

In Example 110, the encoding nucleic acid is characterized in that the viral vector is selected from the following: retrovirus; lentivirus; adenovirus; adeno-associated virus; vaccinia virus; poxvirus; and herpes simplex virus.

Example 112, Limitation on Forms of Formulated Nucleic Acid

In Example 110, the encoding nucleic acid is characterized in that the formulated nucleic acid is selected from the following:
a naked nucleic acid; a cationic peptide-complex nucleic acid (protamine); a positively charged oil-water cationic nanoemulsion including a nucleic acid (cationic nanoemulsion); a nucleic acid which is coupled with a chemically modified dendrimer and complexed with polyethylene glycol and PEG-lipid (modified dendrimer nanoparticle); a nucleic acid complexed with protamine in PEG-lipid nanoparticles (Protamine liposome); a nucleic acid which is complexed with a cationic polymer such as polyethylenimine and PEI (cationic polymer); a nucleic acid which is complexed with a cationic polymer such as a PEI and lipid component (cationic polymer liposome); a nucleic acid which is complexed with a polysaccharide polymer such as chitosan (polysaccharide particle); a nucleic acid which is complexed with a cationic lipid nanoparticle polymer (cationic lipid nanoparticle); a nucleic acid which is complexed with cationic lipid and cholesterol (cationic lipid-cholesterol nanoparticle); and a nucleic acid which is complexed with cationic lipid, cholesterol, and PEG-lipid (cationic lipid-cholesterol-PEG nanoparticle).

Example 113, Pharmaceutical Composition for Immunotherapy Including Formulated Nucleic Acid A pharmaceutical composition for immunotherapy including the following:
a formulated nucleic acid of any one of Examples 100 to 112; and
adjuvants.

Example 114, Pharmaceutical Composition for Obesity Treatment Including Formulated Nucleic Acid A pharmaceutical composition for obesity treatment including the following:
a formulated nucleic acid of any one of Examples 100 to 112; and
adjuvants.

Example 115, Limitation on Adjuvants

A pharmaceutical composition of any one of Examples 113 and 114, which is characterized in that the adjuvant is one or more selected from the following:
lipid nanoparticles (LNPs); aluminum salts; 1;2-dioleyl-3-trimethylammonium-propane chloride; MF59 (Novartis) adjuvant; CD70; CD40 ligand (CD40L); TriMix; protamine acting through TLR7 signaling; and/or bacteria-derived monophosphoryl lipid A.

Example 116, Including Additional Ingredients

The pharmaceutical composition of any one of Examples 113 to 114, wherein the pharmaceutical composition includes one or more additional ingredients selected from the following:
lipids; salts to balance body acidity; sucrose to maintain stability during repeated freezing-thawing; and vaccine stability enhancing substances.

Example 117, Limitation on Additional Ingredients

The pharmaceutical composition of Example 116,
wherein a pharmaceutical composition which is characterized in that the lipid is one or more selected from SM-102, PEG2000-DMG, DPSC, cholesterol, and ALC-0315;
the salt is one or more selected from sodium acetate, potassium chloride, monobasic potassium phosphate, sodium chloride, and dibasic sodium phosphate dehydrate; and
the vaccine stability enhancing substance one or more selected from acetic acid, an acid stabilizer (tromethamine), and ethanol.

Use of Peptides

Example 118, Use for Immunotherapy (First Medical Use)

Use for immunotherapy of a peptide unit of any one of Examples 1 to 90, a peptide of any one of Examples 91 to 95, a nucleic acid of any one of Examples 96 to 106, and/or a pharmaceutical composition of any one of Examples 107 to 109 and Examples 113 to Example 117.

Example 119, Use for Obesity Treatment (First Medical Use)

Use for obesity treatment of a peptide unit of any one of Examples 1 to 90, a peptide of any one of Examples 91 to 95, a nucleic acid of any one of Examples 96 to 106, and/or a pharmaceutical composition of any one of Examples 107 to 109 and Examples 113 to Example 117.

Example 120, Use for Preparation of Immunotherapeutics (Second Medical Use)

Use for preparation of immunotherapeutics of a peptide unit of any one of Examples 1 to 90, a peptide of any one of Examples 91 to 95, a nucleic acid of any one of Examples 96 to 106, and/or a pharmaceutical composition of any one of Examples 107 to 109 and Examples 113 to Example 117.

Example 121, Use for Preparation of Therapeutics for Obesity Treatment (Second Medical Use)

Use for preparation of therapeutics for obesity treatment of a peptide unit of any one of Examples 1 to 90, a peptide of any one of Examples 91 to 95, a nucleic acid of any one of Examples 96 to 106, and/or a pharmaceutical composition of any one of Examples 107 to 109 and Examples 113 to Example 117.

Treatment Methods Using Peptides

Example 122, Immunotherapy Using Peptides an immunotherapy including the following:
administering a peptide unit of any one of Examples 1 to 90, a peptide of any one of Examples 91 to 95, a nucleic acid of any one of Examples 96 to 106, and/or a pharmaceutical composition of any one of Examples 107 to 109 and Examples 113 to Example 117 into the body of a subject.

Example 123, Methods for Obesity Treatment Using Peptides

Methods for obesity treatment using the following:
administering a peptide unit of any one of Examples 1 to 90, a peptide of any one of Examples 91 to 95, a nucleic acid of any one of Examples 96 to 106, and/or a pharmaceutical composition of any one of Examples 107 to 109 and Examples 113 to Example 117 into the body of a subject.

Sequences Similar to Peptide Units and/or Peptides

Example 124, Sequences Similar to Peptide Units

A peptide unit which has a sequence that matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one peptide unit of Examples 1 to 90.

Example 125, Sequences Similar to Peptides

A peptide which has a sequence that matches 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100% or more, with any one peptide unit of Examples 91 to 95.

Experimental Examples

Hereinafter, the invention provided by the present specification will be described in more detail through Experimental Examples and Examples. These Examples are only for the purpose of illustrating the contents disclosed by the present specification, and it will be apparent to those skilled in the art that the scope of the contents disclosed by the present specification is not to be construed as being limited by these Examples.

Experimental Example 1, Experimental Method

Experimental Example 1.1, Preparation of Peptides

This peptide was obtained by requesting a peptide synthesis company (Anygen, Korea, Gwangju City). The peptide of the present invention can be synthesized using conventionally known techniques (e.g., liquid peptide synthesis, solid phase peptide synthesis, convergent of small peptide fragments, etc.), and the synthesis method is not limited. For example, the OTP3 peptide of the present invention can be synthesized using the convergent method of small peptide fragments, in which sites of a long-chain peptide to which a coupling can easily be made are virtually cleaved and various parts are prepared based on this, and then combined with one another to thereby finally synthesize a desired peptide. The above convergent method has limitations in that specific amino acids must exist within the peptide sequence, and thus, the peptide may also be effectively synthesized by a combinatory peptide synthesis method, where the solution phase synthesis method and the solid phase peptide synthesis method are appropriately combined.

Experimental Example 1.2, Confirmation of Prepared Peptide 1—Analysis of Purity The purity of the peptide prepared in Experimental Example 1.1 was measured by performing HPLC analysis (Shimadzu HPLC LabSolutions) using a C-18 reversed-phase column (SHIMADZU C18 analytical column). As for the analysis conditions, the sample was separated and developed into an aqueous solution of 0.05% trifluoroactate (TFA) and 0.05% TFA acetotrile solution at 60° C., and then the purity was confirmed by measuring the peak absorbance at a wavelength of 230 nm.

Experimental Example 1.3, Confirmation of Prepared Peptide 2—Analysis of Molecular Weight The molecular weight of the peptide prepared in Experimental Example 1.1 was analyzed with a mass spectrometer (AXIMA Assurance, MALDI-TOF, Shimadzu).

Experimental Example 1.4, Confirmation of Prepared Peptide 2—Analysis of Quantification The peptide prepared in Experimental Example 1.1 was quantified by measuring the UV extinction coefficient (Ultrospec 3000 Pro UV/VIS spectrophotometer, Pharmacia).

Specifically, the quantification was performed using the extinction coefficient at 280 nm.

Experimental Example 1.5, Preparation of Composition for In Vivo Administration

A composition for in vivo administration was prepared by mixing the peptide prepared in Experimental Example 1.1, alhydrogel (Al(OH)$_3$, manufactured by InvivoGe, Inc.), and PHAD (manufactured by Avanti). The specific process is as follows.

(1) The prepared peptide powder was dissolved in 100% dimethyl sulfoxide (DMSO) to obtain a concentration of 100 mg/L.

(2) PBS was added to the peptide-DMSO solution of (1) and mixed to prepare the peptide at a concentration of 50 mg/mL.

(3) PHAD was dissolved in 100% DMSO to a concentration of 10 mg/mL, and then diluted with distilled water to a concentration of 1 mg/mL.

(4) An alhydrogel adjuvant (Invivogen, USA) and the PHAD solution were added to the mixture of (2). The concentration of the mixed composition was 50 μg for the peptide, 10 μg for the PHAD, and 10% (v/v) for the Alhydrogel adjuvant, per 100 μL, which is the amount for one dose.

(5) After well mixing the mixture of (4), the resultant was reacted overnight while stirring with a rotator in a low temperature room (4° C.).

(6) For DSMO washing, the reactants of (5) were centrifuged at 1,400 rpm for 15 minutes, and the supernatant except for about 1 mL above the pellet was removed. Thereafter, 10 mL of PBS was added thereto and mixed.

(7) The washing process of (6) was repeated 3 times.

(8) After the final washing process, PBS was added thereto so as to adjust the final concentration of the composition. In particular, the peptide concentration was 50 μg/100 μL (in particular, 30 μg/100 μL in Example 4), the PHAD concentration was 10 μg/100 μL, and the hydrogel adjuvant concentration was 10% (v/v).

(9) The amount of peptide adsorbed to the aluminum gel was measured according to the method described in Experimental Example 2.3. As a result, it was confirmed that the adsorption rate was 95% or more and the peptide was used in the experiment.

Experimental Example 1.6, Preparation of Test Subject

In order to test the effect of the composition for in vivo administration prepared in Experimental Example 1.5, C57BL/6, Balbc and/or ICR species were used as experimental mice (purchased from Central Lab Animal Inc.). Although there were some differences in species, the mice purchased were 7-week-old on average and they were acclimatized for one week, and were used for experiments when they were 8 weeks of age. Experimental mice were reared under the conditions of a constant temperature and humidity environment within the temperature range of 23±1° C., relative humidity of 50±5%, and an environment controlled as 12-hour light room/12 hour dark room. Drinking water and food were provided ad libitum. In the case of a normal diet (purchased from Central Lab Animal Inc.), it consisted of 20% protein, 70% carbohydrate, and 10% fat based on total calories, whereas in the case of an obesity-inducing diet (purchased from Research diets), it consisted of a high-fat diet including 20% protein, 20% carbohydrate, and 60% fat based on total calories. Experimental mice were divided into each group to have different dietary conditions and composition administration conditions, and experiments were performed with the number of individuals that could be statistically processed for each experimental group. Detailed conditions are as disclosed in each specific experimental example.

Experimental Example 1.7, Administration of Composition Including Peptide to Test Subject For a test subject prepared in Experimental Example 1.6, different compositions were administered for each experimental group. All administration compositions were administered by an intramuscular injection method, and after disinfecting muscles of both thighs of each mouse with an alcohol swab, 50 μL each with a total amount of 100 μL was injected.

Experimental Example 1.8, Confirmation of Effect of Composition for In Vivo Administration 1—Weight Measurement In order to confirm the weight loss effect on a test subject of the composition administered in the body according to Experimental Example 1.7, body weight and organ weight of the mice were measured for each experimental group. From the time of arrival to the end of the experiment for each experimental group of mice, the average was calculated after measuring three times per week to obtain the average weight value for each week. After completion of the experiment, each mouse was anesthetized, organs were dissected, and weights were measured, and the average was obtained for each experimental group.

Experimental Example 1.9, Confirmation of Effect of Composition for In Vivo Administration 2—Confirmation of Antibody Titer In order to determine whether the composition for in vivo administration administered in Experimental Example 1.7 induced an antibody against the B-cell epitope, a method for confirming the antibody titer using the target antigen is as follows. In particular, the target antigen is RNVPPIFNDVYWIAF (SEQ ID NO: 6) or ApoB100. The time to confirm the antibody titer may vary as needed, and the time was specifically described for each experimental example.

1. Process of Antigen Coating Reaction 1-1) For each injection of a composition for in vivo administration into a test subject, collect about 200 μL of blood from the subject's tail vein one week after the injection.

1-2) After placing the collected blood at 4° C. for one hour, perform centrifugation of the blood sample at 14,000 rpm for 10 minutes to separate the serum, which is the supernatant.

1-3) Dilute the target antigen to a concentration of 50 μg/100 μL in coating buffer (0.05 M, bicarbonate, pH 9.6) and add the antigen to a 96-well plate in an amount of 50 μg per well, and allow them to react overnight at 4° C. so that the peptide is coated on the wall of the well.

1-4) Wash the target antigen-coated plate three times using 300 μL of phosphate buffered saline (PBS)-T (0.05% with Tween-20) per well.

2. Process of Blocking Reaction 2-1) Add 300 μL of a 0.5% casein blocking solution per well in the plate, and allow to react overnight at 4° C.

2-2) Wash the plate three times with 300 µL of PBS-T per well.

3. Process of Primary Antibody Reaction 3-1) As the primary antibody reaction, dilute the separated serum to an appropriate concentration, add it in an amount of 100 µL per well, and allow to react at 37° C. for one hour. In particular, after the initial injection, subject the serum to serial dilution by diluting the same to 1/20 to 1/1,000 in the experiment, and 1/500 to 1/10,000 depending on the subject during the experiment after the second to third injections. As a positive control, use a monoclonal antibody against the peptide of SEQ ID NO: 41 after purification.

3-2) After the reaction of 3-1, wash the plate three times with 300 µL of PBS-T per well.

4. Process of Secondary Antibody Reaction 4-1) As a secondary antibody reaction, add 100 µL of horseradish peroxidase (HRP) conjugated to anti-mouse IgG antibody recognizing a mouse antibody per well, and allow them to react at 37° C. for one hour.

4-2) After the reaction of 4-1), wash the plate three times with 300 µL of PBS-T per well.

5. Process of Confirming Color Development and Absorbance 5-1) Add 100 µL of a o-phenylenediamine dihydrochloride (OPD) solution per well, and allow to react at 37° C. for 10 minutes, and measure the absorbance at OD 450 nm (Synergy HT microplate reader, BioTek).

Obtain the antibody titer in serum by converting the extinction coefficient, which is measured based on 1 mg/mL concentration of the monoclonal antibody against the target antibody as a positive control.

Experimental Example 1.10, Confirmation of Effect of Composition for In Vivo Administration 3—Confirmation of blood lipid concentration The experimental method for confirming the effect of the composition for in vivo administration administered in Experimental Example 1.7 on the blood lipid concentration of a test subject is as follows:

(1) One week after the administration of each composition, collect about 200 µL of blood from a subject's tail vein.

(2) Measurement of blood triglyceride (TG) concentration: Triglyzyme-V (Shinyak Chemical Co., Ltd.) was used. i) After mixing 4 µL of the blood sample and 300 µL of a color developing reagent, the mixture was reacted at 37° C. for 5 minutes. ii) For the red quinone produced, the absorbance was measured at 505 nm, and the concentration was calculated by comparing with that of the reference solution.

(3) Measurement of total cholesterol concentration in blood: Cholestezyme-V (Shinyak Chemical Co., Ltd.) was used. i) After mixing 4 µL of the blood sample and 300 µL of a color developing reagent, the mixture was reacted at 37° C. for 5 minutes. ii) For the red quinone produced, the absorbance was measured at 505 nm, and the concentration was calculated by comparing with that of the reference solution.

(4) Measurement of high density lipoprotein (HDL) concentration in blood: HDL-C555 (Shinyak Chemical Co., Ltd.) was used. i) After mixing 10 µL of the blood sample and 10 µL of a precipitation reagent, the mixture was allowed to react at room temperature for at least 10 minutes. ii) The reactants were centrifuged at 300 rpm or greater, and the supernatant was separated. iii) After mixing 4 µL of the supernatant and 300 µL of a color developing reagent, the mixture was reacted at 37° C. for 5 minutes. iv) For the above reaction, the absorbance was measured at 555 nm and the concentration was calculated by comparing with that of the reference solution.

(5) Measurement of low density lipoprotein (LDL) concentration in blood. i) The reaction was performed using the Direct LDL Cholesterol detection kit (Randox). ii) After the reaction of Step 2, for the quinone produced, the absorbance was measured at 600 nm, and the concentration was calculated by comparing with that of the reference solution.

Experimental Example 1.11, Confirmation of Effect of Composition for In Vivo Administration 4—Confirmation of Lipolysis Ability and Comparison of Size of Adipocytes The method for confirming the effect of the composition for in vivo administration administered in Experimental Example 1.7 on the ability of degrading adipocytes and the size of adipocytes of a test subject by Hormon sensitive lipase (HSL) is as follows:

1. Separation of Adipocytes 1-1) Cut an epididymal fat pad with scissors, add 4 mL per 1 g of KRB buffer including 2% FBS, 2 mM glucose, and 1 mg/mL collagenase, shake and allow them to react at 37° C. for one hour while shaking.

1-2) After the reaction is complete, pass the resultant through a 300 µm nylon mesh to filter out adipose tissue residues and adipose tissue, and then pass the filtrate again through a 40 µm nylon mesh to separate adipocytes and macrophages.

1-3) Wash the adipocytes filtered in 1-2) by adding DMEM with 10% FBS and 1% AA, and remove the liquid in the lower layer with a syringe to obtain adipocytes from which collagenase has been removed.

2. Comparison of Lipolysis Ability 2-1) Seed the adipocytes obtained in 1-3) in a 48-well plate at $1.0 \times 10^1$ cells/well, and add a total of 1 mL of DMEM (10% FBS, 1% AA) thereto for culturing under 37° C. 5% $CO_2$ for two hours.

2-2) For the wells to induce HSL activity, add norepinephrine to a final concentration of $10^{-5}$ M.

2-3) After the reaction is complete, allow 100 µL of the supernatant of each well to react with 100 µL of a free glycerol reagent, and measure the absorbance at 540 nm.

3. Observation of Size of Adipocytes 3-1) Seed the adipocytes obtained in 1-3) in a 48 well plate at $1.0 \times 10^5$ cells/mL per well, treat with 10 µM of DAPI, allow them to react for two hours, and observe under a microscope.

3-2) In order to confirm whether DAPI-stained cells are adipocytes, stain lipids and nuclei together and observe. In particular, treat the cells with 10 µM of DAPI and 1:1,000 of HCS LipidTOX and allow them to react for 24 hours, and then observe under a microscope.

Experimental Example 2, Confirmation of Peptide Effect 1

Experimental Example 2.1, Preparation of Peptides and Experiments Thereof

After preparing peptides according to [Table 1] according to Experimental Example 1.1, the peptides prepared were confirmed according to Experimental Examples 1.2 to 1.4. A composition for in vivo administration including the peptides according to [Table 1] was prepared, according to Experimental Example 1.5.

TABLE 1

Peptides used in Experimental Example 2 and composition for in vivo administration including the same

| Label | Peptide sequence | SEQ ID NO |
|---|---|---|
| Example. 1 | RNVPPIFNDVYWIAFZaK(Cha)VAAWTLKAAaZ | 56 |
| Example. 2 | ZaK(Cha)VAAWTLKAAaZRNVPPIFNDVYWIAF | 57 |

The test subject shown in [Table 2] was prepared according to Experimental Example 1.6.

TABLE 2

Test subject used in Experimental Example 2

| Label | Species | Diet | Composition | n |
|---|---|---|---|---|
| Group 1-1 | C57BL/6J, male | ~13 weeks: normal diet after 13 weeks: high-fat diet | Example. 1 | 6 |
| Group 1-2 | C57BL/6J, male | ~13 weeks: normal diet after 13 weeks: high-fat diet | Example. 2 | 6 |

According to Experimental Example 1.7, the composition for in vivo administration was administered to the test subject. In particular, the administration cycle was as follows: 7 weeks, 9 weeks, 12 weeks, 15 weeks, and 18 weeks of age.

Experimental Example 2.2, Confirmation of Experimental Results

In order to confirm the experimental results of Experimental Example 2.1, the weight of the test subject was measured for each experimental group disclosed in [Table 2] according to Experimental Example 1.8.

Figure 2:
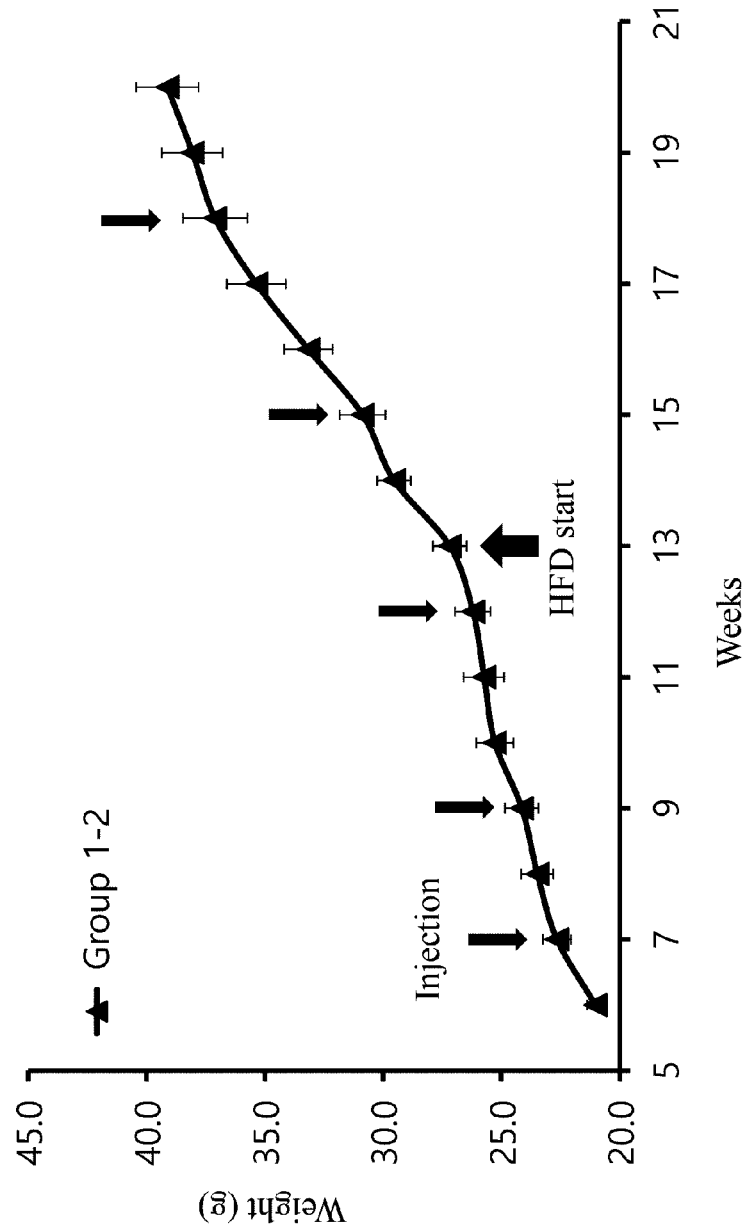
Figure 3:
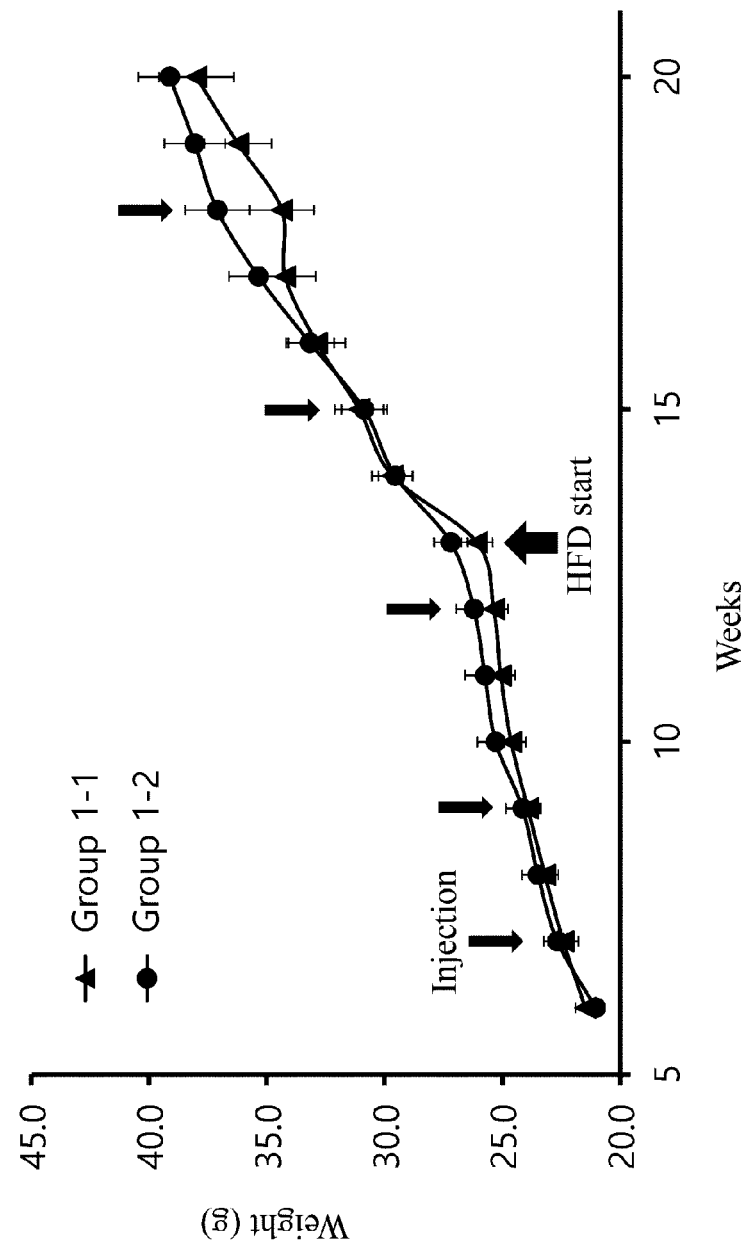
Figure 4:
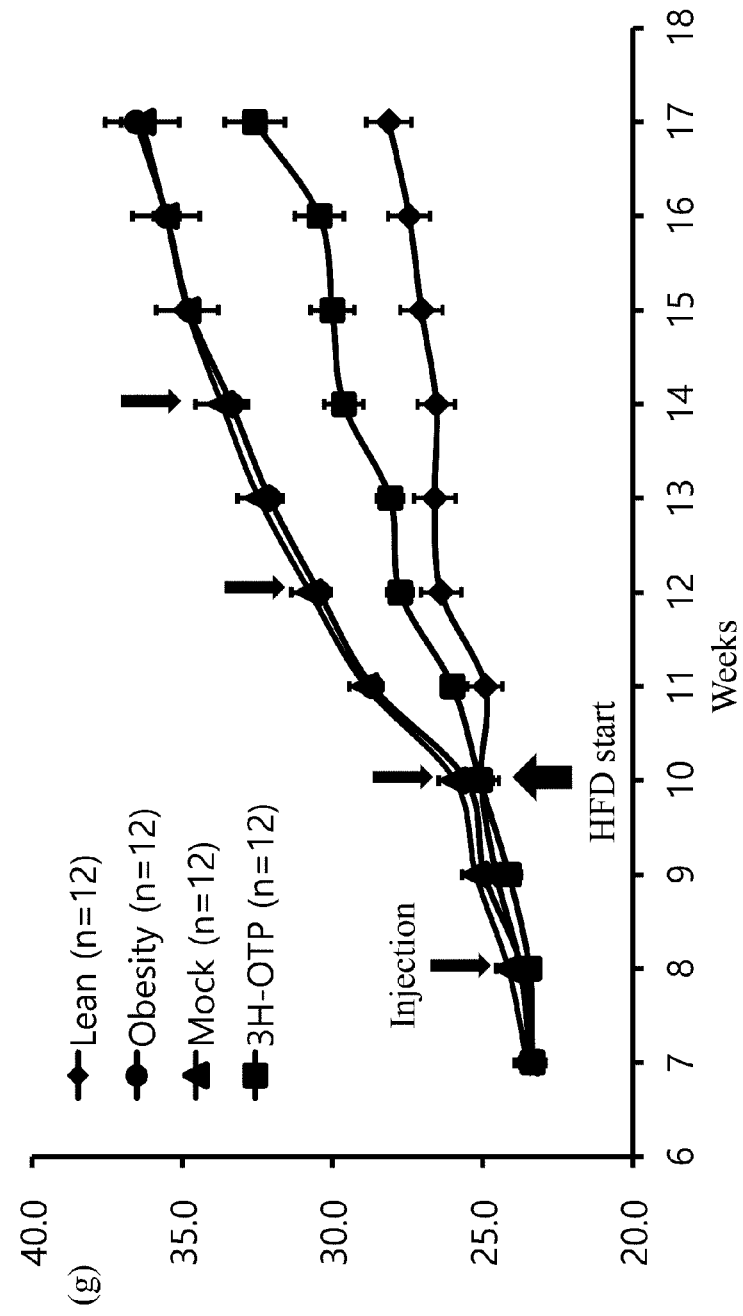
FIG. 4, which shows the results of the peptide effect confirmation experiment according to Experimental Example 3, is a graph showing the measured weight per week of age of a test subject for each experimental group, in which Lean denotes a control group with normal weight, Obesity denotes an obesity group induced by high-fat diet, Mock denotes a group administered with placebo, and 3H-OTP denotes Group 2-1.
Figure 5:
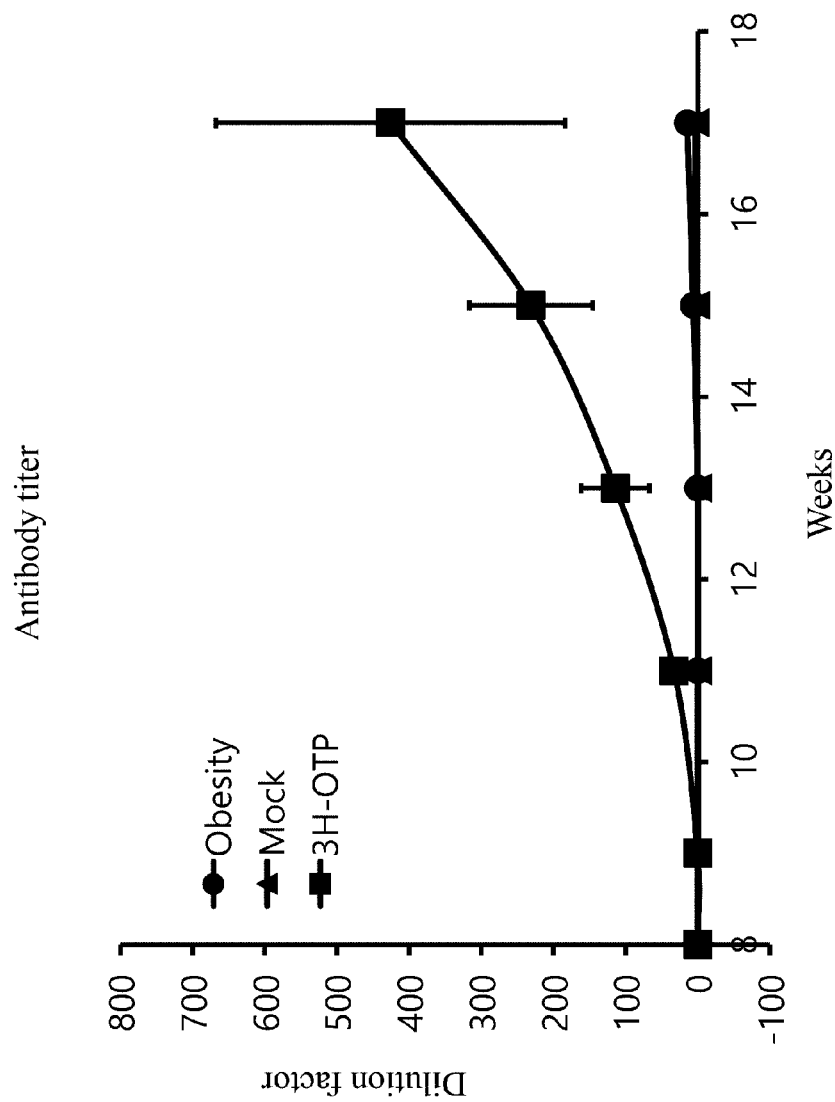
FIG. 5, which shows the results of the peptide effect confirmation experiment according to Experimental Example 3, is a graph showing the measured antibody titer observed in a test subject for each experimental group, in which Obesity denotes an obesity group induced by high-fat diet, Mock denotes a group administered with placebo, and 3H-OTP denotes Group 2-1.
Figure 6:
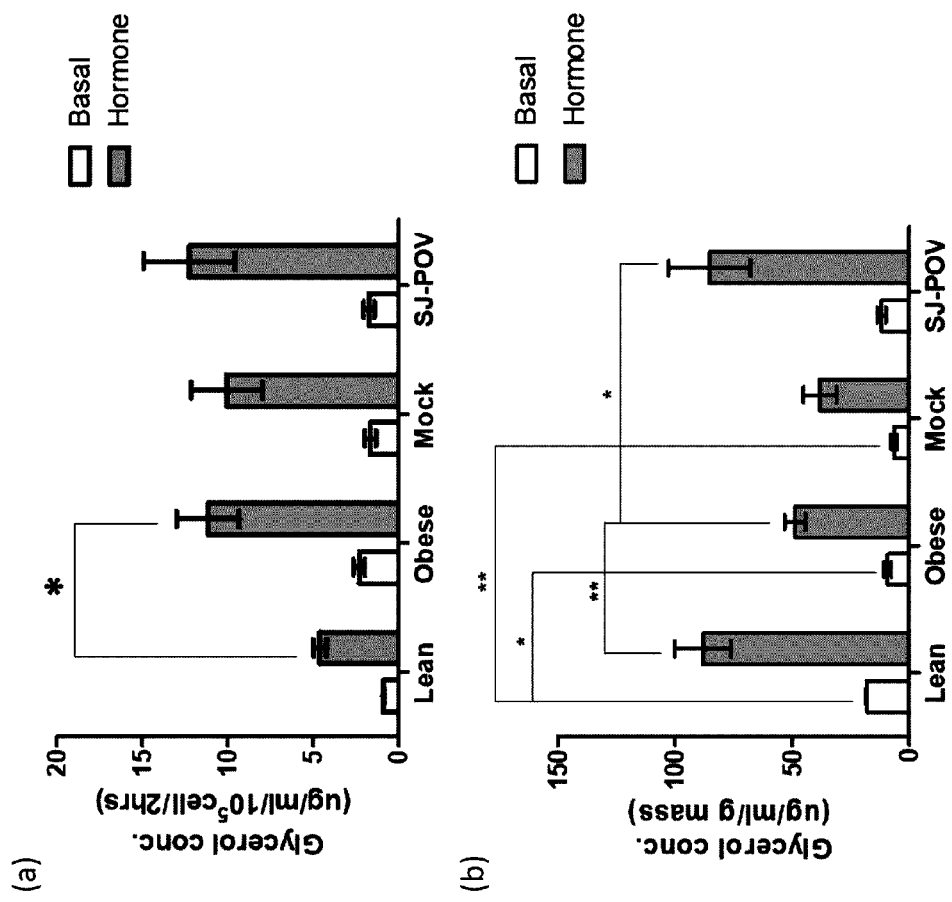
FIG. 6, which shows the results of the peptide effect confirmation experiment according to Experimental Example 3, is a graph showing the measured lipolysis ability of hormone sensitive lipase in adipocytes of a test subject for each experimental group, in which Basal denotes a case where norepinephrine was not treated and Hormone denotes a case where norepinephrine was treated, and Lean denotes a control group with normal weight, Obesity denotes an obesity group induced by high-fat diet, Mock denotes a group administered with placebo, and 3H-OTP denotes Group 2-1 ((a) concentration of glycerol secreted per $10^5$ adipocytes, (b) concentration of glycerol secreted per one gram of adipocytes.
Figure 7:
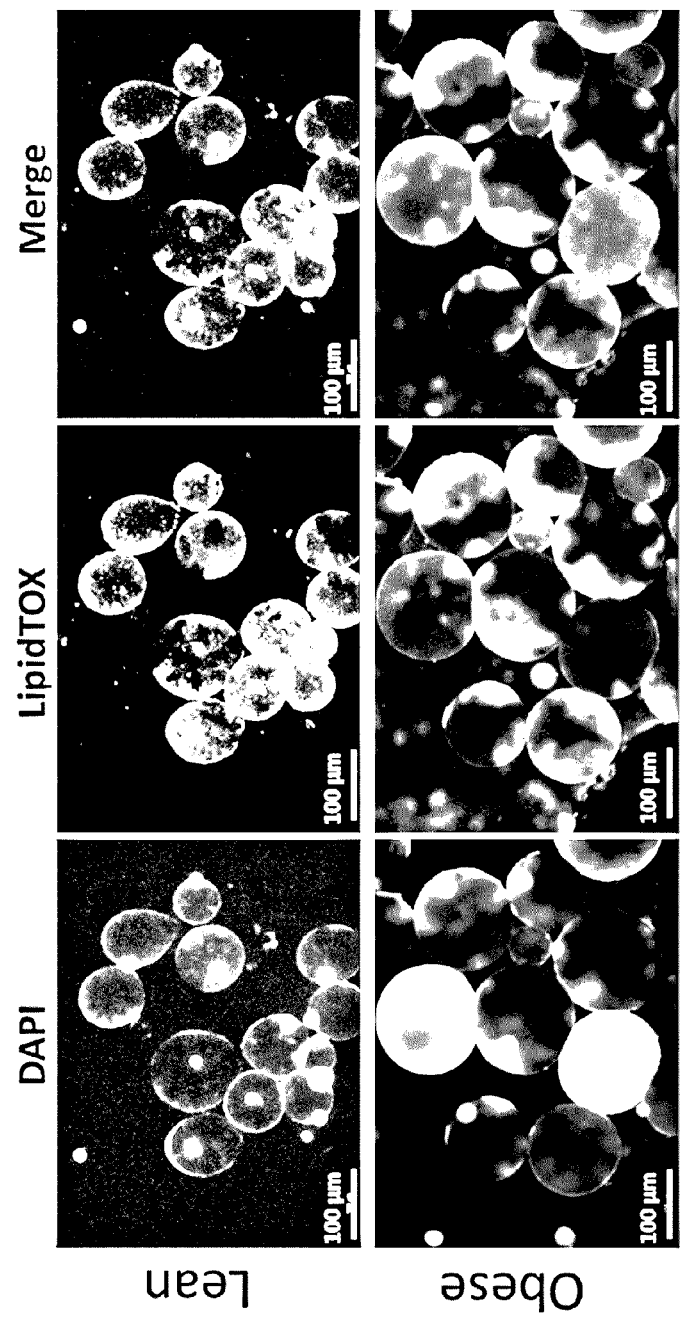
FIG. 7, which shows the results of the peptide effect confirmation experiment according to Experimental Example 3, is images showing the measured size of the adipocytes of a test subject for each experimental group, in which Lean denotes a control group with normal weight and Obese denotes an obesity group induced by high-fat diet (DAPI stained images, LipidTOX stained images, and Merge images are shown, respectively).

The experimental results are shown in FIGS. 1 to 3.

Experimental Example 3, Confirmation of Peptide Effect 2

Experimental Example 3.1, Peptide Preparation and Experiment Thereof

After preparing the peptides according to [Table 3] according to Experimental Example 1.1, the peptides prepared were confirmed according to Experimental Examples 1.2 to 1.4. A composition for in vivo administration including the peptides according to [Table 3] according to Experimental Example 1.5 was prepared.

TABLE 3

Peptides used in Experimental Example 3 and composition for in vivo administration including the same

| Label | Peptide sequence | SEQ ID NO |
|---|---|---|
| Example. 3 | RNVPPIFNDVYWIAFZaK(Cha)VAAWTLKAAaZCRFRGLISLSQVYLS | 108 |

The test subject shown in [Table 4] was prepared according to Experimental Example 1.6.

TABLE 4

Test subject used in Experimental Example 3

| Label | Species | Diet | Composition | n |
|---|---|---|---|---|
| Lean | C57BL/6J, male | ~10 weeks: normal diet after 10 weeks: high-fat diet | PBS-Alum | 12 |
| Obesity | C57BL/6J, male | ~10 weeks: normal diet after 10 weeks: high-fat diet | PBS-Alum | 12 |
| Mock | C57BL/6J, male | ~10 weeks: normal diet after 10 weeks: high-fat diet | Alum-PHAD/PBS | 12 |
| Group 2-1 (3H-OTP) | C57BL/6J, male | ~10 weeks: normal diet after 10 weeks: high-fat diet | Example. 3 | 12 |

In particular, Lean denotes a control group with normal weight, Obese denotes an obesity group induced by high-fat diet, and Mock denotes a group administered with placebo (the same hereinafter).

According to Experimental Example 1.7, the composition for in vivo administration was administered to the test subject. In particular, the administration cycle was as follows: 8 weeks, 10 weeks, 12 weeks, and 14 weeks of age.

Experimental Example 3.2, Confirmation of Experimental Results

In order to confirm the experimental results of Experimental Example 3.1, the following experiments were performed in a test subject for each experimental group disclosed in [Table 4].

(1) According to Experimental Example 1.8, the weight of a test subject for each experimental group was measured.

(2) According to Experimental Example 1.9, the antibody titers observed in a test subject for each experimental group were confirmed.

(3) According to Experimental Example 1.10, the blood lipid concentration of a test subject for each experimental group was measured.

(4) According to Experimental Example 1.11, the lipolysis ability of a test subject for each experimental group was confirmed, and the size of adipocytes was observed.

The experimental results are shown in FIGS. 4 to 9.

Experimental Example 4, Confirmation of Peptide Effect 3

Experimental Example 4.1, Peptide Preparation and Experiment Thereof

After preparing the peptides according to [Table 5] according to Experimental Example 1.1, the peptides prepared were confirmed according to Experimental Examples 1.2 to 1.4. A composition for in vivo administration including the peptides according to [Table 5] according to Experimental Example 1.5 was prepared.

TABLE 5

Peptides used in Experimental Example 4 and composition for in vivo administration including the same

| Label | Peptide sequence | SEQ ID NO |
|---|---|---|
| Example. 3 | RNVPPIFNDVYWIAFZaK(Cha)VAAWTLKAAaZC RFRGLISLSQVYLS | 108 |
| Example. 4 | RNVPPIFNDVYWIAFZaK(Cha)VAAWTLKAAaZC RFRGLISLSQVYLS | 108 |

In particular, in Example. 4, the final peptide concentration was 30 μg/100 μL.

The test subject shown in [Table 6] was prepared according to Experimental Example 1.6.

TABLE 6

Test subject used in Experimental Example 4

| Label | Species | Diet | Composition | n |
|---|---|---|---|---|
| Lean | C57BL/6J, male | ~11 weeks: normal diet after 11 weeks: high-fat diet | PBS-Alum | 8 |
| Obesity | C57BL/6J, male | ~11 weeks: normal diet after 11 weeks: high-fat diet | PBS-Alum | 9 |
| Mock | C57BL/6J, male | ~11 weeks: normal diet after 11 weeks: high-fat diet | Alum-PHAD/PBS | 9 |
| Group 3-1 (3H-OTP 50 ug) | C57BL/6J, male | ~11 weeks: normal diet after 11 weeks: high-fat diet | Example. 3 | 8 |
| Group 3-2 (3H-OTP 30 ug) | C57BL/6J, male | ~11 weeks: normal diet after 11 weeks: high-fat diet | Example. 4 | 8 |

According to Experimental Example 1.7, the composition for in vivo administration was administered to the test subject. In particular, the administration cycle was as follows: 8 weeks, 11 weeks, 14 weeks, 17 weeks, and 20 weeks of age.

Experimental Example 4.2, Confirmation of Experimental Results

In order to confirm the experimental results of Experimental Example 4.1, the following experiments were performed in a test subject for each experimental group disclosed in [Table 6].

(1) According to Experimental Example 1.8, the weight of a test subject for each experimental group was measured.

(2) According to Experimental Example 1.9, the antibody titers observed in a test subject for each experimental group were confirmed.

Figure 10:
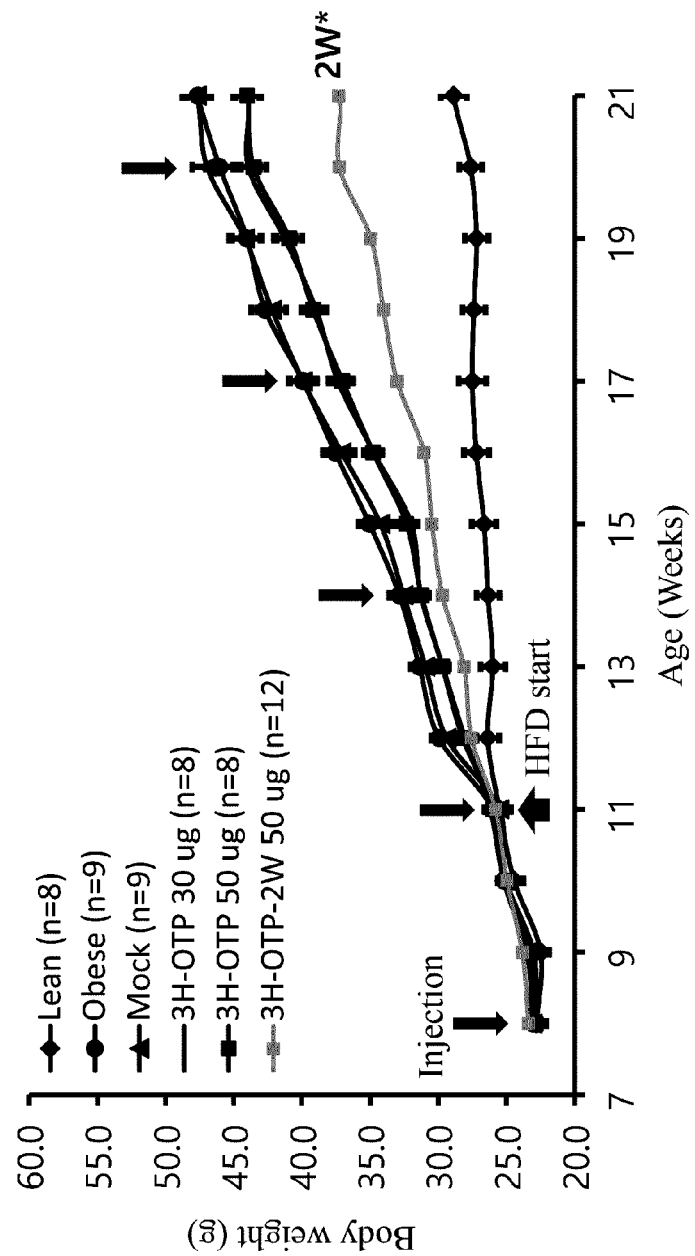
FIG. 10, which shows the results of the peptide effect confirmation experiment according to Experimental Example 4, is a graph showing the measured body weight per week of age of a test subject for each experimental group, in which Lean denotes a control group with normal weight, Obese denotes an obesity group induced by high-fat diet, Mock denotes a group administered with placebo, 3H-OTP 30 μg denotes Group 3-2, and 3H-OTP 50 μg denotes Group 3-1. For a reference purpose, a graph relating to 3H-OTP-2W 50 μg representing Group 2-1 is also shown.
Figure 11:
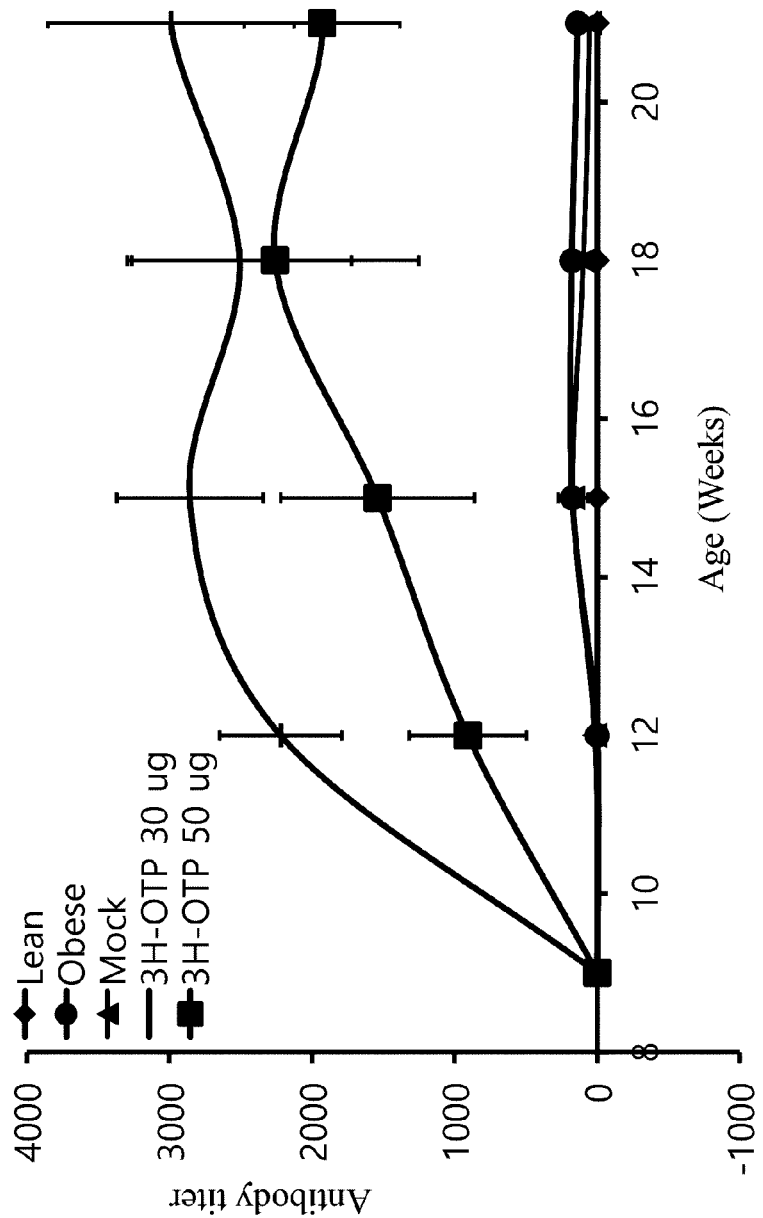
FIG. 11, which shows the results of the peptide effect confirmation experiment according to Experimental Example 4, is a graph showing the measured antibody titer per week of age of a test subject for each experimental group, in which Lean denotes a control group with normal weight, Obese denotes an obesity group induced by high-fat diet, Mock denotes a group administered with placebo, 3H-OTP 30 μg denotes Group 3-2, and 3H-OTP 50 μg denotes Group 3-1.

The experimental results are shown in FIGS. 10 and 11.

Experimental Example 5, Confirmation of Peptide Effect 4

Experimental Example 5.1, Peptide Preparation and Experiment Thereof

After preparing the peptides according to [Table 7] according to Experimental Example 1.1, the peptides prepared were confirmed according to Experimental Examples 1.2 to 1.4. A composition for in vivo administration including the peptides according to [Table 7] according to Experimental Example 1.5 was prepared.

TABLE 7

Peptides used in Experimental Example 5 and composition for in vivo administration including the same

| Label | Peptide sequence | SEQ ID NO |
|---|---|---|
| Example. 3 | RNVPPIFNDVYWIAFZaK(Cha)VAAWTLKAAaZC RFRGLISLSQVYLS | 108 |

The test subject shown in [Table 8] was prepared according to Experimental Example 1.6.

TABLE 8

Test subject used in Experimental Example 5

| Label | Species | Diet | Composition | n |
|---|---|---|---|---|
| Lean | C57BL/6J, male | normal diet | PBS-Alum | 10 |
| Obesity | C57BL/6J, male | ~5 weeks: normal diet after 5 weeks: high-fat diet | PBS-Alum | 10 |
| Group 4-1 (3H-OTP) | C57BL/6J, male | ~5 weeks: normal diet after 5 weeks: high-fat diet | Example. 3 | 10 |

According to Experimental Example 1.7, the composition for in vivo administration was administered to the test subject. In particular, the administration cycle was as follows: 11 weeks, 13 weeks, 15 weeks, and 17 weeks of age.

Experimental Example 5.2, Confirmation of Experimental Results

In order to confirm the experimental results of Experimental Example 5.1, the weight of the test subject was measured for each experimental group disclosed in [Table 8] according to Experimental Example 1.8.

Figure 12:
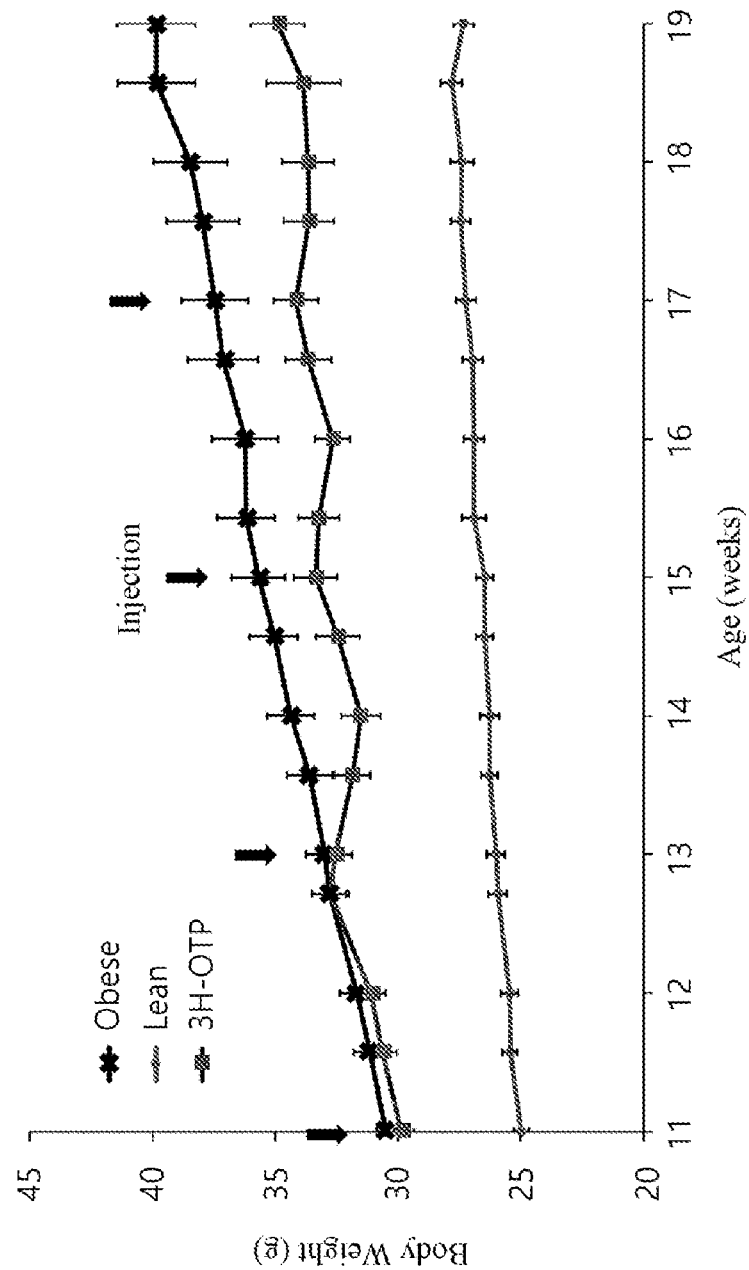
FIG. 12, which shows the results of the peptide effect confirmation experiment according to Experimental Example 5, is a graph showing the measured body weight per week of age of a test subject for each experimental group, in which Lean denotes a control group with normal weight, Obese denotes an obesity group induced by high-fat diet, and 3H-OTP denotes Group 4-1.

The experimental results are shown in FIG. 12.

Experimental Example 6, Confirmation of Peptide Effect 5

Experimental Example 6.1, Peptide Preparation and Experiment Thereof

After preparing the peptides according to [Table 9] according to Experimental Example 1.1, the peptides prepared were confirmed according to Experimental Examples 1.2 to 1.4. A composition for in vivo administration including the peptides according to [Table 9] according to Experimental Example 1.5 was prepared.

TABLE 9

Peptides used in Experimental Example 6 and composition for in vivo administration including the same

| Label | Peptide sequence | SEQ ID NO |
|---|---|---|
| Example. 3 | RNVPPIFNDVYWIAFZaK(Cha)VAAWTLKAAaZC RFRGLISLSQVYLS | 108 |

The test subject shown in [Table 10] was prepared according to Experimental Example 1.6.

TABLE 10

Test subject used in Experimental Example 6

| Label | Species | Diet | Composition | n |
|---|---|---|---|---|
| Lean | C57BL/6J-Rag2em1hwl/Korl, female/male Wild (+/+) | normal diet | PBS-Alum | Female: 3 |
| Group 5-1 (Wild (+/+)) | C57BL/6J-Rag2em1hwl/Korl, female/male Wild (+/+) | ~10 weeks: normal diet after 10 weeks: high-fat diet | PBS-Alum | Female: 4 Male: 3 |
| Group 5-2 (Hetero (+/−)) | C57BL/6J-Rag2em1hwl/Korl, female/male Hetero (+/−) | ~10 weeks: normal diet after 10 weeks: high-fat diet | Example. 3 | Female: 3 Male: 3 |
| Group 5-3 (Homo (−/−)) | C57BL/6J-Rag2em1hwl/Korl, female/male Homo (−/−) | ~10 weeks: normal diet after 10 weeks: high-fat diet | Example. 3 | Female: 3 Male: 1 |

\* The C57BL/6J-Rag2em1hwl/Korl mouse is a mouse in which the Rag2 gene, which is a gene involved in the antibody producing ability in a C57BL/6J mouse, is knocked out.
\*\* Wild (+/+) refers to a wild-type mouse in which no gene is mutated, Hetero (+/−) refers to a heterozygote mouse, and Homo (−/−) refers to a homozygote mouse.
\*\*\* Homo (−/−) mouse does not have the ability to produce antibodies in the body.

According to Experimental Example 1.7, the composition for in vivo administration was administered to the test subject. In particular, the administration cycle was as follows: 8 weeks, 10 weeks, 12 weeks, and 14 weeks of age.

Experimental Example 6.2, Confirmation of Experimental Results

In order to confirm the experimental results of Experimental Example 6.1, the weight of the test subject was measured for each experimental group disclosed in [Table 10] according to Experimental Example 1.8.

Figure 13:
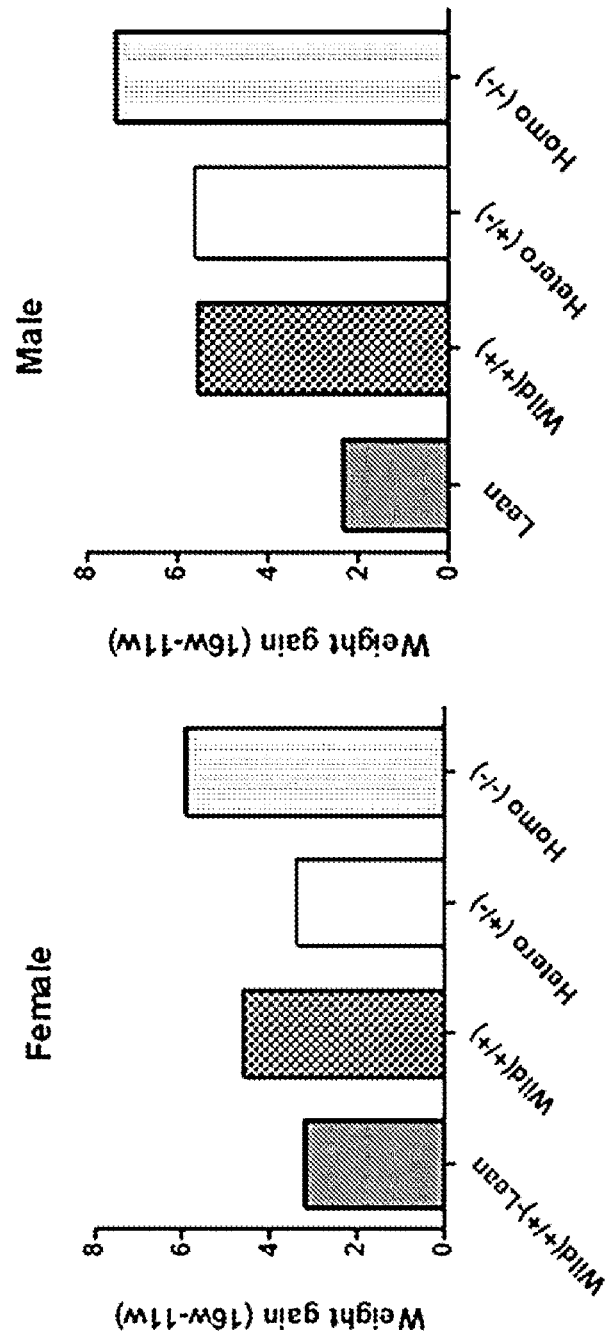
FIG. 13, which shows the results of the peptide effect confirmation experiment according to Experimental Example 6, is graphs showing the increase of body weight at 16 weeks of age compared to that at 11 weeks of age, after measurement of the body weight per week of age of a test subject for each experimental group by age, in which Wild(+/+)-Lean denotes a control group with normal weight, Wild(+/+) denotes Group 5-1, Hetero(+/−) denotes Group 5-2, and Homo(−/−) denotes Group 5-3.
Figure 14:
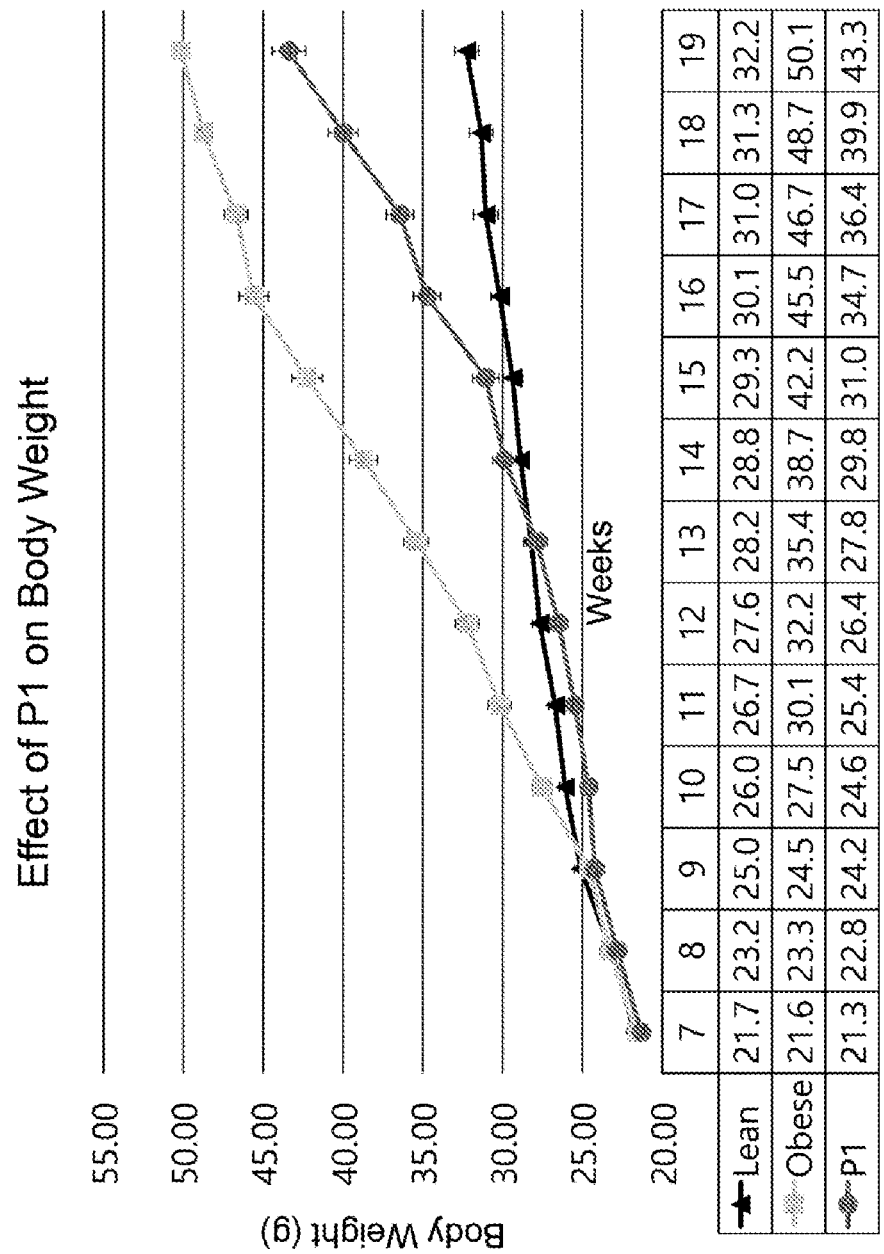
FIGS. 14 to 22, which show the results of the peptide effect confirmation experiment according to Experimental Example 7, and are graphs showing the measured body weight per week of age of a test subject in each experimental group, in which Lean denotes a control group with normal weight, Obese denotes an obesity group induced by high-fat diet, P1 denotes Group 6-1, P2 denotes Group 6-2, P3 denotes Group 6-3, P4 denotes Group 6-4, P5 denotes Group 6-5, P6 denotes Group 6-6, P7 denotes Group 6-7, P8 denotes Group 6-8, and P9 denotes Group 6-9.
Figure 15:
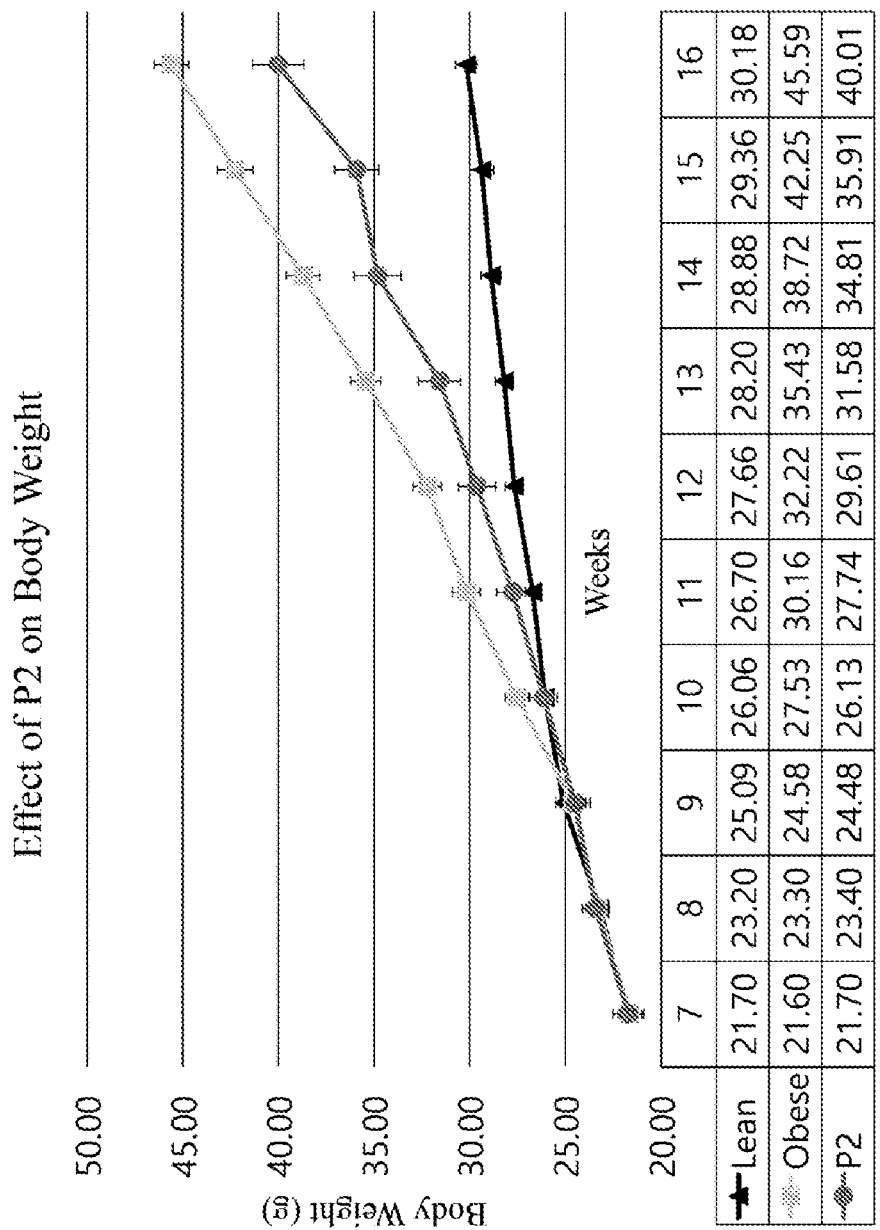
Figure 16:
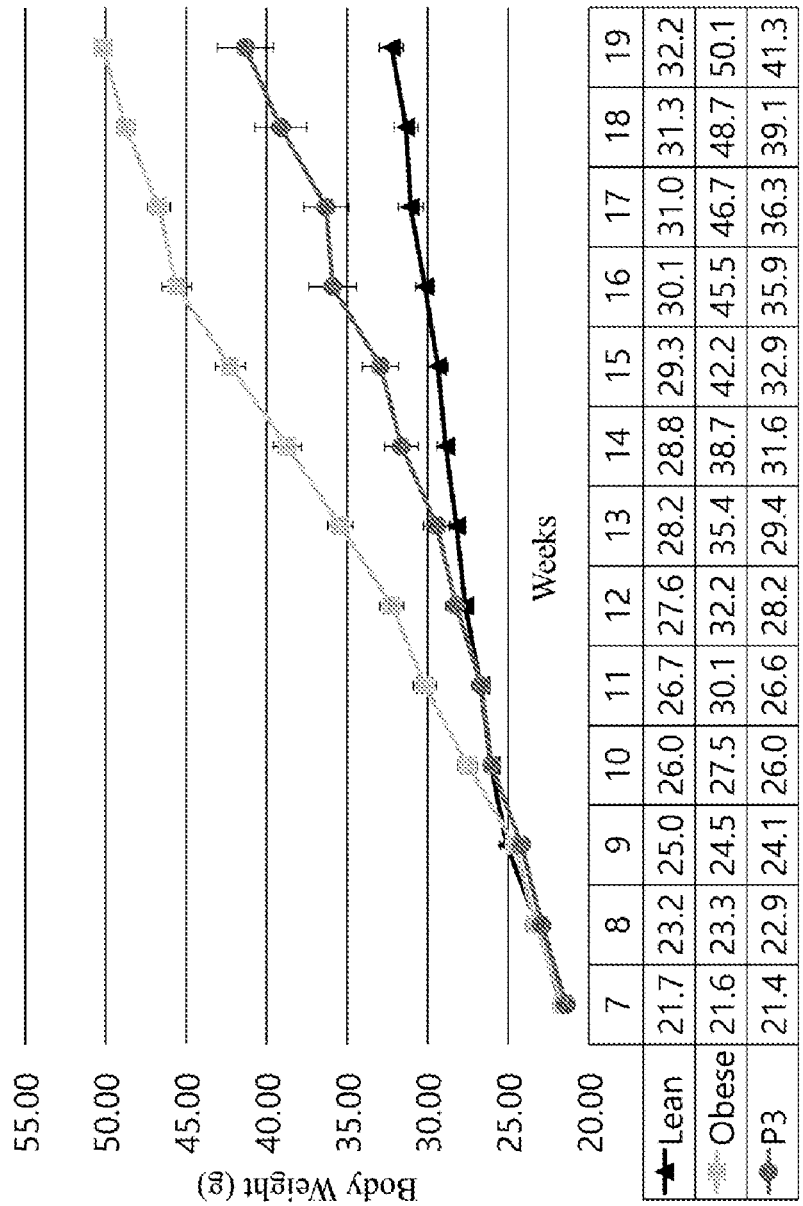
Figure 17:
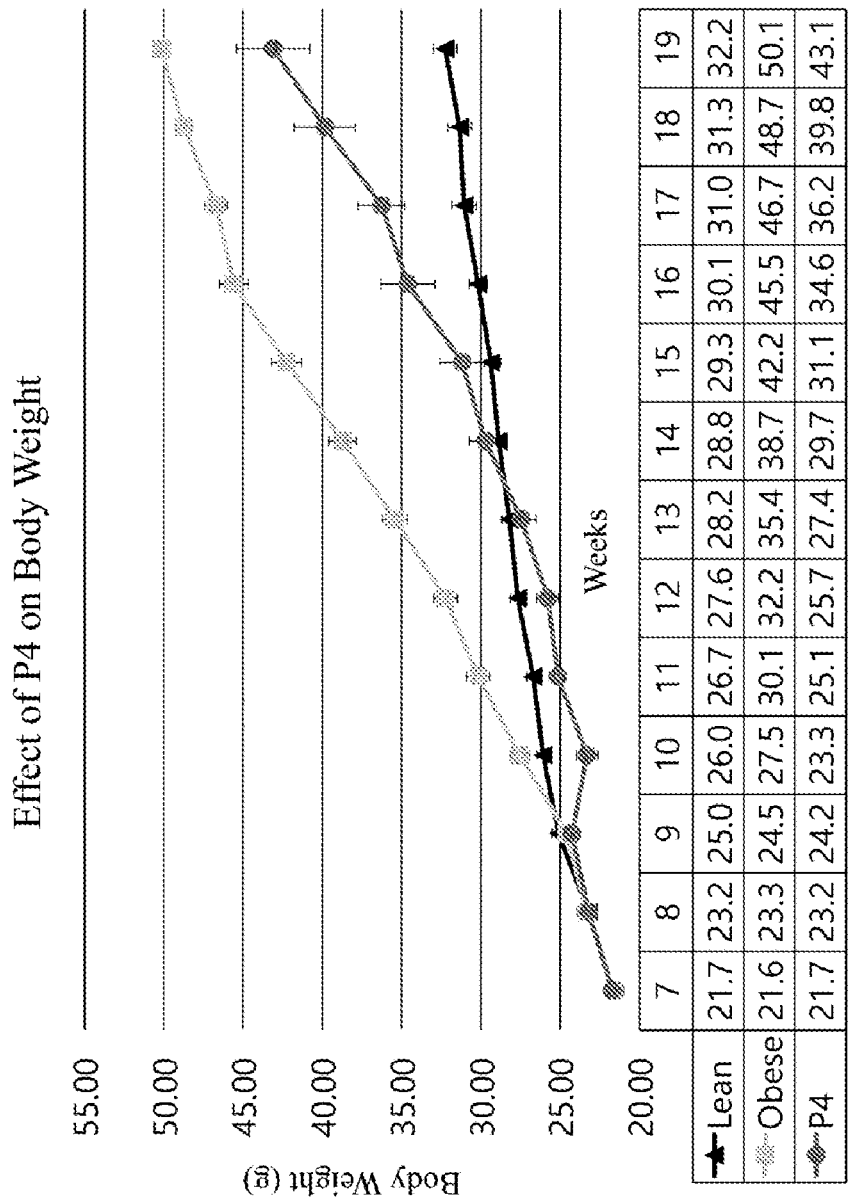
Figure 18:
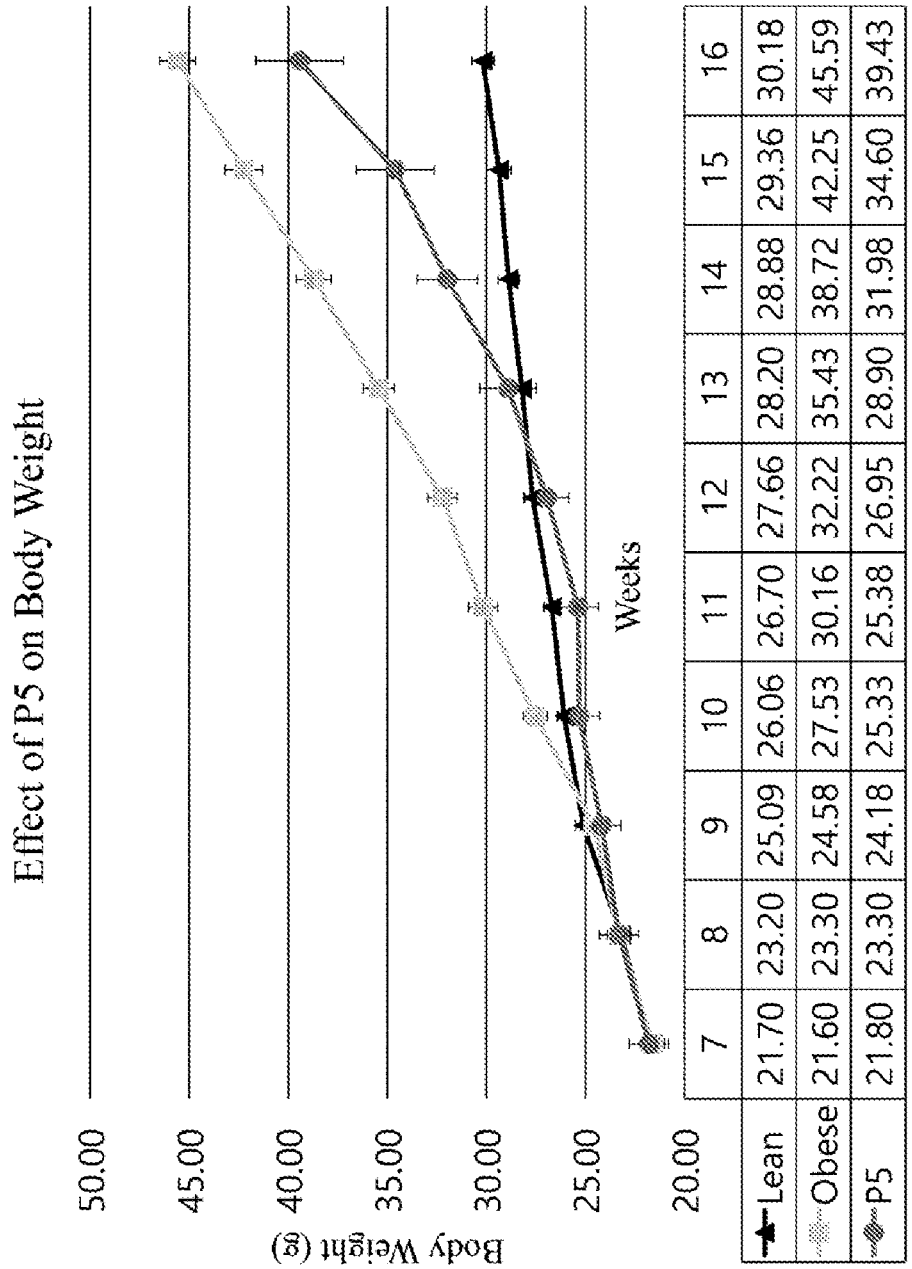
Figure 19:
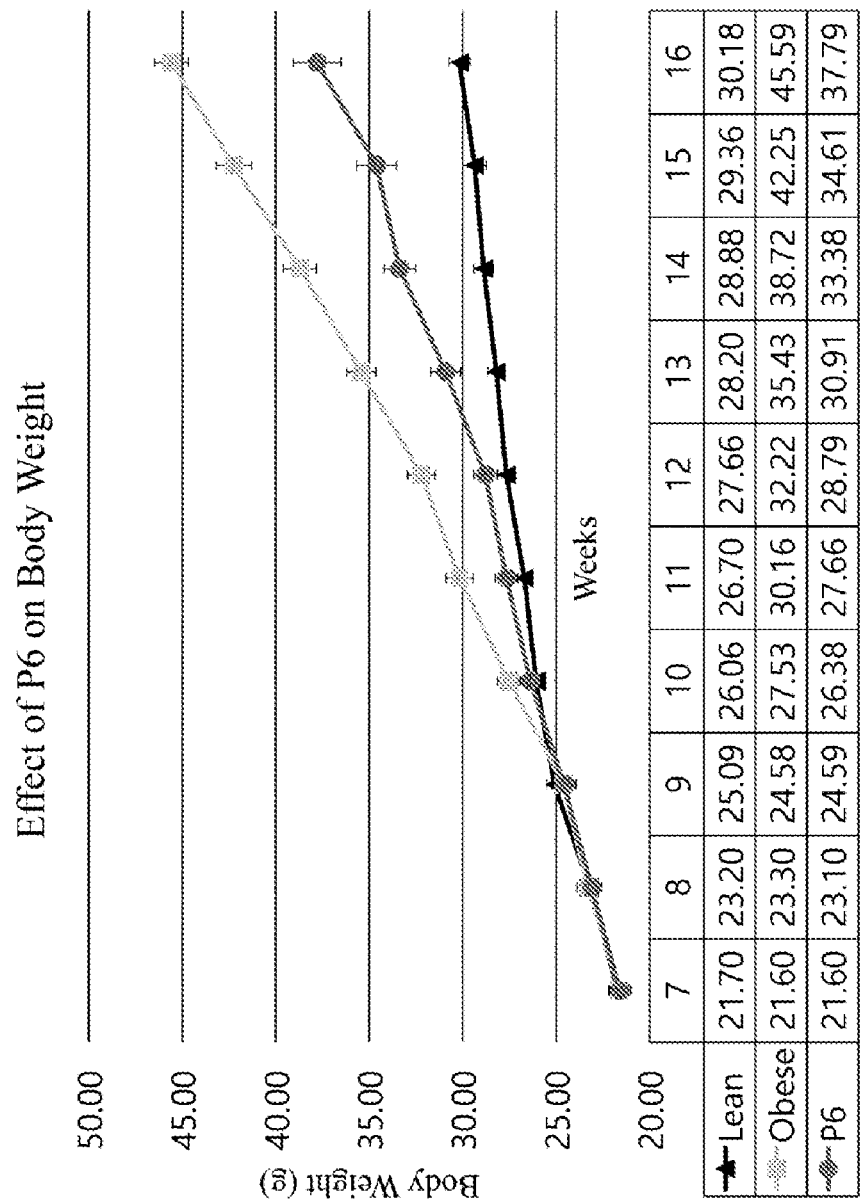
Figure 20:
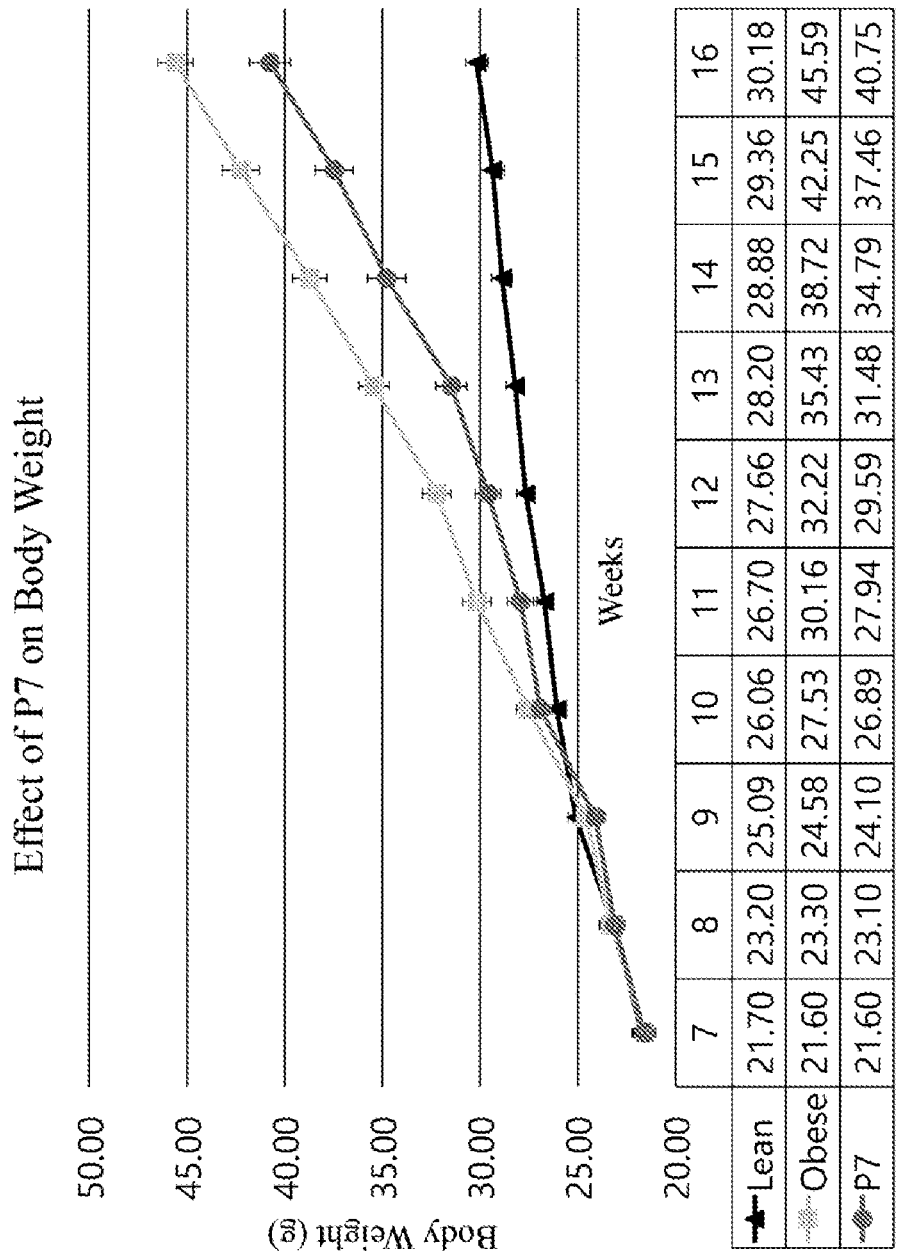
Figure 21:
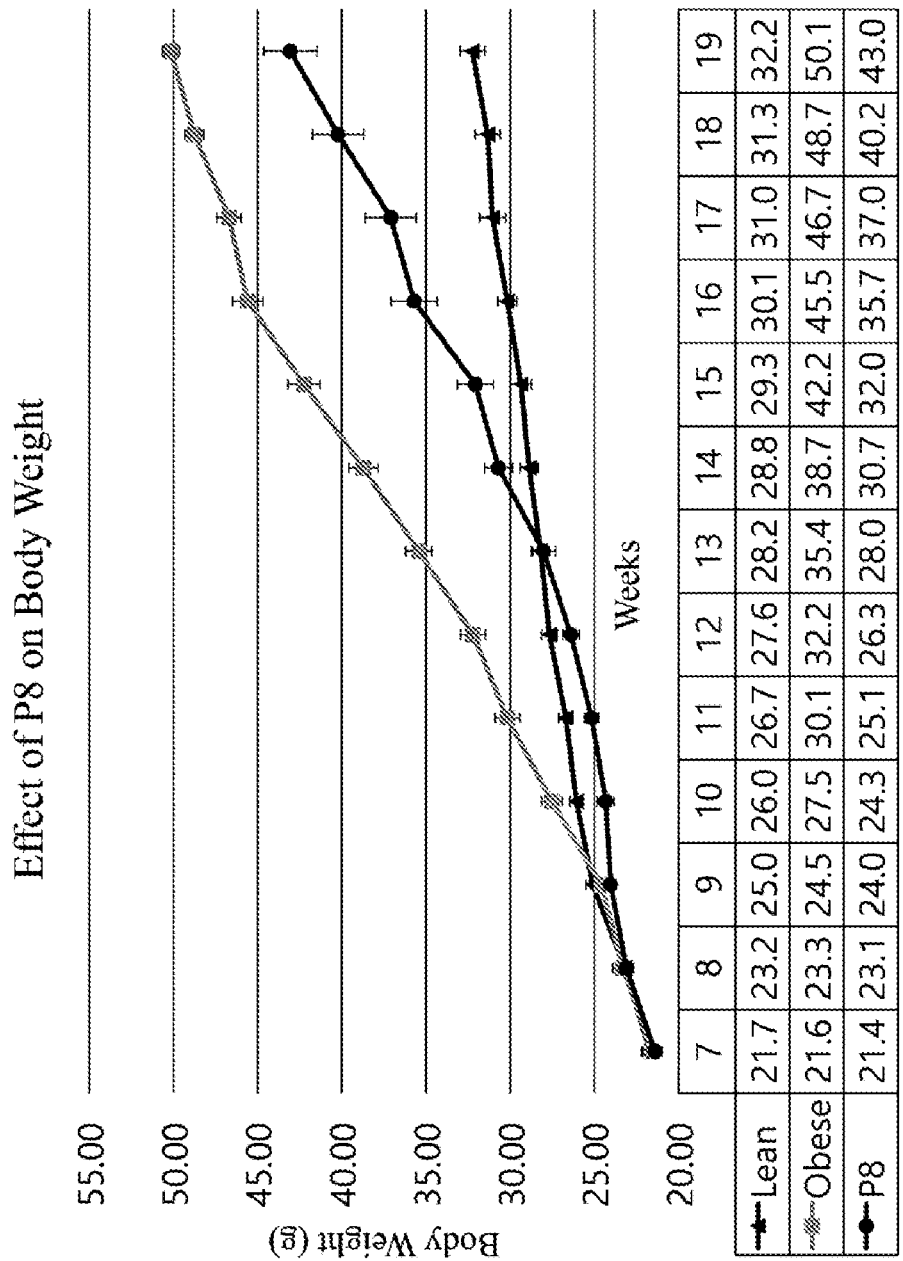
Figure 22:
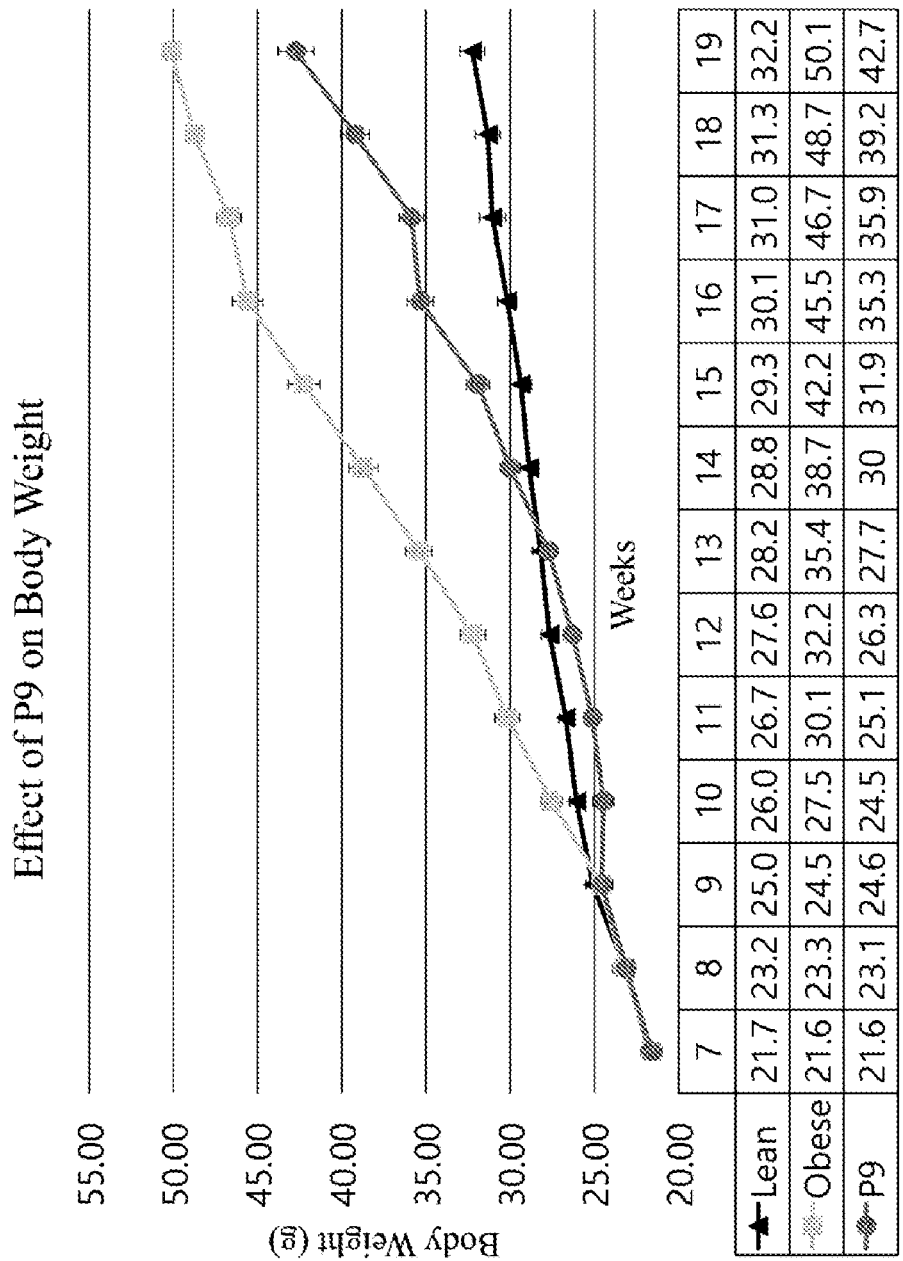

The experimental results are shown in FIG. 13.

Experimental Example 7, Confirmation of Peptide Effect 6

Experimental Example 7.1, Peptide Preparation and Experiment Thereof

After preparing the peptides according to [Table 11] according to Experimental Example 1.1, the peptides prepared were confirmed according to Experimental Examples 1.2 to 1.4. A composition for in vivo administration including the peptides according to [Table 11] according to Experimental Example 1.5 was prepared.

TABLE 11

Peptides used in Experimental Example 7 and composition for in vivo administration including the same

| Label | Peptide sequence | SEQ ID NO |
|---|---|---|
| Example. 5 | RNVPPIFNDVYWIAFZaK(Cha)VAAWTLKAAaZC RFRGLISLSQVYLS | 108 |
| Example. 6 | RNVPPIFNDVYWIAFZaK(Cha)VAAWTLKAAaZG SHHHHHHGSDDDDK | 68 |
| Example. 7 | GSHHHHHHGSDDDDKZaK(Cha)VAAWTLKAAaZR NVPPIFNDVYWIAF | 69 |
| Example. 8 | KTTKQSFDLSVKAQYKKNKHZaK(Cha)VAAWTLK AAaZCRFRGLISLSQVYLS | 114 |
| Example. 9 | RNVPPIFNDVYWIAFCRFRGLISLSQVYLSZaK (Cha)VAAWTLKAAaZ | 84 |
| Example. 10 | RNVPPIFNDVYWIAFZPKYVKQNTLKLATZCRFRG LISLSQVYLS | 121 |
| Example. 11 | RNVPPIFNDVYWIAFZaK(Cha)VAAWTLKAAaZ | 56 |
| Example. 12 | RNVPPIFNDVYWIAFK(Cha)VAAWTLKAA | 62 |
| Example. 13 | RNVPPIFNDVYWIAFK(Cha)VAAWTLKAAHHHHH H | 67 |

The test subject shown in [Table 12] was prepared according to Experimental Example 1.6.

TABLE 12

Test subject used in Experimental Example 7

| Label | Species | Diet | Composition | n |
|---|---|---|---|---|
| Lean | C57BL/6J, male | ~10 weeks: normal diet after 10 weeks: high-fat diet | PBS-Alum | 8 |
| Obese | C57BL/6J, male | ~10 weeks: normal diet after 10 weeks: high-fat diet | PBS-Alum | 12 |
| Group 6-1 (P1) | C57BL/6J, male | ~10 weeks: normal diet after 10 weeks: high-fat diet | Example. 5 | 12 |
| Group 6-2 (P2) | C57BL/6J, male | ~10 weeks: normal diet after 10 weeks: high-fat diet | Example. 6 | 8 |
| Group 6-3 (P3) | C57BL/6J, male | ~10 weeks: normal diet after 10 weeks: high-fat diet | Example. 7 | 8 |
| Group 6-4 (P4) | C57BL/6J, male | ~10 weeks: normal diet after 10 weeks: high-fat diet | Example. 8 | 8 |
| Group 6-5 (P5) | C57BL/6J, male | ~10 weeks: normal diet after 10 weeks: high-fat diet | Example. 9 | 4 |
| Group 6-6 (P6) | C57BL/6J, male | ~10 weeks: normal diet after 10 weeks: high-fat diet | Example. 10 | 8 |

TABLE 12-continued

Test subject used in Experimental Example 7

| Label | Species | Diet | Composition | n |
|---|---|---|---|---|
| Group 6-7 (P7) | C57BL/6J, male | ~10 weeks: normal diet after 10 weeks: high-fat diet | Example. 11 | 8 |
| Group 6-8 (P8) | C57BL/6J, male | ~10 weeks: normal diet after 10 weeks: high-fat diet | Example. 12 | 8 |
| Group 6-9 (P9) | C57BL/6J, male | ~10 weeks: normal diet after 10 weeks: high-fat diet | Example. 13 | 8 |

According to Experimental Example 1.7, the composition for in vivo administration was administered to the test subject. In particular, the administration cycle was as follows: 8 weeks, 10 weeks, 12 weeks, and 14 weeks of age.

Experimental Example 7.2, Confirmation of Experimental Results

In order to confirm the experimental results of Experimental Example 7.1, the following experiments were performed in a test subject for each experimental group disclosed in [Table 12].

(1) According to Experimental Example 1.8, the weight of a test subject for each experimental group was measured.

(2) According to Experimental Example 1.9, the antibody titers observed in a test subject for each experimental group at 11 weeks, 16 weeks, and 19 weeks were confirmed. In particular, the target antigen was determined using RNVP-PIFNDVYWIAF (SEQ ID NO: 6).

The experimental results are shown in FIGS. 14 to 25.

As a result of the experiment, all of the experimental groups 6-1 (P1) to experimental groups 6-9 (P9) showed a distinct weight loss effect compared to the control group (Obese), which were fed with a high-fat diet.

The results of the antibody titer test according to the experimental group can be interpreted as follows:

Since no antigen was administered to the control groups (i.e., Lean and Obese), antibody titers were not shown.

In consideration of the experimental design, in the experimental groups, the antibody titers to SEQ ID NO: 6 included in the peptides used were mainly confirmed. Although antibody titers to sequences other than SEQ ID NO: 6 included in the peptides used were not separately confirmed, the weight loss effect due to a humoral immunity by these was confirmed together.

Specific results will be described below.

In the case of Experimental Group 6-1 (P1), there were individuals showing a large antibody titer depending on the individual, and there were also individuals which showed no antibody titer. These results can be interpreted as follows: for some individuals of the experimental group 6-1 (P1), a humoral immunity to RNVPPIFNDVYWIAF (SEQ ID NO: 6) included in Example 6 was induced, thus showing both the weight loss effect and antibody titer observed; and although for some individuals, a humoral immunity to CRFRGLISLSQVYLS (SEQ ID NO: 7) included in Example 6 was induced, resulting in weight loss, the antigen used in the Enzyme-Linked Immunosorbent Assay (ELISA) consisted only of RNVPPIFNDVYWIAF (SEQ ID NO: 6) and there was no other antigen (i.e., the antigen of SEQ ID NO: 7), therefore, the antibody titer according to the above experiment was not observed even in the presence of the antibody.

In the case of experimental group 6-2 (P2), the antibody titer to RNVPPIFNDVYWIAF (SEQ ID NO: 6) included in Example 7 was observed, and the weight loss effect appeared, it can be interpreted that the B-cell epitope included in the peptide of Example 7 well induced a humoral immunity thereto.

In the case of experimental group 6-3 (P3), the antibody titer to RNVPPIFNDVYWIAF (SEQ ID NO: 6) included in Example 8 was observed, and the weight loss effect appeared, it can be interpreted that that the B-cell epitope included in the peptide of Example 8 well induced a humoral immunity thereto.

In the case of experimental group 6-4 (P4), it can be interpreted that a humoral immunity to KTTKQSFDLSVKAQYKKNKH (SEQ ID NO: 8) and/or CRFRGLISLSQVYLS (SEQ ID NO: 7) included in Example 9 was induced, thus antibody titers against RNVPPIFNDVYWIAF (SEQ ID NO: 6) were not shown, while there was a weight loss effect.

These results can be interpreted that for some individuals of the experimental group 6-5 (P5), a humoral immunity was induced against RNVPPIFNDVYWIAF (SEQ ID NO: 6) included in Example 10, such that both a weight loss effect and an antibody titer are observed, for the other individuals of the experimental group 6-5 (P5), a humoral immunity was induced against CRFRGLISLSQVYLS (SEQ ID NO: 7) included in Example 10, such that a weight loss effect is observed, but the antibody titer according to the above experiment was not observed.

In the case of experimental group 6-7 (P7), although there were some differences between individuals, antibodies to RNVPPIFNDVYWIAF (SEQ ID NO: 6) was observed and the weight loss effect appeared, therefore, it can be interpreted that the B-cell epitope included in the peptide of Example 11 well induced a humoral immunity.

In the case of experimental group 6-8 (P8), since the antibody titer against RNVPPIFNDVYWIAF (SEQ ID NO: 6) included in Example 12 was shown, and the weight loss effect was shown, it can be interpreted that the B-cell epitope included in the peptide of Example 12 well induced a humoral immunity.

In the case of experimental group 6-9 (P9), there were some differences between individuals. However, since the antibody against RNVPPIFNDVYWIAF (SEQ ID NO: 6) was observed and the weight loss effect appeared, it can be interpreted that the B-cell epitope included in the peptide of Example 13 well induced a humoral immunity.

Experimental Example 8, Confirmation of Peptide Effect 7

Experimental Example 8.1, Peptide Preparation and Experiment Thereof

After preparing the peptides according to [Table 13] according to Experimental Example 1.1, the peptides prepared are confirmed according to Experimental Examples 1.2 to 1.4. A composition for in vivo administration including the peptides according to [Table 13] according to Experimental Example 1.5 are prepared.

TABLE 13

Peptides used in Experimental Example 8 and composition for in vivo administration including the same

| Label | Peptide sequence | SEQ ID NO |
|---|---|---|
| Example. 5 | RNVPPIFNDVYWIAFZaK(Cha)VAAWTLKAAaZCRFRGLISLSQVYLS | 108 |
| Example. 14 | RNVPPIFNDVYWIAFZaK(Cha)VAAWTLKAACRFRGLISLSQVYLS | 160 |
| Example. 15 | RNVPPIFNDVYWIAFZaK(Cha)VAAWTLKAACR | 161 |

The test subject shown in [Table 14] is prepared according to Experimental Example 1.6.

TABLE 14

Test subject used in Experimental Example 8

| Label | Species | Diet | Composition | n |
|---|---|---|---|---|
| Lean | C57BL/6J, male | ~10 weeks: normal diet after 10 weeks: high-fat diet | PBS-Alum | 8 |
| Obese | C57BL/6J, male | ~10 weeks: normal diet after 10 weeks: high-fat diet | PBS-Alum | 8 |
| Group 7-1 | C57BL/6J, male | ~10 weeks: normal diet after 10 weeks: high-fat diet | Example. 5 | 8 |
| Group 7-2 | C57BL/6J, male | ~10 weeks: normal diet after 10 weeks: high-fat diet | Example. 14 | 8 |
| Group 7-3 | C57BL/6J, male | ~10 weeks: normal diet after 10 weeks: high-fat diet | Example. 15 | 8 |

According to Experimental Example 1.7, the composition for in vivo administration is administered to the test subject. In particular, the administration cycle, administration timing, and frequency of administration may be appropriately modified according to the experimental design. For example, the composition may be administered four times at intervals of two weeks for a test subject of 8 weeks of age, but is not limited thereto.

The above experimental method may be appropriately modified as necessary.

Experimental Example 8.2, Confirmation of Experimental Results

In order to confirm the experimental results of Experimental Example 8.1, the following experiments are performed in a test subject for each experimental group disclosed in [Table 14].

(1) According to Experimental Example 1.8, the weight of a test subject for each experimental group is measured.

(2) According to Experimental Example 1.9, the antibody titers observing in a test subject for each experimental group are confirmed.

(3) According to Experimental Example 1.10, the blood lipid concentration of a test subject for each experimental group is measured.

(4) According to Experimental Example 1.11, the lipolysis ability of a test subject in each experimental group is confirmed and the size of adipocytes is observed.

Experimental Example 9, Confirmation of Peptide Effect 8

Experimental Example 9.1, Peptide Preparation and Experiment Thereof

According to Experimental Example 1.1, a peptide represented by one or more sequences selected from the group consisting of the following is prepared: SEQ ID NOS: 56 to 158, SEQ ID NOS: 160 to 161, and SEQ ID NOS: 198 to 220.

The peptides prepared are confirmed according to Experimental Examples 1.2 to 1.4. According to Experimental Example 1.5, a composition for in vivo administration including the peptides prepared is prepared.

In particular, the peptide may be prepared by selecting only some sequences from the sequence groups above, and repeated experiments may be performed with multiple combinations as needed.

The test subject for the peptides prepared is prepared according to Experimental Example 1.6. In particular, examples of the control groups and the experimental groups to be used are as shown in [Table 15], and each experimental group is determined with reference to the conditions of Experimental Example 1.6 and [Table 15].

TABLE 15

Test subject used in Experimental Example 9

| Label | Species | Diet | Composition | n |
|---|---|---|---|---|
| Lean | C57BL/6J, male | ~10 weeks: normal diet after 10 weeks: high-fat diet | PBS-Alum | 8 |
| Obese | C57BL/6J, male | ~10 weeks: normal diet after 10 weeks: high-fat diet | PBS-Alum | 8 |
| Experimental group | C57BL/6J, male | ~10 weeks: normal diet after 10 weeks: high-fat diet | One of the prepared Example in Experimental example 9.1 | 8 |

In particular, the experimental groups are prepared as many as the number of the prepared peptides prepared.

According to Experimental Example 1.7, the composition for in vivo administration is administered to the test subject. In particular, the administration cycle, administration timing, and frequency of administration may be appropriately modified according to the experimental design. For example, the composition may be administered four times at intervals of two weeks for a test subject of 8 weeks of age, but is not limited thereto.

The above experimental method may be appropriately modified as necessary.

Experimental Example 9.2, Confirmation of Experimental Results

In order to confirm the experimental results of Experimental Example 9.1, the following experiments are performed in a test subject for each experimental group.

(1) According to Experimental Example 1.8, the weight of a test subject for each experimental group is measured.

(2) According to Experimental Example 1.9, the antibody titers observing in a test subject for each experimental group are confirmed.

(3) According to Experimental Example 1.10, the blood lipid concentration of a test subject for each experimental group is measured.

(4) According to Experimental Example 1.11, the lipolysis ability of a test subject in each experimental group was confirmed and the size of adipocytes is observed.

Experimental Example 10, Confirmation of Peptide Effect 9

Experimental Example 10.1, Peptide Preparation and Experiment Thereof

After preparing the peptides according to Examples 81 to 90 in the paragraph of "Possible Examples of the Invention" according to Experimental Example 1.1, the peptides prepared are confirmed according to Experimental Examples 1.2 to 1.4. According to Experimental Example 1.5, a composition for in vivo administration including the peptides prepared is prepared.

In particular, only parts of the peptides according to Examples 81 to 90 of the paragraph of "Possible Examples of the Invention" may be selected and prepared, and experiments on multiple combinations may be repeated as needed.

The test subject for the peptide prepared is prepared according to Experimental Example 1.6. In particular, the control groups and experimental groups to be used are determined with reference to the conditions of Experimental Example 1.6 and [Table 15].

According to Experimental Example 1.7, the composition for in vivo administration is administered to the test subject. In particular, the administration cycle, administration timing, and frequency of administration may be appropriately modified according to the experimental design. For example, the composition may be administered four times at intervals of two weeks for a test subject of 8 weeks of age, but is not limited thereto.

The above experimental method may be appropriately modified as necessary.

Experimental Example 10.2, Confirmation of Experimental Results

In order to confirm the experimental results of Experimental Example 10.1, the following experiments are performed in a test subject for each experimental group.

(1) According to Experimental Example 1.8, the weight of a test subject for each experimental group is measured.

(2) According to Experimental Example 1.9, the antibody titers observing in a test subject for each experimental group are confirmed.

(3) According to Experimental Example 1.10, the blood lipid concentration of a test subject for each experimental group is measured.

(4) According to Experimental Example 1.11, the lipolysis ability of a test subject in each experimental group is confirmed and the size of adipocytes is observed.

INDUSTRIAL APPLICABILITY

A peptide unit, a peptide, and/or a nucleic acid encoding the same provided herein can be used to prepare an immunotherapeutic, particularly an agent for treating obesity, and the immunotherapeutic may show a therapeutic effect by generating an intended humoral immunity when administered into the body of a subject.

The invention claimed is:

1. A peptide comprising an amino acid sequence, wherein the amino acid sequence comprises RNVPPIFNDVYWI-AFZaK(Cha)VAAWTLKAACR (SEQ ID NO: 161), wherein the "a" denotes D-form alanine, the "(Cha)" denotes L-cyclohexylanine, and the "Z" denotes 6-aminohexanoic acid.

2. The peptide of claim 1,
wherein
the amino acid sequence consists of RNVPPIFNDVYWI-AFZaK(Cha)VAAWTLKAACR (SEQ ID NO: 161), wherein the "a" denotes D-form alanine, the "(Cha)" denotes L-cyclohexylalanine, and the "Z" denotes 6-aminohexanoic acid.

3. The peptide of claim 1, wherein the peptide consists of the amino acid sequence RNVPPIFNDVYWIAFZaK(Cha)VAAWTLKAACR (SEQ ID NO: 161), wherein the "a" denotes D-form alanine, the "(Cha)" denotes L-cyclohexylalanine, and the "Z" denotes 6-aminohexanoic acid.

* * * * *

SEQUENCE LISTING

```
Sequence total quantity: 309
SEQ ID NO: 1           moltype = AA  length = 11
FEATURE                Location/Qualifiers
SITE                   2
                       note = 2nd amino acid(Xaa) is L-cyclohexylalanins.
source                 1..11
                       mol_type = protein
                       note = Th epitope
                       organism = synthetic construct
SEQUENCE: 1
KXVAAWTLKA A                                                              11

SEQ ID NO: 2           moltype = AA  length = 13
FEATURE                Location/Qualifiers
source                 1..13
                       mol_type = protein
                       note = Th epitope
                       organism = synthetic construct
SEQUENCE: 2
PKYVKQNTLK LAT                                                            13

SEQ ID NO: 3           moltype = AA  length = 15
FEATURE                Location/Qualifiers
source                 1..15
                       mol_type = protein
                       note = Th epitope
                       organism = synthetic construct
SEQUENCE: 3
ILMQYIKANS KFIGI                                                          15

SEQ ID NO: 4           moltype = AA  length = 15
FEATURE                Location/Qualifiers
```

```
source                  1..15
                        mol_type = protein
                        note = Th epitope
                        organism = synthetic construct
SEQUENCE: 4
QSIALSSLMV AQAIP                                                              15

SEQ ID NO: 5            moltype = AA  length = 32
FEATURE                 Location/Qualifiers
source                  1..32
                        mol_type = protein
                        note = Th epitope
                        organism = synthetic construct
SEQUENCE: 5
ILMQYIKANS KFIGIPMGLP QSIALSSLMV AQ                                            32

SEQ ID NO: 6            moltype = AA  length = 15
FEATURE                 Location/Qualifiers
source                  1..15
                        mol_type = protein
                        note = B cell epitope
                        organism = synthetic construct
SEQUENCE: 6
RNVPPIFNDV YWIAF                                                              15

SEQ ID NO: 7            moltype = AA  length = 15
FEATURE                 Location/Qualifiers
source                  1..15
                        mol_type = protein
                        note = B cell epitope
                        organism = synthetic construct
SEQUENCE: 7
CRFRGLISLS QVYLS                                                              15

SEQ ID NO: 8            moltype = AA  length = 20
FEATURE                 Location/Qualifiers
source                  1..20
                        mol_type = protein
                        note = B cell epitope
                        organism = synthetic construct
SEQUENCE: 8
KTTKQSFDLS VKAQYKKNKH                                                         20

SEQ ID NO: 9            moltype = AA  length = 11
FEATURE                 Location/Qualifiers
source                  1..11
                        mol_type = protein
                        note = B cell epitope
                        organism = synthetic construct
SEQUENCE: 9
RNVPPIFNDV Y                                                                  11

SEQ ID NO: 10           moltype = AA  length = 11
FEATURE                 Location/Qualifiers
source                  1..11
                        mol_type = protein
                        note = B cell epitope
                        organism = synthetic construct
SEQUENCE: 10
CRFRGLISLS Q                                                                  11

SEQ ID NO: 11           moltype = AA  length = 12
FEATURE                 Location/Qualifiers
source                  1..12
                        mol_type = protein
                        note = B cell epitope
                        organism = synthetic construct
SEQUENCE: 11
KTTKQSFDLS VK                                                                 12

SEQ ID NO: 12           moltype = AA  length = 12
FEATURE                 Location/Qualifiers
source                  1..12
                        mol_type = protein
                        note = B cell epitope
                        organism = synthetic construct
SEQUENCE: 12
RNVPPIFNDV YW                                                                 12
```

```
SEQ ID NO: 13          moltype = AA   length = 12
FEATURE                Location/Qualifiers
source                 1..12
                       mol_type = protein
                       note = B cell epitope
                       organism = synthetic construct
SEQUENCE: 13
CRFRGLISLS QV                                                                    12

SEQ ID NO: 14          moltype = AA   length = 17
FEATURE                Location/Qualifiers
source                 1..17
                       mol_type = protein
                       note = B cell epitope
                       organism = synthetic construct
SEQUENCE: 14
KTTKQSFDLS VKAQYKK                                                               17

SEQ ID NO: 15          moltype = AA   length = 13
FEATURE                Location/Qualifiers
source                 1..13
                       mol_type = protein
                       note = B cell epitope
                       organism = synthetic construct
SEQUENCE: 15
RNVPPIFNDV YWI                                                                   13

SEQ ID NO: 16          moltype = AA   length = 13
FEATURE                Location/Qualifiers
source                 1..13
                       mol_type = protein
                       note = B cell epitope
                       organism = synthetic construct
SEQUENCE: 16
CRFRGLISLS QVY                                                                   13

SEQ ID NO: 17          moltype = AA   length = 18
FEATURE                Location/Qualifiers
source                 1..18
                       mol_type = protein
                       note = B cell epitope
                       organism = synthetic construct
SEQUENCE: 17
KTTKQSFDLS VKAQYKKN                                                              18

SEQ ID NO: 18          moltype = AA   length = 11
FEATURE                Location/Qualifiers
source                 1..11
                       mol_type = protein
                       note = B cell epitope
                       organism = synthetic construct
SEQUENCE: 18
PIFNDVYWIA F                                                                     11

SEQ ID NO: 19          moltype = AA   length = 11
FEATURE                Location/Qualifiers
source                 1..11
                       mol_type = protein
                       note = B cell epitope
                       organism = synthetic construct
SEQUENCE: 19
GLISLSQVYL S                                                                     11

SEQ ID NO: 20          moltype = AA   length = 16
FEATURE                Location/Qualifiers
source                 1..16
                       mol_type = protein
                       note = B cell epitope
                       organism = synthetic construct
SEQUENCE: 20
QSFDLSVKAQ YKKNKH                                                                16

SEQ ID NO: 21          moltype = AA   length = 12
FEATURE                Location/Qualifiers
source                 1..12
                       mol_type = protein
                       note = B cell epitope
                       organism = synthetic construct
SEQUENCE: 21
```

```
PPIFNDVYWI AF                                                                          12

SEQ ID NO: 22          moltype = AA   length = 12
FEATURE                Location/Qualifiers
source                 1..12
                       mol_type = protein
                       note = B cell epitope
                       organism = synthetic construct
SEQUENCE: 22
RGLISLSQVY LS                                                                          12

SEQ ID NO: 23          moltype = AA   length = 17
FEATURE                Location/Qualifiers
source                 1..17
                       mol_type = protein
                       note = B cell epitope
                       organism = synthetic construct
SEQUENCE: 23
KQSFDLSVKA QYKKNKH                                                                     17

SEQ ID NO: 24          moltype = AA   length = 13
FEATURE                Location/Qualifiers
source                 1..13
                       mol_type = protein
                       note = B cell epitope
                       organism = synthetic construct
SEQUENCE: 24
VPPIFNDVYW IAF                                                                         13

SEQ ID NO: 25          moltype = AA   length = 13
FEATURE                Location/Qualifiers
source                 1..13
                       mol_type = protein
                       note = B cell epitope
                       organism = synthetic construct
SEQUENCE: 25
FRGLISLSQV YLS                                                                         13

SEQ ID NO: 26          moltype = AA   length = 18
FEATURE                Location/Qualifiers
source                 1..18
                       mol_type = protein
                       note = B cell epitope
                       organism = synthetic construct
SEQUENCE: 26
TKQSFDLSVK AQYKKNKH                                                                    18

SEQ ID NO: 27          moltype = AA   length = 13
FEATURE                Location/Qualifiers
source                 1..13
                       mol_type = protein
                       note = B cell epitope
                       organism = synthetic construct
SEQUENCE: 27
NVPPIFNDVY WIA                                                                         13

SEQ ID NO: 28          moltype = AA   length = 13
FEATURE                Location/Qualifiers
source                 1..13
                       mol_type = protein
                       note = B cell epitope
                       organism = synthetic construct
SEQUENCE: 28
RFRGLISLSQ VYL                                                                         13

SEQ ID NO: 29          moltype = AA   length = 16
FEATURE                Location/Qualifiers
source                 1..16
                       mol_type = protein
                       note = B cell epitope
                       organism = synthetic construct
SEQUENCE: 29
TKQSFDLSVK AQYKKN                                                                      16

SEQ ID NO: 30          moltype = AA   length = 11
FEATURE                Location/Qualifiers
source                 1..11
                       mol_type = protein
                       note = B cell epitope
```

-continued

```
                       organism = synthetic construct
SEQUENCE: 30
VPPIFNDVYW I                                                                  11

SEQ ID NO: 31          moltype = AA   length = 11
FEATURE                Location/Qualifiers
source                 1..11
                       mol_type = protein
                       note = B cell epitope
                       organism = synthetic construct
SEQUENCE: 31
FRGLISLSQV Y                                                                  11

SEQ ID NO: 32          moltype = AA   length = 16
FEATURE                Location/Qualifiers
source                 1..16
                       mol_type = protein
                       note = B cell epitope
                       organism = synthetic construct
SEQUENCE: 32
TKQSFDLSVK AQYKKN                                                             16

SEQ ID NO: 33          moltype = AA   length = 9
FEATURE                Location/Qualifiers
source                 1..9
                       mol_type = protein
                       note = B cell epitope
                       organism = synthetic construct
SEQUENCE: 33
PPIFNDVYW                                                                      9

SEQ ID NO: 34          moltype = AA   length = 9
FEATURE                Location/Qualifiers
source                 1..9
                       mol_type = protein
                       note = B cell epitope
                       organism = synthetic construct
SEQUENCE: 34
RGLISLSQV                                                                      9

SEQ ID NO: 35          moltype = AA   length = 14
FEATURE                Location/Qualifiers
source                 1..14
                       mol_type = protein
                       note = B cell epitope
                       organism = synthetic construct
SEQUENCE: 35
KQSFDLSVKA QYKK                                                               14

SEQ ID NO: 36          moltype =      length =
SEQUENCE: 36
000

SEQ ID NO: 37          moltype =      length =
SEQUENCE: 37
000

SEQ ID NO: 38          moltype =      length =
SEQUENCE: 38
000

SEQ ID NO: 39          moltype =      length =
SEQUENCE: 39
000

SEQ ID NO: 40          moltype = AA   length = 4
FEATURE                Location/Qualifiers
source                 1..4
                       mol_type = protein
                       note = B cell epitope
                       organism = synthetic construct
SEQUENCE: 40
RNVP                                                                           4

SEQ ID NO: 41          moltype = AA   length = 4
FEATURE                Location/Qualifiers
source                 1..4
                       mol_type = protein
                       note = B cell epitope
```

```
                        organism = synthetic construct
SEQUENCE: 41
WIAF                                                                    4

SEQ ID NO: 42           moltype =    length =
SEQUENCE: 42
000

SEQ ID NO: 43           moltype =    length =
SEQUENCE: 43
000

SEQ ID NO: 44           moltype =    length =
SEQUENCE: 44
000

SEQ ID NO: 45           moltype =    length =
SEQUENCE: 45
000

SEQ ID NO: 46           moltype = AA   length = 4
FEATURE                 Location/Qualifiers
source                  1..4
                        mol_type = protein
                        note = B cell epitope
                        organism = synthetic construct
SEQUENCE: 46
CRFR                                                                    4

SEQ ID NO: 47           moltype = AA   length = 4
FEATURE                 Location/Qualifiers
source                  1..4
                        mol_type = protein
                        note = B cell epitope
                        organism = synthetic construct
SEQUENCE: 47
VYLS                                                                    4

SEQ ID NO: 48           moltype =    length =
SEQUENCE: 48
000

SEQ ID NO: 49           moltype =    length =
SEQUENCE: 49
000

SEQ ID NO: 50           moltype =    length =
SEQUENCE: 50
000

SEQ ID NO: 51           moltype =    length =
SEQUENCE: 51
000

SEQ ID NO: 52           moltype = AA   length = 15
FEATURE                 Location/Qualifiers
source                  1..15
                        mol_type = protein
                        note = Auxiliary part
                        organism = synthetic construct
SEQUENCE: 52
GSHHHHHHGS DDDDK                                                       15

SEQ ID NO: 53           moltype = AA   length = 6
FEATURE                 Location/Qualifiers
source                  1..6
                        mol_type = protein
                        note = Auxiliary part
                        organism = synthetic construct
SEQUENCE: 53
HHHHHH                                                                  6

SEQ ID NO: 54           moltype = AA   length = 20
FEATURE                 Location/Qualifiers
source                  1..20
                        mol_type = protein
                        note = His-tag sequence
                        organism = synthetic construct
SEQUENCE: 54
```

MRGSHHHHHH GSDDDDKIVD                                                        20

SEQ ID NO: 55           moltype = AA   length = 13
FEATURE                 Location/Qualifiers
source                  1..13
                        mol_type = protein
                        note = Linker peptide
                        organism = synthetic construct
SEQUENCE: 55
GGGGSGGGGG GSS                                                               13

SEQ ID NO: 56           moltype = AA   length = 30
FEATURE                 Location/Qualifiers
source                  1..30
                        mol_type = protein
                        note = Unit peptide
                        organism = synthetic construct
SITE                    17
                        note = 17th aminoacid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SITE                    16
                        note = 16th amino acid(Xaa) is a 6-aminohexanoic acid.
SEQUENCE: 56
RNVPPIFNDV YWIAFXXKXV AAWTLKAAXX                                             30

SEQ ID NO: 57           moltype = AA   length = 30
FEATURE                 Location/Qualifiers
SITE                    1
                        note = 1st amino acid(Xaa) is a 6-aminohexanoic acid.
source                  1..30
                        mol_type = protein
                        note = Unit peptide
                        organism = synthetic construct
SITE                    2
                        note = 2nd aminoacid(Xaa) is a D-form alanine.
SITE                    4
                        note = 4th amino acid(Xaa) isL-cyclohexylalanins.
SITE                    14
                        note = 14th amino acid(Xaa) is a D-form alanine.
SITE                    15
                        note = 15th amino acid(Xaa) is a 6-aminohexanoic acid.
SEQUENCE: 57
XXKXVAAWTL KAAXXRNVPP IFNDVYWIAF                                             30

SEQ ID NO: 58           moltype = AA   length = 30
FEATURE                 Location/Qualifiers
SITE                    16
                        note = 16th amino acid(Xaa) is a 6-aminohexanoic acid.
source                  1..30
                        mol_type = protein
                        note = Unit peptide
                        organism = synthetic construct
SITE                    17
                        note = 17th aminoacid(Xaa) is a D-form alanine.
SITE                    19
                        note = 19th amino acid(Xaa) isL-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 58
CRFRGLISLS QVYLSXXKXV AAWTLKAAXX                                             30

SEQ ID NO: 59           moltype = AA   length = 30
FEATURE                 Location/Qualifiers
SITE                    1
                        note = 1st amino acid(Xaa) is a 6-aminohexanoic acid.
source                  1..30
                        mol_type = protein
                        note = Unit peptide
                        organism = synthetic construct
SITE                    2
                        note = 2nd aminoacid(Xaa) is a D-form alanine.
SITE                    4

```
                        note = 4th amino acid(Xaa) isL-cyclohexylalanins.
SITE                    14
                        note = 14th amino acid(Xaa) is a D-form alanine.
SITE                    15
                        note = 15th amino acid(Xaa) is a 6-aminohexanoic acid.
SEQUENCE: 59
XXKXVAAWTL KAAXXCRFRG LISLSQVYLS                                          30

SEQ ID NO: 60           moltype = AA  length = 35
FEATURE                 Location/Qualifiers
SITE                    21
                        note = 21st amino acid(Xaa) is a 6-aminohexanoic acid.
source                  1..35
                        mol_type = protein
                        note = Unit peptide
                        organism = synthetic construct
SITE                    22
                        note = 22nd aminoacid(Xaa) is a D-form alanine.
SITE                    24
                        note = 24th amino acid(Xaa) isL-cyclohexylalanins.
SITE                    34
                        note = 34th amino acid(Xaa) is a D-form alanine.
SITE                    35
                        note = 35th amino acid(Xaa) is a 6-aminohexanoic acid.
SEQUENCE: 60
KTTKQSFDLS VKAQYKKNKH XXKXVAAWTL KAAXX                                    35

SEQ ID NO: 61           moltype = AA  length = 35
FEATURE                 Location/Qualifiers
SITE                    1
                        note = 1st amino acid(Xaa) is a 6-aminohexanoic acid.
source                  1..35
                        mol_type = protein
                        note = Unit peptide
                        organism = synthetic construct
SITE                    2
                        note = 2nd aminoacid(Xaa) is a D-form alanine.
SITE                    4
                        note = 4th amino acid(Xaa) is L-cyclohexylalanins.
SITE                    14
                        note = 14th amino acid(Xaa) is a D-form alanine.
SITE                    15
                        note = 15th amino acid(Xaa) is a 6-aminohexanoic acid.
SEQUENCE: 61
XXKXVAAWTL KAAXXKTTKQ SFDLSVKAQY KKNKH                                    35

SEQ ID NO: 62           moltype = AA  length = 26
FEATURE                 Location/Qualifiers
SITE                    17
                        note = 17th amino acid(Xaa) is L-cyclohexylalanins.
source                  1..26
                        mol_type = protein
                        note = Unit peptide
                        organism = synthetic construct
SEQUENCE: 62
RNVPPIFNDV YWIAFKXVAA WTLKAA                                              26

SEQ ID NO: 63           moltype = AA  length = 26
FEATURE                 Location/Qualifiers
SITE                    2
                        note = 2nd amino acid(Xaa) is L-cyclohexylalanins.
source                  1..26
                        mol_type = protein
                        note = Unit peptide
                        organism = synthetic construct
SEQUENCE: 63
KXVAAWTLKA ARNVPPIFND VYWIAF                                              26

SEQ ID NO: 64           moltype = AA  length = 22
FEATURE                 Location/Qualifiers
SITE                    13
                        note = 13rd amino acid(Xaa) is L-cyclohexylalanins.
source                  1..22
                        mol_type = protein
                        note = Unit peptide
                        organism = synthetic construct
SEQUENCE: 64
RNVPPIFNDV YKXVAAWTLK AA                                                  22
```

```
SEQ ID NO: 65              moltype = AA   length = 22
FEATURE                    Location/Qualifiers
SITE                       13
                           note = 13rd amino acid(Xaa) is L-cyclohexylalanins.
source                     1..22
                           mol_type = protein
                           note = Unit peptide
                           organism = synthetic construct
SEQUENCE: 65
PIFNDVYWIA FKXVAAWTLK AA                                                   22

SEQ ID NO: 66              moltype = AA   length = 20
FEATURE                    Location/Qualifiers
SITE                       11
                           note = 11st amino acid(Xaa) is L-cyclohexylalanins.
source                     1..20
                           mol_type = protein
                           note = Unit peptide
                           organism = synthetic construct
SEQUENCE: 66
PPIFNDVYWK XVAAWTLKAA                                                      20

SEQ ID NO: 67              moltype = AA   length = 32
FEATURE                    Location/Qualifiers
SITE                       17
                           note = 17th amino acid(Xaa) is L-cyclohexylalanins.
source                     1..32
                           mol_type = protein
                           note = Unit peptide
                           organism = synthetic construct
SEQUENCE: 67
RNVPPIFNDV YWIAFKXVAA WTLKAAHHHH HH                                        32

SEQ ID NO: 68              moltype = AA   length = 45
FEATURE                    Location/Qualifiers
SITE                       16
                           note = 16th amino acid(Xaa) is a 6-aminohexanoic acid.
source                     1..45
                           mol_type = protein
                           note = Unit peptide
                           organism = synthetic construct
SITE                       17
                           note = 17th aminoacid(Xaa) is a D-form alanine.
SITE                       19
                           note = 19th amino acid(Xaa) is L-cyclohexylalanins.
SITE                       29
                           note = 29th amino acid(Xaa) is a D-form alanine.
SITE                       30
                           note = 30th amino acid(Xaa) is a 6-aminohexanoic acid.
SEQUENCE: 68
RNVPPIFNDV YWIAFXXKXV AAWTLKAAXX GSHHHHHHGS DDDDK                          45

SEQ ID NO: 69              moltype = AA   length = 45
FEATURE                    Location/Qualifiers
SITE                       16
                           note = 16th amino acid(Xaa) is a 6-aminohexanoic acid.
source                     1..45
                           mol_type = protein
                           note = Unit peptide
                           organism = synthetic construct
SITE                       17
                           note = 17th aminoacid(Xaa) is a D-form alanine.
SITE                       19
                           note = 19th amino acid(Xaa) isL-cyclohexylalanins.
SITE                       29
                           note = 29th amino acid(Xaa) is a D-form alanine.
SITE                       30
                           note = 30th amino acid(Xaa) is a 6-aminohexanoic acid.
SEQUENCE: 69
GSHHHHHHGS DDDDKXXKXV AAWTLKAAXX RNVPPIFNDV YWIAF                          45

SEQ ID NO: 70              moltype = AA   length = 45
FEATURE                    Location/Qualifiers
SITE                       31
                           note = 31st amino acid(Xaa) is a 6-aminohexanoic acid.
source                     1..45
                           mol_type = protein
                           note = Unit peptide
                           organism = synthetic construct
```

```
SITE                   32
                       note = 32nd aminoacid(Xaa) is a D-form alanine.
SITE                   34
                       note = 34th amino acid(Xaa) isL-cyclohexylalanins.
SITE                   44
                       note = 44th amino acid(Xaa) is a D-form alanine.
SITE                   45
                       note = 45th amino acid(Xaa) is a 6-aminohexanoic acid.
SEQUENCE: 70
RNVPPIFNDV YWIAFGSHHH HHHGSDDDDK XXKXVAAWTL KAAXX                           45

SEQ ID NO: 71          moltype = AA  length = 45
FEATURE                Location/Qualifiers
SITE                   16
                       note = 16th amino acid(Xaa) is a 6-aminohexanoic acid.
source                 1..45
                       mol_type = protein
                       note = Unit peptide
                       organism = synthetic construct
SITE                   19
                       note = 19th amino acid(Xaa) isL-cyclohexylalanins.
SITE                   29
                       note = 29th amino acid(Xaa) is a D-form alanine.
SITE                   30
                       note = 30th amino acid(Xaa) is a 6-aminohexanoic acid.
SITE                   17
                       note = 17th aminoacid(Xaa) is a D-form alanine.
SEQUENCE: 71
GSHHHHHHGS DDDDKXXKXV AAWTLKAAXX CRFRGLISLS QVYLS                           45

SEQ ID NO: 72          moltype = AA  length = 45
FEATURE                Location/Qualifiers
source                 1..45
                       mol_type = protein
                       note = Unit peptide
                       organism = synthetic construct
SITE                   31
                       note = 31st amino acid(Xaa) is a 6-aminohexanoic acid.
SITE                   32
                       note = 32nd aminoacid(Xaa) is a D-form alanine.
SITE                   34
                       note = 34th amino acid(Xaa) isL-cyclohexylalanins.
SITE                   44
                       note = 44th amino acid(Xaa) is a D-form alanine.
SITE                   45
                       note = 45th amino acid(Xaa) is a 6-aminohexanoic acid.
SEQUENCE: 72
GSHHHHHHGS DDDDKCRFRG LISLSQVYLS XXKXVAAWTL KAAXX                           45

SEQ ID NO: 73          moltype = AA  length = 45
FEATURE                Location/Qualifiers
source                 1..45
                       mol_type = protein
                       note = Unit peptide
                       organism = synthetic construct
SITE                   16
                       note = 16th amino acid(Xaa) is a 6-aminohexanoic acid.
SITE                   17
                       note = 17th aminoacid(Xaa) is a D-form alanine.
SITE                   19
                       note = 19th amino acid(Xaa) isL-cyclohexylalanins.
SITE                   29
                       note = 29th amino acid(Xaa) is a D-form alanine.
SITE                   30
                       note = 30th amino acid(Xaa) is a 6-aminohexanoic acid.
SEQUENCE: 73
CRFRGLISLS QVYLSXXKXV AAWTLKAAXX GSHHHHHHGS DDDDK                           45

SEQ ID NO: 74          moltype = AA  length = 50
FEATURE                Location/Qualifiers
source                 1..50
                       mol_type = protein
                       note = Unit peptide
                       organism = synthetic construct
SITE                   16
                       note = 16th amino acid(Xaa) is a 6-aminohexanoic acid.
SITE                   17
                       note = 17th aminoacid(Xaa) is a D-form alanine.
SITE                   19
```

```
                      note = 19th amino acid(Xaa) isL-cyclohexylalanins.
SITE                  29
                      note = 29th amino acid(Xaa) is a D-form alanine.
SITE                  30
                      note = 30th amino acid(Xaa) is a 6-aminohexanoic acid.
SEQUENCE: 74
GSHHHHHHGS DDDDKXXKXV AAWTLKAAXX KTTKQSFDLS VKAQYKKNKH                50

SEQ ID NO: 75         moltype = AA  length = 50
FEATURE               Location/Qualifiers
source                1..50
                      mol_type = protein
                      note = Unit peptide
                      organism = synthetic construct
SITE                  36
                      note = 36th amino acid(Xaa) is a 6-aminohexanoic acid.
SITE                  37
                      note = 37th aminoacid(Xaa) is a D-form alanine.
SITE                  39
                      note = 39th amino acid(Xaa) isL-cyclohexylalanins.
SITE                  49
                      note = 49th amino acid(Xaa) is a D-form alanine.
SITE                  50
                      note = 50th amino acid(Xaa) is a 6-aminohexanoic acid.
SEQUENCE: 75
GSHHHHHHGS DDDDKKTTKQ SFDLSVKAQY KKNKHXXKXV AAWTLKAAXX                50

SEQ ID NO: 76         moltype = AA  length = 50
FEATURE               Location/Qualifiers
source                1..50
                      mol_type = protein
                      note = Unit peptide
                      organism = synthetic construct
SITE                  21
                      note = 21st amino acid(Xaa) is a 6-aminohexanoic acid.
SITE                  22
                      note = 22nd aminoacid(Xaa) is a D-form alanine.
SITE                  24
                      note = 24th amino acid(Xaa) is L-cyclohexylalanins.
SITE                  34
                      note = 34th amino acid(Xaa) is a D-form alanine.
SITE                  35
                      note = 35th amino acid(Xaa) is a 6-aminohexanoic acid.
SEQUENCE: 76
KTTKQSFDLS VKAQYKKNKH XXKXVAAWTL KAAXXGSHHH HHHGSDDDDK                50

SEQ ID NO: 77         moltype = AA  length = 50
FEATURE               Location/Qualifiers
source                1..50
                      mol_type = protein
                      note = Unit peptide
                      organism = synthetic construct
SITE                  36
                      note = 36th amino acid(Xaa) is a 6-aminohexanoic acid.
SITE                  37
                      note = 37th aminoacid(Xaa) is a D-form alanine.
SITE                  39
                      note = 39th amino acid(Xaa) isL-cyclohexylalanins.
SITE                  49
                      note = 49th amino acid(Xaa) is a D-form alanine.
SITE                  50
                      note = 50th amino acid(Xaa) is a 6-aminohexanoic acid.
SEQUENCE: 77
MRGSHHHHHH GSDDDDKIVD RNVPPIFNDV YWIAFXXKXV AAWTLKAAXX                50

SEQ ID NO: 78         moltype = AA  length = 65
FEATURE               Location/Qualifiers
source                1..65
                      mol_type = protein
                      note = Unit peptide
                      organism = synthetic construct
SITE                  51
                      note = 51st amino acid(Xaa) is a 6-aminohexanoic acid.
SITE                  52
                      note = 52nd aminoacid(Xaa) is a D-form alanine.
SITE                  54
                      note = 54th amino acid(Xaa) is L-cyclohexylalanins.
SITE                  64
                      note = 64th amino acid(Xaa) is a D-form alanine.
```

```
SITE                       65
                           note = 65th amino acid(Xaa) is a 6-aminohexanoic acid.
SEQUENCE: 78
MRGSHHHHHH GSDDDDKIVD GSHHHHHHGS DDDDKRNVPP IFNDVYWIAF XXKXVAAWTL    60
KAAXX                                                                65

SEQ ID NO: 79              moltype = AA  length = 65
FEATURE                    Location/Qualifiers
source                     1..65
                           mol_type = protein
                           note = Unit peptide
                           organism = synthetic construct
SITE                       36
                           note = 36th amino acid(Xaa) is a 6-aminohexanoic acid.
SITE                       37
                           note = 37th aminoacid(Xaa) is a D-form alanine.
SITE                       39
                           note = 39th amino acid(Xaa) is L-cyclohexylalanins.
SITE                       49
                           note = 49th amino acid(Xaa) is a D-form alanine.
SITE                       50
                           note = 50th amino acid(Xaa) is a 6-aminohexanoic acid.
SEQUENCE: 79
MRGSHHHHHH GSDDDDKIVD RNVPPIFNDV YWIAFXXKXV AAWTLKAAXX GSHHHHHHGS    60
DDDDK                                                                65

SEQ ID NO: 80              moltype = AA  length = 30
FEATURE                    Location/Qualifiers
source                     1..30
                           mol_type = protein
                           note = Unit peptide
                           organism = synthetic construct
SEQUENCE: 80
RNVPPIFNDV YWIAFILMQY IKANSKFIGI                                     30

SEQ ID NO: 81              moltype = AA  length = 47
FEATURE                    Location/Qualifiers
source                     1..47
                           mol_type = protein
                           note = Unit peptide
                           organism = synthetic construct
SEQUENCE: 81
RNVPPIFNDV YWIAFILMQY IKANSKFIGI PMGLPQSIAL SSLMVAQ                  47

SEQ ID NO: 82              moltype = AA  length = 32
FEATURE                    Location/Qualifiers
source                     1..32
                           mol_type = protein
                           note = Unit peptide
                           organism = synthetic construct
SITE                       17
                           note = 17th amino acid(Xaa) is a 6-aminohexanoic acid.
SITE                       18
                           note = 18th amino acid(Xaa) is a D-form alanine.
SITE                       20
                           note = 20th amino acid(Xaa) is L-cyclohexylalanins.
SITE                       30
                           note = 30th amino acid(Xaa) is a D-form alanine.
SITE                       31
                           note = 31st amino acid(Xaa) is a 6-aminohexanoic acid.
SEQUENCE: 82
CRNVPPIFND VYWIAFXXKX VAAWTLKAAX XC                                  32

SEQ ID NO: 83              moltype = AA  length = 45
FEATURE                    Location/Qualifiers
source                     1..45
                           mol_type = protein
                           note = Unit peptide
                           organism = synthetic construct
SITE                       31
                           note = 31st amino acid(Xaa) is a 6-aminohexanoic acid.
SITE                       32
                           note = 32nd amino acid(Xaa) is a D-form alanine.
SITE                       34
                           note = 34th amino acid(Xaa) is L-cyclohexylalanins.
SITE                       44
                           note = 44th amino acid(Xaa) is a D-form alanine.
SITE                       45
                           note = 45th amino acid(Xaa) is a 6-aminohexanoic acid.
```

```
SEQUENCE: 83
RNVPPIFNDV YWIAFRNVPP IFNDVYWIAF XXKXVAAWTL KAAXX          45

SEQ ID NO: 84           moltype = AA   length = 45
FEATURE                 Location/Qualifiers
source                  1..45
                        mol_type = protein
                        note = Unit peptide
                        organism = synthetic construct
SITE                    31
                        note = 31st amino acid(Xaa) is a 6-aminohexanoic acid.
SITE                    32
                        note = 32nd amino acid(Xaa) is a D-form alanine.
SITE                    34
                        note = 34th amino acid(Xaa) is L-cyclohexylalanins.
SITE                    44
                        note = 44th amino acid(Xaa) is a D-form alanine.
SITE                    45
                        note = 45th amino acid(Xaa) is a 6-aminohexanoic acid.
SEQUENCE: 84
RNVPPIFNDV YWIAFCRFRG LISLSQVYLS XXKXVAAWTL KAAXX          45

SEQ ID NO: 85           moltype = AA   length = 50
FEATURE                 Location/Qualifiers
source                  1..50
                        mol_type = protein
                        note = Unit peptide
                        organism = synthetic construct
SITE                    36
                        note = 36th amino acid(Xaa) is a 6-aminohexanoic acid.
SITE                    37
                        note = 37th amino acid(Xaa) is a D-form alanine.
SITE                    39
                        note = 39th amino acid(Xaa) is L-cyclohexylalanins.
SITE                    49
                        note = 49th amino acid(Xaa) is a D-form alanine.
SITE                    50
                        note = 50th amino acid(Xaa) is a 6-aminohexanoic acid.
SEQUENCE: 85
RNVPPIFNDV YWIAFKTTKQ SFDLSVKAQY KKNKHXXKXV AAWTLKAAXX     50

SEQ ID NO: 86           moltype = AA   length = 45
FEATURE                 Location/Qualifiers
source                  1..45
                        mol_type = protein
                        note = Unit peptide
                        organism = synthetic construct
SITE                    31
                        note = 31st amino acid(Xaa) is a 6-aminohexanoic acid.
SITE                    32
                        note = 32nd amino acid(Xaa) is a D-form alanine.
SITE                    34
                        note = 34th amino acid(Xaa) is L-cyclohexylalanins.
SITE                    44
                        note = 44th amino acid(Xaa) is a D-form alanine.
SITE                    45
                        note = 45th amino acid(Xaa) is a 6-aminohexanoic acid.
SEQUENCE: 86
CRFRGLISLS QVYLSRNVPP IFNDVYWIAF XXKXVAAWTL KAAXX          45

SEQ ID NO: 87           moltype = AA   length = 45
FEATURE                 Location/Qualifiers
source                  1..45
                        mol_type = protein
                        note = Unit peptide
                        organism = synthetic construct
SITE                    31
                        note = 31st amino acid(Xaa) is a 6-aminohexanoic acid.
SITE                    32
                        note = 32nd amino acid(Xaa) is a D-form alanine.
SITE                    34
                        note = 34th amino acid(Xaa) is L-cyclohexylalanins.
SITE                    44
                        note = 44th amino acid(Xaa) is a D-form alanine.
SITE                    45
                        note = 45th amino acid(Xaa) is a 6-aminohexanoic acid.
SEQUENCE: 87
CRFRGLISLS QVYLSCRFRG LISLSQVYLS XXKXVAAWTL KAAXX          45
```

```
SEQ ID NO: 88                moltype = AA  length = 50
FEATURE                      Location/Qualifiers
source                       1..50
                             mol_type = protein
                             note = Unit peptide
                             organism = synthetic construct
SITE                         36
                             note = 36th amino acid(Xaa) is a 6-aminohexanoic acid.
SITE                         37
                             note = 37th amino acid(Xaa) is a D-form alanine.
SITE                         39
                             note = 39th amino acid(Xaa) is L-cyclohexylalanins.
SITE                         49
                             note = 49th amino acid(Xaa) is a D-form alanine.
SITE                         50
                             note = 50th amino acid(Xaa) is a 6-aminohexanoic acid.
SEQUENCE: 88
CRFRGLISLS QVYLSKTTKQ SFDLSVKAQY KKNKHXXKXV AAWTLKAAXX                    50

SEQ ID NO: 89                moltype = AA  length = 50
FEATURE                      Location/Qualifiers
source                       1..50
                             mol_type = protein
                             note = Unit peptide
                             organism = synthetic construct
SITE                         36
                             note = 36th amino acid(Xaa) is a 6-aminohexanoic acid.
SITE                         37
                             note = 37th amino acid(Xaa) is a D-form alanine.
SITE                         39
                             note = 39th amino acid(Xaa) is L-cyclohexylalanins.
SITE                         49
                             note = 49th amino acid(Xaa) is a D-form alanine.
SITE                         50
                             note = 50th amino acid(Xaa) is a 6-aminohexanoic acid.
SEQUENCE: 89
KTTKQSFDLS VKAQYKKNKH RNVPPIFNDV YWIAFXXKXV AAWTLKAAXX                    50

SEQ ID NO: 90                moltype = AA  length = 50
FEATURE                      Location/Qualifiers
source                       1..50
                             mol_type = protein
                             note = Unit peptide
                             organism = synthetic construct
SITE                         36
                             note = 36th amino acid(Xaa) is a 6-aminohexanoic acid.
SITE                         37
                             note = 37th amino acid(Xaa) is a D-form alanine.
SITE                         39
                             note = 39th amino acid(Xaa) is L-cyclohexylalanins.
SITE                         49
                             note = 49th amino acid(Xaa) is a D-form alanine.
SITE                         50
                             note = 50th amino acid(Xaa) is a 6-aminohexanoic acid.
SEQUENCE: 90
KTTKQSFDLS VKAQYKKNKH CRFRGLISLS QVYLSXXKXV AAWTLKAAXX                    50

SEQ ID NO: 91                moltype = AA  length = 55
FEATURE                      Location/Qualifiers
source                       1..55
                             mol_type = protein
                             note = Unit peptide
                             organism = synthetic construct
SITE                         41
                             note = 41st amino acid(Xaa) is a 6-aminohexanoic acid.
SITE                         42
                             note = 42nd amino acid(Xaa) is a D-form alanine.
SITE                         44
                             note = 44th amino acid(Xaa) is L-cyclohexylalanins.
SITE                         54
                             note = 54th amino acid(Xaa) is a D-form alanine.
SITE                         55
                             note = 55th amino acid(Xaa) is a 6-aminohexanoic acid.
SEQUENCE: 91
KTTKQSFDLS VKAQYKKNKH KTTKQSFDLS VKAQYKKNKH XXKXVAAWTL KAAXX              55

SEQ ID NO: 92                moltype = AA  length = 41
FEATURE                      Location/Qualifiers
source                       1..41
```

```
                      mol_type = protein
                      note = Unit peptide
                      organism = synthetic construct
SITE                  32
                      note = 32nd amino acid(Xaa) is L-cyclohexylalanins.
SEQUENCE: 92
RNVPPIFNDV YWIAFCRFRG LISLSQVYLS KXVAAWTLKA A                       41

SEQ ID NO: 93         moltype = AA   length = 33
FEATURE               Location/Qualifiers
source                1..33
                      mol_type = protein
                      note = Unit peptide
                      organism = synthetic construct
SITE                  24
                      note = 24th amino acid(Xaa) is L-cyclohexylalanins.
SEQUENCE: 93
PIFNDVYWIA FGLISLSQVY LSKXVAAWTL KAA                                33

SEQ ID NO: 94         moltype = AA   length = 33
FEATURE               Location/Qualifiers
source                1..33
                      mol_type = protein
                      note = Unit peptide
                      organism = synthetic construct
SITE                  24
                      note = 24th amino acid(Xaa) is L-cyclohexylalanins.
SEQUENCE: 94
RNVPPIFNDV YCRFRGLISL SQKXVAAWTL KAA                                33

SEQ ID NO: 95         moltype = AA   length = 33
FEATURE               Location/Qualifiers
source                1..33
                      mol_type = protein
                      note = Unit peptide
                      organism = synthetic construct
SITE                  24
                      note = 24th amino acid(Xaa) is L-cyclohexylalanins.
SEQUENCE: 95
PIFNDVYWIA FCRFRGLISL SQKXVAAWTL KAA                                33

SEQ ID NO: 96         moltype = AA   length = 29
FEATURE               Location/Qualifiers
source                1..29
                      mol_type = protein
                      note = Unit peptide
                      organism = synthetic construct
SITE                  20
                      note = 20th amino acid(Xaa) is L-cyclohexylalanins.
SEQUENCE: 96
PPIFNDVYWR GLISLSQVKX VAAWTLKAA                                     29

SEQ ID NO: 97         moltype = AA   length = 47
FEATURE               Location/Qualifiers
source                1..47
                      mol_type = protein
                      note = Unit peptide
                      organism = synthetic construct
SITE                  32
                      note = 32nd amino acid(Xaa) is L-cyclohexylalanins.
SEQUENCE: 97
RNVPPIFNDV YWIAFCRFRG LISLSQVYLS KXVAAWTLKA AHHHHHH                 47

SEQ ID NO: 98         moltype = AA   length = 65
FEATURE               Location/Qualifiers
source                1..65
                      mol_type = protein
                      note = Unit peptide
                      organism = synthetic construct
SITE                  51
                      note = 51st amino acid(Xaa) is a 6-aminohexanoic acid.
SITE                  52
                      note = 52nd amino acid(Xaa) is a D-form alanine.
SITE                  54
                      note = 54th amino acid(Xaa) is L-cyclohexylalanins.
SITE                  64
                      note = 64th amino acid(Xaa) is a D-form alanine.
SITE                  65
                      note = 65th amino acid(Xaa) is a 6-aminohexanoic acid.
```

```
SEQUENCE: 98
MRGSHHHHHH GSDDDDKIVD RNVPPIFNDV YWIAFCRFRG LISLSQVYLS XXKXVAAWTL    60
KAAXX                                                               65

SEQ ID NO: 99           moltype = AA   length = 63
FEATURE                 Location/Qualifiers
source                  1..63
                        mol_type = protein
                        note = Unit peptide
                        organism = synthetic construct
SITE                    51
                        note = 51st amino acid(Xaa) is a 6-aminohexanoic acid.
SITE                    52
                        note = 52nd amino acid(Xaa) is a D-form alanine.
SITE                    54
                        note = 54th amino acid(Xaa) is L-cyclohexylalanins.
SEQUENCE: 99
MRGSHHHHHH GSDDDDKIVD RNVPPIFNDV YWIAFCRFRG LISLSQVYLS XXKXVAAWTL    60
KAA                                                                 63

SEQ ID NO: 100          moltype = AA   length = 43
FEATURE                 Location/Qualifiers
source                  1..43
                        mol_type = protein
                        note = Unit peptide
                        organism = synthetic construct
SITE                    31
                        note = 31st amino acid(Xaa) is a 6-aminohexanoic acid.
SITE                    32
                        note = 32nd amino acid(Xaa) is a D-form alanine.
SITE                    34
                        note = 34th amino acid(Xaa) is L-cyclohexylalanins.
SEQUENCE: 100
RNVPPIFNDV YWIAFCRFRG LISLSQVYLS XXKXVAAWTL KAA                     43

SEQ ID NO: 101          moltype = AA   length = 76
FEATURE                 Location/Qualifiers
source                  1..76
                        mol_type = protein
                        note = Unit peptide
                        organism = synthetic construct
SITE                    64
                        note = 64th amino acid(Xaa) is a 6-aminohexanoic acid.
SITE                    65
                        note = 65th amino acid(Xaa) is a D-form alanine.
SITE                    67
                        note = 67th amino acid(Xaa) is L-cyclohexylalanins.
SEQUENCE: 101
MRGSHHHHHH GSDDDDKIVD RNVPPIFNDV YWIAFGGGGS GGGGGGSSRN VPPIFNDVYW    60
IAFXXKXVAA WTLKAA                                                   76

SEQ ID NO: 102          moltype = AA   length = 56
FEATURE                 Location/Qualifiers
source                  1..56
                        mol_type = protein
                        note = Unit peptide
                        organism = synthetic construct
SITE                    44
                        note = 44th amino acid(Xaa) is a 6-aminohexanoic acid.
SITE                    45
                        note = 45th amino acid(Xaa) is a D-form alanine.
SITE                    47
                        note = 47th amino acid(Xaa) is L-cyclohexylalanins.
SEQUENCE: 102
RNVPPIFNDV YWIAFGGGGS GGGGGGSSRN VPPIFNDVYW IAFXXKXVAA WTLKAA        56

SEQ ID NO: 103          moltype = AA   length = 58
FEATURE                 Location/Qualifiers
source                  1..58
                        mol_type = protein
                        note = Unit peptide
                        organism = synthetic construct
SITE                    44
                        note = 44th amino acid(Xaa) is a 6-aminohexanoic acid.
SITE                    45
                        note = 45th amino acid(Xaa) is a D-form alanine.
SITE                    47
                        note = 47th amino acid(Xaa) is L-cyclohexylalanins.
SITE                    57
```

```
                      note = 57th amino acid(Xaa) is a D-form alanine.
SITE                  58
                      note = 58th amino acid(Xaa) is a 6-aminohexanoic acid.
SEQUENCE: 103
RNVPPIFNDV YWIAFGGGGS GGGGGGSSRN VPPIFNDVYW IAFXXKXVAA WTLKAAXX    58

SEQ ID NO: 104        moltype = AA  length = 45
FEATURE               Location/Qualifiers
source                1..45
                      mol_type = protein
                      note = Unit peptide
                      organism = synthetic construct
SEQUENCE: 104
RNVPPIFNDV YWIAFRNVPP IFNDVYWIAF ILMQYIKANS KFIGI                 45

SEQ ID NO: 105        moltype = AA  length = 62
FEATURE               Location/Qualifiers
source                1..62
                      mol_type = protein
                      note = Unit peptide
                      organism = synthetic construct
SEQUENCE: 105
RNVPPIFNDV YWIAFRNVPP IFNDVYWIAF ILMQYIKANS KFIGIPMGLP QSIALSSLMV 60
AQ                                                                62

SEQ ID NO: 106        moltype = AA  length = 47
FEATURE               Location/Qualifiers
source                1..47
                      mol_type = protein
                      note = Unit peptide
                      organism = synthetic construct
SITE                  32
                      note = 32nd amino acid(Xaa) is a 6-aminohexanoic acid.
SITE                  33
                      note = 33rd amino acid(Xaa) is a D-form alanine.
SITE                  35
                      note = 35th amino acid(Xaa) is L-cyclohexylalanins.
SITE                  45
                      note = 45th amino acid(Xaa) is a D-form alanine.
SITE                  46
                      note = 46th amino acid(Xaa) is a 6-aminohexanoic acid.
SEQUENCE: 106
CRNVPPIFND VYWIAFCRFR GLISLSQVYL SXXKXVAAWT LKAAXXC               47

SEQ ID NO: 107        moltype = AA  length = 45
FEATURE               Location/Qualifiers
source                1..45
                      mol_type = protein
                      note = Unit peptide
                      organism = synthetic construct
SITE                  16
                      note = 16th amino acid(Xaa) is a 6-aminohexanoic acid.
SITE                  17
                      note = 17th amino acid(Xaa) is a D-form alanine.
SITE                  19
                      note = 19th amino acid(Xaa) is L-cyclohexylalanins.
SITE                  29
                      note = 29th amino acid(Xaa) is a D-form alanine.
SITE                  30
                      note = 30th amino acid(Xaa) is a 6-aminohexanoic acid.
SEQUENCE: 107
RNVPPIFNDV YWIAFXXKXV AAWTLKAAXX RNVPPIFNDV YWIAF                 45

SEQ ID NO: 108        moltype = AA  length = 45
FEATURE               Location/Qualifiers
source                1..45
                      mol_type = protein
                      note = Unit peptide
                      organism = synthetic construct
SITE                  16
                      note = 16th amino acid(Xaa) is a 6-aminohexanoic acid.
SITE                  17
                      note = 17th amino acid(Xaa) is a D-form alanine.
SITE                  19
                      note = 19th amino acid(Xaa) is L-cyclohexylalanins.
SITE                  29
                      note = 29th amino acid(Xaa) is a D-form alanine.
SITE                  30
                      note = 30th amino acid(Xaa) is a 6-aminohexanoic acid.
```

```
SEQUENCE: 108
RNVPPIFNDV YWIAFXXKXV AAWTLKAAXX CRFRGLISLS QVYLS              45

SEQ ID NO: 109          moltype = AA  length = 50
FEATURE                 Location/Qualifiers
source                  1..50
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 109
RNVPPIFNDV YWIAFXXKXV AAWTLKAAXX KTTKQSFDLS VKAQYKKNKH         50

SEQ ID NO: 110          moltype = AA  length = 45
FEATURE                 Location/Qualifiers
source                  1..45
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 110
CRFRGLISLS QVYLSXXKXV AAWTLKAAXX RNVPPIFNDV YWIAF              45

SEQ ID NO: 111          moltype = AA  length = 45
FEATURE                 Location/Qualifiers
source                  1..45
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 111
CRFRGLISLS QVYLSXXKXV AAWTLKAAXX CRFRGLISLS QVYLS              45

SEQ ID NO: 112          moltype = AA  length = 50
FEATURE                 Location/Qualifiers
source                  1..50
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 112
RNVPPIFNDV YWIAFXXKXV AAWTLKAAXX KTTKQSFDLS VKAQYKKNKH         50
```

```
SEQ ID NO: 113            moltype = AA  length = 50
FEATURE                   Location/Qualifiers
source                    1..50
                          mol_type = protein
                          note = Unit peptide
                          organism = synthetic construct
SITE                      21
                          note = 21st amino acid(Xaa) is a 6-aminohexanoic acid.
SITE                      22
                          note = 22nd amino acid(Xaa) is a D-form alanine.
SITE                      24
                          note = 24th amino acid(Xaa) is L-cyclohexylalanins.
SITE                      34
                          note = 34th amino acid(Xaa) is a D-form alanine.
SITE                      35
                          note = 35th amino acid(Xaa) is a 6-aminohexanoic acid.
SEQUENCE: 113
KTTKQSFDLS VKAQYKKNKH XXKXVAAWTL KAAXXRNVPP IFNDVYWIAF              50

SEQ ID NO: 114            moltype = AA  length = 50
FEATURE                   Location/Qualifiers
source                    1..50
                          mol_type = protein
                          note = Unit peptide
                          organism = synthetic construct
SITE                      21
                          note = 21st amino acid(Xaa) is a 6-aminohexanoic acid.
SITE                      22
                          note = 22nd amino acid(Xaa) is a D-form alanine.
SITE                      24
                          note = 24th amino acid(Xaa) is L-cyclohexylalanins.
SITE                      34
                          note = 34th amino acid(Xaa) is a D-form alanine.
SITE                      35
                          note = 35th amino acid(Xaa) is a 6-aminohexanoic acid.
SEQUENCE: 114
KTTKQSFDLS VKAQYKKNKH XXKXVAAWTL KAAXXCRFRG LISLSQVYLS              50

SEQ ID NO: 115            moltype = AA  length = 55
FEATURE                   Location/Qualifiers
source                    1..55
                          mol_type = protein
                          note = Unit peptide
                          organism = synthetic construct
SITE                      21
                          note = 21st amino acid(Xaa) is a 6-aminohexanoic acid.
SITE                      22
                          note = 22nd amino acid(Xaa) is a D-form alanine.
SITE                      24
                          note = 24th amino acid(Xaa) is L-cyclohexylalanins.
SITE                      34
                          note = 34th amino acid(Xaa) is a D-form alanine.
SITE                      35
                          note = 35th amino acid(Xaa) is a 6-aminohexanoic acid.
SEQUENCE: 115
KTTKQSFDLS VKAQYKKNKH XXKXVAAWTL KAAXXKTTKQ SFDLSVKAQY KKNKH        55

SEQ ID NO: 116            moltype = AA  length = 33
FEATURE                   Location/Qualifiers
source                    1..33
                          mol_type = protein
                          note = Unit peptide
                          organism = synthetic construct
SITE                      13
                          note = 13rd amino acid(Xaa) is L-cyclohexylalanins.
SEQUENCE: 116
PIFNDVYWIA FKXVAAWTLK AACRFRGLIS LSQ                                33

SEQ ID NO: 117            moltype = AA  length = 29
FEATURE                   Location/Qualifiers
source                    1..29
                          mol_type = protein
                          note = Unit peptide
                          organism = synthetic construct
VARIANT                   11
                          note = Xaa can be any naturally occurring amino acid.
SEQUENCE: 117
PPIFNDVYWK XVAAWTLKAA RGLISLSQV                                    29
```

```
SEQ ID NO: 118            moltype = AA   length = 65
FEATURE                   Location/Qualifiers
source                    1..65
                          mol_type = protein
                          note = Unit peptide
                          organism = synthetic construct
SITE                      36
                          note = 36th amino acid(Xaa) is a 6-aminohexanoic acid.
SITE                      37
                          note = 37th amino acid(Xaa) is a D-form alanine.
SITE                      39
                          note = 39th amino acid(Xaa) is L-cyclohexylalanins.
SITE                      49
                          note = 49th amino acid(Xaa) is a D-form alanine.
SITE                      50
                          note = 50th amino acid(Xaa) is a 6-aminohexanoic acid.
SEQUENCE: 118
MRGSHHHHHH GSDDDDKIVD RNVPPIFNDV YWIAFXXKXV AAWTLKAAXX RNVPPIFNDV    60
YWIAF                                                               65

SEQ ID NO: 119            moltype = AA   length = 108
FEATURE                   Location/Qualifiers
source                    1..108
                          mol_type = protein
                          note = Unit peptide
                          organism = synthetic construct
SEQUENCE: 119
MRGSHHHHHH GSDDDDKIVD RNVPPIFNDV YWIAFGGGGS GGGGGGSSIL MQYIKANSKF    60
IGIPMGLPQS IALSSLMVAQ GGGGSGGGGG GSSCRFRGLI SLSQVYLS                108

SEQ ID NO: 120            moltype = AA   length = 45
FEATURE                   Location/Qualifiers
source                    1..45
                          mol_type = protein
                          note = Unit peptide
                          organism = synthetic construct
SEQUENCE: 120
RNVPPIFNDV YWIAFILMQY IKANSKFIGI CRFRGLISLS QVYLS                    45

SEQ ID NO: 121            moltype = AA   length = 45
FEATURE                   Location/Qualifiers
source                    1..45
                          mol_type = protein
                          note = Unit peptide
                          organism = synthetic construct
SITE                      16
                          note = 16th amino acid(Xaa) is a 6-aminohexanoic acid.
SITE                      17
                          note = 17th amino acid(Xaa) is a D-form alanine.
SITE                      19
                          note = 19th amino acid(Xaa) is L-cyclohexylalanins.
SITE                      29
                          note = 29th amino acid(Xaa) is a D-form alanine.
SITE                      30
                          note = 30th amino acid(Xaa) is a 6-aminohexanoic acid.
SEQUENCE: 121
RNVPPIFNDV YWIAFXPKYV KQNTLKLATX CRFRGLISLS QVYLS                    45

SEQ ID NO: 122            moltype = AA   length = 47
FEATURE                   Location/Qualifiers
source                    1..47
                          mol_type = protein
                          note = Unit peptide
                          organism = synthetic construct
SITE                      17
                          note = 17th amino acid(Xaa) is a 6-aminohexanoic acid.
SITE                      18
                          note = 18th amino acid(Xaa) is a D-form alanine.
SITE                      20
                          note = 20th amino acid(Xaa) is L-cyclohexylalanins.
SITE                      30
                          note = 30th amino acid(Xaa) is a D-form alanine.
SITE                      31
                          note = 31st amino acid(Xaa) is a 6-aminohexanoic acid.
SEQUENCE: 122
CRNVPPIFND VYWIAFXXKX VAAWTLKAAX XRNVPPIFND VYWIAFC                  47

SEQ ID NO: 123            moltype = AA   length = 45
FEATURE                   Location/Qualifiers
```

```
source                  1..45
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 123
RNVPPIFNDV YWIAFXXKXV AAWTLKAAXX ILMQYIKANS KFIGI                     45

SEQ ID NO: 124          moltype = AA   length = 45
FEATURE                 Location/Qualifiers
source                  1..45
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 124
CRFRGLISLS QVYLSXXKXV AAWTLKAAXX ILMQYIKANS KFIGI                     45

SEQ ID NO: 125          moltype = AA   length = 50
FEATURE                 Location/Qualifiers
source                  1..50
                        mol_type = protein
                        note = Unit peptide
                        organism = synthetic construct
SITE                    21
                        note = 21st amino acid(Xaa) is a 6-aminohexanoic acid.
SITE                    22
                        note = 22nd amino acid(Xaa) is a D-form alanine.
SITE                    24
                        note = 24th amino acid(Xaa) is L-cyclohexylalanins.
SITE                    34
                        note = 34th amino acid(Xaa) is a D-form alanine.
SITE                    35
                        note = 35th amino acid(Xaa) is a 6-aminohexanoic acid.
SEQUENCE: 125
KTTKQSFDLS VKAQYKKNKH XXKXVAAWTL KAAXXILMQY IKANSKFIGI                50

SEQ ID NO: 126          moltype = AA   length = 45
FEATURE                 Location/Qualifiers
source                  1..45
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 126
ILMQYIKANS KFIGIXXKXV AAWTLKAAXX RNVPPIFNDV YWIAF                     45

SEQ ID NO: 127          moltype = AA   length = 45
FEATURE                 Location/Qualifiers
source                  1..45
                        mol_type = protein
                        note = Unit peptide
```

```
                            organism = synthetic construct
SITE                        16
                            note = 16th amino acid(Xaa) is a 6-aminohexanoic acid.
SITE                        17
                            note = 17th amino acid(Xaa) is a D-form alanine.
SITE                        19
                            note = 19th amino acid(Xaa) is L-cyclohexylalanins.
SITE                        29
                            note = 29th amino acid(Xaa) is a D-form alanine.
SITE                        30
                            note = 30th amino acid(Xaa) is a 6-aminohexanoic acid.
SEQUENCE: 127
ILMQYIKANS KFIGIXXKXV AAWTLKAAXX CRFRGLISLS QVYLS               45

SEQ ID NO: 128              moltype = AA  length = 50
FEATURE                     Location/Qualifiers
source                      1..50
                            mol_type = protein
                            note = Unit peptide
                            organism = synthetic construct
SITE                        16
                            note = 16th amino acid(Xaa) is a 6-aminohexanoic acid.
SITE                        17
                            note = 17th amino acid(Xaa) is a D-form alanine.
SITE                        19
                            note = 19th amino acid(Xaa) is L-cyclohexylalanins.
SITE                        29
                            note = 29th amino acid(Xaa) is a D-form alanine.
SITE                        30
                            note = 30th amino acid(Xaa) is a 6-aminohexanoic acid.
SEQUENCE: 128
ILMQYIKANS KFIGIXXKXV AAWTLKAAXX KTTKQSFDLS VKAQYKKNKH          50

SEQ ID NO: 129              moltype = AA  length = 33
FEATURE                     Location/Qualifiers
source                      1..33
                            mol_type = protein
                            note = Unit peptide
                            organism = synthetic construct
SITE                        13
                            note = 13rd amino acid(Xaa) is L-cyclohexylalanins.
SITE                        24
                            note = 24th amino acid(Xaa)is L-cyclohexylalanins.
SEQUENCE: 129
PIFNDVYWIA FKXVAAWTLK AAKXVAAWTL KAA                            33

SEQ ID NO: 130              moltype = AA  length = 31
FEATURE                     Location/Qualifiers
source                      1..31
                            mol_type = protein
                            note = Unit peptide
                            organism = synthetic construct
SITE                        11
                            note = 11st amino acid(Xaa) is L-cyclohexylalanins.
SITE                        21
                            note = 21st amino acid(Xaa)is L-cyclohexylalanins.
SEQUENCE: 130
PPIFNDVYWK XVAAWTLKAA KXVAAWTLKA A                              31

SEQ ID NO: 131              moltype = AA  length = 65
FEATURE                     Location/Qualifiers
source                      1..65
                            mol_type = protein
                            note = Unit peptide
                            organism = synthetic construct
SITE                        36
                            note = 36th amino acid(Xaa) is a 6-aminohexanoic acid.
SITE                        37
                            note = 37th amino acid(Xaa) is a D-form alanine.
SITE                        39
                            note = 39th amino acid(Xaa) is L-cyclohexylalanins.
SITE                        49
                            note = 49th amino acid(Xaa) is a D-form alanine.
SITE                        50
                            note = 50th amino acid(Xaa) is a 6-aminohexanoic acid.
SEQUENCE: 131
MRGSHHHHHH GSDDDDKIVD RNVPPIFNDV YWIAFXXKXV AAWTLKAAXX ILMQYIKANS   60
KFIGI                                                              65
```

```
SEQ ID NO: 132            moltype = AA  length = 50
FEATURE                   Location/Qualifiers
source                    1..50
                          mol_type = protein
                          note = Unit peptide
                          organism = synthetic construct
SITE                      36
                          note = 36th amino acid(Xaa) is a 6-aminohexanoic acid.
SITE                      37
                          note = 37th amino acid(Xaa) is a D-form alanine.
SITE                      39
                          note = 39th amino acid(Xaa) is L-cyclohexylalanins.
SITE                      49
                          note = 49th amino acid(Xaa) is a D-form alanine.
SITE                      50
                          note = 50th amino acid(Xaa) is a 6-aminohexanoic acid.
SEQUENCE: 132
MRGSHHHHHH GSDDDDKIVD ILMQYIKANS KFIGIXXKXV AAWTLKAAXX                    50

SEQ ID NO: 133            moltype = AA  length = 78
FEATURE                   Location/Qualifiers
source                    1..78
                          mol_type = protein
                          note = Unit peptide
                          organism = synthetic construct
SITE                      49
                          note = 49th amino acid(Xaa) is a 6-aminohexanoic acid.
SITE                      50
                          note = 50th amino acid(Xaa) is a D-form alanine.
SITE                      52
                          note = 52nd amino acid(Xaa) is L-cyclohexylalanins.
SITE                      62
                          note = 62nd amino acid(Xaa) is a D-form alanine.
SITE                      63
                          note = 63rd amino acid(Xaa) is a 6-aminohexanoic acid.
SEQUENCE: 133
MRGSHHHHHH GSDDDDKIVD RNVPPIFNDV YWIAFGGGGS GGGGGGSSXX KXVAAWTLKA         60
AXXILMQYIK ANSKFIGI                                                      78

SEQ ID NO: 134            moltype = AA  length = 125
FEATURE                   Location/Qualifiers
source                    1..125
                          mol_type = protein
                          note = Unit peptide
                          organism = synthetic construct
SEQUENCE: 134
MRGSHHHHHH GSDDDDKIVD RNVPPIFNDV YWIAFGGGGS GGGGGGSSIL MQYIKANSKF         60
IGIPMGLPQS IALSSLMVAQ GGGGSGGGGG GSSILMQYIK ANSKFIGIPM GLPQSIALSS        120
LMVAQ                                                                   125

SEQ ID NO: 135            moltype = AA  length = 43
FEATURE                   Location/Qualifiers
source                    1..43
                          mol_type = protein
                          note = Unit peptide
                          organism = synthetic construct
SITE                      16
                          note = 16th amino acid(Xaa) is a 6-aminohexanoic acid.
SITE                      17
                          note = 17th aminoacid(Xaa) is a D-form alanine.
SITE                      19
                          note = 19th amino acid(Xaa) is L-cyclohexylalanins.
SITE                      29
                          note = 29th amino acid(Xaa) is a D-form alanine.
SITE                      30
                          note = 30th amino acid(Xaa) is a 6-aminohexanoic acid.
SITE                      32
                          note = 32nd amino acid is L-cyclohexylalanins.
SITE                      42
                          note = 42nd amino acid(Xaa) is a D-form alanine.
SITE                      43
                          note = 43rd amino acid is a 6-aminohexanoic acid.
SEQUENCE: 135
RNVPPIFNDV YWIAFXXKXV AAWTLKAAXX KXLAAFTIRA AXX                           43

SEQ ID NO: 136            moltype = AA  length = 47
FEATURE                   Location/Qualifiers
source                    1..47
                          mol_type = protein
```

```
                        note = Unit peptide
                        organism = synthetic construct
SITE                    17
                        note = 17th amino acid(Xaa) is a 6-aminohexanoic acid.
SITE                    18
                        note = 18th amino acid(Xaa) is a D-form alanine.
SITE                    20
                        note = 20th amino acid(Xaa) is L-cyclohexylalanins.
SITE                    30
                        note = 30th amino acid(Xaa) is a D-form alanine.
SITE                    31
                        note = 31st amino acid(Xaa) is a 6-aminohexanoic acid.
SEQUENCE: 136
CRNVPPIFND VYWIAFXXKX VAAWTLKAAX XILMQYIKAN SKFIGIC                  47

SEQ ID NO: 137          moltype = AA  length = 60
FEATURE                 Location/Qualifiers
source                  1..60
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 137
RNVPPIFNDV YWIAFXXKXV AAWTLKAAXX ILMQYIKANS KFIGIRNVPP IFNDVYWIAF    60

SEQ ID NO: 138          moltype = AA  length = 60
FEATURE                 Location/Qualifiers
source                  1..60
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 138
RNVPPIFNDV YWIAFXXKXV AAWTLKAAXX ILMQYIKANS KFIGICRFRG LISLSQVYLS    60

SEQ ID NO: 139          moltype = AA  length = 65
FEATURE                 Location/Qualifiers
source                  1..65
                        mol_type = protein
                        note = Unit peptide
                        organism = synthetic construct
SITE                    16
                        note = 16th amino acid(Xaa) is a 6-aminohexanoic acid.
SITE                    17
                        note = 17th amino acid(Xaa) is a D-form alanine.
SITE                    19
                        note = 19th amino acid(Xaa) is L-cyclohexylalanins.
SITE                    29
                        note = 29th amino acid(Xaa) is a D-form alanine.
SITE                    30
                        note = 30th amino acid(Xaa) is a 6-aminohexanoic acid.
SEQUENCE: 139
RNVPPIFNDV YWIAFXXKXV AAWTLKAAXX ILMQYIKANS KFIGIKTTKQ SFDLSVKAQY    60
KKNKH                                                                65

SEQ ID NO: 140          moltype = AA  length = 60
FEATURE                 Location/Qualifiers
source                  1..60
                        mol_type = protein
                        note = Unit peptide
                        organism = synthetic construct
```

```
SITE                      16
                          note = 16th amino acid(Xaa) is a 6-aminohexanoic acid.
SITE                      17
                          note = 17th amino acid(Xaa) is a D-form alanine.
SITE                      19
                          note = 19th amino acid(Xaa) is L-cyclohexylalanins.
SITE                      29
                          note = 29th amino acid(Xaa) is a D-form alanine.
SITE                      30
                          note = 30th amino acid(Xaa) is a 6-aminohexanoic acid.
SEQUENCE: 140
CRFRGLISLS QVYLSXXKXV AAWTLKAAXX ILMQYIKANS KFIGIRNVPP IFNDVYWIAF   60

SEQ ID NO: 141            moltype = AA   length = 60
FEATURE                   Location/Qualifiers
source                    1..60
                          mol_type = protein
                          note = Unit peptide
                          organism = synthetic construct
SITE                      16
                          note = 16th amino acid(Xaa) is a 6-aminohexanoic acid.
SITE                      17
                          note = 17th amino acid(Xaa) is a D-form alanine.
SITE                      19
                          note = 19th amino acid(Xaa) is L-cyclohexylalanins.
SITE                      29
                          note = 29th amino acid(Xaa) is a D-form alanine.
SITE                      30
                          note = 30th amino acid(Xaa) is a 6-aminohexanoic acid.
SEQUENCE: 141
CRFRGLISLS QVYLSXXKXV AAWTLKAAXX ILMQYIKANS KFIGICRFRG LISLSQVYLS   60

SEQ ID NO: 142            moltype = AA   length = 65
FEATURE                   Location/Qualifiers
source                    1..65
                          mol_type = protein
                          note = Unit peptide
                          organism = synthetic construct
SITE                      16
                          note = 16th amino acid(Xaa) is a 6-aminohexanoic acid.
SITE                      17
                          note = 17th amino acid(Xaa) is a D-form alanine.
SITE                      19
                          note = 19th amino acid(Xaa) is L-cyclohexylalanins.
SITE                      29
                          note = 29th amino acid(Xaa) is a D-form alanine.
SITE                      30
                          note = 30th amino acid(Xaa) is a 6-aminohexanoic acid.
SEQUENCE: 142
CRFRGLISLS QVYLSXXKXV AAWTLKAAXX ILMQYIKANS KFIGIKTTKQ SFDLSVKAQY   60
KKNKH                                                               65

SEQ ID NO: 143            moltype = AA   length = 65
FEATURE                   Location/Qualifiers
source                    1..65
                          mol_type = protein
                          note = Unit peptide
                          organism = synthetic construct
SITE                      21
                          note = 21st amino acid(Xaa) is a 6-aminohexanoic acid.
SITE                      22
                          note = 22nd amino acid(Xaa) is a D-form alanine.
SITE                      24
                          note = 24th amino acid(Xaa) is L-cyclohexylalanins.
SITE                      34
                          note = 34th amino acid(Xaa) is a D-form alanine.
SITE                      35
                          note = 35th amino acid(Xaa) is a 6-aminohexanoic acid.
SEQUENCE: 143
KTTKQSFDLS VKAQYKKNKH XXKXVAAWTL KAAXXILMQY IKANSKFIGI RNVPPIFNDV   60
YWIAF                                                               65

SEQ ID NO: 144            moltype = AA   length = 65
FEATURE                   Location/Qualifiers
source                    1..65
                          mol_type = protein
                          note = Unit peptide
                          organism = synthetic construct
SITE                      21
```

```
                         note = 21st amino acid(Xaa) is a 6-aminohexanoic acid.
SITE                     22
                         note = 22nd aminoacid(Xaa) is a D-form alanine.
SITE                     24
                         note = 24th amino acid(Xaa) isL-cyclohexylalanins.
SITE                     34
                         note = 34th amino acid(Xaa) is a D-form alanine.
SITE                     35
                         note = 35th amino acid(Xaa) is a 6-aminohexanoic acid.
SEQUENCE: 144
KTTKQSFDLS VKAQYKKNKH XXKXVAAWTL KAAXXILMQY IKANSKFIGI CRFRGLISLS    60
QVYLS                                                               65

SEQ ID NO: 145           moltype = AA   length = 70
FEATURE                  Location/Qualifiers
source                   1..70
                         mol_type = protein
                         note = Unit peptide
                         organism = synthetic construct
SITE                     21
                         note = 21st amino acid(Xaa) is a 6-aminohexanoic acid.
SITE                     22
                         note = 22nd amino acid(Xaa) is a D-form alanine.
SITE                     24
                         note = 24th amino acid(Xaa) is L-cyclohexylalanins.
SITE                     34
                         note = 34th amino acid(Xaa) is a D-form alanine.
SITE                     35
                         note = 35th amino acid(Xaa) is a 6-aminohexanoic acid.
SEQUENCE: 145
KTTKQSFDLS VKAQYKKNKH XXKXVAAWTL KAAXXILMQY IKANSKFIGI KTTKQSFDLS    60
VKAQYKKNKH                                                          70

SEQ ID NO: 146           moltype = AA   length = 80
FEATURE                  Location/Qualifiers
source                   1..80
                         mol_type = protein
                         note = Unit peptide
                         organism = synthetic construct
SITE                     36
                         note = 36th amino acid(Xaa) is a 6-aminohexanoic acid.
SITE                     37
                         note = 37th amino acid(Xaa) is a D-form alanine.
SITE                     39
                         note = 39th amino acid(Xaa) is L-cyclohexylalanins.
SITE                     49
                         note = 49th amino acid(Xaa) is a D-form alanine.
SITE                     50
                         note = 50th amino acid(Xaa) is a 6-aminohexanoic acid.
SEQUENCE: 146
MRGSHHHHHH GSDDDDKIVD RNVPPIFNDV YWIAFXXKXV AAWTLKAAXX ILMQYIKANS    60
KFIGIRNVPP IFNDVYWIAF                                               80

SEQ ID NO: 147           moltype = AA   length = 140
FEATURE                  Location/Qualifiers
source                   1..140
                         mol_type = protein
                         note = Unit peptide
                         organism = synthetic construct
SEQUENCE: 147
MRGSHHHHHH GSDDDDKIVD RNVPPIFNDV YWIAFGGGGS GGGGGGSSIL MQYIKANSKF    60
IGIPMGLPQS IALSSLMVAQ ILMQYIKANS KFIGIPMGLP QSIALSSLMV AQGGGGSGGG   120
GGGSSCRFRG LISLSQVYLS                                              140

SEQ ID NO: 148           moltype = AA   length = 44
FEATURE                  Location/Qualifiers
source                   1..44
                         mol_type = protein
                         note = Unit peptide
                         organism = synthetic construct
SITE                     13
                         note = 13rd amino acid(Xaa) is L-cyclohexylalanins.
SITE                     24
                         note = 24th amino acid(Xaa)is L-cyclohexylalanins.
SEQUENCE: 148
PIFNDVYWIA FKXVAAWTLK AAKXVAAWTL KAACRFRGLI SLSQ                    44

SEQ ID NO: 149           moltype = AA   length = 40
FEATURE                  Location/Qualifiers
```

| | |
|---|---|
| source | 1..40 |
| | mol_type = protein |
| | note = Unit peptide |
| | organism = synthetic construct |
| SITE | 11 |
| | note = 11st amino acid(Xaa) is L-cyclohexylalanins. |
| SITE | 22 |
| | note = 22nd amino acid(Xaa)is L-cyclohexylalanins. |
| SEQUENCE: 149 | |

```
PPIFNDVYWK XVAAWTLKAA KXVAAWTLKA ARGLISLSQV                    40
```

| | |
|---|---|
| SEQ ID NO: 150 | moltype = AA  length = 62 |
| FEATURE | Location/Qualifiers |
| source | 1..62 |
| | mol_type = protein |
| | note = Unit peptide (cyclic) |
| | organism = synthetic construct |
| SITE | 17 |
| | note = 17th amino acid(Xaa) is a 6-aminohexanoic acid. |
| SITE | 18 |
| | note = 18th amino acid(Xaa) is a D-form alanine. |
| SITE | 20 |
| | note = 20th amino acid(Xaa) is L-cyclohexylalanins. |
| SITE | 30 |
| | note = 30th amino acid(Xaa) is a D-form alanine. |
| SITE | 31 |
| | note = 31st amino acid(Xaa) is a 6-aminohexanoic acid. |
| SEQUENCE: 150 | |

```
CRNVPPIFND VYWIAFXXKX VAAWTLKAAX XILMQYIKAN SKFIGIRNVP PIFNDVYWIA   60
FC                                                                62
```

| | |
|---|---|
| SEQ ID NO: 151 | moltype = AA  length = 80 |
| FEATURE | Location/Qualifiers |
| source | 1..80 |
| | mol_type = protein |
| | note = Concatamer |
| | organism = synthetic construct |
| SITE | 36 |
| | note = Each of 36th, 50th, 66th, and 80th amino acid(Xaa) is a 6-aminohexanoic acid. |
| SITE | 50 |
| | note = Each of 36th, 50th, 66th, and 80th amino acid(Xaa) is a 6-aminohexanoic acid. |
| SITE | 66 |
| | note = Each of 36th, 50th, 66th, and 80th amino acid(Xaa) is a 6-aminohexanoic acid. |
| SITE | 80 |
| | note = Each of 36th, 50th, 66th, and 80th amino acid(Xaa) is a 6-aminohexanoic acid. |
| SITE | 37 |
| | note = Each of 37th, 49th, 67th, and 79th aminoacid(Xaa) is a D-form alanine. |
| SITE | 49 |
| | note = Each of 37th, 49th, 67th, and 79th aminoacid(Xaa) is a D-form alanine. |
| SITE | 67 |
| | note = Each of 37th, 49th, 67th, and 79th aminoacid(Xaa) is a D-form alanine. |
| SITE | 79 |
| | note = Each of 37th, 49th, 67th, and 79th aminoacid(Xaa) is a D-form alanine. |
| SITE | 39 |
| | note = Each of 39th and 69th aminoacid(Xaa) is L-cyclohexylalanins. |
| SITE | 69 |
| | note = Each of 39th and 69th aminoacid(Xaa) is L-cyclohexylalanins. |
| SEQUENCE: 151 | |

```
MRGSHHHHHH GSDDDDKIVD RNVPPIFNDV YWIAFXXKXV AAWTLKAAXX RNVPPIFNDV   60
YWIAFXXKXV AAWTLKAAXX                                              80
```

| | |
|---|---|
| SEQ ID NO: 152 | moltype = AA  length = 90 |
| FEATURE | Location/Qualifiers |
| source | 1..90 |
| | mol_type = protein |
| | note = Concatamer |
| | organism = synthetic construct |
| SITE | 31 |
| | note = Each of 31st, 45th, 76th, and 90th amino acid(Xaa) |

```
                              is a 6-aminohexanoic acid.
SITE                       45
                              note = Each of 31st, 45th, 76th, and 90th amino acid(Xaa)
                              is a 6-aminohexanoic acid.
SITE                       76
                              note = Each of 31st, 45th, 76th, and 90th amino acid(Xaa)
                              is a 6-aminohexanoic acid.
SITE                       90
                              note = Each of 31st, 45th, 76th, and 90th amino acid(Xaa)
                              is a 6-aminohexanoic acid.
SITE                       32
                              note = Each of 32nd, 44th, 77th, and 89th aminoacid(Xaa) is
                              a D-form alanine.
SITE                       44
                              note = Each of 32nd, 44th, 77th, and 89th aminoacid(Xaa) is
                              a D-form alanine.
SITE                       77
                              note = Each of 32nd, 44th, 77th, and 89th aminoacid(Xaa) is
                              a D-form alanine.
SITE                       89
                              note = Each of 32nd, 44th, 77th, and 89th aminoacid(Xaa) is
                              a D-form alanine.
SITE                       34
                              note = Each of 34th and 79th aminoacid(Xaa) is
                              L-cyclohexylalanins.
SITE                       79
                              note = Each of 34th and 79th aminoacid(Xaa) is
                              L-cyclohexylalanins.
SEQUENCE: 152
RNVPPIFNDV YWIAFCRFRG LISLSQVYLS XXKXVAAWTL KAAXXRNVPP IFNDVYWIAF   60
CRFRGLISLS QVYLSXXKXV AAWTLKAAXX                                   90

SEQ ID NO: 153             moltype = AA  length = 90
FEATURE                    Location/Qualifiers
source                     1..90
                              mol_type = protein
                              note = Concatamer
                              organism = synthetic construct
SITE                       16
                              note = Each of 16th, 30th, 61st, and 75th amino acid(Xaa)
                              is a6-aminohexanoic acid.
SITE                       30
                              note = Each of 16th, 30th, 61st, and 75th amino acid(Xaa)
                              is a6-aminohexanoic acid.
SITE                       61
                              note = Each of 16th, 30th, 61st, and 75th amino acid(Xaa)
                              is a6-aminohexanoic acid.
SITE                       75
                              note = Each of 16th, 30th, 61st, and 75th amino acid(Xaa)
                              is a6-aminohexanoic acid.
SITE                       17
                              note = Each of 17th, 29th, 62nd, and 74th aminoacid(Xaa) is
                              a D-form alanine.
SITE                       29
                              note = Each of 17th, 29th, 62nd, and 74th aminoacid(Xaa) is
                              a D-form alanine.
SITE                       62
                              note = Each of 17th, 29th, 62nd, and 74th aminoacid(Xaa) is
                              a D-form alanine.
SITE                       74
                              note = Each of 17th, 29th, 62nd, and 74th aminoacid(Xaa) is
                              a D-form alanine.
SITE                       19
                              note = Each of 19th and 64th aminoacid(Xaa) is
                              L-cyclohexylalanins.
SITE                       64
                              note = Each of 19th and 64th aminoacid(Xaa) is
                              L-cyclohexylalanins.
SEQUENCE: 153
RNVPPIFNDV YWIAFXXKXV AAWTLKAAXX CRFRGLISLS QVYLSRNVPP IFNDVYWIAF   60
XXKXVAAWTL KAAXXCRFRG LISLSQVYLS                                   90

SEQ ID NO: 154             moltype = AA  length = 90
FEATURE                    Location/Qualifiers
source                     1..90
                              mol_type = protein
                              note = Concatamer
                              organism = synthetic construct
SITE                       16
```

```
                            note = Each of 16th, 30th, 61st, and 75th amino acid(Xaa)
                             is a 6-aminohexanoic acid.
SITE                        30
                            note = Each of 16th, 30th, 61st, and 75th amino acid(Xaa)
                             is a 6-aminohexanoic acid.
SITE                        61
                            note = Each of 16th, 30th, 61st, and 75th amino acid(Xaa)
                             is a 6-aminohexanoic acid.
SITE                        75
                            note = Each of 16th, 30th, 61st, and 75th amino acid(Xaa)
                             is a 6-aminohexanoic acid.
SITE                        17
                            note = Each of 17th, 29th, 62nd and 74th aminoacid(Xaa) is
                             a D-form alanine.
SITE                        29
                            note = Each of 17th, 29th, 62nd and 74th aminoacid(Xaa) is
                             a D-form alanine.
SITE                        62
                            note = Each of 17th, 29th, 62nd and 74th aminoacid(Xaa) is
                             a D-form alanine.
SITE                        74
                            note = Each of 17th, 29th, 62nd and 74th aminoacid(Xaa) is
                             a D-form alanine.
SITE                        19
                            note = Each of 19th and 64th aminoacid(Xaa) is
                             L-cyclohexylalanins.
SITE                        64
                            note = Each of 19th and 64th aminoacid(Xaa) is
                             L-cyclohexylalanins.
SEQUENCE: 154
RNVPPIFNDV YWIAFXXKXV AAWTLKAAXX ILMQYIKANS KFIGIRNVPP IFNDVYWIAF    60
XXKXVAAWTL KAAXXILMQY IKANSKFIGI                                    90

SEQ ID NO: 155              moltype = AA  length = 120
FEATURE                     Location/Qualifiers
source                      1..120
                            mol_type = protein
                            note = Concatamer
                            organism = synthetic construct
SITE                        16
                            note = Each of 16th, 30th, 76th, and 90th amino acid(Xaa)
                             is a 6-aminohexanoic acid.
SITE                        30
                            note = Each of 16th, 30th, 76th, and 90th amino acid(Xaa)
                             is a 6-aminohexanoic acid.
SITE                        76
                            note = Each of 16th, 30th, 76th, and 90th amino acid(Xaa)
                             is a 6-aminohexanoic acid.
SITE                        90
                            note = Each of 16th, 30th, 76th, and 90th amino acid(Xaa)
                             is a 6-aminohexanoic acid.
SITE                        17
                            note = Each of 17th, 29th, 77th, and 89th aminoacid(Xaa) is
                             a D-form alanine.
SITE                        29
                            note = Each of 17th, 29th, 77th, and 89th aminoacid(Xaa) is
                             a D-form alanine.
SITE                        29
                            note = Each of 17th, 29th, 77th, and 89th aminoacid(Xaa) is
                             a D-form alanine.
SITE                        77
                            note = Each of 17th, 29th, 77th, and 89th aminoacid(Xaa) is
                             a D-form alanine.
SITE                        89
                            note = Each of 17th, 29th, 77th, and 89th aminoacid(Xaa) is
                             a D-form alanine.
SITE                        19
                            note = Each of 19th and 79th aminoacid(Xaa) is
                             L-cyclohexylalanins.
SITE                        79
                            note = Each of 19th and 79th aminoacid(Xaa) is
                             L-cyclohexylalanins.
SEQUENCE: 155
RNVPPIFNDV YWIAFXXKXV AAWTLKAAXX ILMQYIKANS KFIGIRNVPP IFNDVYWIAF    60
RNVPPIFNDV YWIAFXXKXV AAWTLKAAXX ILMQYIKANS KFIGIRNVPP IFNDVYWIAF   120

SEQ ID NO: 156              moltype = AA  length = 75
FEATURE                     Location/Qualifiers
source                      1..75
```

```
                           mol_type = protein
                           note = String-of-Beads
                           organism = synthetic construct
SITE                       16
                           note = Each of 16th, 30th, 61st, and 75th amino acid(Xaa)
                           is a 6-aminohexanoic acid.
SITE                       30
                           note = Each of 16th, 30th, 61st, and 75th amino acid(Xaa)
                           is a 6-aminohexanoic acid.
SITE                       61
                           note = Each of 16th, 30th, 61st, and 75th amino acid(Xaa)
                           is a 6-aminohexanoic acid.
SITE                       75
                           note = Each of 16th, 30th, 61st, and 75th amino acid(Xaa)
                           is a 6-aminohexanoic acid.
SITE                       17
                           note = Each of 17th, 29th, 62nd, and 74th aminoacid(Xaa) is
                           a D-form alanine.
SITE                       29
                           note = Each of 17th, 29th, 62nd, and 74th aminoacid(Xaa) is
                           a D-form alanine.
SITE                       62
                           note = Each of 17th, 29th, 62nd, and 74th aminoacid(Xaa) is
                           a D-form alanine.
SITE                       74
                           note = Each of 17th, 29th, 62nd, and 74th aminoacid(Xaa) is
                           a D-form alanine.
SITE                       19
                           note = Each of 19th and 64th aminoacid(Xaa) is
                           L-cyclohexylalanins.
SITE                       64
                           note = Each of 19th and 64th aminoacid(Xaa) is
                           L-cyclohexylalanins.
SEQUENCE: 156
RNVPPIFNDV YWIAFXXKXV AAWTLKAAXX RNVPPIFNDV YWIAFCRFRG LISLSQVYLS    60
XXKXVAAWTL KAAXX                                                   75

SEQ ID NO: 157             moltype = AA  length = 152
FEATURE                    Location/Qualifiers
source                     1..152
                           mol_type = protein
                           note = String-of-Beads
                           organism = synthetic construct
SITE                       16
                           note = 16th, 30th, 46th, 62nd, 76th, 92nd, 108th, and 122nd
                           Xaa is a 6-aminohexanoic acid.
SITE                       30
                           note = 16th, 30th, 46th, 62nd, 76th, 92nd, 108th, and 122nd
                           Xaa is a 6-aminohexanoic acid.
SITE                       46
                           note = 16th, 30th, 46th, 62nd, 76th, 92nd, 108th, and 122nd
                           Xaa is a 6-aminohexanoic acid.
SITE                       62
                           note = 16th, 30th, 46th, 62nd, 76th, 92nd, 108th, and 122nd
                           Xaa is a 6-aminohexanoic acid.
SITE                       76
                           note = 16th, 30th, 46th, 62nd, 76th, 92nd, 108th, and 122nd
                           Xaa is a 6-aminohexanoic acid.
SITE                       92
                           note = 16th, 30th, 46th, 62nd, 76th, 92nd, 108th, and 122nd
                           Xaa is a 6-aminohexanoic acid.
SITE                       108
                           note = 16th, 30th, 46th, 62nd, 76th, 92nd, 108th, and 122nd
                           Xaa is a 6-aminohexanoic acid.
SITE                       122
                           note = 16th, 30th, 46th, 62nd, 76th, 92nd, 108th, and 122nd
                           Xaa is a 6-aminohexanoic acid.
SITE                       17
                           note = 17th, 29th, 63rd, 75th, 109th, and 121st Xaa is a
                           D-form alanine.
SITE                       29
                           note = 17th, 29th, 63rd, 75th, 109th, and 121st Xaa is a
                           D-form alanine.
SITE                       63
                           note = 17th, 29th, 63rd, 75th, 109th, and 121st Xaa is a
                           D-form alanine.
SITE                       75
                           note = 17th, 29th, 63rd, 75th, 109th, and 121st Xaa is a
                           D-form alanine.
```

```
SITE                    109
                        note = 17th, 29th, 63rd, 75th, 109th, and 121st Xaa is a
                        D-form alanine.
SITE                    121
                        note = 17th, 29th, 63rd, 75th, 109th, and 121st Xaa is a
                        D-form alanine.
SITE                    19
                        note = 19th, 65th, and 111st Xaa isL-cyclohexylalanins.
SITE                    65
                        note = 19th, 65th, and 111st Xaa isL-cyclohexylalanins.
SITE                    111
                        note = 19th, 65th, and 111st Xaa isL-cyclohexylalanins.
SEQUENCE: 157
RNVPPIFNDV YWIAFXXKXV AAWTLKAAXX RNVPPIFNDV YWIAFXRNVP PIFNDVYWIA    60
FXXKXVAAWT LKAAXXILMQ YIKANSKFIG IXRNVPPIFN DVYWIAFXXK XVAAWTLKAA   120
XXILMQYIKA NSKFIGICRF RGLISLSQVY LS                                152

SEQ ID NO: 158          moltype = AA  length = 272
FEATURE                 Location/Qualifiers
source                  1..272
                        mol_type = protein
                        note = String-of-Beads
                        organism = synthetic construct
SITE                    16
                        note = 6-aminohexanoic acid
SITE                    30
                        note = 6-aminohexanoic acid
SITE                    61
                        note = 6-aminohexanoic acid
SITE                    75
                        note = 6-aminohexanoic acid
SITE                    106
                        note = 6-aminohexanoic acid
SITE                    120
                        note = 6-aminohexanoic acid
SITE                    136
                        note = 6-aminohexanoic acid
SITE                    150
                        note = 6-aminohexanoic acid
SITE                    166
                        note = 6-aminohexanoic acid
SITE                    182
                        note = 6-aminohexanoic acid
SITE                    196
                        note = 6-aminohexanoic acid
SITE                    212
                        note = 6-aminohexanoic acid
SITE                    228
                        note = 6-aminohexanoic acid
SITE                    242
                        note = 6-aminohexanoic acid
SITE                    17
                        note = D-form alanine
SITE                    29
                        note = D-form alanine
SITE                    62
                        note = D-form alanine
SITE                    74
                        note = D-form alanine
SITE                    107
                        note = D-form alanine
SITE                    119
                        note = D-form alanine
SITE                    137
                        note = D-form alanine
SITE                    149
                        note = D-form alanine
SITE                    183
                        note = D-form alanine
SITE                    195
                        note = D-form alanine
SITE                    229
                        note = D-form alanine
SITE                    241
                        note = D-form alanine
SITE                    19
                        note = L-cyclohexylalanins
SITE                    64
                        note = L-cyclohexylalanins
```

-continued

```
SITE                    109
                        note = L-cyclohexylalanins
SITE                    139
                        note = L-cyclohexylalanins
SITE                    185
                        note = L-cyclohexylalanins
SITE                    231
                        note = L-cyclohexylalanins
SEQUENCE: 158
RNVPPIFNDV YWIAFXXKXV AAWTLKAAXX RNVPPIFNDV YWIAFCRFRG LISLSQVYLS  60
XXKXVAAWTL KAAXXRNVPP IFNDVYWIAF CRFRGLISLS QVYLSXXKXV AAWTLKAAXX  120
RNVPPIFNDV YWIAFXXKXV AAWTLKAAXX RNVPPIFNDV YWIAFXRNVP PIFNDVYWIA  180
FXXKXVAAWT LKAAXXILMQ YIKANSKFIG IXRNVPPIFN DVYWIAFXXK XVAAWTLKAA  240
XXILMQYIKA NSKFIGICRF RGLISLSQVY LS                                272

SEQ ID NO: 159          moltype = AA  length = 6
FEATURE                 Location/Qualifiers
source                  1..6
                        mol_type = protein
                        note = Auxiliary part
                        organism = synthetic construct
SEQUENCE: 159
RRRRRR                                                             6

SEQ ID NO: 160          moltype = AA  length = 43
FEATURE                 Location/Qualifiers
source                  1..43
                        mol_type = protein
                        note = Unit peptide
                        organism = synthetic construct
SITE                    19
                        note = Xaa at position 19 is L-cyclohexylalanine
SITE                    16
                        note = Xaa at position 16 is 6-aminohexanoic acid
SITE                    17
                        note = Xaa at position 17 is D-form alanine
SEQUENCE: 160
RNVPPIFNDV YWIAFXXKXV AAWTLKAACR FRGLISLSQV YLS                    43

SEQ ID NO: 161          moltype = AA  length = 30
FEATURE                 Location/Qualifiers
source                  1..30
                        mol_type = protein
                        note = Unit peptide
                        organism = synthetic construct
SITE                    16
                        note = Xaa at position 16 is 6-aminohexanoic acid
SITE                    17
                        note = Xaa at position 17 is D-form alanine
SITE                    19
                        note = Xaa at position 19 is L-cyclohexylalanine
SEQUENCE: 161
RNVPPIFNDV YWIAFXXKXV AAWTLKAACR                                   30

SEQ ID NO: 162          moltype = AA  length = 10
FEATURE                 Location/Qualifiers
source                  1..10
                        mol_type = protein
                        note = Th epitope
                        organism = synthetic construct
SEQUENCE: 162
PLGFFPDHQL                                                         10

SEQ ID NO: 163          moltype = AA  length = 16
FEATURE                 Location/Qualifiers
source                  1..16
                        mol_type = protein
                        note = Th epitope
                        organism = synthetic construct
SEQUENCE: 163
WPEANQVGAG AFGPGF                                                  16

SEQ ID NO: 164          moltype = AA  length = 15
FEATURE                 Location/Qualifiers
source                  1..15
                        mol_type = protein
                        note = Th epitope
                        organism = synthetic construct
SEQUENCE: 164
```

-continued

```
MQWNSTALHQ ALQDP                                                         15

SEQ ID NO: 165          moltype = AA  length = 26
FEATURE                 Location/Qualifiers
source                  1..26
                        mol_type = protein
                        note = Th epitope
                        organism = synthetic construct
SEQUENCE: 165
MQWNSTTFHQ TLQDPRVRGL YFPAGG                                             26

SEQ ID NO: 166          moltype = AA  length = 10
FEATURE                 Location/Qualifiers
source                  1..10
                        mol_type = protein
                        note = Th epitope
                        organism = synthetic construct
SEQUENCE: 166
FFLLTRILTI                                                               10

SEQ ID NO: 167          moltype = AA  length = 15
FEATURE                 Location/Qualifiers
source                  1..15
                        mol_type = protein
                        note = Th epitope
                        organism = synthetic construct
SEQUENCE: 167
FFLLTRILTI PQSLD                                                         15

SEQ ID NO: 168          moltype = AA  length = 15
FEATURE                 Location/Qualifiers
source                  1..15
                        mol_type = protein
                        note = Th epitope
                        organism = synthetic construct
SEQUENCE: 168
TSLNFLGGTT VCLGQ                                                         15

SEQ ID NO: 169          moltype = AA  length = 16
FEATURE                 Location/Qualifiers
source                  1..16
                        mol_type = protein
                        note = Th epitope
                        organism = synthetic construct
SEQUENCE: 169
QSPTSNHSPT SCPPIC                                                        16

SEQ ID NO: 170          moltype = AA  length = 19
FEATURE                 Location/Qualifiers
source                  1..19
                        mol_type = protein
                        note = Th epitope
                        organism = synthetic construct
SEQUENCE: 170
IIFLFILLLC LIFLLVLLD                                                     19

SEQ ID NO: 171          moltype = AA  length = 14
FEATURE                 Location/Qualifiers
source                  1..14
                        mol_type = protein
                        note = Th epitope
                        organism = synthetic construct
SEQUENCE: 171
CTTPAQGNSM FPSC                                                          14

SEQ ID NO: 172          moltype = AA  length = 8
FEATURE                 Location/Qualifiers
source                  1..8
                        mol_type = protein
                        note = Th epitope
                        organism = synthetic construct
SEQUENCE: 172
CTKPTDGN                                                                 8

SEQ ID NO: 173          moltype = AA  length = 8
FEATURE                 Location/Qualifiers
source                  1..8
                        mol_type = protein
                        note = Th epitope
```

-continued

```
                               organism = synthetic construct
SEQUENCE: 173
WASVRFSW                                                               8

SEQ ID NO: 174          moltype = AA   length = 9
FEATURE                 Location/Qualifiers
source                  1..9
                        mol_type = protein
                        note = Th epitope
                        organism = synthetic construct
SEQUENCE: 174
LLPIFFCLW                                                              9

SEQ ID NO: 175          moltype = AA   length = 20
FEATURE                 Location/Qualifiers
source                  1..20
                        mol_type = protein
                        note = Th epitope
                        organism = synthetic construct
SEQUENCE: 175
MDIDPYKEFG ATVELLSFLP                                                 20

SEQ ID NO: 176          moltype = AA   length = 10
FEATURE                 Location/Qualifiers
source                  1..10
                        mol_type = protein
                        note = Th epitope
                        organism = synthetic construct
SEQUENCE: 176
FLPSDFFPSV                                                            10

SEQ ID NO: 177          moltype = AA   length = 20
FEATURE                 Location/Qualifiers
source                  1..20
                        mol_type = protein
                        note = Th epitope
                        organism = synthetic construct
SEQUENCE: 177
RDLLDTASAL YREALESPEH                                                 20

SEQ ID NO: 178          moltype = AA   length = 20
FEATURE                 Location/Qualifiers
source                  1..20
                        mol_type = protein
                        note = Th epitope
                        organism = synthetic construct
SEQUENCE: 178
PHHTALRQAI LCWGELMTLA                                                 20

SEQ ID NO: 179          moltype = AA   length = 15
FEATURE                 Location/Qualifiers
source                  1..15
                        mol_type = protein
                        note = Th epitope
                        organism = synthetic construct
SEQUENCE: 179
GRETVIEYLV SFGVW                                                      15

SEQ ID NO: 180          moltype = AA   length = 15
FEATURE                 Location/Qualifiers
source                  1..15
                        mol_type = protein
                        note = Th epitope
                        organism = synthetic construct
SEQUENCE: 180
EYLVSFGVWI RTPPA                                                      15

SEQ ID NO: 181          moltype = AA   length = 20
FEATURE                 Location/Qualifiers
source                  1..20
                        mol_type = protein
                        note = Th epitope
                        organism = synthetic construct
SEQUENCE: 181
VSFGVWIRTP PAYRPPNAPI                                                 20

SEQ ID NO: 182          moltype = AA   length = 10
FEATURE                 Location/Qualifiers
source                  1..10
```

```
SEQ ID NO: 182                  moltype = AA   length = 10
FEATURE                         Location/Qualifiers
source                          1..10
                                mol_type = protein
                                note = Th epitope
                                organism = synthetic construct
SEQUENCE: 182
TVVRRRGRSP                                                                      10

SEQ ID NO: 183                  moltype = AA   length = 15
FEATURE                         Location/Qualifiers
source                          1..15
                                mol_type = protein
                                note = Th epitope
                                organism = synthetic construct
SEQUENCE: 183
VGPLTVNEKR RLKLI                                                                15

SEQ ID NO: 184                  moltype = AA   length = 15
FEATURE                         Location/Qualifiers
source                          1..15
                                mol_type = protein
                                note = Th epitope
                                organism = synthetic construct
SEQUENCE: 184
RHYLHTLWKA GILYK                                                                15

SEQ ID NO: 185                  moltype = AA   length = 15
FEATURE                         Location/Qualifiers
source                          1..15
                                mol_type = protein
                                note = Th epitope
                                organism = synthetic construct
SEQUENCE: 185
ESRLVVDFSQ FSRGN                                                                15

SEQ ID NO: 186                  moltype = AA   length = 15
FEATURE                         Location/Qualifiers
source                          1..15
                                mol_type = protein
                                note = Th epitope
                                organism = synthetic construct
SEQUENCE: 186
LQSLTNLLSS NLSWL                                                                15

SEQ ID NO: 187                  moltype = AA   length = 15
FEATURE                         Location/Qualifiers
source                          1..15
                                mol_type = protein
                                note = Th epitope
                                organism = synthetic construct
SEQUENCE: 187
SSNLSWLSLD VSAAF                                                                15

SEQ ID NO: 188                  moltype = AA   length = 15
FEATURE                         Location/Qualifiers
source                          1..15
                                mol_type = protein
                                note = Th epitope
                                organism = synthetic construct
SEQUENCE: 188
LHLYSHPIIL GFRKI                                                                15

SEQ ID NO: 189                  moltype = AA   length = 15
FEATURE                         Location/Qualifiers
source                          1..15
                                mol_type = protein
                                note = Th epitope
                                organism = synthetic construct
SEQUENCE: 189
KQCFRKLPVN RPIDW                                                                15

SEQ ID NO: 190                  moltype = AA   length = 15
FEATURE                         Location/Qualifiers
source                          1..15
                                mol_type = protein
                                note = Th epitope
                                organism = synthetic construct
SEQUENCE: 190
LCQVFADATP TGWGL                                                                15

SEQ ID NO: 191                  moltype = AA   length = 15
```

```
FEATURE                 Location/Qualifiers
source                  1..15
                        mol_type = protein
                        note = Th epitope
                        organism = synthetic construct
SEQUENCE: 191
AANWILRGTS FVYVP                                                              15

SEQ ID NO: 192          moltype = AA  length = 15
FEATURE                 Location/Qualifiers
source                  1..15
                        mol_type = protein
                        note = Th epitope
                        organism = synthetic construct
SEQUENCE: 192
EIRLKVFVLG GCRHK                                                              15

SEQ ID NO: 193          moltype = AA  length = 17
FEATURE                 Location/Qualifiers
source                  1..17
                        mol_type = protein
                        note = Auxiliary part
                        organism = synthetic construct
SITE                    16
                        note = Xaa at position 16 is 6-aminohexanoic acid.
SITE                    17
                        note = Xaa at position 17 is D-form alanine.
SEQUENCE: 193
GSHHHHHHGS DDDDKXX                                                            17

SEQ ID NO: 194          moltype = AA  length = 17
FEATURE                 Location/Qualifiers
source                  1..17
                        mol_type = protein
                        note = Auxiliary part
                        organism = synthetic construct
SITE                    1
                        note = Xaa at position 1 is D-form alanine.
SITE                    2
                        note = Xaa at position 2 is 6-aminohexanoic acid.
SEQUENCE: 194
XXGSHHHHHH GSDDDDK                                                            17

SEQ ID NO: 195          moltype = AA  length = 11
FEATURE                 Location/Qualifiers
source                  1..11
                        mol_type = protein
                        note = Th epitope
                        organism = synthetic construct
SEQUENCE: 195
KFVAAWTLKA A                                                                  11

SEQ ID NO: 196          moltype = AA  length = 11
FEATURE                 Location/Qualifiers
source                  1..11
                        mol_type = protein
                        note = Th epitope
                        organism = synthetic construct
SEQUENCE: 196
KYVAAWTLKA A                                                                  11

SEQ ID NO: 197          moltype = AA  length = 11
FEATURE                 Location/Qualifiers
source                  1..11
                        mol_type = protein
                        note = Th epitope
                        organism = synthetic construct
VARIANT                 2
                        note = Xaa can be any naturally occurring amino acid
SEQUENCE: 197
KXVAAWTLKA A                                                                  11

SEQ ID NO: 198          moltype = AA  length = 45
FEATURE                 Location/Qualifiers
source                  1..45
                        mol_type = protein
                        note = Unit peptide
                        organism = synthetic construct
VARIANT                 16
```

```
                        note = X can be any amino acid.
VARIANT                 17
                        note = X can be any amino acid.
VARIANT                 19
                        note = X can be any amino acid.
VARIANT                 29
                        note = X can be any amino acid.
VARIANT                 30
                        note = X can be any amino acid.
SEQUENCE: 198
RNVPPIFNDV YWIAFXXKXV AAWTLKAAXX CRFRGLISLS QVYLS             45

SEQ ID NO: 199          moltype = AA   length = 45
FEATURE                 Location/Qualifiers
source                  1..45
                        mol_type = protein
                        note = Unit peptide
                        organism = synthetic construct
VARIANT                 16
                        note = X can be any amino acid.
VARIANT                 17
                        note = X can be any amino acid.
VARIANT                 19
                        note = X can be any amino acid.
VARIANT                 29
                        note = X can be any amino acid.
VARIANT                 30
                        note = X can be any amino acid.
SEQUENCE: 199
RNVPPIFNDV YWIAFXXKXV AAWTLKAAXX GSHHHHHHGS DDDDK             45

SEQ ID NO: 200          moltype = AA   length = 45
FEATURE                 Location/Qualifiers
source                  1..45
                        mol_type = protein
                        note = Unit peptide
                        organism = synthetic construct
VARIANT                 16
                        note = X can be any amino acid.
VARIANT                 17
                        note = X can be any amino acid.
VARIANT                 19
                        note = X can be any amino acid.
VARIANT                 29
                        note = X can be any amino acid.
VARIANT                 30
                        note = X can be any amino acid.
SEQUENCE: 200
GSHHHHHHGS DDDDKXXKXV AAWTLKAAXX RNVPPIFNDV YWIAF             45

SEQ ID NO: 201          moltype = AA   length = 50
FEATURE                 Location/Qualifiers
source                  1..50
                        mol_type = protein
                        note = Unit peptide
                        organism = synthetic construct
VARIANT                 21
                        note = X can be any amino acid.
VARIANT                 22
                        note = X can be any amino acid.
VARIANT                 24
                        note = X can be any amino acid.
VARIANT                 34
                        note = X can be any amino acid.
VARIANT                 35
                        note = X can be any amino acid.
SEQUENCE: 201
KTTKQSFDLS VKAQYKKNKH XXKXVAAWTL KAAXXCRFRG LISLSQVYLS        50

SEQ ID NO: 202          moltype = AA   length = 45
FEATURE                 Location/Qualifiers
source                  1..45
                        mol_type = protein
                        note = Unit peptide
                        organism = synthetic construct
VARIANT                 31
                        note = X can be any amino acid.
VARIANT                 32
                        note = X can be any amino acid.
```

```
VARIANT                 34
                        note = X can be any amino acid.
VARIANT                 44
                        note = X can be any amino acid.
VARIANT                 45
                        note = X can be any amino acid.
SEQUENCE: 202
RNVPPIFNDV YWIAFCRFRG LISLSQVYLS XXKXVAAWTL KAAXX               45

SEQ ID NO: 203          moltype = AA   length = 45
FEATURE                 Location/Qualifiers
source                  1..45
                        mol_type = protein
                        note = Unit peptide
                        organism = synthetic construct
VARIANT                 16
                        note = X can be any amino acid.
VARIANT                 30
                        note = X can be any amino acid.
SEQUENCE: 203
RNVPPIFNDV YWIAFXPKYV KQNTLKLATX CRFRGLISLS QVYLS               45

SEQ ID NO: 204          moltype = AA   length = 30
FEATURE                 Location/Qualifiers
source                  1..30
                        mol_type = protein
                        note = Unit peptide
                        organism = synthetic construct
VARIANT                 16
                        note = X can be any amino acid.
VARIANT                 17
                        note = X can be any amino acid.
VARIANT                 19
                        note = X can be any amino acid.
VARIANT                 29
                        note = X can be any amino acid.
VARIANT                 30
                        note = X can be any amino acid.
SEQUENCE: 204
RNVPPIFNDV YWIAFXXKXV AAWTLKAAXX                                30

SEQ ID NO: 205          moltype = AA   length = 26
FEATURE                 Location/Qualifiers
source                  1..26
                        mol_type = protein
                        note = Unit peptide
                        organism = synthetic construct
VARIANT                 17
                        note = X can be any amino acid.
SEQUENCE: 205
RNVPPIFNDV YWIAFKXVAA WTLKAA                                    26

SEQ ID NO: 206          moltype = AA   length = 32
FEATURE                 Location/Qualifiers
source                  1..32
                        mol_type = protein
                        note = Unit peptide
                        organism = synthetic construct
VARIANT                 17
                        note = X can be any amino acid.
SEQUENCE: 206
RNVPPIFNDV YWIAFKXVAA WTLKAAHHHH HH                             32

SEQ ID NO: 207          moltype = AA   length = 43
FEATURE                 Location/Qualifiers
source                  1..43
                        mol_type = protein
                        note = Unit peptide
                        organism = synthetic construct
VARIANT                 16
                        note = X can be any amino acid.
VARIANT                 17
                        note = X can be any amino acid.
VARIANT                 19
                        note = X can be any amino acid.
SEQUENCE: 207
RNVPPIFNDV YWIAFXXKXV AAWTLKAACR FRGLISLSQV YLS                 43

SEQ ID NO: 208          moltype = AA   length = 30
```

```
FEATURE                 Location/Qualifiers
source                  1..30
                        mol_type = protein
                        note = Unit peptide
                        organism = synthetic construct
VARIANT                 16
                        note = X can be any amino acid.
VARIANT                 17
                        note = X can be any amino acid.
VARIANT                 19
                        note = X can be any amino acid.
SEQUENCE: 208
RNVPPIFNDV YWIAFXXKXV AAWTLKAACR                                            30

SEQ ID NO: 209          moltype = AA   length = 45
FEATURE                 Location/Qualifiers
source                  1..45
                        mol_type = protein
                        note = Unit peptide
                        organism = synthetic construct
VARIANT                 16
                        note = X can be any amino acid.
VARIANT                 17
                        note = X can be any amino acid.
VARIANT                 29
                        note = X can be any amino acid.
VARIANT                 30
                        note = X can be any amino acid.
SEQUENCE: 209
RNVPPIFNDV YWIAFXXKFV AAWTLKAAXX CRFRGLISLS QVYLS                           45

SEQ ID NO: 210          moltype = AA   length = 30
FEATURE                 Location/Qualifiers
source                  1..30
                        mol_type = protein
                        note = Unit peptide
                        organism = synthetic construct
VARIANT                 16
                        note = X can be any amino acid.
VARIANT                 17
                        note = X can be any amino acid.
VARIANT                 29
                        note = X can be any amino acid.
VARIANT                 30
                        note = X can be any amino acid.
SEQUENCE: 210
RNVPPIFNDV YWIAFXXKFV AAWTLKAAXX                                            30

SEQ ID NO: 211          moltype = AA   length = 43
FEATURE                 Location/Qualifiers
source                  1..43
                        mol_type = protein
                        note = Unit peptide
                        organism = synthetic construct
VARIANT                 16
                        note = X can be any amino acid.
VARIANT                 17
                        note = X can be any amino acid.
SEQUENCE: 211
RNVPPIFNDV YWIAFXXKFV AAWTLKAACR FRGLISLSQV YLS                             43

SEQ ID NO: 212          moltype = AA   length = 30
FEATURE                 Location/Qualifiers
source                  1..30
                        mol_type = protein
                        note = Unit peptide
                        organism = synthetic construct
VARIANT                 16
                        note = X can be any amino acid.
VARIANT                 17
                        note = X can be any amino acid.
SEQUENCE: 212
RNVPPIFNDV YWIAFXXKFV AAWTLKAACR                                            30

SEQ ID NO: 213          moltype = AA   length = 23
FEATURE                 Location/Qualifiers
source                  1..23
                        mol_type = protein
                        note = Unit peptide
```

```
                                            organism = synthetic construct
SEQUENCE: 213
RNVPPIFNDV YWIAFCTKPT DGN                                                    23

SEQ ID NO: 214          moltype = AA   length = 24
FEATURE                 Location/Qualifiers
source                  1..24
                        mol_type = protein
                        note = Unit peptide
                        organism = synthetic construct
SEQUENCE: 214
RNVPPIFNDV YWIAFLLPIF FCLW                                                   24

SEQ ID NO: 215          moltype = AA   length = 25
FEATURE                 Location/Qualifiers
source                  1..25
                        mol_type = protein
                        note = Unit peptide
                        organism = synthetic construct
SEQUENCE: 215
RNVPPIFNDV YWIAFFLPSD FFPSV                                                  25

SEQ ID NO: 216          moltype = AA   length = 55
FEATURE                 Location/Qualifiers
source                  1..55
                        mol_type = protein
                        note = Unit peptide
                        organism = synthetic construct
SITE                    22
                        note = Xaa at position 22 and position 39 are D-form
                          alanine.
SITE                    39
                        note = Xaa at position 22 and position 39 are D-form
                          alanine.
SITE                    21
                        note = Xaa at position 21 and position 40 are
                          6-aminohexanoic acid.
SITE                    40
                        note = Xaa at position 21 and position 40 are
                          6-aminohexanoic acid.
SEQUENCE: 216
KTTKQSFDLS VKAQYKKNKH XXWPEANQVG AGAFGPGFXX CRFRGLISLS QVYLS                 55

SEQ ID NO: 217          moltype = AA   length = 59
FEATURE                 Location/Qualifiers
source                  1..59
                        mol_type = protein
                        note = Unit peptide
                        organism = synthetic construct
SITE                    22
                        note = Xaa at position 22 and position 43 are D-form
                          alanine.
SITE                    43
                        note = Xaa at position 22 and position 43 are D-form
                          alanine.
SITE                    21
                        note = Xaa at position 21 and position 44 are
                          6-aminohexanoic acid.
SITE                    44
                        note = Xaa at position 21 and position 44 are
                          6-aminohexanoic acid.
SEQUENCE: 217
KTTKQSFDLS VKAQYKKNKH XXMDIDPYKE FGATVELLSF LPXXCRFRGL ISLSQVYLS            59

SEQ ID NO: 218          moltype = AA   length = 71
FEATURE                 Location/Qualifiers
source                  1..71
                        mol_type = protein
                        note = Unit peptide
                        organism = synthetic construct
SITE                    22
                        note = Xaa at position 22 and position 55 are D-form
                          alanine.
SITE                    55
                        note = Xaa at position 22 and position 55 are D-form
                          alanine.
SITE                    21
                        note = Xaa at position 21 and position 56 are
                          6-aminohexanoic acid.
```

|  |  |  |
|---|---|---|
| SITE |  | 56 |
|  |  | note = Xaa at position 21 and position 56 are 6-aminohexanoic acid. |
| SEQUENCE: 218 |  |  |
| KTTKQSFDLS VKAQYKKNKH XXILMQYIKA NSKFIGIPMG LPQSIALSSL MVAQXXCRFR | | 60 |
| GLISLSQVYL S | | 71 |
| | | |
| SEQ ID NO: 219 | moltype = AA  length = 36 | |
| FEATURE | Location/Qualifiers | |
| source | 1..36 | |
|  | mol_type = protein | |
|  | note = Unit peptide | |
|  | organism = synthetic construct | |
| SEQUENCE: 219 | | |
| RNVPPIFNDV YWIAFILMQY IKANSKFIGI HHHHHH | | 36 |
| | | |
| SEQ ID NO: 220 | moltype = AA  length = 41 | |
| FEATURE | Location/Qualifiers | |
| source | 1..41 | |
|  | mol_type = protein | |
|  | note = Unit peptide | |
|  | organism = synthetic construct | |
| SEQUENCE: 220 | | |
| RNVPPIFNDV YWIAFMDIDP YKEFGATVEL LSFLPHHHHH H | | 41 |
| | | |
| SEQ ID NO: 221 | moltype = AA  length = 15 | |
| FEATURE | Location/Qualifiers | |
| source | 1..15 | |
|  | mol_type = protein | |
|  | note = B-cell epitope | |
|  | organism = synthetic construct | |
| SEQUENCE: 221 | | |
| RFRGLISLSQ VYLDP | | 15 |
| | | |
| SEQ ID NO: 222 | moltype = AA  length = 15 | |
| FEATURE | Location/Qualifiers | |
| source | 1..15 | |
|  | mol_type = protein | |
|  | note = B-cell epitope | |
|  | organism = synthetic construct | |
| SEQUENCE: 222 | | |
| SVCGCPVGHH DVVGL | | 15 |
| | | |
| SEQ ID NO: 223 | moltype = AA  length = 21 | |
| FEATURE | Location/Qualifiers | |
| source | 1..21 | |
|  | mol_type = protein | |
|  | note = Th epitope | |
|  | organism = synthetic construct | |
| SEQUENCE: 223 | | |
| DIEKKIAKME KASSVFNVVN S | | 21 |
| | | |
| SEQ ID NO: 224 | moltype = AA  length = 16 | |
| FEATURE | Location/Qualifiers | |
| source | 1..16 | |
|  | mol_type = protein | |
|  | note = Th epitope | |
|  | organism = synthetic construct | |
| SEQUENCE: 224 | | |
| YSGPLKAEIA QRLEDV | | 16 |
| | | |
| SEQ ID NO: 225 | moltype = AA  length = 11 | |
| FEATURE | Location/Qualifiers | |
| source | 1..11 | |
|  | mol_type = protein | |
|  | note = Th epitope | |
|  | organism = synthetic construct | |
| VARIANT | 2 | |
|  | note = X can be any amino acid. | |
| SEQUENCE: 225 | | |
| KXVKANTLKA A | | 11 |
| | | |
| SEQ ID NO: 226 | moltype = AA  length = 11 | |
| FEATURE | Location/Qualifiers | |
| source | 1..11 | |
|  | mol_type = protein | |
|  | note = Th epitope | |
|  | organism = synthetic construct | |
| VARIANT | 2 | |

```
                        note = X can be any amino acid.
SEQUENCE: 226
KXVKANTLKA A                                                            11

SEQ ID NO: 227          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 227
KXVKAWTLKA A                                                            11

SEQ ID NO: 228          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 228
KXVKAWTLKA A                                                            11

SEQ ID NO: 229          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 229
KXVWANTLKA A                                                            11

SEQ ID NO: 230          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 230
KXVWANTLKA A                                                            11

SEQ ID NO: 231          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 231
KXVWAYTLKA A                                                            11

SEQ ID NO: 232          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 232
KXVWAVTLKA A                                                            11

SEQ ID NO: 233          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 233
```

```
KXVYAWTLKA A                                                                    11

SEQ ID NO: 234          moltype = AA  length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 234
KXVYAWTLKA A                                                                    11

SEQ ID NO: 235          moltype = AA  length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 235
RXVRANTLKA A                                                                    11

SEQ ID NO: 236          moltype = AA  length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 236
KXVKAHTLKA A                                                                    11

SEQ ID NO: 237          moltype = AA  length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 237
KXVKAHTLKA A                                                                    11

SEQ ID NO: 238          moltype = AA  length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 238
KXVAANTLKA A                                                                    11

SEQ ID NO: 239          moltype = AA  length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 239
KXVAANTLKA A                                                                    11

SEQ ID NO: 240          moltype = AA  length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 240
KXVAAYTLKA A                                                                    11
```

```
SEQ ID NO: 241          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 241
KXVAAYTLKA A                                                                    11

SEQ ID NO: 242          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 242
KXVAAWTLKA A                                                                    11

SEQ ID NO: 243          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 243
KXVAAKTLKA A                                                                    11

SEQ ID NO: 244          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 244
KXVAAHTLKA A                                                                    11

SEQ ID NO: 245          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 245
KXVAAATLKA A                                                                    11

SEQ ID NO: 246          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 246
KXVAAWTLKA A                                                                    11

SEQ ID NO: 247          moltype = AA   length = 11
FEATURE                 Location/Qualifiers
source                  1..11
                        mol_type = protein
                        note = Th epitope
                        organism = synthetic construct
VARIANT                 2
                        note = X can be any amino acid.
SEQUENCE: 247
KXVMAATLKA A                                                                    11

SEQ ID NO: 248          moltype = DNA   length = 135
FEATURE                 Location/Qualifiers
```

```
                          source           1..135
                                           mol_type = other DNA
                                           note = DNA encoding unit peptide
                                           organism = synthetic construct
SEQUENCE: 248
cgtaatgttc ctcctatctt caatgatgtt tattggattg cattcnnnnn naagnnngtg    60
gcagcttgga ccctgaaggc agcannnnnn tgccgtttcc gtggactgat ttccctgtcc   120
caggtttatc tgtcc                                                    135

SEQ ID NO: 249           moltype = DNA  length = 135
FEATURE                  Location/Qualifiers
source                   1..135
                         mol_type = other DNA
                         note = DNA encoding unit peptide
                         organism = synthetic construct
SEQUENCE: 249
cgtaatgttc ctcctatctt caatgatgtt tattggattg cattcnnnnn naagttcgtg    60
gcagcttgga ccctgaaggc agcannnnnn tgccgtttcc gtggactgat ttccctgtcc   120
caggtttatc tgtcc                                                    135

SEQ ID NO: 250           moltype = DNA  length = 135
FEATURE                  Location/Qualifiers
source                   1..135
                         mol_type = other DNA
                         note = DNA encoding unit peptide
                         organism = synthetic construct
SEQUENCE: 250
cgtaatgttc ctcctatctt caatgatgtt tattggattg cattcnnnnn naagtatgtg    60
gcagcttgga ccctgaaggc agcannnnnn tgccgtttcc gtggactgat ttccctgtcc   120
caggtttatc tgtcc                                                    135

SEQ ID NO: 251           moltype = DNA  length = 135
FEATURE                  Location/Qualifiers
source                   1..135
                         mol_type = other DNA
                         note = DNA encoding unit peptide
                         organism = synthetic construct
SEQUENCE: 251
cgtaatgttc ctcctatctt caatgatgtt tattggattg cattcnnnnn naagnnngtg    60
gcagcttgga ccctgaaggc agcannnnnn ggatcgcatc accatcacca tcacggatcc   120
gatgatgatg acaag                                                    135

SEQ ID NO: 252           moltype = DNA  length = 135
FEATURE                  Location/Qualifiers
source                   1..135
                         mol_type = other DNA
                         note = DNA encoding unit peptide
                         organism = synthetic construct
SEQUENCE: 252
cgtaatgttc ctcctatctt caatgatgtt tattggattg cattcnnnnn naagttcgtg    60
gcagcttgga ccctgaaggc agcannnnnn ggatcgcatc accatcacca tcacggatcc   120
gatgatgatg acaag                                                    135

SEQ ID NO: 253           moltype = DNA  length = 135
FEATURE                  Location/Qualifiers
source                   1..135
                         mol_type = other DNA
                         note = DNA encoding unit peptide
                         organism = synthetic construct
SEQUENCE: 253
cgtaatgttc ctcctatctt caatgatgtt tattggattg cattcnnnnn naagtatgtg    60
gcagcttgga ccctgaaggc agcannnnnn ggatcgcatc accatcacca tcacggatcc   120
gatgatgatg acaag                                                    135

SEQ ID NO: 254           moltype = DNA  length = 135
FEATURE                  Location/Qualifiers
source                   1..135
                         mol_type = other DNA
                         note = DNA encoding unit peptide
                         organism = synthetic construct
SEQUENCE: 254
ggatcgcatc accatcacca tcacggatcc gatgatgatg acaagnnnnn naagnnngtg    60
gcagcttgga ccctgaaggc agcannnnnn cgtaatgttc ctcctatctt caatgatgtt   120
tattggattg cattc                                                    135

SEQ ID NO: 255           moltype = DNA  length = 135
FEATURE                  Location/Qualifiers
source                   1..135
                         mol_type = other DNA
```

```
                            note = DNA encoding unit peptide
                            organism = synthetic construct
SEQUENCE: 255
ggatcgcatc accatcacca tcacggatcc gatgatgatg acaagnnnnn naagttcgtg       60
gcagcttgga ccctgaaggc agcannnnnn cgtaatgttc ctcctatctt caatgatgtt     120
tattggattg cattc                                                      135

SEQ ID NO: 256          moltype = DNA  length = 135
FEATURE                 Location/Qualifiers
source                  1..135
                        mol_type = other DNA
                        note = DNA encoding unit peptide
                        organism = synthetic construct
SEQUENCE: 256
ggatcgcatc accatcacca tcacggatcc gatgatgatg acaagnnnnn naagtatgtg       60
gcagcttgga ccctgaaggc agcannnnnn cgtaatgttc ctcctatctt caatgatgtt     120
tattggattg cattc                                                      135

SEQ ID NO: 257          moltype = DNA  length = 135
FEATURE                 Location/Qualifiers
source                  1..135
                        mol_type = other DNA
                        note = DNA encoding unit peptide
                        organism = synthetic construct
SEQUENCE: 257
aaaacgacaa agcaatcatt tgatttaagt gtaaaagctc agtatnnnnn naagnnngtg       60
gcagcttgga ccctgaaggc agcannnnnn tgccgtttcc gtggactgat ttccctgtcc     120
caggtttatc tgtcc                                                      135

SEQ ID NO: 258          moltype = DNA  length = 135
FEATURE                 Location/Qualifiers
source                  1..135
                        mol_type = other DNA
                        note = DNA encoding unit peptide
                        organism = synthetic construct
SEQUENCE: 258
aaaacgacaa agcaatcatt tgatttaagt gtaaaagctc agtatnnnnn naagttcgtg       60
gcagcttgga ccctgaaggc agcannnnnn tgccgtttcc gtggactgat ttccctgtcc     120
caggtttatc tgtcc                                                      135

SEQ ID NO: 259          moltype = DNA  length = 135
FEATURE                 Location/Qualifiers
source                  1..135
                        mol_type = other DNA
                        note = DNA encoding unit peptide
                        organism = synthetic construct
SEQUENCE: 259
aaaacgacaa agcaatcatt tgatttaagt gtaaaagctc agtatnnnnn naagtatgtg       60
gcagcttgga ccctgaaggc agcannnnnn tgccgtttcc gtggactgat ttccctgtcc     120
caggtttatc tgtcc                                                      135

SEQ ID NO: 260          moltype = DNA  length = 135
FEATURE                 Location/Qualifiers
source                  1..135
                        mol_type = other DNA
                        note = DNA encoding unit peptide
                        organism = synthetic construct
SEQUENCE: 260
cgtaatgttc ctcctatctt caatgatgtt tattggattg cattctgccg tttccgtgga       60
ctgatttccc tgtcccaggt ttatctgtcc nnnnnnaagn nngtgcagc ttggaccctg      120
aaggcagcan nnnn                                                       135

SEQ ID NO: 261          moltype = DNA  length = 135
FEATURE                 Location/Qualifiers
source                  1..135
                        mol_type = other DNA
                        note = DNA encoding unit peptide
                        organism = synthetic construct
SEQUENCE: 261
cgtaatgttc ctcctatctt caatgatgtt tattggattg cattctgccg tttccgtgga       60
ctgatttccc tgtcccaggt ttatctgtcc nnnnnnaagt tcgtggcagc ttggaccctg     120
aaggcagcan nnnn                                                       135

SEQ ID NO: 262          moltype = DNA  length = 135
FEATURE                 Location/Qualifiers
source                  1..135
                        mol_type = other DNA
                        note = DNA encoding unit peptide
                        organism = synthetic construct
```

```
SEQUENCE: 262
cgtaatgttc ctcctatctt caatgatgtt tattggattg cattctgccg tttccgtgga    60
ctgatttccc tgtcccaggt ttatctgtcc nnnnnnaagt atgtggcagc ttggaccctg   120
aaggcagcan nnnnn                                                    135

SEQ ID NO: 263          moltype = DNA   length = 135
FEATURE                 Location/Qualifiers
source                  1..135
                        mol_type = other DNA
                        note = DNA encoding unit peptide
                        organism = synthetic construct
SEQUENCE: 263
cgtaatgttc ctcctatctt caatgatgtt tattggattg cattcnnncc taagtatgtg    60
aagcagaata cactgaagct ggcaaccnnn tgccgtttcc gtggactgat ttccctgtcc   120
caggtttatc tgtcc                                                    135

SEQ ID NO: 264          moltype = DNA   length = 90
FEATURE                 Location/Qualifiers
source                  1..90
                        mol_type = other DNA
                        note = DNA encoding unit peptide
                        organism = synthetic construct
SEQUENCE: 264
cgtaatgttc ctcctatctt caatgatgtt tattggattg cattcnnnnn naagnnngtg    60
gcagcttgga ccctgaaggc agcannnnnn                                     90

SEQ ID NO: 265          moltype = DNA   length = 90
FEATURE                 Location/Qualifiers
source                  1..90
                        mol_type = other DNA
                        note = DNA encoding unit peptide
                        organism = synthetic construct
SEQUENCE: 265
cgtaatgttc ctcctatctt caatgatgtt tattggattg cattcnnnnn naagttcgtg    60
gcagcttgga ccctgaaggc agcannnnnn                                     90

SEQ ID NO: 266          moltype = DNA   length = 90
FEATURE                 Location/Qualifiers
source                  1..90
                        mol_type = other DNA
                        note = DNA encoding unit peptide
                        organism = synthetic construct
SEQUENCE: 266
cgtaatgttc ctcctatctt caatgatgtt tattggattg cattcnnnnn naagtatgtg    60
gcagcttgga ccctgaaggc agcannnnnn                                     90

SEQ ID NO: 267          moltype = DNA   length = 78
FEATURE                 Location/Qualifiers
source                  1..78
                        mol_type = other DNA
                        note = DNA encoding unit peptide
                        organism = synthetic construct
SEQUENCE: 267
cgtaatgttc ctcctatctt caatgatgtt tattggattg cattcaagnn ngtggcagct    60
tggaccctga aggcagca                                                  78

SEQ ID NO: 268          moltype = DNA   length = 78
FEATURE                 Location/Qualifiers
source                  1..78
                        mol_type = other DNA
                        note = DNA encoding unit peptide
                        organism = synthetic construct
SEQUENCE: 268
cgtaatgttc ctcctatctt caatgatgtt tattggattg cattcaagtt cgtggcagct    60
tggaccctga aggcagca                                                  78

SEQ ID NO: 269          moltype = DNA   length = 78
FEATURE                 Location/Qualifiers
source                  1..78
                        mol_type = other DNA
                        note = DNA encoding unit peptide
                        organism = synthetic construct
SEQUENCE: 269
cgtaatgttc ctcctatctt caatgatgtt tattggattg cattcaagta tgtggcagct    60
tggaccctga aggcagca                                                  78

SEQ ID NO: 270          moltype = DNA   length = 96
FEATURE                 Location/Qualifiers
source                  1..96
```

```
                         mol_type = other DNA
                         note = DNA encoding unit peptide
                         organism = synthetic construct
SEQUENCE: 270
cgtaatgttc ctcctatctt caatgatgtt tattggattg cattcaagnn ngtggcagct    60
tggaccctga aggcagcaca tcaccatcac catcac                              96

SEQ ID NO: 271           moltype = DNA   length = 96
FEATURE                  Location/Qualifiers
source                   1..96
                         mol_type = other DNA
                         note = DNA encoding unit peptide
                         organism = synthetic construct
SEQUENCE: 271
cgtaatgttc ctcctatctt caatgatgtt tattggattg cattcaagtt cgtggcagct    60
tggaccctga aggcagcaca tcaccatcac catcac                              96

SEQ ID NO: 272           moltype = DNA   length = 96
FEATURE                  Location/Qualifiers
source                   1..96
                         mol_type = other DNA
                         note = DNA encoding unit peptide
                         organism = synthetic construct
SEQUENCE: 272
cgtaatgttc ctcctatctt caatgatgtt tattggattg cattcaagta tgtggcagct    60
tggaccctga aggcagcaca tcaccatcac catcac                              96

SEQ ID NO: 273           moltype = DNA   length = 129
FEATURE                  Location/Qualifiers
source                   1..129
                         mol_type = other DNA
                         note = DNA encoding unit peptide
                         organism = synthetic construct
SEQUENCE: 273
cgtaatgttc ctcctatctt caatgatgtt tattggattg cattcnnnnn naagnnngtg    60
gcagcttgga ccctgaaggc agcatgccgt ttccgtggac tgatttccct gtcccaggtt   120
tatctgtcc                                                           129

SEQ ID NO: 274           moltype = DNA   length = 129
FEATURE                  Location/Qualifiers
source                   1..129
                         mol_type = other DNA
                         note = DNA encoding unit peptide
                         organism = synthetic construct
SEQUENCE: 274
cgtaatgttc ctcctatctt caatgatgtt tattggattg cattcnnnnn naagttcgtg    60
gcagcttgga ccctgaaggc agcatgccgt ttccgtggac tgatttccct gtcccaggtt   120
tatctgtcc                                                           129

SEQ ID NO: 275           moltype = DNA   length = 129
FEATURE                  Location/Qualifiers
source                   1..129
                         mol_type = other DNA
                         note = DNA encoding unit peptide
                         organism = synthetic construct
SEQUENCE: 275
cgtaatgttc ctcctatctt caatgatgtt tattggattg cattcnnnnn naagtatgtg    60
gcagcttgga ccctgaaggc agcatgccgt ttccgtggac tgatttccct gtcccaggtt   120
tatctgtcc                                                           129

SEQ ID NO: 276           moltype = DNA   length = 90
FEATURE                  Location/Qualifiers
source                   1..90
                         mol_type = other DNA
                         note = DNA encoding unit peptide
                         organism = synthetic construct
SEQUENCE: 276
cgtaatgttc ctcctatctt caatgatgtt tattggattg cattcnnnnn naagnnngtg    60
gcagcttgga ccctgaaggc agcatgccgt                                     90

SEQ ID NO: 277           moltype = DNA   length = 90
FEATURE                  Location/Qualifiers
source                   1..90
                         mol_type = other DNA
                         note = DNA encoding unit peptide
                         organism = synthetic construct
SEQUENCE: 277
cgtaatgttc ctcctatctt caatgatgtt tattggattg cattcnnnnn naagttcgtg    60
gcagcttgga ccctgaaggc agcatgccgt                                     90
```

```
SEQ ID NO: 278         moltype = DNA  length = 90
FEATURE                Location/Qualifiers
source                 1..90
                       mol_type = other DNA
                       note = DNA encoding unit peptide
                       organism = synthetic construct
SEQUENCE: 278
cgtaatgttc ctcctatctt caatgatgtt tattggattg cattcnnnnn naagtatgtg   60
gcagcttgga ccctgaaggc agcatgccgt                                    90

SEQ ID NO: 279         moltype = RNA  length = 135
FEATURE                Location/Qualifiers
source                 1..135
                       mol_type = other RNA
                       note = RNA encoding unit peptide
                       organism = synthetic construct
SEQUENCE: 279
cgtaatgttc ctcctatctt caatgatgtt tattggattg cattcnnnnn naagnnngtg   60
gcagcttgga ccctgaaggc agcannnnnn tgccgtttcc gtggactgat ttccctgtcc  120
caggtttatc tgtcc                                                   135

SEQ ID NO: 280         moltype = RNA  length = 135
FEATURE                Location/Qualifiers
source                 1..135
                       mol_type = other RNA
                       note = RNA encoding unit peptide
                       organism = synthetic construct
SEQUENCE: 280
cgtaatgttc ctcctatctt caatgatgtt tattggattg cattcnnnnn naagttcgtg   60
gcagcttgga ccctgaaggc agcannnnnn tgccgtttcc gtggactgat ttccctgtcc  120
caggtttatc tgtcc                                                   135

SEQ ID NO: 281         moltype = RNA  length = 135
FEATURE                Location/Qualifiers
source                 1..135
                       mol_type = other RNA
                       note = RNA encoding unit peptide
                       organism = synthetic construct
SEQUENCE: 281
cgtaatgttc ctcctatctt caatgatgtt tattggattg cattcnnnnn naagtatgtg   60
gcagcttgga ccctgaaggc agcannnnnn tgccgtttcc gtggactgat ttccctgtcc  120
caggtttatc tgtcc                                                   135

SEQ ID NO: 282         moltype = RNA  length = 135
FEATURE                Location/Qualifiers
source                 1..135
                       mol_type = other RNA
                       note = RNA encoding unit peptide
                       organism = synthetic construct
SEQUENCE: 282
cgtaatgttc ctcctatctt caatgatgtt tattggattg cattcnnnnn naagnnngtg   60
gcagcttgga ccctgaaggc agcannnnnn ggatcgcatc accatcacca tcacggatcc  120
gatgatgatg acaag                                                   135

SEQ ID NO: 283         moltype = RNA  length = 135
FEATURE                Location/Qualifiers
source                 1..135
                       mol_type = other RNA
                       note = RNA encoding unit peptide
                       organism = synthetic construct
SEQUENCE: 283
cgtaatgttc ctcctatctt caatgatgtt tattggattg cattcnnnnn naagttcgtg   60
gcagcttgga ccctgaaggc agcannnnnn ggatcgcatc accatcacca tcacggatcc  120
gatgatgatg acaag                                                   135

SEQ ID NO: 284         moltype = RNA  length = 135
FEATURE                Location/Qualifiers
source                 1..135
                       mol_type = other RNA
                       note = RNA encoding unit peptide
                       organism = synthetic construct
SEQUENCE: 284
cgtaatgttc ctcctatctt caatgatgtt tattggattg cattcnnnnn naagtatgtg   60
gcagcttgga ccctgaaggc agcannnnnn ggatcgcatc accatcacca tcacggatcc  120
gatgatgatg acaag                                                   135

SEQ ID NO: 285         moltype = RNA  length = 135
FEATURE                Location/Qualifiers
```

```
source                  1..135
                        mol_type = other RNA
                        note = RNA encoding unit peptide
                        organism = synthetic construct
SEQUENCE: 285
ggatcgcatc accatcacca tcacggatcc gatgatgatg acaagnnnnn naagnnngtg    60
gcagcttgga ccctgaaggc agcannnnnn cgtaatgttc ctcctatctt caatgatgtt   120
tattggattg cattc                                                    135

SEQ ID NO: 286          moltype = RNA  length = 135
FEATURE                 Location/Qualifiers
source                  1..135
                        mol_type = other RNA
                        note = RNA encoding unit peptide
                        organism = synthetic construct
SEQUENCE: 286
ggatcgcatc accatcacca tcacggatcc gatgatgatg acaagnnnnn naagttcgtg    60
gcagcttgga ccctgaaggc agcannnnnn cgtaatgttc ctcctatctt caatgatgtt   120
tattggattg cattc                                                    135

SEQ ID NO: 287          moltype = RNA  length = 135
FEATURE                 Location/Qualifiers
source                  1..135
                        mol_type = other RNA
                        note = RNA encoding unit peptide
                        organism = synthetic construct
SEQUENCE: 287
ggatcgcatc accatcacca tcacggatcc gatgatgatg acaagnnnnn naagtatgtg    60
gcagcttgga ccctgaaggc agcannnnnn cgtaatgttc ctcctatctt caatgatgtt   120
tattggattg cattc                                                    135

SEQ ID NO: 288          moltype = RNA  length = 135
FEATURE                 Location/Qualifiers
source                  1..135
                        mol_type = other RNA
                        note = RNA encoding unit peptide
                        organism = synthetic construct
SEQUENCE: 288
aaaacgacaa agcaatcatt tgatttaagt gtaaaagctc agtatnnnnn naagnnngtg    60
gcagcttgga ccctgaaggc agcannnnnn tgccgtttcc gtggactgat ttccctgtcc   120
caggtttatc tgtcc                                                    135

SEQ ID NO: 289          moltype = RNA  length = 135
FEATURE                 Location/Qualifiers
source                  1..135
                        mol_type = other RNA
                        note = RNA encoding unit peptide
                        organism = synthetic construct
SEQUENCE: 289
aaaacgacaa agcaatcatt tgatttaagt gtaaaagctc agtatnnnnn naagttcgtg    60
gcagcttgga ccctgaaggc agcannnnnn tgccgtttcc gtggactgat ttccctgtcc   120
caggtttatc tgtcc                                                    135

SEQ ID NO: 290          moltype = RNA  length = 135
FEATURE                 Location/Qualifiers
source                  1..135
                        mol_type = other RNA
                        note = RNA encoding unit peptide
                        organism = synthetic construct
SEQUENCE: 290
aaaacgacaa agcaatcatt tgatttaagt gtaaaagctc agtatnnnnn naagtatgtg    60
gcagcttgga ccctgaaggc agcannnnnn tgccgtttcc gtggactgat ttccctgtcc   120
caggtttatc tgtcc                                                    135

SEQ ID NO: 291          moltype = RNA  length = 135
FEATURE                 Location/Qualifiers
source                  1..135
                        mol_type = other RNA
                        note = RNA encoding unit peptide
                        organism = synthetic construct
SEQUENCE: 291
cgtaatgttc ctcctatctt caatgatgtt tattggattg cattctgccg tttccgtgga    60
ctgatttccc tgtcccaggt ttatctgtcc nnnnnnaagn nngtggcagc ttggaccctg   120
aaggcagcan nnnnn                                                    135

SEQ ID NO: 292          moltype = RNA  length = 135
FEATURE                 Location/Qualifiers
source                  1..135
                        mol_type = other RNA
```

```
                        note = RNA encoding unit peptide
                        organism = synthetic construct
SEQUENCE: 292
cgtaatgttc ctcctatctt caatgatgtt tattggattg cattctgccg tttccgtgga    60
ctgatttccc tgtcccaggt ttatctgtcc nnnnnnaagt tcgtggcagc ttggaccctg   120
aaggcagcan nnnnn                                                    135

SEQ ID NO: 293          moltype = RNA  length = 135
FEATURE                 Location/Qualifiers
source                  1..135
                        mol_type = other RNA
                        note = RNA encoding unit peptide
                        organism = synthetic construct
SEQUENCE: 293
cgtaatgttc ctcctatctt caatgatgtt tattggattg cattctgccg tttccgtgga    60
ctgatttccc tgtcccaggt ttatctgtcc nnnnnnaagt atgtggcagc ttggaccctg   120
aaggcagcan nnnnn                                                    135

SEQ ID NO: 294          moltype = RNA  length = 135
FEATURE                 Location/Qualifiers
source                  1..135
                        mol_type = other RNA
                        note = RNA encoding unit peptide
                        organism = synthetic construct
SEQUENCE: 294
cgtaatgttc ctcctatctt caatgatgtt tattggattg cattcnnncc taagtatgtg    60
aagcagaata cactgaagct ggcaaccnnn tgccgtttcc gtggactgat ttccctgtcc   120
caggtttatc tgtcc                                                    135

SEQ ID NO: 295          moltype = RNA  length = 90
FEATURE                 Location/Qualifiers
source                  1..90
                        mol_type = other RNA
                        note = RNA encoding unit peptide
                        organism = synthetic construct
SEQUENCE: 295
cgtaatgttc ctcctatctt caatgatgtt tattggattg cattcnnnnn naagnnngtg    60
gcagcttgga ccctgaaggc agcannnnnn                                    90

SEQ ID NO: 296          moltype = RNA  length = 90
FEATURE                 Location/Qualifiers
source                  1..90
                        mol_type = other RNA
                        note = RNA encoding unit peptide
                        organism = synthetic construct
SEQUENCE: 296
cgtaatgttc ctcctatctt caatgatgtt tattggattg cattcnnnnn naagttcgtg    60
gcagcttgga ccctgaaggc agcannnnnn                                    90

SEQ ID NO: 297          moltype = RNA  length = 90
FEATURE                 Location/Qualifiers
source                  1..90
                        mol_type = other RNA
                        note = RNA encoding unit peptide
                        organism = synthetic construct
SEQUENCE: 297
cgtaatgttc ctcctatctt caatgatgtt tattggattg cattcnnnnn naagtatgtg    60
gcagcttgga ccctgaaggc agcannnnnn                                    90

SEQ ID NO: 298          moltype = RNA  length = 78
FEATURE                 Location/Qualifiers
source                  1..78
                        mol_type = other RNA
                        note = RNA encoding unit peptide
                        organism = synthetic construct
SEQUENCE: 298
cgtaatgttc ctcctatctt caatgatgtt tattggattg cattcaagnn ngtggcagct    60
tggaccctga aggcagca                                                 78

SEQ ID NO: 299          moltype = RNA  length = 78
FEATURE                 Location/Qualifiers
source                  1..78
                        mol_type = other RNA
                        note = RNA encoding unit peptide
                        organism = synthetic construct
SEQUENCE: 299
cgtaatgttc ctcctatctt caatgatgtt tattggattg cattcaagtt cgtggcagct    60
tggaccctga aggcagca                                                 78
```

```
SEQ ID NO: 300          moltype = RNA   length = 78
FEATURE                 Location/Qualifiers
source                  1..78
                        mol_type = other RNA
                        note = RNA encoding unit peptide
                        organism = synthetic construct
SEQUENCE: 300
cgtaatgttc ctcctatctt caatgatgtt tattggattg cattcaagta tgtggcagct   60
tggaccctga aggcagca                                                 78

SEQ ID NO: 301          moltype = RNA   length = 96
FEATURE                 Location/Qualifiers
source                  1..96
                        mol_type = other RNA
                        note = RNA encoding unit peptide
                        organism = synthetic construct
SEQUENCE: 301
cgtaatgttc ctcctatctt caatgatgtt tattggattg cattcaagnn ngtggcagct   60
tggaccctga aggcagcaca tcaccatcac catcac                             96

SEQ ID NO: 302          moltype = RNA   length = 96
FEATURE                 Location/Qualifiers
source                  1..96
                        mol_type = other RNA
                        note = RNA encoding unit peptide
                        organism = synthetic construct
SEQUENCE: 302
cgtaatgttc ctcctatctt caatgatgtt tattggattg cattcaagtt cgtggcagct   60
tggaccctga aggcagcaca tcaccatcac catcac                             96

SEQ ID NO: 303          moltype = RNA   length = 96
FEATURE                 Location/Qualifiers
source                  1..96
                        mol_type = other RNA
                        note = RNA encoding unit peptide
                        organism = synthetic construct
SEQUENCE: 303
cgtaatgttc ctcctatctt caatgatgtt tattggattg cattcaagta tgtggcagct   60
tggaccctga aggcagcaca tcaccatcac catcac                             96

SEQ ID NO: 304          moltype = RNA   length = 129
FEATURE                 Location/Qualifiers
source                  1..129
                        mol_type = other RNA
                        note = RNA encoding unit peptide
                        organism = synthetic construct
SEQUENCE: 304
cgtaatgttc ctcctatctt caatgatgtt tattggattg cattcnnnnn naagnnngtg   60
gcagcttgga ccctgaaggc agcatgccgt ttccgtggac tgatttccct gtcccaggtt  120
tatctgtcc                                                          129

SEQ ID NO: 305          moltype = RNA   length = 129
FEATURE                 Location/Qualifiers
source                  1..129
                        mol_type = other RNA
                        note = RNA encoding unit peptide
                        organism = synthetic construct
SEQUENCE: 305
cgtaatgttc ctcctatctt caatgatgtt tattggattg cattcnnnnn naagttcgtg   60
gcagcttgga ccctgaaggc agcatgccgt ttccgtggac tgatttccct gtcccaggtt  120
tatctgtcc                                                          129

SEQ ID NO: 306          moltype = RNA   length = 129
FEATURE                 Location/Qualifiers
source                  1..129
                        mol_type = other RNA
                        note = RNA encoding unit peptide
                        organism = synthetic construct
SEQUENCE: 306
cgtaatgttc ctcctatctt caatgatgtt tattggattg cattcnnnnn naagtatgtg   60
gcagcttgga ccctgaaggc agcatgccgt ttccgtggac tgatttccct gtcccaggtt  120
tatctgtcc                                                          129

SEQ ID NO: 307          moltype = RNA   length = 90
FEATURE                 Location/Qualifiers
source                  1..90
                        mol_type = other RNA
                        note = RNA encoding unit peptide
                        organism = synthetic construct
```

```
SEQUENCE: 307
cgtaatgttc ctcctatctt caatgatgtt tattggattg cattcnnnnn naagnnngtg    60
gcagcttgga ccctgaaggc agcatgccgt                                    90

SEQ ID NO: 308          moltype = RNA  length = 90
FEATURE                 Location/Qualifiers
source                  1..90
                        mol_type = other RNA
                        note = RNA encoding unit peptide
                        organism = synthetic construct
SEQUENCE: 308
cgtaatgttc ctcctatctt caatgatgtt tattggattg cattcnnnnn naagttcgtg    60
gcagcttgga ccctgaaggc agcatgccgt                                    90

SEQ ID NO: 309          moltype = RNA  length = 90
FEATURE                 Location/Qualifiers
source                  1..90
                        mol_type = other RNA
                        note = RNA encoding unit peptide
                        organism = synthetic construct
SEQUENCE: 309
cgtaatgttc ctcctatctt caatgatgtt tattggattg cattcnnnnn naagtatgtg    60
gcagcttgga ccctgaaggc agcatgccgt                                    90
```